(12) United States Patent
Fairman et al.

(10) Patent No.: US 11,998,599 B2
(45) Date of Patent: *Jun. 4, 2024

(54) POLYPEPTIDE-ANTIGEN CONJUGATES WITH NON-NATURAL AMINO ACIDS

(71) Applicant: Vaxcyte, Inc., San Carlos, CA (US)

(72) Inventors: Jeffery Fairman, Mountain View, CA (US); Jon H. Heinrichs, Doylestown, PA (US); Wei Chan, San Francisco, CA (US)

(73) Assignee: Vaxcyte, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/859,251

(22) Filed: Dec. 29, 2017

(65) Prior Publication Data

US 2018/0333484 A1 Nov. 22, 2018

Related U.S. Application Data

(60) Provisional application No. 62/591,160, filed on Nov. 27, 2017, provisional application No. 62/568,201, filed on Oct. 4, 2017, provisional application No. 62/530,803, filed on Jul. 10, 2017, provisional application No. 62/441,115, filed on Dec. 30, 2016.

(51) Int. Cl.
*A61K 39/385* (2006.01)
*A61K 39/09* (2006.01)
*A61K 47/64* (2017.01)
*A61P 29/00* (2006.01)
*A61P 31/04* (2006.01)
*A61P 37/00* (2006.01)
*A61K 39/00* (2006.01)

(52) U.S. Cl.
CPC .......... *A61K 39/385* (2013.01); *A61K 39/092* (2013.01); *A61K 47/6415* (2017.08); *A61K 47/646* (2017.08); *A61P 29/00* (2018.01); *A61P 31/04* (2018.01); *A61P 37/00* (2018.01); *A61K 2039/575* (2013.01); *A61K 2039/6037* (2013.01); *A61K 2039/627* (2013.01)

(58) Field of Classification Search
CPC .......... A61P 37/04; A61P 31/00; A61P 43/00; A61P 37/02; A61K 39/092; A61K 39/00; A61K 2039/70; A61K 2039/6087; A61K 2039/55544; A61K 39/116; A61K 2039/627; A61K 2039/55583; A61K 2039/55516; A61K 2039/60; A61K 35/74; A61K 2039/6093; A61K 38/164; A61K 39/40; C12N 9/2417; G01N 33/56911; G01N 33/56938; G01N 2333/31; Y10S 424/831; Y10S 530/806
See application file for complete search history.

(56) References Cited

U.S. PATENT DOCUMENTS

| | | |
|---|---|---|
| 4,902,506 A | 2/1990 | Anderson et al. |
| 5,360,897 A | 11/1994 | Anderson et al. |
| 5,565,204 A | 10/1996 | Kuo et al. |
| 5,614,382 A | 3/1997 | Metcalf |
| 5,623,057 A | 4/1997 | Marburg et al. |
| 5,785,973 A | 7/1998 | Bixler et al. |
| 6,329,512 B1 | 12/2001 | Yang et al. |
| 6,548,276 B2 | 4/2003 | Swartz et al. |
| 6,855,321 B1 | 2/2005 | Rappuoli et al. |
| 6,927,042 B2 | 8/2005 | Schultz et al. |
| 6,994,986 B2 | 2/2006 | Swartz et al. |
| 7,018,637 B2 | 3/2006 | Chong et al. |
| 7,041,479 B2 | 5/2006 | Swartz et al. |
| 7,129,333 B2 | 10/2006 | Schultz et al. |
| 7,217,791 B2 | 5/2007 | Chen et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,560,535 B2 | 7/2009 | Schultz et al. |
| 7,709,001 B2 | 5/2010 | Hausdorff et al. |
| 7,718,791 B2 | 5/2010 | Bahler et al. |
| 7,825,226 B2 | 11/2010 | Schultz et al. |
| 7,867,498 B2 | 1/2011 | Rappuoli et al. |
| 7,871,794 B2 | 1/2011 | Knapp et al. |

(Continued)

FOREIGN PATENT DOCUMENTS

| | | |
|---|---|---|
| CN | 101374548 A | 2/2009 |
| CN | 102716480 A | 10/2012 |

(Continued)

OTHER PUBLICATIONS

Ogawa T. The potential protective immune responses to synthetic peptides containing conserved epitopes of Porphyromonas gingivalis fimbrial protein. J Med Microbiol. Nov. 1994;41(5):349-58. (Year: 1994).*

(Continued)

*Primary Examiner* — Aradhana Sasan
*Assistant Examiner* — Jia-Hai Lee
(74) *Attorney, Agent, or Firm* — Cooley LLP

(57) ABSTRACT

Methods for the production of immunogenic compositions containing a non-natural amino acid are disclosed. The non-natural amino acid can be a site for attachment of antigens, such as bacterial capsular polysaccharides, to make immunogenic conjugates. Bio-orthogonal attachment chemistry incorporated into the non-natural amino acids allows for more efficient and potent antigen presentation to the immune system, simplified purification, and more well-defined structure of these semi-synthetic immunogens.

17 Claims, 5 Drawing Sheets
Specification includes a Sequence Listing.

(56) References Cited

U.S. PATENT DOCUMENTS

| | | |
|---|---|---|
| 7,935,787 B2 | 5/2011 | Khandke et al. |
| 7,955,605 B2 | 6/2011 | Prasad |
| 8,030,074 B2 | 10/2011 | Schultz et al. |
| 8,114,648 B2 | 2/2012 | Schultz et al. |
| 8,183,010 B2 | 5/2012 | Swartz et al. |
| 8,192,746 B2 | 6/2012 | Caulfield et al. |
| 8,298,759 B2 | 10/2012 | Voloshin et al. |
| 8,329,184 B2 | 12/2012 | Biemans et al. |
| 8,357,529 B2 | 1/2013 | Swartz et al. |
| 8,481,054 B2 | 7/2013 | Nahm et al. |
| 8,492,115 B2 | 7/2013 | Swartz et al. |
| 8,551,527 B2 | 10/2013 | Chouvenc et al. |
| 8,562,999 B2 | 10/2013 | Khandke et al. |
| 8,603,484 B2 | 12/2013 | Prasad |
| 8,642,042 B2 | 2/2014 | Mekalanos |
| 8,652,480 B2 | 2/2014 | Yuan et al. |
| 8,715,958 B2 | 5/2014 | Goerke et al. |
| 8,753,645 B2 | 6/2014 | Biemans et al. |
| 8,753,649 B2 | 6/2014 | Lee et al. |
| 8,758,764 B2 | 6/2014 | Masignani et al. |
| 8,778,631 B2 | 7/2014 | Voloshin et al. |
| 8,795,689 B2 | 8/2014 | Crinean |
| 8,808,707 B1 | 8/2014 | Siber et al. |
| 8,895,024 B2 | 11/2014 | Hausdorff et al. |
| 8,895,724 B2 | 11/2014 | Hausdorff et al. |
| 8,912,322 B2 | 12/2014 | Popik et al. |
| 8,999,697 B2 | 4/2015 | Yuan et al. |
| 9,040,253 B2 | 5/2015 | Roy et al. |
| 9,095,567 B2 | 8/2015 | Khandke et al. |
| 9,175,033 B2 | 11/2015 | Lee |
| 9,265,839 B2 | 2/2016 | Biemans et al. |
| 9,265,840 B2 | 2/2016 | Biemans et al. |
| 9,315,468 B2 | 4/2016 | Boon et al. |
| 9,358,284 B2 | 6/2016 | Saul et al. |
| 9,399,060 B2 | 7/2016 | Hausdorff et al. |
| 9,410,170 B2 | 8/2016 | Calhoun et al. |
| 9,422,345 B2 | 8/2016 | Blais et al. |
| 9,474,795 B2 | 10/2016 | Lee et al. |
| 9,480,736 B2 | 11/2016 | Hausdorff et al. |
| 9,492,559 B2 | 11/2016 | Emini et al. |
| 9,493,517 B2 | 11/2016 | Costantino et al. |
| 9,649,372 B2 | 5/2017 | Harper et al. |
| 9,650,621 B2 | 5/2017 | Thanos et al. |
| 9,669,084 B2 | 6/2017 | Siber et al. |
| 9,675,681 B2 | 6/2017 | Yuan et al. |
| 9,682,934 B2 | 6/2017 | Stafford et al. |
| 9,682,984 B2 | 6/2017 | Bonde-Larsen et al. |
| 9,778,266 B2 | 10/2017 | Nahm et al. |
| 9,840,493 B2 | 12/2017 | Yang et al. |
| 9,938,516 B2 | 4/2018 | Zimmerman et al. |
| 9,981,035 B2 | 5/2018 | Hausdorff et al. |
| 9,981,045 B2 | 5/2018 | Prasad |
| 9,988,619 B2 | 6/2018 | Zimmerman et al. |
| 9,994,527 B2 | 6/2018 | Stafford et al. |
| 10,034,949 B2 | 7/2018 | Shin et al. |
| 10,112,900 B2 | 10/2018 | Stafford et al. |
| 10,124,050 B2 | 11/2018 | Watson et al. |
| 10,137,088 B2 | 11/2018 | Zale et al. |
| 10,179,909 B2 | 1/2019 | Zimmerman et al. |
| 10,190,145 B2 | 1/2019 | Yam et al. |
| 10,316,322 B2 | 6/2019 | Groff et al. |
| 10,597,664 B2 | 3/2020 | Oganesyan et al. |
| 2004/0102388 A1 | 5/2004 | High et al. |
| 2004/0202668 A1* | 10/2004 | Boutriau ............ A61K 39/12 424/184.1 |
| 2006/0228380 A1* | 10/2006 | Hausdorff ......... A61K 39/385 424/244.1 |
| 2006/0228381 A1 | 10/2006 | Bahler et al. |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2008/0102498 A1 | 5/2008 | Bahler et al. |
| 2009/0117148 A1* | 5/2009 | Costantino ............ A61P 43/00 424/197.11 |
| 2009/0162394 A1 | 6/2009 | Biemans et al. |
| 2009/0269370 A1 | 10/2009 | Cohen et al. |
| 2010/0034847 A1 | 2/2010 | Borkowski et al. |
| 2012/0321658 A1 | 12/2012 | Biemans et al. |
| 2013/0189300 A1 | 7/2013 | Costantino et al. |
| 2013/0273098 A1 | 10/2013 | Blue et al. |
| 2013/0344103 A1 | 12/2013 | Biemans et al. |
| 2014/0066598 A1 | 3/2014 | Stafford et al. |
| 2014/0154286 A1 | 6/2014 | Malley et al. |
| 2015/0017187 A1 | 1/2015 | Thanos et al. |
| 2015/0017192 A1 | 1/2015 | Usera et al. |
| 2015/0190520 A1 | 7/2015 | Shin et al. |
| 2015/0216996 A1 | 8/2015 | Gu et al. |
| 2016/0101187 A1 | 4/2016 | Berti et al. |
| 2016/0251336 A1 | 9/2016 | Yang et al. |
| 2016/0257945 A1 | 9/2016 | Zimmerman et al. |
| 2016/0257946 A1 | 9/2016 | Zimmerman et al. |
| 2016/0324948 A1 | 11/2016 | Gu et al. |
| 2016/0324949 A1 | 11/2016 | Han et al. |
| 2016/0370376 A1 | 12/2016 | Polukhtin et al. |
| 2016/0375118 A1 | 12/2016 | Park et al. |
| 2017/0002012 A1 | 1/2017 | Van Delft et al. |
| 2017/0007713 A1 | 1/2017 | Gu et al. |
| 2017/0008858 A1 | 1/2017 | Van Delft et al. |
| 2017/0021006 A1 | 1/2017 | Watson et al. |
| 2017/0143821 A1 | 5/2017 | Porro |
| 2017/0196962 A1 | 7/2017 | Nizet et al. |
| 2017/0224802 A1 | 8/2017 | Crinean |
| 2017/0224804 A1 | 8/2017 | Gu et al. |
| 2017/0252423 A1 | 9/2017 | Siber et al. |
| 2017/0267637 A1 | 9/2017 | Stafford et al. |
| 2017/0283469 A1 | 10/2017 | Thanos et al. |
| 2018/0000922 A1 | 1/2018 | Cooper et al. |
| 2018/0002732 A1 | 1/2018 | Chandler et al. |
| 2018/0051065 A1 | 2/2018 | Yin |
| 2018/0086734 A1 | 3/2018 | Yang et al. |
| 2018/0099039 A1 | 4/2018 | Emini et al. |
| 2018/0136224 A1 | 5/2018 | Nahm et al. |
| 2018/0147288 A1 | 5/2018 | Robinson et al. |
| 2018/0161445 A1 | 6/2018 | Dhere et al. |
| 2018/0207262 A1 | 7/2018 | Biemans et al. |
| 2018/0250390 A1 | 9/2018 | Hausdorff et al. |
| 2018/0303923 A1 | 10/2018 | Bertaud et al. |
| 2019/0000952 A1 | 1/2019 | Lin et al. |
| 2019/0047958 A1 | 2/2019 | Stafford et al. |
| 2019/0070282 A1 | 3/2019 | Watson et al. |
| 2019/0070283 A1 | 3/2019 | Han et al. |
| 2019/0070287 A1 | 3/2019 | Fanger et al. |
| 2019/0161781 A1 | 5/2019 | Yam et al. |
| 2019/0248841 A1 | 8/2019 | Faridmoayer et al. |
| 2020/0054739 A1 | 2/2020 | Fairman et al. |
| 2020/0113993 A1 | 4/2020 | Forrest et al. |

FOREIGN PATENT DOCUMENTS

| | | |
|---|---|---|
| CN | 102807621 A | 12/2012 |
| CN | 102861326 A | 1/2013 |
| CN | 104080479 A | 10/2014 |
| CN | 106102770 A | 11/2016 |
| EP | 0 071 515 A1 | 2/1983 |
| EP | 0 245 045 A2 | 11/1987 |
| EP | 0 375 778 A1 | 7/1990 |
| EP | 1 601 689 B1 | 11/2007 |
| EP | 1 791 860 B1 | 4/2008 |
| EP | 1 861 420 B1 | 11/2009 |
| EP | 1 976 697 B1 | 6/2011 |
| EP | 1 896 065 B1 | 7/2011 |
| EP | 2 044 194 B1 | 10/2011 |
| EP | 2 382 986 A2 | 11/2011 |
| EP | 2 402 025 A2 | 1/2012 |
| EP | 2 094 298 B1 | 2/2012 |
| EP | 1 868 645 B1 | 3/2012 |
| EP | 2 086 582 B1 | 11/2012 |
| EP | 2 417 983 B1 | 6/2013 |
| EP | 2 676 679 A2 | 12/2013 |
| EP | 2 322 631 B1 | 11/2014 |
| EP | 2 815 762 A2 | 12/2014 |
| EP | 2 099 487 A1 | 6/2015 |
| EP | 2 544 708 B1 | 6/2015 |
| EP | 2 932 979 A1 | 10/2015 |

(56) References Cited

FOREIGN PATENT DOCUMENTS

| | | |
|---|---|---|
| EP | 2 932 980 A1 | 10/2015 |
| EP | 2 094 304 B1 | 11/2015 |
| EP | 3 009 146 A1 | 4/2016 |
| EP | 3 020 411 A1 | 5/2016 |
| EP | 2 865 392 B1 | 11/2016 |
| EP | 3 096 785 A2 | 11/2016 |
| EP | 3 096 786 A2 | 11/2016 |
| EP | 2 129 693 B1 | 12/2016 |
| EP | 2 351 578 B1 | 1/2017 |
| EP | 2 726 494 B1 | 1/2017 |
| EP | 3 130 348 A1 | 2/2017 |
| EP | 3 004 062 B1 | 7/2017 |
| EP | 2 796 546 B1 | 8/2017 |
| EP | 3 269 385 A1 | 1/2018 |
| EP | 3 269 386 A1 | 1/2018 |
| EP | 2 716 661 B1 | 3/2018 |
| EP | 3 296 741 A1 | 3/2018 |
| EP | 2 950 815 B1 | 4/2018 |
| EP | 3 302 542 A1 | 4/2018 |
| EP | 3 311 836 A1 | 4/2018 |
| EP | 2 907 525 B1 | 5/2018 |
| EP | 3 325 008 A1 | 5/2018 |
| EP | 2 436 700 B1 | 6/2018 |
| EP | 3 377 098 A1 | 9/2018 |
| EP | 3 055 321 B1 | 10/2018 |
| EP | 3 017 827 B1 | 11/2018 |
| EP | 3 406 635 A1 | 11/2018 |
| EP | 3 436 061 A2 | 2/2019 |
| EP | 3 470 080 A1 | 4/2019 |
| EP | 3 170 837 B1 | 8/2019 |
| EP | 2 945 641 B1 | 1/2020 |
| JP | 2001-190665 A | 7/2001 |
| JP | 2009-520761 A | 5/2009 |
| JP | 2011-212183 A | 10/2011 |
| JP | 2012-521403 A | 9/2012 |
| JP | 2014-518061 A | 7/2014 |
| JP | 2015-501329 A | 1/2015 |
| JP | 2015-529208 A | 10/2015 |
| JP | 2017-504661 A | 2/2017 |
| JP | 2020-504760 A | 7/2018 |
| JP | 2019-513821 A | 5/2019 |
| WO | WO-89/06974 A2 | 8/1989 |
| WO | WO-89/06974 A3 | 8/1989 |
| WO | WO-94/09115 A1 | 4/1994 |
| WO | WO-98/51339 A1 | 11/1998 |
| WO | WO-02/40497 A1 | 5/2002 |
| WO | WO-03/007985 A2 | 1/2003 |
| WO | WO-03/007985 A3 | 1/2003 |
| WO | WO-2004/043376 A2 | 5/2004 |
| WO | WO-2004/043376 A3 | 5/2004 |
| WO | WO-2004/067030 A2 | 8/2004 |
| WO | WO-2004/067030 A3 | 8/2004 |
| WO | WO-2004/067574 A1 | 8/2004 |
| WO | WO-2006/000920 A3 | 1/2005 |
| WO | WO-2005/033148 A1 | 4/2005 |
| WO | WO-2005/105141 A2 | 11/2005 |
| WO | WO-2005/105141 A3 | 11/2005 |
| WO | WO-2006/000920 A2 | 1/2006 |
| WO | WO-2006/110352 A2 | 10/2006 |
| WO | WO-2006/110352 A3 | 10/2006 |
| WO | WO-2006/110381 A1 | 10/2006 |
| WO | WO-2008/045852 A2 | 4/2008 |
| WO | WO-2008/045852 A3 | 4/2008 |
| WO | WO-2008/079653 A1 | 7/2008 |
| WO | WO-2008/079732 A2 | 7/2008 |
| WO | WO-2008/079732 A3 | 7/2008 |
| WO | WO-2008/081014 A2 | 7/2008 |
| WO | WO-2008/081014 A3 | 7/2008 |
| WO | WO-2008/118752 A2 | 10/2008 |
| WO | WO-2008/118752 A3 | 10/2008 |
| WO | WO-2008/143709 A2 | 11/2008 |
| WO | WO-2008/143709 A3 | 11/2008 |
| WO | WO-2009/000824 A2 | 12/2008 |
| WO | WO-2009/000824 A3 | 12/2008 |
| WO | WO-2009/000825 A2 | 12/2008 |
| WO | WO-2009/000825 A3 | 12/2008 |
| WO | WO-2009/106085 A1 | 9/2009 |
| WO | WO-2010/080484 A1 | 7/2010 |
| WO | WO-2010/080486 A2 | 7/2010 |
| WO | WO-2010/080486 A3 | 7/2010 |
| WO | WO2010150230 A1 * | 12/2010 | ............ C07K 14/34 |
| WO | WO-2011/110241 A1 | 9/2011 |
| WO | WO-2011/110531 A2 | 9/2011 |
| WO | WO-2011/110531 A3 | 9/2011 |
| WO | WO-2011/151760 A2 | 12/2011 |
| WO | WO-2011/151760 A3 | 12/2011 |
| WO | WO-2012/121973 A1 | 9/2012 |
| WO | WO-2013/009564 A1 | 1/2013 |
| WO | WO-2013/068949 A1 | 5/2013 |
| WO | WO-2014/036492 A1 | 3/2014 |
| WO | WO-2014/102265 A1 | 7/2014 |
| WO | WO-2014/111344 A1 | 7/2014 |
| WO | WO2015054658 A1 * | 4/2015 | ........... C07D 401/12 |
| WO | WO-2015/110940 A2 | 7/2015 |
| WO | WO-2015/110940 A3 | 7/2015 |
| WO | WO-2015/110941 A2 | 7/2015 |
| WO | WO-2015/110941 A3 | 7/2015 |
| WO | WO-2015/117093 A1 | 8/2015 |
| WO | WO-2016/020413 A1 | 2/2016 |
| WO | WO-2016/113644 A1 | 7/2016 |
| WO | WO-2016/207905 A2 | 12/2016 |
| WO | WO-2016/207905 A3 | 12/2016 |
| WO | WO-2017/067962 A1 | 4/2017 |
| WO | WO-2017/173415 A2 | 10/2017 |
| WO | WO-2017/173415 A3 | 10/2017 |
| WO | WO-2018/064444 A1 | 4/2018 |
| WO | WO-2018/126229 A9 | 7/2018 |
| WO | WO-2018/134693 A1 | 7/2018 |
| WO | WO-2018/144438 A1 | 8/2018 |
| WO | WO-2018/147641 A1 | 8/2018 |
| WO | WO-2018/156465 A1 | 8/2018 |
| WO | WO-2018/156467 A1 | 8/2018 |
| WO | WO-2018/156468 A1 | 8/2018 |
| WO | WO-2018/156491 A1 | 8/2018 |
| WO | WO-2018/206635 A1 | 11/2018 |
| WO | WO-2019/050813 A1 | 3/2019 |
| WO | WO-2019/050814 A1 | 3/2019 |
| WO | WO-2019/050815 A1 | 3/2019 |
| WO | WO-2019/050816 A1 | 3/2019 |
| WO | WO-2019/050818 A1 | 3/2019 |
| WO | WO-2019/070994 A1 | 4/2019 |
| WO | WO-2019/139692 A2 | 7/2019 |
| WO | WO-2019/139692 A3 | 7/2019 |
| WO | WO-2019/152921 A1 | 8/2019 |
| WO | WO-2019/152925 A1 | 8/2019 |
| WO | WO-2019/212842 A1 | 11/2019 |
| WO | WO-2019/212846 A1 | 11/2019 |
| WO | WO-2019/220304 A1 | 11/2019 |

OTHER PUBLICATIONS

Selva et al. Rapid and easy identification of capsular serotypes of *Streptococcus pneumoniae* by use of fragment analysis by automated fluorescence-based capillary electrophoresis. J Clin Microbiol. Nov. 2012;50(11):3451-7. (Year: 2012).*

NCBI AMV91693 toxin CRM197. https://www.ncbi.nlm.nih.gov/protein/AMV91693.1?report=genbank&log$=protalign&blast_rank=1&RID=NGAS5FVZ016[Sep. 8, 2020 11:57:14 PM] (Year: 2020).*

Dagan et al. Glycoconjugate vaccines and immune interference: A review. Vaccine 28 (2010) 5513-5523. (Year: 2010).*

Durando et al. Experience with pneumococcal polysaccharide conjugate vaccine (conjugated to CRM197 carrier protein) in children and adults. Clin Microbiol Infect 2013; 19(suppl. 1): 1-9. (Year: 2013).*

Lyn Jones. Recent advances in the molecular design of synthetic vaccines. Nature chemistry. 2015 (7): 952-960. (Year: 2015).*

Moginger et al. Cross Reactive Material 197 glycoconjugate vaccines contain privileged conjugation sites. Sci Rep. Feb. 4, 2016;6:20488. (Year: 2016).*

Zarei et al. Hib Vaccines: Past, Present, and Future Perspectives. Journal of Immunology Research vol. 2016, Article ID 7203587, 18 pages. (Year: 2016).*

(56) References Cited

OTHER PUBLICATIONS

Guo et al. Genetic diversity of fluoroquinolone-nonsusceptible *Streptococcus pneumoniae* clinical isolates and the first identification of serotype 20B in China. Eur J Clin Microbiol Infect Dis (2014) 33:465-470. (Year: 2014).*
Adamo, R. et al. (2013). Synthetically defined glycoprotein vaccines: Current status and future directions, Chem. Sci. 4:2995-3008.
Andrews, N.J. et al. (2014). "Serotype-specific effectiveness and correlates of protection for the 13-valent pneumococcal conjugate vaccine: a postlicensure indirect cohort study," Lancet Infect Dis. 14:839-846.
Astronomo, R.D. et al. (2010). Carbohydrate vaccines: developing sweet solutions to sticky situations? Nature Reviews. 9:308-324.
Avci, F.Y. et al. (2013). "Carbohydrates and T cells: A sweet twosome," Seminars in Immunology. 25:146-151.
Bain, J.D. et al. (1989). "Biosynthetic site-specific incorporation of a non-natural amino acid into a polypeptide," J. Am. Chem. Soc. 111:8013-8014.
Baraldo et al. (2004). "N19 polyepitope as a carrier for enhanced immunogenicity and protective efficacy of meningococcal conjugate vaccines," Infect. Immun. 72:4884-4887.
Bardotti, A. et al. (2008). "Physicochemical characterization of glycoconjugate vaccines for prevention of meningococcal diseases," Vaccine 26:2284-2296.
Barrett, D.J. (1985). "Human immune responses to polysaccharide antigens: an analysis of bacterial polysaccharide vaccines in infants," Adv Pediatr. 32: 139-158.
Baskin, J.M. et al. (2007). "Copper-free click chemistry for dynamic in vivo imaging," PNAS. 104:16793-16797.
Bazewicz, C.G. et al. (2013). "Sensitive, site-specific, and stable vibrational probe of local protein environments: 4-azidomethyl-L-phenylalanine," J. Phys. Chem. B. 117:8987-8993.
Beatty, K.E. et al. (2006). "Fluorescence visualization of newly synthesized proteins in mammalian cells," Angew. Chem. Int. Ed. 45:7364-7367.
Beatty, K.E. et al. (2005). "Selective dye-labeling of newly synthesized proteins in bacterial cells," J. Am. Chem. Soc. 127:14150-14151.
Beißbarth, T. et al. (2005). "A systematic approach for comprehensive T-cell epitope discovery using peptide libraries," Bioinformatics 21 (Suppl 1):i29-i37.
Berkowitz, B. et al. (1972). "Evidence for active immunity to morphine in mice," Science 178:1290-1292.
Bonten, M. et al. (2014). Community Acquired Pneumonia Immunization Trial in Adults (CAPiTA). Abstract No. 0541. 9th International Symposium on Pneumococci and Pneumococcal disease.
Broker, M. et al. (2011). "Biochemical and biological characteristics of cross-reacting material 197 CRM197, a non-toxic mutant of diphtheria toxin: use as a conjugation protein in vaccines and other potential clinical applications," Biologicals 39:195-204.
Broker, M. et al. (2017). "Polysaccharide conjugate vaccine protein carriers as a "neglected valency"—Potential and limitations," Vaccine 35:3286-3294.
Buttery, J.P. et al. (2005). "Immunogenicity and safety of a combination pneumococcal-meningococcal vaccine in infants: a randomized controlled trial," JAMA 293:1751-1758.
Calix, J.J. et al. (2012). "Biochemical, genetic, and serological characterization of two capsule subtypes among *Streptococcus pneumoniae* Serotype 20 strains: discovery of a new pneumococcal serotype." J. Biol. Chem. 287:27885-94.
Chang, J.Y. et al. (1998). "Unique chemical reactivity of His-21 of CRM197, a mutated diphtheria toxin," J. Febs Lett. 427:362-366.
Chin, J.W. (2014). "Expanding and reprogramming the genetic code of cells and animals," Annu. Rev. Biochem. 83:379-408.
Chong, S. (2014). "Overview of cell-free protein synthesis: historic landmarks, commercial systems, and expanding applications," Curr. Protoc. Mol. Biol. 108:16.30.1-11.
Costantino, P. et al. (2011). "The design of semi-synthetic and synthetic glycoconjugate vaccines," Expert Opin. Drug Disc. 6:1045-1066.

Coutinho, A. et al. (1973). "B cell mitogenic properties of thymus-independent antigens," Nature New Biol. 245: 12-14.
Crotti, S. et al. (2014). "Defined conjugation of glycans to the lysines of CRM197 guided by their reactivity mapping," Chembiochem. 15:836-843.
Dagan, R. et al. (1998). "Reduced response to multiple vaccines sharing common protein epitopes that are administered simultaneously to infants," Infect Immun. 66:2093-2098.
De Benedetto, G. (2015/2016). "Characterization of polysaccharide-based vaccines against invasive nontyphoidal *Salmonella* disease (INTS)," Universita Degli Studi Di Trieste, 174 total pages.
Declaration of Ron Dagan, MD, EPO Opposition to Wyeth LLC, EP 1868645 (Pfizer submission May 4, 2015).
De Graaf, A.J. et al. (2009). "Nonnatural amino acids for site-specific protein conjugation," Bioconjugate Chem. 20:1281-1295.
DeLisi, C. et al. (1985). "T-cell antigenic sites tend to be amphipathic structures," PNAS 82:7048-7052.
De Velasco, E.A. et al. (1995). "Synthetic peptides representing t-cell epitopes act as carriers in pneumococcal polysaccharide conjugate vaccines," Infection & Immunity 65:961-968.
Desai, D.V. et al. (2014). "T-cell epitope prediction methods: an overview," Methods Mol. Biol. 1184:333-364.
Diethelm-Okita, B.M. et al. (1997). "Epitope repertoire of human CD4+ T cells on tetanus toxin: identification of immunodominant sequence segments," J. Infect. Dis. 175:382-391.
Diethelm-Okita, B.M. et al. (2000). "Universal epitopes for human CD4+ cells on tetanus and diphtheria toxins," J. Infect. Dis. 181:1001-1009.
Ederwine, J. et al. (1992). "Analysis of gene expression in single live neurons," PNAS 89:3010-3014.
Endo, Y. et al. (2006). "Cell-free expression systems for eukaryotic protein production," Curr Opin Biotechnol. 17:373-380.
Falugi, F. et al. (2001). "Rationally designed strings of promiscuous CD4(+) T cell epitopes provide help to Haemophilus influenzae type b oligosaccharide: a model for new conjugate vaccines," Eur. J. Immunol. 31:3816-3824.
Feikin, D. et al. (2013). "Serotype-specific changes in Invasive Pneumococcal Disease after pneumoccocal conjugate vaccine introduction: A pooled analysis of multiple sites," Serotype Replacement Study Group. PLoS Med. 10:e1001517.
Frasch, Preparation of bacterial polysaccharide-protein conjugates: Analytical and manufacturing challenges, Vaccine 27, 6468-70 (2009).
Fridman, A. et al. (2012). "An efficient T-cell epitope discovery strategy using in silico prediction and the iTopia assay platform," Oncoimmunol. 1:1258-1270.
Geno, K.A. et al. (2015). "Pneumococcal Capsules and Their Types: Past, Present, and Future," Clin. Microbiol. Rev. 28:871-899.
Glesby, M.J. et al. (2015). "Immunogenicity and Safety of 13-Valent Pneumococcal Conjugate Vaccine in HIV-Infected Adults Previously Vaccinated With Pneumococcal Polysaccharide Vaccine," J. Infect. Dis. 212:18-27.
Goetsch, L. et al. (2003). "Identification of B- and T-cell epitopes of BB, a carrier protein derived from the G protein of *Streptococcus* strain G148," Clin. Diagn. Lab. Immunol. 10:125-132.
Gonzalez, D. et al. (2003). "Immunization with Porphyromonas gingivalis capsular polysaccharide prevents P. gingivalis-elicited oral bone loss in a murine model," Infect. Immun. 71:2283-2287.
Goffin, P. et al. (2017). "High-yield production of recombinant CRM197, a non toxic mutant of diphtheria toxin, in the periplasm of *Escherichia coli*," Biotechnol. J. 12:1700168, 11 total pages.
Goldblatt, D. (2000). "Editorial Review: Conjugate Vaccines," Clin Exp Immunol. 119:1-3.
Grayson, E.J. et al. (2011). "A coordinated synthesis and conjugation strategy for the preparation of homogeneous glycocojugate vaccine candidates," 50:4127-4132.
Guttormsen, H.K. et al. (1999). "Cognate stimulatory B-Cell-T-Cell interactions are critical for T-cell help recruited by glycoconjugate vaccines," Infect Immun. 67:6375-6384.
Hatsukami, D.K. et al. (2005). "Safety and immunogenicity of a nicotine conjugate vaccine in current smokers," 78:456-467.

(56) References Cited

OTHER PUBLICATIONS

Heckler, T.G. et al. (1984). "T4 RNA ligase mediated preparation of novel "chemically misacylated" tRNAPheS," Biochem. 23:1468-1473.
Henikoff, S. et al. (1992). "Amino acid substitution matrices from protein blocks," PNAS 89:10915.
Henrichsen, J. (1995). "Six newly recognized types of Streptococcus pneumoniae," J. Clin. Microbiol. 33:2759-2762.
Hermans, J.P.G. et al. (1988). "Synthesis of two analogues of a fragment of the complex polysaccharide C substance from Streptococcus pneumonia type 1," Recl. Trav. Chim. Pays-Bas, 107:600-606.
Hovijitra, N.T. et al. (2009). "Cell-free synthesis of functional aquaporin Z in synthetic liposomes," Biotechnol Bioeng. 104:40-49.
Howard, J.G. et al. (1971). "Studies on immunological paralysis. V. The influence of molecular weight on the immunogenicity, tolerogenicity and antibody-neutralizing activity of the 3 pneumococcal polysaccharide," 21:535-545.
Hu, Q.Y. et al. (2016). "Towards the next generation of biomedicines by site-selective conjugation," Chem Soc. Rev. 45:1691-1719.
Hua, C.Z. et al. (2016). "Serum Concentrations of Antibodies against Outer Membrane Protein P6, Protein D, and T- and B-Cell Combined Antigenic Epitopes of Nontypeable Haemophilus influenzae in Children and Adults of Different Ages," Clin. Vaccine Immunol. 23:155-161.
Hutchins, B.M. et al. (2011). "Selective formation of covalent protein heterodymers with an unnatural amino acid," Chemical Biology 18:299-303.
Huang, N. et al. (2015). "Liver X receptors contribute to periodontal pathogen-elicited inflammation and oral bone loss," Mol. Oral Microbiol. 30:438-450.
Institut Merieux (1980). Brevet Belge 80:26320, FR2 495 939, (With English abstract).
International Search Report dated Jul. 3, 2018, for PCT Application No. PCT/US2017/069129, filed on Dec. 29, 2017, 8 pages.
Jermutus, L. et al. (1998). "Recent advances in producing and selecting functional proteins by using cell-free translation," Curr Opin Biotechnol. 9:534-548.
Jewett, M.C. et al. (2004). "Rapid expression and purification of 100 nmol quantities of active protein using cell-free protein synthesis," Biotechnol Prog. 20:102-109.
Jewett, M.C. et al. (2002). "Prokaryotic systems for in vitro expression," Weiner MP, Lu Q, editors. Gene cloning and expression technologies. Westborough, MA: Eaton Publishing. pp. 391-411.
Jin, Z. et al. (2007). "Haemophilus influenzae type a infection and its prevention," Infect. Immun. 75:2650-2654.
Jones, C. (2005). "Vaccines based on the cell surface carbohydrates of pathogenic bacteria," Anals of the Bras. Academy of Sciences 77:293-324.
Jones, C. et al. (2002). "Use and validation of NMR assays for the identity and O-acetyl content of capsular polysaccharides from Neisseria meningitidis used in vaccine manufacture," J. Pharm. Biomed. Analysis 30:1233-1247.
Kabat, E.A. et al. (1958). "The effect of variation in molecular weight on the antigenicity of dextran in man," Arch. Blochem. Biophys. 78:306-318.
Kalin, M. (1998). "Pneumococcal serotypes and their clinical relevance," Thorax 53:159-162.
Kim, J.O. et al. (1999). "Relationship between cell surface carbohydrates and intrastrain variation on Opsonophagocytosis of Streptococcus pneumonia," Infection and Immunity 67:2327-2333.
Kim, C.H. et al. (2013). "Protein conjugation with genetically encoded unnatural amino acids," Current Opinion in Chemical Biology 17:412-419.
Kosten, T.R. et al. (2002). "Human therapeutic cocaine vaccine: safety and immunogenicity," Vaccine 20:1196-1204.
Kuberan, B. et al. (2000). "Carbohydrate based vaccines," Curr. Org. Chem. 4:653-677.
Laferriere, C.A. et al. (1997). "The synthesis of Streptococcus pneumoniae polysaccharide-tetanus toxoid conjugates and the effect of chain length on immunogenicity," Vaccine 15:179.
Lagos, R. et al. (2009). "Immunology of combining CRM(197) conjugates for Streptococcus pneumoniae, Neisseria meningitis and Haemophilus influenzae in Chilean infants," Vaccine 27:2299-2305.
Laine, M.L. et al. (1996). "Novel polysaccharide capsular serotypes ion Porphyromonas gingivalis," J. Periodontal Res. 31:278-284.
Lee, C.J. (2002). "Quality control of polyvalent pneumococcal polysaccharide-protein conjugate vaccine by nephelometry," Biologicals 30:97-103.
Lees et al. (2008). Conjugation Chemistry, Chap. 11, Pneumococcal Vaccines: The Impact of Conjugate Vaccine, pp. 163-174.
Lees, A. et al. (1996). "Activation of soluble polysaccharides with 1-cyano-4-dimethylaminopyridinium tetrafluoroborate for use in protein-polysaccharide conjugate vaccines and immunological reagents," Vaccine 14:190-198.
Lei, Q.P. et al. (2000). "Quantification of free polysaccharide in meningococcal polysaccharide-diphtheria toxoid conjugate vaccines," Dev. Biol. 103:259-264.
Lemercinier et al. (1996). "Full 1H NMR assignment and detailed O-acetylation patterns of capsular polysaccharides from Neisseria meningitidis used in vaccine production," Carb. Res. 296:83-96.
Leonard, E.G. et al. (2003). "Antigen processing of the heptavalent pneumococcal conjugate vaccine carrier protein CRM(197) differs depending on the serotype of the attached polysaccharide," Infect Immun 71(7):4186-9.
Li, J. et al. (2016). "Epigenetic switch driven by DNA inversions dictates phase variation in Streptococcus pneumonia," PLoS Pathogens 12:e1005762, 36 total pages.
Lim, S. et al. (2016). "Bioconjugation of therapeutic proteins and enzymes using the expanded set of genetically encoded amino acids," Crit. Rev. in Biotechnol. 36:803-815.
Lu, Y. et al. (2013). "Escherichia coli-based cell free production of flagellin and ordered flagellin display on virus-like particles," Biotechnol Bioeng 110:2073-2085.
Lu, Y. et al. (2014). "Production and stabilization of the trimeric influenza hemagglutinin stem domain for potentially broadly protective influenza vaccines," PNAS. 111:125-130.
Maciel, M., Jr. et al. (2008). "Comprehensive analysis of T cell epitope discovery strategies using 17DD yellow fever virus structural proteins and BALB/c (H2d) mice model," Virol. 378:105-117.
Manso, A.S. et al. (2014). "A random six-phase switch regulates pneumococcal virulence via global epigenetic changes," Nat. Comm. 5:5055, 9 total pages.
Maza, J.C. et al. (2015). "Synthesis and Incorporation of Unnatural Amino Acids To Probe and Optimize Protein Bioconjugations," Bioconjugate Chem. 26:1884-1889.
Micoli, F. et al. (2018). "Protein carriers for glycoconjugate vaccines: History, selection criteria, characterization and new trends," Molecules 23:1451.
Miyataki, N et al. (1993). "Removal of N-terminal formyl groups and deblocking of pyrrolidone carboxylic acid of proteins with anhydrous hydrazine vapor," Eur. J. Biochem. 212:785-789.
Moginger, U. et al. (2016). "Cross reactive material 197 glycoconjugate vaccines contain privileged conjugation sites," Sci. Reports 6:20488.
Musher, D. et al. (1990). "Pneumococcal Polysaccharide Vaccine in Young Adults and Older Bronchitics: Determination of IgG Responses by ELISA and the Effect of Adsorption of Serum with Non-Type-Specific Cell Wall Polysaccharide," Infect Dis. 161:728-735.
Nguyen, D.P. et al. (2009). "Genetic encoding and labeling of aliphatic azides and alkynes in recombinant proteins via a pyrrolysyl-tRNA Synthetase/tRNA(CUA) pair and click chemistry," JACS 131:8720-8721.
Noren, C.J. et al. (1989). "A general method for site-specific incorporation of unnatural amino acids into proteins," Science 244:182-188.
Nwe, K. et al. (2009). Growing applications of "Click chemistry" for bioconjugation in contemporary biomedical research, Cancer Biotherapy and Radiopharmaceuticals. 24:289-302.
O'Brien, K.L. et al. (2007). "Predictors of pneumococcal conjugate vaccine immunogenicity among infants and toddlers in an American Indian PnCRM197 efficacy trial," J Infect Dis. 196:104-114.

(56) References Cited

OTHER PUBLICATIONS

Orr, N. et al. (1999). "Expression and immunogenicity of a mutant diphtheria toxin molecule, CRM(197), and its fragments in *Salmonella typhi* vaccine strain CVD 908-htrA," Infect. Immunol. 67:4290-4294.

Pantosti, A. et al. (1991). "Immunochemical characterization of two surface polysaccharides of Bacteroides fragilis," Infect. Immunol. 59:2075-2082.

Patel, K.G. et al. (2011). "Surface functionalization of virus-like particles by direct conjugation using azide-alkyne click chemistry," Bioconjug Chem. 22:376-387.

Pecetta, S. et al. (2016). "Evaluation of the non-toxic mutant of the diphtheria toxin K51E/E148K as carrier protein for meningococcal vaccines," Vaccine 34:1405-1411.

Peltola, H. et al. (1977). "Haemophilus influenzae type b capsular polysaccharide vaccine in children: a double-blind field study of 100,000 vaccinees 3 months to 5 years of age in Finland,"Pediatrics 60:730-737.

Pillai, S. et al. (1995). "Immunogenicity of genetically engineered glutathione S-transferase fusion proteins containing a T-cell epitope from diphtheria toxin," Infect Immun 63:1535-40.

Pobre, K. et al. (2014). "Carrier priming or suppression: understanding carrier priming enhancement of anti-polysaccharide antibody response to conjugate vaccines," Vaccine 32:1423-1430.

Poolman et al. (Feb. 2011), "Impact of the Conjugation Method on the Immunogenicity of *Streptococcus pneumoniae* Serotype 19F Polysaccharide Conjugate Vaccines," Clinical and Vaccine.

Powell & Newman (1995). Vaccine Design, Chaps. 8 and 9. ISBN: 030644867X.

Presolski, S.I. et al. (2011). "Copper-catalyzed azide-alkyne click chemistry for bioconjugation," Curr. Protoc. Chem. Biol. 3:153-162.

Prevnar 13 Package Insert (2017). 43 total pages.

Prevnar 13 VRBPAC Briefing Document Nov. 18, 2009, 248 total pages.

Quast, R.B. et al. (2015). "Cotranslational incorporation of non-standard amino acids using cell-free protein synthesis," FEBS Letters 589:1703-1712.

Raju, R. et al. (1995). "Epitopes for human CD4+ cells on diphtheria toxin: Structural features of sequence segments forming epitopes recognized by most subjects," Eur J Immunol 25:3207-3214.

Reece, J.C. et al. (1993). "Mapping the major human T helper epitopes of Tetanus toxin," IJ. Immunol. 151:6175-6184.

Richter, S.S. et al. (2013). "Pneumococcal serotypes before and after introduction of conjugate vaccines, United States, 1999-2011(1)," Emerg Infect Dis. 19:1074-1083.

Safari et al. (2012). The future of synthetic carbohydrate vaccines: Immunological studies on *Streptococcus pneumoniae* type 14, Chapter 24, pp. 617-634.

Schneerson, R. et al. (1980). "Preparation, characterization, and immunogenicity of Haemophilus influenzae type b polysaccharide-protein conjugates," J Exp Med. 152:361-376.

Schifferle, R.E. et al. (1989). "Characterization of a polysaccharide anigen from Bacteroidis gingivalis," J. Immunol. 143:3035-3042.

Shimizu, Y. et al. (2006). "Cell-free translation systems of protein engineering," FEBS Journal 273:4133-4140.

Schultz, P.G. et al. (2010). "Adding new chemistries to the genetic code," Annu. Rev. Biochem. 79:413-444.

Skinner, J, et al. (2011). "Pre-clinical evaluation of a 15-valent pneumococcal conjugate vaccine (PCV15-CRM197) in an infant-rhesus monkey immunogenicity model," Vaccine. 29:8870-8876.

Sletten, E.M. et al. (2011). "From mechanism to mouse: a tale of two bioorthogonal reactions," Acc. Chem. Res. 44:666-676.

Sobanjo, A. et al. (2015). "Safety, Tolerability and Immunogenicity of 15-valent Pneumococcal Conjugate Vaccine in Toddlers Previously Vaccinated With 7-valent Pneumococcal Conjugate Vaccine," Pediatr Infect Dis J. 34:186-194.

Spirin, A.S. et al. (1988). "A continuous cell-free translation system capable of producing polypeptides in high yield," Science. 242:1162-1164.

Tomczyk, S. et al. (2014). Use of 13-valent pneumococcal conjugate vaccine and 23-valent pneumococcal polysaccharide vaccine among adults aged ≥65 years: recommendations of the Advisory Committee on Immunization Practices (ACIP). Centers for Disease Control and Prevention (CDC). MMWR Morb Mortal Wkly Rep. 63: 822-825.

Tontini, M. et al. (2016). "Preclinical studies on new proteins as carrier for glycoconjugate vaccines," Vaccine 34:4235-4242.

Trotter, C. et al. (2004). "Effectiveness of meningococcal serogroup C conjugate vaccine 4 years after introduction," The Lancet 364:24-30.

Turner, A.E.B. et al. (2017). "Novel polysaccharide-protein conjugates provide an immunogenic 13-valent pneumococcal conjugate vaccine for S. pneumonia," Synth. And Systems Biotechnol. 2:49-58.

Van Gelder, R.N. et al. (1990). "Amplified RNA synthesized from limited quantities of heterogeneous cDNA," PNAS 87:1663-1667.

Van Winkelhoff, A.J. et al. (1993). "K-antigens in porphyromonas gingivalis are associated with virulence," Oral Microbiol. Immunol. 8:259-265.

Wang, Q. et al. (2009). "Expanding the genetic code for biological studies," Chem. and Biol., Current Biology, London, GB, 16(3):323-336.

Wang, L. et al. (2001). "Expanding the genetic code of *Escherichia coli*," Science 292:498-500.

Weiser, J.N. et al. (1999). Effect of intrastrain variation in the amount of capsular polysaccharide on genetic transformation of *Streptococcus pneumonia*: Implications for virulence studies of encapsulated strains. Infect Immun. Jul. 1999; 67(7): 3690-3692.

Weiser, J.N. et al. (1994). "Phase variation in Pneumococcal opacity: Relationship between colonial morphology and nasopharyngeal colonization," Infection and Immunity 62:2582-2589.

Wessels, M.R. et al. (1998). "Structural properties of group B streptococcal type III polysaccharide conjugate vaccines that influence immunogenicity and efficacy," Infect. Immun. 66:2186-2192.

WHO Technical Report Series, Annex 4, No. 927, 2005, 3 total pages.

Wiertz et al. (1992). "Identification of T cell epitopes occurring in a meningococcal class 1 outer membrane protein using overlapping peptides assembled with simultaneous multiple peptide synthesis," J. Exp. Med. 176:79-88.

Wizemann, T.M. et al. (2001). "Use of a whole genome approach to identify vaccine molecules affording protection against *Streptococcus pneumoniae* infection," Infect. Immun. 69:1593-1598.

Written Opinion of the International Searching Authority dated Jul. 3, 2018, for PCT Application No. PCT/US2017/069129, filed on Dec. 29, 2017, 8 pages.

Wu, D. et al. (2013). "Development of pneumococcal polysaccharide conjugate vaccine with long spacer arm," Vaccine 31:5623-5626.

Wyeth Grounds of Appeal, EPO Opposition to Wyeth LLC, EP 1868645 (Pfizer submission May 4, (2015).

Young, T.S. et al. (2010). "Beyond the canonical 20 amino acids: Expanding the genetic lexicon," J. Biol. Chem. 285:11039-11044.

Yu, J. et al. (2011). "Development of an automated and multiplexed serotyping assay for *Streptococcus pneumonia*," Clin. Vacc. Immunol. 18:1900-1907.

Zangwill, K.M. et al. (2003). "Safety and immunogenicity of a heptavalent pneumococcal conjugate vaccine in infants," Vaccine. 21:1894-1900.

Zawada, J.F. et al. (2011). "Microscale to manufacturing scale-up of cell free cytokine production—A new approach for shortening protein production development timeliness," Biotechnol. Bioeng. 108:1570-1578.

Zhang, X. et al. (2013). "Applications of azide-based bioorthogonal click," Chemistry in Glycobiology 18:7145-7159.

Zhu, J. et al. (2009). "Synthetic carbohydrate-based anticancer vaccines: The memorial Sloan-Kettering experience," Expert Rev. Vaccines 10:1399-1413.

(56) References Cited

OTHER PUBLICATIONS

Zimmerman, E.S. et al. (2014). "Production of site-specific antibody-drug conjugates using optimized non-natural amino acids in a cell-free expression system," Bioconjugate Chem. 25:351-361.

Zubay, G. (1973). "In vitro synthesis of protein in microbial systems," Annu Rev Genet. 7:267-287.

Gruber, W.C. et al. (2012). "Development and clinical evaluation of Prevnar 13, a 13-valent pneumococcal $CRM_{197}$ conjugate vaccine," Annals of the New York Academy of Sciences 1263:15-26.

Park, I.H. et al. (2008). "Differential effects of pneumococcal vaccines against serotypes 6A and 6C," The Journal of Infectious Diseases 198:1818-1822.

Avci, F. et al. (2019). Glycoconjugates: What it would take to master these three well-known yet little-understood immunogens for vaccine development, mSphere 4:e00520-19, 8 total pages.

Gamblin, D. et al. (2009). Glycoprotein synthesis: An update, Chem. Rev. 109:131-163.

International Search Report dated Oct. 11, 2019, for PCT Application No. PCT/US2019/040143, filed on Jul. 1, 2019, 6 pages.

International Search Report dated Dec. 20, 2019, for PCT Application No. PCT/US2019/040131, filed on Jul. 1, 2019, 13 pages.

Kapoor, N. et al. (2018). "Malaria derived glycosylphosphatidylinositol anchor enhances anti-Pfs25 functional antibodies that block malaria transmission," Biochem. 57:516-519.

Nahn, M.H. et al. (2016). "Protocol for opsonophagocytic killing assay for antibodies against Group B *Streptococcus* (UAB GBS OPA)," Version B.04, Mar. 2016, located at https://www.vaccine.uab.edu/uploads/mdocs/UAB-GBS-OPA.pdf, 24 total pages.

Nahn, M.H. et al. (2014). "Protocol for multiplexed opsonophagocytic killing assay (UAB-MOPA) for antibodies against *Streptococcus pneumoniae*," Version E.02, Dec. 2014, located at https://www.vaccine.uab.edu/uploads/mdocs/UAB-MOPA.pdf, 43 total pages.

Written Opinion of the International Searching Authority dated Oct. 11, 2019, for PCT Application No. PCT/US2019/040143, filed on Jul. 1, 2019, 9 pages.

Written Opinion of the International Searching Authority dated Dec. 20, 2019, for PCT Application No. PCT/US2019/040131, filed on Jul. 1, 2019, 19 pages.

Hosaka et al. (1991). "Arg-X-Lys/Arg-Arg motif as a signal for precursor cleavage catalyzed by furin within the constitutive secretory pathway," J Biol Chem. 266:12127-12130.

Non-Final Office Action dated Jun. 7, 2021, for U.S. Appl. No. 16/459,303, filed Jul. 1, 2019, 17 pages.

Dagan, R. et al. (2010). "Glycoconjugate vaccines and immune interference: A review," Vaccine 28:5513-5523.

Pollabauer, E.M. et al. (2009). "The influence of carrier protein on the immunogenicity of simultaneously administered conjugate vaccines in infants," Vaccine 27:1674-1679.

Behrens, C. et al. (2021). "Development of a Next Generation 30+ Valent Pneumococcal Conjugate Vaccine (VAX-XP) Using Site-Specific Carrier Protein Conjugation," Vaxcyte, Inc. Poster, 1 total page.

Fairman, J. et al. (2021), "Non-clinical immunological comparison of a Next-Generation 24-valent pneumococcal conjugate vaccine (VAX-24) using site-specific carrier protein conjugation to the current standard of care (PCV13 and PPV23)," Vaccine 39:3197-3206.

Hurley, D. et al. (2019). Safety, tolerability, & immunogenicity of a 20-Valent Pneumococcal Conjugate Vaccine (PCV20) in adults 60-64 years of age, Presented at 29th European Congress of Clinical Microbiology & Infectious Disease, Apr. 13-16, 2019, Amsterdam.

Ladhani, S.N. et al. (2018), "Rapid increase in non-vaccine serotypes causing invasive pneumococcal disease in England and Wales, 2000-17: a prospective national observational cohort study," Lancet Infect. Dis. 18:441-451.

Moore, M.R. et al. (2015). "Effect of use of 13-valent pneumococcal conjugate vaccine in children on invasive pneumococcal disease in children and adults in the USA: analysis of multisite, population-based surveillance," Lancet Infect. Dis. 15:301-309.

Stefanetti, G. et al. (2015). "Click Chemistry Applied to the Synthesis of *Salmonella typhimurium* O-Antigen Glycoconjugate Vaccine on Solid Phase with Sugar Recycling," Bioconjugate Chemistry 26:2507-2513.

Yeh, S.H. et al. (2010). "Immunogenicity and safety of 13-valent pneumococcal conjugate vaccine in infants and toddlers," Pediatrics 126:e493-e505.

CAS Registry$^{SM}$: Exact and pattern searching of protein sequences, Nov. 2008, 2 total pages.

Final Office Action dated Jan. 7, 2022, for U.S. Appl. No. 16/459,303, filed Jul. 1, 2019, 18 pages,.

Izidoro, M.A. et al. (2009). "A study of human furin specificity using synthetic peptides derived from natural substrates, and effects of potassium ions," Arch. Biochem. Biophys. 487:105-114.

ClinicalTrials.Gov (2018). Trial to Evaluate the Safety and Immunogenicity of a Multivalent Pneumococcal Vaccine in Healthy Infants, ClinicalTrials.Gov Identifier NCT03512288, 39 total pages.

Non-Final Office Action dated Sep. 9, 2022, for U.S. Appl. No. 16/459,303, filed Jul. 1, 2019, 19 pages.

Prevnar 20 Package Insert (2021). 18 total pages.

Prevnar 20 BLA Clinical Review Memorandum (Jun. 8, 2021). STN: 125731/0, 117 total pages.

Vaxcyte, Inc. (2022). VAX-24 Phase ½ Proof-of-Concept Study Topline Results, located at https://www.sec.gov/Archives/edgar/data/1649094/000119312522267147/d413834dex992.htm, 35 total pages.

Vaxcyte, Inc. (2022). Vaxcyte Reports Positive Topline Data from Phase ½ Proof-of-Concept Study of its 24-Valent Pneumococcal Conjugate Vaccine Candidate Being Investigated for the Prevention of Invasive Pneumococcal Disease in Adults Aged 18-64—Press Release, located at https://investors.vaxcyte.com/news-releases/news-release-details/vaxcyte-reports-positive-topline-data-phase-12-proof-concept, 3 total pages.

Duowei, Y. et al. (Jul. 31, 2007). Molecular Biology, Nanjing Normal University Press, p. 149, 7 total pages (with English translation).

Nakayama, K. (1994). "Kex2-like endoproteases involved in processing of precursors for bioactive peptides and proteins," Biophysics 34(3):124-130 (pp. 30-36), 9 total pages (with English Translation).

Notice of Allowance dated Nov. 7, 2023, for U.S. Appl. No. 16/459,303, filed Jul. 1, 2019, 8 pages.

\* cited by examiner

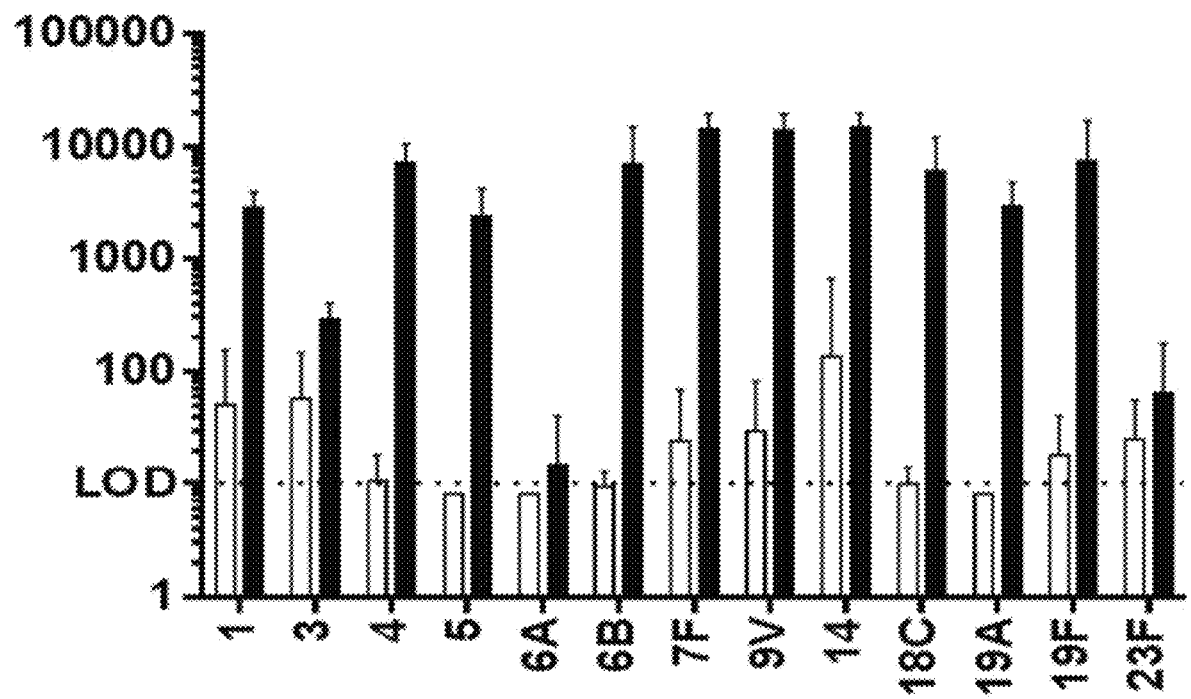
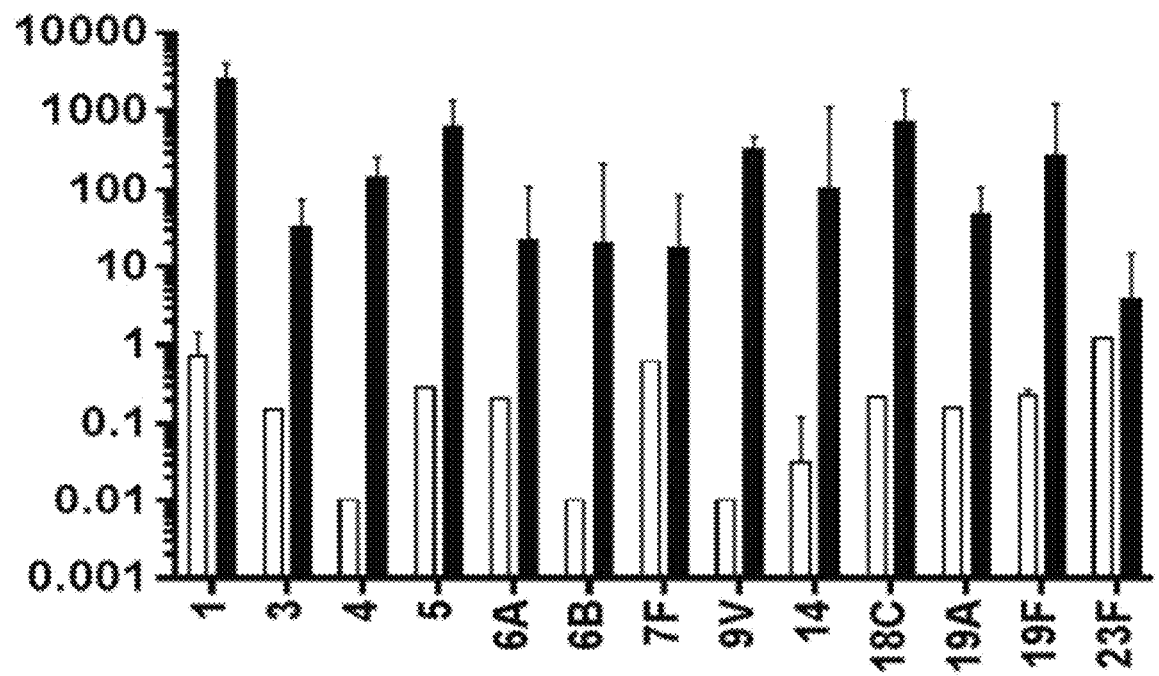

POLYPEPTIDE-ANTIGEN CONJUGATES WITH NON-NATURAL AMINO ACIDS

CROSS-REFERENCE TO RELATED APPLICATIONS

This application claims the benefit of U.S. provisional patent application 62/441,115, filed Dec. 30, 2016, U.S. provisional patent application 62/530,803, filed Jul. 10, 2017, U.S. provisional patent application 62/568,201, filed Oct. 4, 2017, and U.S. provisional patent application 62/591,160, filed Nov. 27, 2017, each of which is incorporated by reference in its entirety.

DESCRIPTION OF THE TEXT FILE SUBMITTED ELECTRONICALLY

The Sequence Listing associated with this application is provided in text format in lieu of a paper copy, and is hereby incorporated by reference into the specification. The name of the text file containing the Sequence Listing is STRO_001_04_US_ST25.txt. The text file is 17 KB, created on Jun. 16, 2020, and is being submitted electronically via EFS-Web.

BACKGROUND OF THE INVENTION

Vaccines based on isolated antigenic macromolecules (e.g. the first-generation meningococcus, pneumococcus, and *Haemophilus* polysaccharide vaccines) represented significant improvements over earlier vaccine formulations based around live attenuated or inactivated organism vaccines.

Purified macromolecules are significantly easier to manufacture, have an improved safety profile, and can generate a more productive specific immune response (e.g. they can be directed against an antigen that is more conserved or is important for pathogenesis). Moreover, they offer a simplified template for vaccine production, where an immune response can be directed against a specific site or a specific organism simply by providing the proper immunogen. However, this strategy suffers from an inconvenient fact—that not every macromolecule generates a strong immune response. Many lipids, polysaccharides, and certain protein antigens (and most small molecules) generate immune responses that are inherently weak, transient, and/or defective in certain patient populations (examples include infants or the elderly). These weak immune responses are thought to result from antigen structures that primarily activate B-cells, or otherwise fail to activate T-cell dependent pathways that are involved in immunological memory and antibody maturation.

SUMMARY OF THE INVENTION

The present disclosure is directed to methods, compositions, and techniques for the production of immunogenic compositions containing a non-natural amino acid are disclosed. Bio-orthogonal attachment chemistry incorporated into the non-natural amino acid allows for more efficient and potent antigen presentation to the immune system, simplified purification, and more well-defined structure of these semi-synthetic immunogens.

In one embodiment, the present disclosure provides a conjugate comprising a polypeptide and an antigen, wherein the polypeptide is a carrier protein comprising at least one T-cell activating epitope and at least one non-natural amino acid, or "nnAA," wherein the antigen is conjugated to the nnAA. In another embodiment, the carrier protein comprises at least one T-cell activating epitope from a protein selected from the group consisting of *Corynebacterium diphtheriae* toxin, *Clostridium tetani* tetanospasmin (also known as tetanus toxin), *Haemophilus influenzae* protein D (PD, HiD), outer membrane protein complex of serogroup B meningococcus (OMPC) and CRM197. In another embodiment, the carrier protein comprises at least 2, at least 3, at least 4, at least 5, at least 6, at least 7, at least 8, or at least 9 nnAAs. In another embodiment, the at least one nnAA is replaced for a lysine in the native carrier protein. For instance, the carrier protein comprises CRM197 in which at least 2 (e.g., at least 3, at least 4, at least 5, or at least 6) of the 39 lysine residues in native CRM197 have been replaced by nnAAs. In another embodiment, the at least one nnAA is replaced for a phenylalanine in the native carrier protein. In another embodiment, the at least 2, at least 3, at least 4, at least 5, at least 6, at least 7, at least 8, or at least 9 nnAAs are replaced for a lysine in the native carrier protein. In another embodiment, the at least 2, at least 3, at least 4, at least 5, at least 6, at least 7, at least 8, or at least 9 nnAAs are replaced for a phenylalanine in the native carrier protein. In another embodiment, the at least 2, at least 3, at least 4, at least 5, at least 6, at least 7, at least 8, or at least 9 nnAAs are replaced for a lysine, a phenylalanine or both a lysine and a phenylalanine in the native carrier protein. In another embodiment, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof. In another embodiment, the carrier protein has at least 80% sequence identity to a protein selected from the group consisting of diphtheria toxin (DT), tetanus toxin (TT), *Haemophilus influenzae* protein D (PD), and CRM197. In another embodiment, the carrier protein has at least 80% sequence identity to SEQ ID NO: 1. In another embodiment, the at least one T-cell activating epitope is from CRM197 according to SEQ ID NO:1. In another embodiment, the at least one nnAA is replaced for K25, K34, K38, K40, K213, K215, K228, K245, K265, K386, K523, or K527 of SEQ ID NO: 1. In another embodiment, the at least one nnAA is replaced for F13, F54, F124, F128, F141, F168, F251, F390, F531, or F532 of SEQ ID NO:1. In another embodiment, the at least two nnAA are replaced for K25, K34, K38, K40, K213, K215, K228, K245, K265, K386, K523, K527, F13, F54, F124, F128, F141, F168, F251, F390, F531, or F532 of SEQ ID NO: 1. In another embodiment, the at least one nnAA is replaced for K265 of SEQ ID NO: 1. In another embodiment, the at least one nnAA is replaced for K386 of SEQ ID NO: 1. In another embodiment, the at least one nnAA is replaced for K265 and K386 of SEQ ID NO: 1. In another embodiment, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl) propanoic acid, or any combination thereof. In another embodiment, the antigen is conjugated to the nnAA via a triazole linking moiety. In another embodiment, the antigen is a polysaccharide. In another embodiment, the antigen is a capsular polysaccharide of *Streptococcus pneumoniae*, *Neisseria meningitidis*, *Haemophilus influenzae* (in particular type b i.e. Hib), *Streptococcus pyogenes*, or *Streptococcus agalactiae*. In another embodiment, the antigen is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the antigen is a capsular polysaccharide derived from one of the six serotypes of *Porphyromonas gingivalis* (e.g., K1, K2, K3, K4, K5 and/or K6).

In a related embodiment, the conjugate comprises a polypeptide and an antigen, wherein the polypeptide is a carrier protein comprising at least one T-cell activating epitope and at least one, and preferably at least two, nnAA, wherein the antigen is conjugated to the at least one nnAA and further wherein the at least one nnAA is a 2,3-disubstituted propanoic acid bearing an amino substituent at the 2-position and an azido-containing substituent, a 1,2,4,5-tetrazinyl-containing substituent, or an ethynyl-containing substituent at the 3-position.

In another related embodiment, the conjugate comprises a polypeptide and an antigen, wherein the polypeptide is a carrier protein comprising at least one T-cell activating epitope and at least one, and preferably at least two, nnAA residue, wherein the antigen is conjugated to the nnAA and further wherein the nnAA residue corresponds to an amino acid having the structure of formula XII:

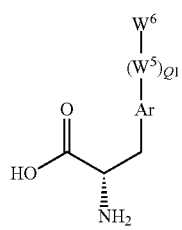

(XII)

wherein:
Ar comprises a 5-membered or 6-membered aromatic ring optionally containing at least one heteroatom;
$W^5$ is selected from $C_1$-$C_{10}$ alkylene, —NH—, —O— and —S—;
Q1 is zero or 1; and
$W^6$ is selected from azido, 1,2,4,5-tetrazinyl optionally C-substituted with a lower alkyl group, and ethynyl, such that the nnAA residue in the polypeptide has the structure of formula XIII

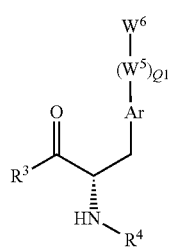

(XIII)

in which $R^3$ is OH or an amino acid residue of the carrier protein, and $R^4$ is H or an amino acid residue of the carrier protein.

In one embodiment, the present disclosure provides a polypeptide comprising at least one nnAA replaced for a naturally occurring amino acid within the native polypeptide according to SEQ ID NO:1, wherein the at least one nnAA is replaced for K25, K34, K38, K40, K213, K215, K228, K245, K265, K386, K523, or K527 of SEQ ID NO:1, wherein the nnAA comprises a linking moiety. In another embodiment, the present disclosure provides a polypeptide comprising at least one nnAA replaced for a naturally occurring amino acid within the native polypeptide according to SEQ ID NO:1, wherein the at least one nnAA is replaced for F13, F54, F124, F128, F141, F168, F251, F390, F531, or F532 of SEQ ID NO:1, wherein the nnAA comprises a linking moiety. In another embodiment, the present disclosure provides a polypeptide comprising at least two nnAA replaced for a naturally occurring amino acid within the native polypeptide according to SEQ ID NO:1, wherein the at least one nnAA is replaced for K25, K34, K38, K40, K213, K215, K228, K245, K265, K386, K523, K527, F13, F54, F124, F128, F141, F168, F251, F390, F531, or F532 of SEQ ID NO: 1, wherein the nnAA comprises a linking moiety. In another embodiment, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof. In another embodiment, K265 of SEQ ID NO:1 is replaced. In another embodiment, K386 of SEQ ID NO:1 is replaced. In another embodiment, K265 and K386 of SEQ ID NO:1 are replaced. In another embodiment, the polypeptide comprises at least 2, at least 3, at least 4, at least 5, at least 6, at least 7, at least 8, or at least 9 nnAAs. In another embodiment, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof.

In a related embodiment, the at least one, and preferably at least two, nnAA in the polypeptide is a 2,3-disubstituted propanoic acid bearing an amino substituent at the 2-position and an azido-containing substituent, a 1,2,4,5-tetrazinyl-containing substituent, or an ethynyl-containing substituent at the 3-position.

In another related embodiment, the at least one, and preferably at least two, nnAA in the polypeptide has the structure of formula XII

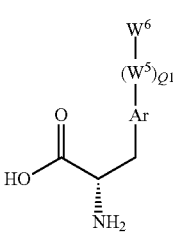

(XII)

wherein:
    Ar comprises a 5-membered or 6-membered aromatic ring optionally containing at least one heteroatom;
    $W^5$ is selected from $C_1$-$C_{10}$ alkylene, —NH—, —O— and —S—;
    Q1 is zero or 1; and
    $W^6$ is selected from azido, 1,2,4,5-tetrazinyl optionally C-substituted with a lower alkyl group, and ethynyl.

In one embodiment, the present disclosure provides a composition comprising polypeptide-antigen conjugates, wherein the polypeptide is a carrier protein comprising at least one T-cell activating epitope and at least one nnAA, and wherein the antigen is conjugated to the nnAA. In another embodiment, the polypeptide-antigen conjugates are crosslinked through protein-antigen-protein linkages. In another embodiment, the composition comprises multiple carrier-protein antigen conjugates, wherein each conjugate comprises a different antigen (e.g. capsular polysaccharides from different pneumococcal serotypes). In another embodiment, the antigens are derived from different serotypes (e.g. for pneumococcus) or serogroups (e.g. for meningococcus) of the same organism. In another embodiment, the antigen is a polysaccharide. In another embodiment, the antigen is a capsular polysaccharide of *Streptococcus pneumoniae, Neisseria meningitidis, Haemophilus influenzae* (e.g. Hib), *Streptococcus pyogenes*, or *Streptococcus agalactiae*. In another embodiment, the antigen is a capsular polysaccharide derived from one of the six serotypes of *Porphyromonas gingivalis* (e.g., K1, K2, K3, K4, K5 and/or K6). In another embodiment, the antigen is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the composition comprises a protein carrier-antigen conjugate as described herein wherein there are at least 14, 20, 21, 24 or 25, different carrier protein-capsular polysaccharide conjugates, each conjugate comprising a different capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F. In another embodiment, the ratio of the polysaccharide to the carrier protein (w/w) is greater than 1. In another embodiment, the carrier protein comprises at least 2, at least 3, at least 4, at least 5, at least 6, at least 7, at least 8, or at least 9 nnAAs. In another embodiment, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof. In another embodiment, the carrier protein has at least 80% sequence identity to a protein selected from diphtheria toxin (DT), tetanus toxin (TT), *Haemophilus* protein D (PD), outer membrane protein complex of serogroup B meningococcus (OMPC), and CRM197. In another embodiment, the carrier protein has at least 80% sequence identity to CRM197. In another embodiment, the carrier protein has at least 80% sequence identity to SEQ ID NO: 1. In another embodiment, carrier protein has at least 80% sequence identity to SEQ ID NO: 1, further wherein the at least one nnAA replaces a naturally occurring amino acid therein. In another embodiment, the at least one nnAA replaces an amino acid selected from the group consisting of K25, K34, K38, K40, K213, K215, K228, K245, K265, K386, K523, or K527 of SEQ ID NO:1. In another embodiment, the at least one, and preferably at least two, nnAA replaces an amino acid selected from the group consisting of F13, F54, F124, F128, F141, F168, F251, F390, F531, or F532 of SEQ ID NO: 1. In another embodiment, the at least one, and preferably at least two, nnAA replaces an amino acid selected from the group consisting of K25, K34, K38, K40, K213, K215, K228, K245, K265, K386, K523, K527, F13, F54, F124, F128, F141, F168, F251, F390, F531, or F532 of SEQ ID NO: 1. In another embodiment, the antigen is conjugated to the nnAA via a linking moiety. In another embodiment, the antigen is conjugated to the nnAA via a triazole linking moiety.

In a related embodiment, the polypeptide-antigen conjugates in the composition comprise, as the polypeptide, a carrier protein comprising at least one T-cell activating epitope and at least one, and preferably at least two, nnAA, wherein the antigen is conjugated to the nnAA and further wherein the at least one nnAA is a 2,3-disubstituted propanoic acid bearing an amino substituent at the 2-position and an azido-containing substituent, a 1,2,4,5-tetrazinyl-containing substituent, or an ethynyl-containing substituent at the 3-position.

In another related embodiment, the polypeptide-antigen conjugates in the composition comprise, as the polypeptide, a carrier protein comprising at least one T-cell activating epitope and at least one, and preferably at least two, nnAA, wherein the antigen is conjugated to the nnAA and further wherein the at least one nnAA in the polypeptide has the structure of formula XII

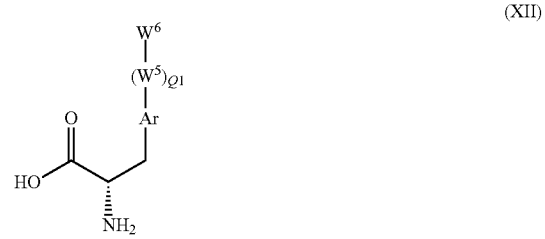

(XII)

wherein:
    Ar comprises a 5-membered or 6-membered aromatic ring optionally containing at least one heteroatom;
    $W^5$ is selected from $C_1$-$C_{10}$ alkylene, —NH—, —O— and —S—;
    Q1 is zero or 1; and
    $W^6$ is selected from azido, 1,2,4,5-tetrazinyl optionally C-substituted with a lower alkyl group, and ethynyl.

In one embodiment, the present disclosure provides a method for producing a conjugate, comprising: (a) providing an activated antigen comprising a plurality of functional groups comprising a first chemical handle capable of conjugating to a second chemical handle of an nnAA; (b) combining the activated antigen with a polypeptide comprising at least one of the nnAA under conditions wherein the first and second chemical handles react to form an antigen-polypeptide conjugate, wherein the polypeptide comprises at least one T-cell activating epitope; and (c) recovering a composition comprising the conjugate. In another embodiment, the antigen is a polysaccharide. In another embodiment, the antigen is a capsular polysaccharide of *Streptococcus pneumoniae, Neisseria meningitidis, Haemophilus influenzae* (e.g. Hib), *Streptococcus pyogenes*, or *Streptococcus agalactiae*. In another embodiment, the antigen is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the antigen is a capsular polysaccharide derived from one of the six serotypes of *Porphyromonas gingivalis* (e.g., K1, K2, K3, K4, K5 and/or K6). In another embodiment, the antigen was reacted with a first reagent selected from the group consisting of CDAP, CDI, or periodate in the production of the activated antigen. In another embodiment, the first reagent is less than 1M periodate. In another embodiment, the plurality of functional groups comprises hydroxyl groups. In another embodiment, the plurality of functional groups comprises an aldehyde group. In another embodiment, the antigen was reacted with a second reagent comprising a functional group selected from the group consisting of propargyl, DIFO, DBCO, and DBCO(PEG)n-NH$_2$. In another embodiment, the antigen was reacted with a second reagent comprising DBCO-NH$_2$. In another embodiment, the first chemical handle comprises an alkyne group. In another embodiment, the second chemical handle comprises an azido group. In another embodiment, the antigen to the polypeptide ratio of the conjugate in the composition (w/w) is greater than 1.

In a related embodiment, the method for producing a conjugate comprises: (a) activating an antigen to incorporate at least one first chemical handle therein, wherein the first chemical handle is capable of conjugating to a second chemical handle of an nnAA in the polypeptide; (b) combining the activated antigen with a polypeptide comprising at least one of the nnAA under conditions wherein the first and second chemical handles react to form an antigen-polypeptide conjugate, wherein the polypeptide comprises at least one T-cell activating epitope; and (c) recovering a composition comprising the conjugate. In one aspect of this embodiment, activating the antigen comprises incorporating at least one alkynyl group into the antigen as the first chemical handle.

In another related embodiment, a method is provided for producing a polypeptide-antigen conjugate, comprising activating an antigen by incorporating at least one alkynyl group therein as the first chemical handle, and reacting the antigen with a polypeptide comprising at least one nnAA, and preferably at least two nnAA, bearing an azido group as the second chemical handle, thereby enabling a non-catalytic covalent bioconjugation reaction between the polypeptide and the antigen. In a preferred embodiment, the alkynyl group is constrained to increase reactivity, e.g., in a ring structure such as a diaryl-strained cyclooctyne.

In one embodiment, the present disclosure provides a method of eliciting an immunoprotective antibody response to an antigen in a subject, comprising administering to the subject a conjugate as described herein in an excipient suitable for parenteral administration.

In one embodiment, the present disclosure provides a method of eliciting an immunoprotective antibody response to an antigen in a subject, comprising administering to the subject a composition as described herein in an excipient suitable for parenteral administration.

In one embodiment, the present disclosure provides a method for synthesis of a polypeptide comprising at least 2 non-natural amino acids (nnAAs) in a cell-free expression mixture maintained at a temperature between about 10 degrees Celsius and about 30 degrees Celsius, wherein the polypeptide produced comprises both a soluble and an insoluble fraction, and wherein the ratio of the soluble fraction to the insoluble fraction is at least 30% (w/w). For instance, for 100 g of total polypeptide the insoluble fraction would be 70 g or less, and the soluble fraction would be 30 g or more. In another embodiment, the temperature is above about 20 degrees Celsius. In another embodiment, the temperature is below about 20 degrees Celsius. In another embodiment, the temperature is between about 14 degrees Celsius and about 18 degrees Celsius. In another embodiment, the polypeptide is encoded by a nucleic acid comprising a suppression codon. In another embodiment, the cell-free expression mixture comprises an orthogonal tRNA/aminoacyl-tRNA synthetase pair specific for the nnAA. In another embodiment, the tRNA concentration is at least 20 µM (i.e. the concentration of the orthogonal tRNA). In another embodiment, the nnAA concentration is less than about 2 mM and the concentration of the aminoacyl-tRNA synthetase is less than about 5 µM (i.e. the concentration of the orthogonal synthetase). In another embodiment, the method comprises conjugating the polypeptide to an active moiety. In another embodiment, the active moiety is selected from the group consisting of a hapten, a bacterial antigen, a viral antigen, a peptide toxin, a macrolide, a polyether, and any combination thereof. In another embodiment, the expression mixture comprises a cellular extract of *E. coli*, wheat germ, or rabbit reticulocyte. In another embodiment, the expression mixture comprises at least 30% cellular extract. In another embodiment, the polypeptide comprises at least 2, at least 3, at least 4, at least 5, at least 6, at least 7, at least 8, or at least 9 nnAAs. In another embodiment, the nnAA is selected from the group consisting of 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, 2-amino-3-(4-(azidomethyl)phenyl) propanoic acid, and any combination thereof. In another embodiment, the polypeptide produced comprises both a soluble and an insoluble fraction, and wherein the ratio of the soluble fraction to the insoluble fraction is at least 60% (w/w). In another embodiment, the polypeptide produced comprises both a soluble and an insoluble fraction, and wherein the ratio of the soluble fraction to the insoluble fraction is at least 80% (w/w). For instance, for 100 g of total polypeptide, the insoluble fraction would be 20 g or less, and the soluble fraction would be 80 g or more.

In one embodiment, the present disclosure provides an improved method of making a protein-conjugate vaccine wherein an antigen is conjugated to a carrier protein that provides a T-cell dependent immune response, the improvement comprising employing as the carrier protein a polypeptide comprising at least one non-natural amino acid, the non-natural amino acid comprising a bio-orthogonal reactive moiety through which the antigen is conjugated to the polypeptide. In another embodiment, the antigen is a bacterial polysaccharide. In another embodiment, the polypeptide comprises at least two non-natural amino acids comprising a bio-orthogonal reactive moiety through which the antigen is conjugated to the polypeptide. In another embodiment, the polypeptide comprises at least one T-cell activating epitope that does not comprise a non-natural amino acid comprising a bio-orthogonal reactive moiety through which the antigen is conjugated to the polypeptide. In another embodiment, the T-cell activating epitope is from a protein selected from the group consisting of *Corynebacterium diphtheriae* toxin, *Clostridium tetani* tetanospasmin, *Haemophilus influenzae* protein D (PD, HiD), outer membrane protein complex of serogroup B meningococcus (OMPC) and CRM197. In another embodiment, the antigen is a bacterial polysaccharide and the bacteria is selected from the group consisting of *Streptococcus pneumoniae, Neisseria meningitidis, Haemophilus influenzae* (e.g. Hib), *Streptococcus pyogenes*, and *Streptococcus agalactiae*. In another embodiment, at least one of the non-natural amino acids is selected from group consisting of 2-amino-3-(4-azidophenyl)propanoic acid (pAF), 2-amino-3-(4-(azidomethyl)phenyl)propanoic acid (pAMF), 2-amino-3-(5-(azidomethyl) pyridin-2-yl)propanoic acid, 2-amino-3-(4-(azidomethyl) pyridin-2-yl)propanoic acid, 2-amino-3-(6-(azidomethyl) pyridin-3-yl)propanoic acid, 2-amino-5-azidopentanoic acid, and 2-amino-3-(4-(azidomethyl)phenyl)propanoic acid.

In one embodiment, the present disclosure provides a method for producing a carrier protein incorporating a plurality of non-natural amino acids in its structure, comprising: (a) providing a nucleic acid encoding a carrier protein, wherein the nucleic acid comprises a plurality of suppression codons; (b) creating a reaction mixture by combining the nucleic acid with a cell-free bacterial extract comprising the non-natural amino acids, a tRNA complementary to the suppression codons, and an aminoacyl-tRNA synthetase; and (c) incubating the reaction mixture of (b) under conditions sufficient to selectively incorporate the non-natural amino acid at the site corresponding to each suppression codon in the carrier protein. In another embodiment, the non-natural amino acid is 4-azidomethylphenylalanine (pAMF). In another embodiment, step (c) comprises incubating the reaction mixture at less than 20 degrees Celsius. In another embodiment, the method additionally comprises purifying the carrier protein immediately after (c). In another embodiment, the suppression codon is selectively substituted at codon 25, 34, 38, 40, 213, 215, 228, 245, 265, 386, 523, or 527 of SEQ ID NO:2. In another embodiment, the reaction mixture in (b) further comprises biological components necessary for protein synthesis. In another embodiment, the tRNA in (b) is capable of being charged with pAMF. In another embodiment, the aminoacyl-tRNA synthetase in (b) preferentially aminoacylates the tRNA with pAMF compared to the 20 natural amino acids.

In another embodiment, the present disclosure provides a composition comprising at least 14, 20, 21, 24, or 25 distinct carrier protein-antigen conjugates wherein the antigen is a capsular polysaccharide and (a) the capsular polysaccharide in each distinct carrier protein-antigen conjugate is from a different serotype of *Streptococcus pneumoniae*; (b) the carrier protein of the carrier protein-antigen conjugates comprises a polypeptide comprising at least one a T-cell activating epitope and at least two non-natural amino acids (nnAA); and (c) the capsular polysaccharides are conjugated to the nnAA. In preferred versions of this embodiment, the at least one T-cell activating epitope is from CRM197 according to SEQ ID NO:1; the polypeptide has at least 80% or 95% sequence identity to SEQ ID NO: 1; and (i) the polypeptide comprises 2-9 nnAA; (ii) the polypeptide comprises 4-6 nnAA; and/or (iii) at least one nnAA is substituted for an amino acid residue selected from the group consisting of (a) K25, K34, K38, K40, K213, K215, K228, K245, K265, K386, K523, K527 of CRM197, (b) F13, F54, F124, F128, F141, F168, F251, F390, F531, or F532 of SEQ ID NO:1, or (c) K25, K34, K38, K40, K213, K215, K228, K245, K265, K386, K523, K527, F13, F54, F124, F128, F141, F168, F251, F390, F531, or F532 of SEQ ID NO: 1. Preferred versions of the previous embodiments include compositions comprising at least 14, 20, 21, 24, or 25 distinct carrier protein-antigen conjugates wherein each distinct carrier protein-antigen conjugate includes an antigen selected individually from the capsular polysaccharides of a *Streptococcus pneumoniae* serotype selected from the group consisting of serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F; compositions of at least 24 distinct carrier protein-antigen conjugates wherein the capsular polysaccharide of 24 of the distinct carrier protein-antigen conjugates are from *Streptococcus pneumoniae* serotypes 1, 2, 3, 4, 5, 6A, 6B, 7F, 8, 9V, 9N, 10A, 11A, 12F, 14, 15B, 17F, 18C, 19A, 19F, 20, 22F, 23F and 33F; compositions comprising at least 25 distinct carrier protein-antigen conjugates wherein the capsular polysaccharide of at least one of the distinct carrier protein-antigen conjugates is from a *Streptococcus pneumoniae* serotype selected from the group consisting of 6C, 7C, 13, 15A, 15C, 16, 16F, 23A, 23B, 24F, 31, 34, 35B, 33F, 35F, 37 and 38; and compositions comprising at least 25 distinct carrier protein-antigen conjugates wherein the capsular polysaccharide of at least one of the distinct carrier protein-antigen conjugates is from a *Streptococcus pneumoniae* serotype selected from the group consisting of 15A and 35B, or alternatively from the group consisting of 20A, 20B and 24B.

In one embodiment the disclosure provides a composition comprising at least 14, 20, 21, 24, or 25 distinct carrier protein-antigen conjugates wherein the antigen is a capsular polysaccharide of *Streptococcus pneumoniae* wherein (a) the capsular polysaccharide in each distinct carrier protein-antigen conjugate is from a different serotype of *Streptococcus pneumoniae*; (b) the carrier protein of the carrier protein-antigen conjugates is a polypeptide comprising at least one T-cell activating epitope and at least two non-natural amino acids (nnAA) and the capsular polysaccharides are conjugated to the nnAA, (c) there is a distinct carrier protein-antigen conjugate comprising a capsular polysaccharide for each of *Streptococcus pneumoniae* serotypes 1, 3, 4, 5, 6A, 6B, 7F, 9V, 14, 18C, 19A, 19F and 23F, and (d) there is at least one additional distinct carrier protein-antigen conjugate comprising a capsular polysaccharide from a *Streptococcus pneumoniae* serotypes selected from the group consisting of serotypes 2, 6C, 8, 9N, 10A, 12F, 15A, 15B, 15C, 16F, 17F, 20, 20A, 20B, 22F, 23A, 23B, 24F, 24B, 31, 33F, 34, 35B, 35F and 38. For instance, the composition can include (i) at least 20 or 21 distinct carrier protein-antigen conjugates, including a conjugate for each of *Streptococcus pneumoniae* serotypes 1, 3, 4, 5, 6A, 6B, 7F, 8, 9V, 10A, 11A, 12F, 14, 15B, 18C, 19A, 19F, 22F, 23F and 33F, or (ii) at least 24 distinct carrier protein-antigen conjugates wherein there is a distinct carrier protein-antigen conjugate comprising a capsular polysaccharide for each of *Streptococcus pneumoniae* serotypes 1, 2, 3, 4, 5, 6A, 6B, 7F, 8, 9V, 9N, 10A, 11A, 12F, 14, 15B, 17F, 18C, 19A, 19F, 20, 22F, 23F and 33F.

In one embodiment the disclosure provides a polypeptide-antigen conjugate, wherein the polypeptide includes 3 or more nnAA residues and the conjugate has a molecular weight of at least 500 kDa. The polypeptide can be a CRMI97 (e.g. comprising an amino acid sequence which has at least 90% sequence identity to SEQ ID NO: 1, as discussed in section 5a below) containing 3 or more nnAA residues (e.g. from 3-9 or 3-8 or 3-7 or 3-6 nnAA residues). The antigen can be a bacterial polysaccharide, such as a pneumococcal capsular polysaccharide. The conjugate can have a molecular weight of at least 600 kDa, at least 800 kDa, at least 900 kDa, or at least 1 MDa e.g. between 1-5 MDa. As discussed further herein, multiple preparations of such conjugates, wherein each preparation is made with a pneumococcal capsular polysaccharide from a different *Streptococcus pneumoniae* serotype, can be combined into compositions of the present invention useful as multivalent vaccines. Preferred selections of *Streptococcus pneumoniae* serotypes represented in such conjugates are also discussed further herein.

In one embodiment the disclosure provides a polypeptide-antigen conjugate, wherein the polypeptide includes 4 or more nnAA residues. The polypeptide can be a CRMl97 (e.g. comprising an amino acid sequence which has at least 90% sequence identity to SEQ ID NO: 1, as discussed in section 5a below) containing 4 or more nnAA residues (e.g. from 4-9 or 4-8 or 4-7 or 4-6 nnAA residues). The antigen can be a bacterial polysaccharide, such as a pneumococcal capsular polysaccharide. The conjugate can have a molecular weight of at least 500 kDa, (e.g., at least 600 kDa, at least 800 kDa, at least 900 kDa, or at least 1 MDa e.g. between 1-5 MDa). As discussed further herein, multiple preparations of such conjugates, wherein each preparation is made with a pneumococcal capsular polysaccharide from a different *Streptococcus pneumoniae* serotype, can be combined into compositions of the present invention useful as multivalent vaccines. Preferred selections of *Streptococcus pneumoniae* serotypes represented in such conjugates are also discussed further herein.

In one embodiment the disclosure provides a protein suitable for preparing an immunogenic polysaccharide-protein conjugate, wherein the protein (i) includes at least one nnAA and (ii) has a solubility of at least 50 mg/L at 20° C. in pH 7.4 Tris buffer. The polypeptide comprises at least one T-cell activating epitope (as discussed above); for example, it can be a CRM197 (e.g. comprising an amino acid sequence which has at least 90% sequence identity to SEQ ID NO: 1, as discussed in section 5a below) containing 2 or more nnAA residues e.g. from 3-9 or 4-9 or 3-8 or 4-8 or 3-7 or 4-7 or 3-6 or 4-6 nnAA residues. The protein can be conjugated to a bacterial polysaccharide, such as a pneumococcal capsular polysaccharide, to make a conjugate. Solubility can be at least 100 mg/L, at least 200 mg/L, or even at least 250 mg/L. As discussed further herein, multiple preparations of such conjugates, wherein each preparation is made with a pneumococcal capsular polysaccharide from a different *Streptococcus pneumoniae* serotype, can be combined into compositions of the present invention useful as multivalent vaccines. Preferred selections of *Streptococcus pneumoniae* serotypes represented in such conjugates are also discussed further herein.

BRIEF DESCRIPTION OF THE DRAWINGS

The features and advantages of the embodiments described herein are further explained by reference to the following detailed description and accompanying drawings that sets forth illustrative embodiments.

In FIG. 2A the ladder shows from top to bottom 10, 15, 20, 25, 37, 50, 75, 100, 150, and 250 kDa. In FIG. 2B the fluorescent markers are at 25 and 75 kDa. Lanes are as follows: L=ladder, W=wild-type; C=C-terminus TAG; then lanes 1-12 have TAG to replace Lys at positions 11, 25, 34, 38, 40, 52, 60, 77, 83, 91, 96 and 103 respectively.

FIG. 3 shows opsonophagocytic (OPA) activity (GMT) following administration of monovalent pneumococcal polysaccharide-eCRM conjugates in mice. Serotypes are shown on the X-axis. White bars are adjuvanted polysaccharides, whereas black bars are adjuvanted conjugates.

FIG. 4 shows IgG responses (GMT) following administration of monovalent pneumococcal polysaccharide-eCRM conjugates in mice. Serotypes are shown on the X-axis. White bars are adjuvanted but unconjugated polysaccharides; black bars are adjuvanted conjugates.

DETAILED DESCRIPTION OF THE INVENTION

Figure 1:
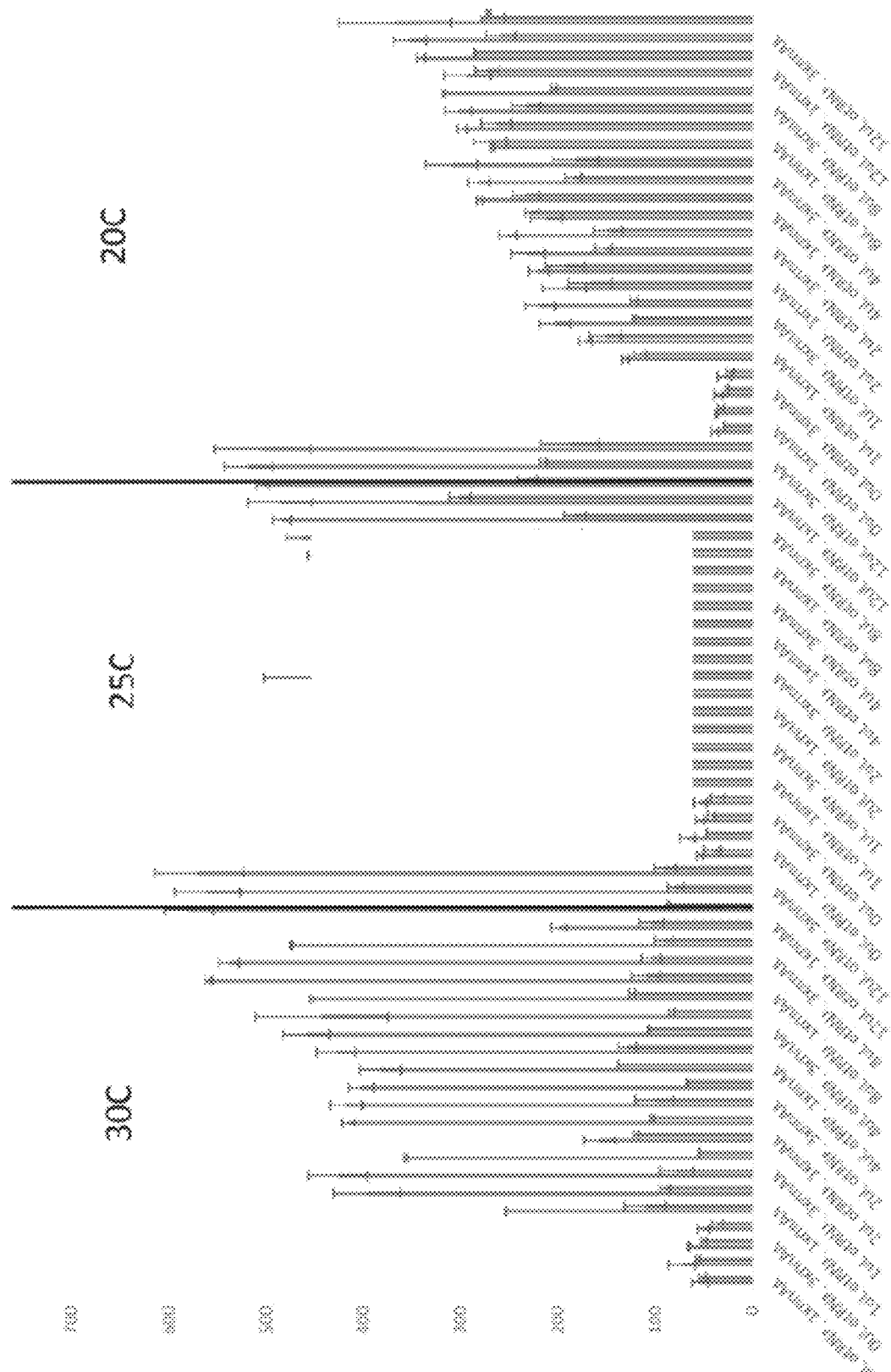
FIG. 1. shows the yield of a 6 nnAA-containing eCRM produced at 30, 25, or 20 degrees Celsius in CFPS reactions optionally supplemented with increasing amounts of tRNA (otRNA) or nnAA/aaRS synthetase (nnAA). Two bars are shown in each column, representing both total and soluble yield.

In protein-conjugate vaccines the immune response to a "weak" antigen is amplified by attachment to a known "strong" protein antigen. In these semi-synthetic biomolecules, proteins that produce strong, long-lived T-cell dependent immune responses ("T-cell dependent antigens") are typically attached to a "weak" antigen by nonspecific oxidation/reduction chemistry. The T-cell activating features on these immunogenic proteins recruit helper T-cells to B-cells that recognize the attached weak antigen, and so allow a strong, long-lived immune response to an otherwise weakly immunogenic molecule.

The current methods and building blocks used for protein-conjugate vaccine production hamper the wider application of conjugate vaccines for disease treatment and prevention. First, relatively few strong protein antigens are chemically resistant, nontoxic, and scalable enough to be used as carriers in conjugate vaccines. Second, the oxidation/reduction chemistry generally used for conjugate vaccine production makes it difficult to preserve epitopes on the carrier and antigen needed for maximum immunogenicity. Third, the relatively low efficiency of these oxidation/reduction reactions complicates quality control and purification, especially at commercial scale.

Recombinant protein production allows the optimization of antigenicity and nontoxicity of carrier proteins, but the existing carrier proteins are difficult to produce in recombinant cells and wholly engineered proteins are difficult to produce in high yields. Gentler conjugation reactions minimize the denaturation/obstruction of carrier and antigen epitopes, but the lower efficiency of these reactions results in less loading of the antigen on the carrier protein and more complicated purification schemes. Importantly, relatively lower antigen to carrier results in a higher likelihood of immune "interference" by antibody responses to the carrier protein itself, or the recognized phenomenon of carrier-induced epitopic suppression.

Thus, a need has been identified for strategies and reagents that allow the combination of these technologies to produce higher-immunogenicity, more easily manufactured conjugate vaccines. Accordingly, described herein are, inter alia, (1) polypeptides, including enhanced carrier proteins, comprising non-natural amino acids; (2) antigens that are suitable to conjugate to polypeptides, including enhanced carrier proteins, comprising non-natural amino acids; (3) polypeptide-antigen conjugates of (1) and (2), including antigens conjugated to enhanced carrier proteins comprising non-natural amino acids; (4) vaccine compositions comprising the foregoing; and (5) methods of making and using the foregoing.

1. Definitions

The term "suppression codon" refers to a nucleotide triplet that is introduced into a polynucleotide at a predetermined location and is recognized by a specific tRNA that can recognize a stop codon (e.g., an amber, ochre or opal stop codon) and allows translation to read through the codon to produce the protein, thereby suppressing the stop codon.

A "non-natural amino acid" (nnAA) refers to an amino acid that is not one of the 20 common amino acids or pyrolysine or selenocysteine; other terms that are used synonymously with the term "non-natural amino acid" are "non-naturally encoded amino acid," "unnatural amino acid," "non-naturally occurring amino acid," and variously hyphenated and non-hyphenated versions thereof. Non-natural amino acids with bio-orthogonal reactive chemical side chains are able to be used as a chemical "handle" to conjugate various payloads to discrete sites in a protein.

The term "sequence identity" or "percent identity" in the context of two or more nucleic acids or polypeptide sequences, refers to two or more sequences that are the same or have a specified percentage of amino acid residues or nucleotides that are the same, when compared and aligned for maximum correspondence over a comparison window, as measured using a sequence comparison algorithm (e.g., BLASTP for amino acid sequences). For purposes of this document, the percent identity is determined over the full-length sequence, such as the reference sequence set forth in SEQ ID NO: 1. The method for calculating the sequence identity as provided herein is the BLASTP program having its defaults set at a wordlength (W) of 3, an expectation (E) of 10, and the BLOSUM62 scoring matrix (see, e.g., Henikoff & Henikoff, 1989, *Proc Natl Acad Sci USA* 89:10915). See e.g., the BLAST alignment tool available on the WWW at blast.ncbi.nlm.nih.gov/Blast.cgi or elsewhere.

The term "antigen" refers to any molecule or a linear molecular fragment that is able to be recognized by the highly variable antigen receptors (B-cell receptors, T-cell receptors, or both) of the adaptive immune system. Non-limiting examples of antigens include polysaccharides or glycans (e.g., bacterial capsular polysaccharides), polynucleotides, polyamino acids, lipids, and small molecules (e.g., haptens, drugs of abuse).

The term "T-cell activating epitope" refers to a structural unit of molecular structure which is capable of inducing T-cell immunity. The function of carrier proteins which include T-cell activating epitopes is well known and documented for conjugates. Without wishing to be bound by theory, a T-cell activating epitope in the carrier protein enables the covalently-attached antigen to be processed by antigen-presenting cells and presented to $CD4^{+ve}$ T cells to induce immunological memory against the antigen.

The term "B-cell epitope" refers generally to those features of a macromolecular structure which are capable of inducing a B cell response. In contrast to a T-cell epitope, a B-cell epitope need not comprise a peptide, since processing by antigen-presenting cells and loading onto the peptide-binding cleft of MHC is not required for B-cell activation.

As used herein, "carrier protein" refers to a non-toxic or detoxified polypeptide containing a T-cell activating epitope which is able to be attached to an antigen (e.g., a polysaccharide) to enhance the humoral response to the conjugated antigen in a subject. The term includes any of the bacterial proteins used as epitope carriers in FDA-approved vaccines. In some embodiments, the carrier protein is *Corynebacterium diphtheriae* toxin, *Clostridium tetani* tetanospasmin, *Haemophilus influenzae* protein D (PD, HiD), outer membrane protein complex of serogroup B meningococcus (OMPC), CRM197, or malaria ookinete specific surface protein Pfs25. In another embodiment, the carrier protein is BB, derived from the G protein of *Streptococcus* strain G148. A "native carrier protein" has only naturally occurring amino acids. An "enhanced carrier protein" has at least one non-natural amino acid replaced for a naturally occurring amino acid in the carrier protein.

As used herein, the term "immunogenic polypeptide" refers to a polypeptide comprising at least one T-cell activating epitope, wherein the T-cell epitope is derived from a protein capable of inducing immunologic memory in animals.

The term "eCRM" or "enhanced CRM" as used interchangeably herein refers to a modified version of the G52E codon variant of diphtheria toxin, wherein at least one of the natural amino acid residues is substituted for a non-natural amino acid and the polypeptide retains at least one T-cell activating epitope.

As used herein, the terms "modified," "replaced," "enhanced," and "substituted" are considered synonymous when used to describe residues of a polypeptide, and in all cases refer to the replacement of a non-natural amino acid for a naturally occurring amino acid within a polypeptide chain.

As used herein, the term "T-independent antigen" refers to an antigen that induces the features of B-cell mediated immunity, or which does not induce processes associated with helper T-cell mediated immunity such as isotype switching or immunologic memory.

The term "polysaccharide" as used herein, is used in its ordinary sense, including, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and optionally from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating units. Oligosaccharides typically have from about 6, 7, 8, 9, or 10 repeating units to about 15, 20, 25, 30, or 35 to about 40 or 45 repeating units.

As used herein, the term "glycan" refers to any linear or branched polymer consisting of monosaccharide (e.g. glucose) residues joined to each other by glycosidic linkages. Examples of glycans include glycogen, starch, hyaluronic acid, and cellulose. Other examples of "glycans" include bacterial capsular polysaccharides.

As used herein, the term "molecular weight" of a polysaccharide or of a carrier protein-polysaccharide conjugate refers to molecular weight calculated by size exclusion chromatography (SEC) combined with multiangle laser light scattering (MALS).

The term "lower alkyl" as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties. See also US-2014/0066598. The term "lower alkylene" refers to an alkylene radical of a lower alkyl.

The compounds of the various embodiments disclosed herein, or their pharmaceutically acceptable salts that contain one or more asymmetric centers and give rise to enantiomers, diastereomers, and other stereoisomeric forms that are defined, in terms of absolute stereochemistry, as (R) or (S), or as (D) or (L) for amino acids. The present disclosure is meant to include all such isomers, as well as their racemic and optically pure forms. The nnAA used herein are generally α-amino acids with a chiral center at the α-carbon, and they are preferably (L) isomers.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). Except as described below, all bonds are identified in the chemical structure diagrams herein, except for all bonds on some carbon atoms, which are assumed to be bonded to sufficient hydrogen atoms to complete the valency.

2. General Methods

Unless defined otherwise, all technical and scientific terms used herein have the commonly understood meaning. Practitioners are particularly directed to Green & Sambrook (eds.) *Molecular Cloning: A Laboratory Manual*, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), and Plotkin, S. A., Orenstein, W. A., & Offit, P. A., *Vaccines*, 6 ed, Elsevier, London (2013), which are incorporated herein by reference, for definitions and terms. Standard methods also appear in Bindereif, Schon, & Westhof (2005) *Handbook of RNA Biochemistry*, Wiley-VCH, Weinheim, Germany which describes detailed methods for RNA manipulation and analysis, and is incorporated herein by reference. Examples of appropriate molecular techniques for generating recombinant nucleic acids, and instructions of many cloning exercises are found in Green & Sambrook (Id.); Ausubel, F. M., et al., (Id.); Berger & Kimmel, *Guide to Molecular Cloning Techniques, Methods in Enzymology* (Volume 152 Academic Press, Inc., San Diego, Calif. 1987); and *PCR Protocols: A Guide to Methods and Applications* (Academic Press, San Diego, Calif. 1990), which are incorporated by reference herein. Examples of appropriate bio-organic techniques for activating and derivatizing biomolecules with chemical handles, and instructions to design such syntheses are found in Hermanson, G. T, *Bioconjugate Techniques*, $2^{nd}$ ed., Elsevier, London (2008). For examples of techniques and components necessary for parenteral administration of biomolecules described herein, practitioners are directed to Remington, Essentials of Pharmaceutics, Pharmaceutical Press, London (2012). Methods for protein purification, chromatography, electrophoresis, centrifugation, and crystallization are described in Coligan et al. (2000) *Current Protocols in Protein Science*, Vol. 1, John Wiley and Sons, Inc., New York. Methods for cell-free synthesis are described in Spirin & Swartz (2008) *Cell-free Protein Synthesis*, Wiley-VCH, Weinheim, Germany. Methods for incorporation of non-natural amino acids into proteins using cell-free synthesis are described in Shimizu et al. (2006) *FEBS Journal*, 273, 4133-4140 and also in Chong (2014) *Curr Protoc Mol Biol.* 108:16.30.1-11.

PCR amplification methods are described, for example, in Innis et al., PCR Protocols: A Guide to Methods and Applications, Academic Press Inc. San Diego, Calif., 1990 and Domingues (ed.) *PCR: Methods and Protocols* ISBN 1493970593 (2017). An amplification reaction typically includes the DNA that is to be amplified, a thermostable DNA polymerase, two oligonucleotide primers, deoxynucleotide triphosphates (dNTPs), reaction buffer and magnesium. Typically a desirable number of thermal cycles is between 1 and 25. Methods for primer design and optimization of PCR conditions are found in molecular biology texts such as Ausubel et al., *Short Protocols in Molecular Biology*, 5th Edition, Wiley, 2002, and Innis et al., *PCR Protocols*, Academic Press, 1990. Computer programs are useful in the design of primers with the required specificity and optimal amplification properties (e.g., Oligo Version 5.0 (National Biosciences)). In some embodiments, the PCR primers additionally contain recognition sites for restriction endonucleases, to facilitate insertion of the amplified DNA fragment into specific restriction enzyme sites in a vector. If restriction sites are to be added to the 5' end of the PCR primers, it is preferable to include a few (e.g., two or three) extra 5' bases to allow more efficient cleavage by the enzyme. In some embodiments, the PCR primers also contain an RNA polymerase promoter site, such as T7 or SP6, to allow for subsequent in vitro transcription. Methods for in vitro transcription are found in sources such as Van Gelder et al., *Proc. Natl. Acad Sci.* U.S.A. 87:1663-1667, 1990; Eberwine et al., *Proc. Natl. Acad Sci.* U.S.A. 89:3010-3014, 1992.

The molecular weight of a polysaccharide or of a carrier protein-polysaccharide conjugate is measured by size exclusion chromatography (SEC) combined with multiangle laser light scattering (MALS). The SEC MALS-UV-RI setup consists of an Agilent HPLC 1100 (including degasser, quaternary pump, temperature-controlled auto-sampler, temperature controlled column compartment and UV-VIS diode array detector) in line with a DAWN-HELEOS multiangle laser light scattering detector and Optilab T-rEX differential refractive interferometer (Wyatt Technology, Santa Barbara, Calif.) for the detection of eluting species. The following series of columns is attached to this system: TSKgel Guard PWXL 6.0 mm ID×4.0 cm long, 12 μm particle; TSKgel 6000 PWXL 7.8 mm ID×30 cm long, 13 μm particle; and a TSKgel 3000 PWXL 7.8 mm ID×30 cm long, 7 μm particle. The column compartment is set to 25° C. and the sample compartment is set to 4° C. A mobile phase consisting of 0.2 μm filtered 1×PBS with 5% v/v acetonitrile is used at a 0.5 mL/min flow rate. Samples are injected within a concentration range of 0.2-1.5 mg/mL polysaccharide and the injected volume is adjusted to yield a total injected mass of 30-40 μg. Agilent Open Lab software is used to control the HPLC, and Wyatt Astra 7 software is used for data collection and analysis. The technique reveals the distribution of absolute molecular weights for conjugates in a sample, and results for a population are expressed as an average value.

In some embodiments, *S. pneumoniae* isolated capsular polysaccharides are obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/

118752). In other embodiments, *S. pneumoniae* isolated capsular polysaccharides are obtained from a commercial source (e.g., ATCC).

3. Polypeptides

Described herein are polypeptides comprising at least one nnAA residue. Suitable polypeptides include any biologically active polypeptide. In some embodiments, the polypeptide is an immunogenic polypeptide. In some embodiments, the nnAA residue is substituted for native residues of a specified polypeptide. In other embodiments, the nnAA residue is appended before, appended after, or inserted within the sequence of a specified polypeptide. In further embodiments, the polypeptide comprises at least 1, at least 2, at least 3, at least 4, at least 5, at least 6, at least 7, at least 8, or at least 9 nnAA residues. In another embodiment, the polypeptide comprises 1, 2, 3, 4, 5, 6, 7, 8, or 9 nnAA residues. In another embodiment, the polypeptide comprises 2-9 nnAA residues, and preferably 4-6 nnAA residues. In yet further embodiments, the polypeptide comprises 2 or more nnAA residues that are chemically distinct.

In one embodiment, the disclosure provides an immunogenic polypeptide comprising an nnAA residue. In another embodiment, the polypeptide comprises at least 2, at least 3, at least 4, at least 5, at least 6, at least 7, at least 8, or at least 9 nnAA residues. In another embodiment, the at least two non-natural amino acid residues comprise at least two different non-natural amino acids. In another embodiment, the at least two different non-natural amino acids are selected from the group consisting of 2-amino-3-(4-azidophenyl) propanoic acid (pAF), 2-amino-3-(4-(azidomethyl)phenyl) propanoic acid (pAMF), 2-amino-3-(5-(azidomethyl)pyridin-2-yl)propanoic acid, 2-amino-3-(4-(azidomethyl) pyridin-2-yl)propanoic acid, 2-amino-3-(6-(azidomethyl) pyridin-3-yl)propanoic acid, 2-amino-5-azidopentanoic acid, or 2-amino-3-(4-(azidomethyl)phenyl)propanoic acid, and any combination thereof. In another embodiment, the polypeptide comprises a T-cell activating epitope of a carrier protein. In another embodiment, the polypeptide is a carrier protein. In another embodiment, the nnAA is not in a T-cell activating epitope of the carrier protein. In another embodiment, the nnAA is substituted for a lysine residue. In another embodiment, the polypeptide is conjugated to an antigen. In another embodiment, the antigen is conjugated to the nnAA. In another embodiment, the antigen comprises a T-cell independent antigen selected from the group consisting of a hapten, a bacterial capsular polysaccharide, a bacterial lipopolysaccharide, or a tumor-derived glycan. In another embodiment, the antigen comprises a bacterial non-capsular polysaccharide, such as an exopolysaccharide e.g. the *S. aureus* exopolysaccharide.

In one embodiment, the disclosure provides a carrier protein comprising an nnAA residue. In another embodiment, the carrier protein comprises at least 2, at least 3, at least 4, at least 5, at least 6, at least 7, at least 8, or at least 9 nnAA residues. In another embodiment, the non-natural amino acid is selected from the group consisting of 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, or 2-amino-3-(4-(azidomethyl)phenyl) propanoic acid, and any combination thereof. In another embodiment, the nnAA is substituted for a lysine residue. In another embodiment, the nnAA residue is at a position that is not in a T-cell activating epitope of the carrier protein. In another embodiment, the substitution is selected from the group consisting of K25, K34, K38, K40, K213, K215, K228, K265, K386, K523 and K527, and any combination thereof of SEQ ID NO: 1. In another embodiment, the substitution comprises a combination of K25, K213, K245, K265, K386, and K523 of SEQ ID NO:1. In another embodiment, the carrier protein comprises an antigen. In another embodiment, the antigen comprises a T-independent antigen selected from the group consisting of a hapten, a bacterial capsular polysaccharide, a bacterial lipopolysaccharide, or a tumor-derived glycan. In another embodiment, the antigen is a polysaccharide. In another embodiment, polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the polypeptide is capable of generating a T-cell dependent immune response.

In one embodiment, the disclosure provides for a protein comprising an antigen conjugated to an amino acid residue of the carrier protein, wherein no antigen is conjugated to a natural amino acid residue of the carrier protein. In another embodiment, no antigen is conjugated to a lysine residue of the carrier protein. In another embodiment, the amino acid is not in a T-cell activating epitope of the carrier protein. In another embodiment, the antigen comprises a T independent antigen selected from the group consisting of a hapten, a bacterial capsular polysaccharide, a bacterial lipopolysaccharide, or a tumor-derived glycan. In another embodiment, the antigen is a polysaccharide. In another embodiment, the polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof.

Ideally, the carrier protein should have a solubility of at least 50 mg/L (e.g. at least 100 mg/L, at least 150 mg/L, at least 200 mg/L, or at least 250 mg/L) when expressed in a cell-free protein synthesis system.

Where a carrier includes more than one nnAA residue, it is preferred to include only a single species of nnAA (e.g. the only nnAA in the carrier is pAMF). This permits the same conjugation chemistry to be used simultaneously at each nnAA. If it is desired to attach two different antigens to a single carrier molecule, this can be achieved by using different nnAA species within a single carrier and conjugating each antigen to a different nnAA, but conjugation to a single species of nnAA in a carrier is preferred. Moreover, where a composition includes multiple different conjugates (e.g. different pneumococcal serotypes) it is preferred that each conjugate includes the same single species of nnAA. Furthermore, where a composition includes multiple different conjugates (e.g. different pneumococcal serotypes) it is preferred that each conjugate includes the same carrier protein.

In another embodiment, the disclosure provides for a polynucleotide encoding the polypeptide described herein. In another embodiment, the disclosure provides for an expression vector comprising the polynucleotide encoding the polypeptide described herein. In another embodiment, the disclosure provides for a host cell comprising the expression vector.

4. Non-Natural Amino Acids

The nnAA residue optionally comprises any of the non-natural amino acids described in this application, or others that have been identified as compatible with cell-based or cell-free protein synthesis (see, e.g., Schultz et al. *Annu Rev Biochem.* 2010; 79:413-44 particularly pp. 418-420; and Chin et al. *Annu Rev Biochem.* 2014; 83:5.1-5.30, which are hereby incorporated by reference).

Examples of non-natural amino acids that can be used in the methods of the embodiments include: a non-natural analog of a tyrosine amino acid; a non-natural analog of a glutamine amino acid; a non-natural analog of a phenylalanine amino acid; a non-natural analog of a serine amino acid; a non-natural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analog containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline, etc.

Particularly preferred nnAA for use with the invention are those which can be incorporated during translation (in a cellular or a cell-free system) and which provide a functional group which is not found in any of the 20 naturally occurring amino acids. Various techniques for incorporating such amino acids into polypeptides are known e.g. see Young & Schultz (2010) *J Biol Chem* 285:11039-44, Maza et al. (2015) *Bioconjugate Chem.* 26:1884-9, and Zimmerman et al. (2014) *Bioconjugate Chem.* 25:351-61.

In particular, the nnAA residue optionally comprises a chemical group suitable for "click" chemistry reaction with a corresponding group on a separate antigen molecule or hapten. Suitable chemical groups for "click" chemistry include, but are not limited to azide ($N_3$), alkyne (C≡C), alkene (C═C) and 1,2,4,5-tetrazine

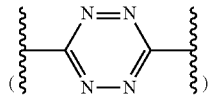 [SMILES: *c1nnc(*)nn1]

groups.

The conjugate comprises a polypeptide and an antigen, wherein the polypeptide is a carrier protein comprising at least one T-cell activating epitope and at least one nnAA, preferably at least two nnAA, wherein the antigen is conjugated to the at least one nnAA. In some embodiments, the at least one nnAA is a 2,3-disubstituted propanoic acid bearing an amino substituent at the 2-position and an azido-containing substituent, a 1,2,4,5-tetrazinyl-containing substituent, or an ethynyl-containing substituent at the 3-position.

In another related embodiment, the conjugate comprises a polypeptide and an antigen, wherein the polypeptide is a carrier protein comprising at least one T-cell activating epitope and at least one an nnAA residue, wherein the antigen is conjugated to the nnAA and further wherein the nnAA residue corresponds to an amino acid having the structure of formula XII

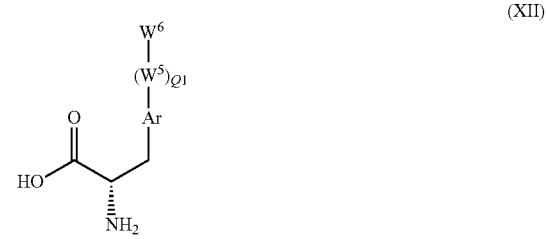

wherein:
Ar comprises a 5-membered or 6-membered aromatic ring optionally containing at least one heteroatom;
$W^5$ is selected from $C_1$-$C_{10}$ alkylene, —NH—, —O— and —S—;
Q1 is zero or 1; and
$W^6$ is selected from azido, 1,2,4,5-tetrazinyl optionally C-substituted with a lower alkyl group, and ethynyl,
such that the nnAA residue in the polypeptide has the structure of formula XIII

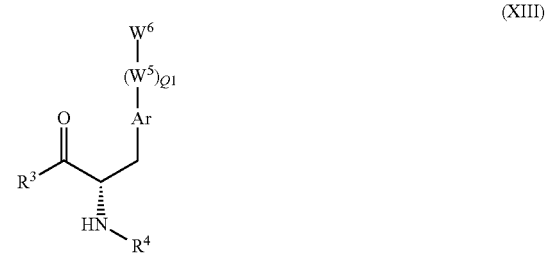

in which $R^3$ is OH or an amino acid residue of the carrier protein, and $R^4$ is H or an amino acid residue of the carrier protein.

In one embodiment, the present disclosure provides a polypeptide comprising at least one nnAA replaced for a naturally occurring amino acid within the native polypeptide according to SEQ ID NO:1, wherein the at least one nnAA is replaced for K25, K34, K38, K40, K213, K215, K228, K245, K265, K386, K523, or K527 of SEQ ID NO: 1, wherein the nnAA comprises a linking moiety. In another embodiment, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl) phenyl)propanoic acid, or any combination thereof. In another embodiment, K265 of SEQ ID NO:1 is replaced. In another embodiment, K386 of SEQ ID NO:1 is replaced. In another embodiment, K265 and K386 of SEQ ID NO:1 are replaced. In another embodiment, the polypeptide comprises at least 2, at least 3, at least 4, at least 5, at least 6, at least 7, at least 8, or at least 9 nnAAs. In another embodiment, the nnAA is selected from 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, and 2-amino-3-(4-(azidomethyl)phenyl)propanoic acid, or any combination thereof.

In another embodiment, the nnAA in the polypeptide is a 2,3-disubstituted propanoic acid bearing an amino substituent at the 2-position and an azido-containing substituent, a 1,2,4,5-tetrazinyl-containing substituent, or an ethynyl-containing substituent at the 3-position. In a preferred embodiment, the substituent at the 3-position is an azido-containing substituent, and, in a more preferred embodiment, the azido-containing substituent comprises a terminal azido group bound to the carbon atom at the 3-position through a linking group. For example, the linking group may comprise an arylene moiety that is optionally substituted and optionally heteroatom-containing. For instance, the linking group may comprise a 5- or 6-membered arylene moiety containing 0 to 4 heteroatoms and 0 to 4 non-hydrogen ring substituents.

In a more preferred embodiment, the nnAA has the structure of formula XII

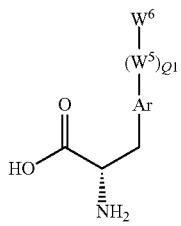

(XII)

wherein:
Ar comprises a 5-membered or 6-membered aromatic ring optionally containing at least one heteroatom;
$W^5$ is selected from $C_1$-$C_{10}$ alkylene, —NH—, —O— and —S—;
Q1 is zero or 1; and
$W^6$ is selected from azido, 1,2,4,5-tetrazinyl optionally C-substituted with a lower alkyl group, and ethynyl.

It will be appreciated that in this case the corresponding nnAA residue in the polypeptide has the structure of formula XIII

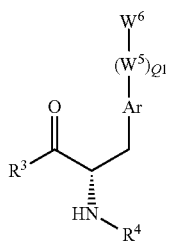

(XIII)

in which $R^3$ is OH or an amino acid residue of the carrier protein, and $R^4$ is H or an amino acid residue of the carrier protein.

In some embodiments, Ar does not contain any heteroatoms, in which case the preferred linker is an unsubstituted phenylene group (i.e. Ar is —$C_6H_4$—). In other embodiments, Ar contains a nitrogen heteroatom and at least one additional heteroatom selected from N, O, and S. Exemplary nitrogen heterocycles are described infra and Ar may be e.g. a pyridine or a pyridazine. In a particularly preferred embodiment, Q is 1, $W^5$ is lower alkylene, and $W^6$ is azido.

Azido-Containing Amino Acids:

In some embodiments, the nnAA residue comprises an azido-containing nnAA. In particular embodiments, the nnAA residue comprises an azido-containing nnAA of formula I:

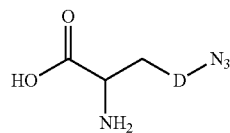

wherein:
D is —Ar—W3- or —W1-Y1-C(O)—Y2-W2-;
Ar is

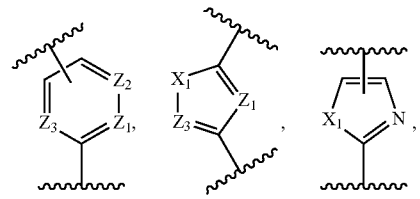

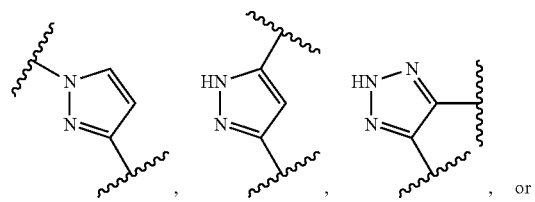

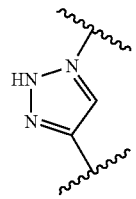

;

each of W1, W2, and W3 is independently a single bond or lower alkylene;
each $X_1$ is independently —NH—, —O—, or —S—;
each Y1 is independently a single bond, —NH—, or —O—;
each Y2 is independently a single bond, —NH—, —O—, or an N-linked or C-linked pyrrolidinylene; and
one of $Z_1$, $Z_2$, and $Z_3$ is —N— and the others of $Z_1$, $Z_2$, and $Z_3$ are independently —CH—.

In other embodiments, the nnAA residue comprises an azido-containing amino acid of formula II:

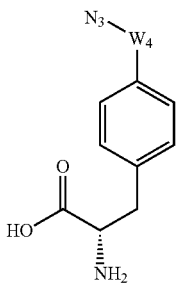

wherein:

$W_4$ is $C_1$-$C_{10}$ alkylene.

In one embodiment the nnAA residue comprises an azido-containing amino acid selected from the group consisting of 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, or 2-amino-3-(4-(azidomethyl)phenyl)propanoic acid, and any combination thereof. In a further embodiment, the nnAA residue comprises 2-amino-3-(4-(azidomethyl)phenyl)propanoic acid (pAMF). pAMF provides very favorable reaction kinetics for producing conjugates (e.g. much faster than using pAF when reacting with an alkyne-containing carbohydrate antigen in a SPAAC method).

Preparation of azido-containing amino acids according to formulas I and II are found, for example, in Stafford et al. US2014-0066598A1, particularly paragraphs [0331]-[0333], which are incorporated by reference. The process involves substitution of hydroxyl groups for chloride on derivatives of the corresponding aryl amino acids using thionyl chloride, followed by nucleophilic displacement of the chloride with azide. Suitable aryl side-chain containing amino acids are also acquired commercially.

1,2,4,5-Tetrazinyl-Containing Amino Acids:

In some embodiments, the non-natural amino acid residue comprises a 1,2,4,5-tetrazine containing nnAA. In particular embodiments, the non-natural amino acid comprises a 1,2,4,5-tetrazine containing nnAA of formula III:

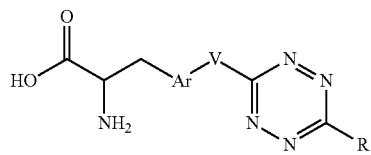

wherein:
Ar is

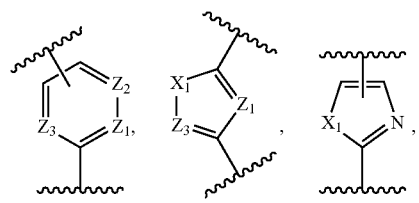

-continued

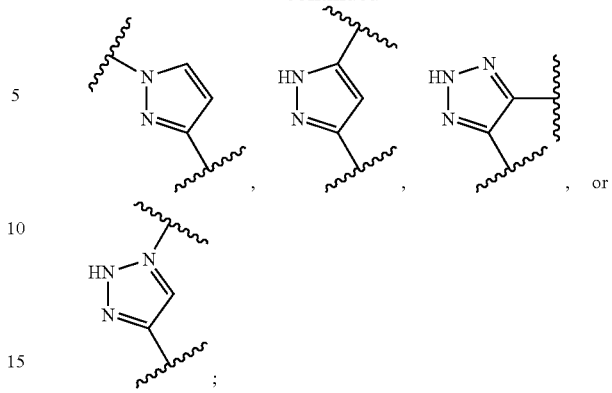

V is a single bond, lower alkylene, or —W1-W2-;
one of W1 and W2 is absent or lower alkylene, and the other is —NH—, —O—, or —S—;
each one of $Z_1$, $Z_2$, and $Z_3$ is —CH— or —N— and the others of $Z_1$, $Z_2$, and $Z_3$ are each independently —CH—; and $X_1$ is independently —NH—, —O—, or —S—;
R is lower alkyl;
and, optionally, when Ar is

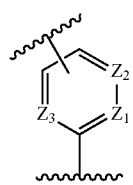

and V is —NH—, then one of $Z_1$, $Z_2$, and $Z_3$ is —N— provided the non-natural amino acid is not:

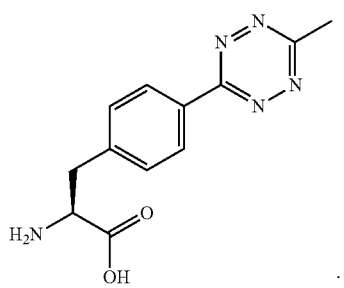 [SMILES: Cc1nnc(-c2ccc(C[C@H](N)C(=O)O)cc2)nn1]

Preparation of 1,2,4,5-tetrazine-containing amino acids according to formula III is found, for example, in Yang et al. US2016-0251336A1, particularly paragraphs [0341]-[0377], which are incorporated by reference. The process involves Negishi coupling of an amino/carboxyl protected derivative of (R)-2-amino-3-iodopropanoic acid with an aminopyridyl bromide to introduce Ar, followed by reaction with a methylthio-1,2,4,5-tetrazine derivative to introduce the tetrazine moiety into the amino acid.

Alkyne-Containing Amino Acids:

In some embodiments, the nnAA residue comprises an alkyne-containing nnAA. In one embodiment, this is a propargyl group. A variety of propargyl-containing amino acids, including syntheses thereof, are found in Beatty et al. Angew. Chem. Int. Ed. 2006, 45, 7364-7; Beatty et al. J. Am.

*Chem. Soc.* 2005(127): 14150-1; Nguyen et al. *J Am Chem Soc.* 2009(131):8720-1. Such propargyl-containing amino acids are suitable for incorporation as nnAAs into proteins using cell-based systems. In some embodiments, the nnAA residue comprises a propargyl-containing nnAA selected from the group consisting of homopropargylglycine, ethynylphenylalanine, and N6-[(2-propynyloxy)carbonyl]-L-lysine.

5. Modified Carrier Proteins

In one aspect, the polypeptide comprising at least one nnAA residue is a modified version of a native carrier protein (e.g., eCRM), or a polypeptide comprising one or a plurality of T-cell activating epitopes of a native carrier protein. Carrier proteins suitable for such modification include, but are not limited to, proteins used in conjugate vaccines such as *Corynebacterium diphtheriae* toxin, *Clostridium tetani* tetanospasmin, *Haemophilus influenzae* protein D (PD, HiD), outer membrane protein complex of serogroup B meningococcus (OMPC), or CRM197.

The amino acid and nucleic acid sequences of many native carrier proteins are publicly available. As noted, however, such non-modified (or native) carrier proteins have limitations, including non-discriminate antigen conjugation to any surface-exposed amino acid. As a result, the T-cell activating epitopes are often sites where antigen conjugation occurs. In a preferred embodiment of the present disclosure, the immunogenic polypeptide is a carrier protein modified by the inclusion of at least one nnAA residue for use as a site of conjugation. As discussed above, the nnAA can be substituted for a native residue or added to the polypeptide by appending before, appending after, or inserting within the sequence of the polypeptide. The use of non-natural amino acids, as described herein, allows the selective placement of non-natural amino acids for conjugation and as a result the T-cell activating epitopes of the enhanced carrier protein can be avoided in antigen conjugation.

Table 1 shows the amino acid and nucleic acid sequences (SEQ ID NOs: 1 & 2) of an example native carrier protein: CRM197. Those of skill in the art will recognize the addition of a N-terminal methionine to the amino acid sequence of conventional CRM197 produced by fermentation of *C. diphtheriae*, and the resulting addition of 1 to the conventional amino acid residue position numbering. The methionine is present because of the inclusion of a start codon in the cell-free protein synthesis method which was used to produce these carriers herein. In some aspects, the enhanced carrier protein comprising the nnAA residues has at least 80% sequence identity, at least 85% sequence identity, at least 90% sequence identity, or at least 95% sequence identity to a homologous native or non-toxic carrier protein used in a conjugate vaccine.

Carrier proteins having sequence identity to SEQ ID NO:1 (CRM197) include other mutant diphtheria toxin proteins, such as the non-toxic K51E/E148K double mutant which has also been used as a carrier protein in conjugates (Pecetta et al. 2016 *Vaccine* 34:1405-11). In all of these variants of SEQ ID NO:1 the natural toxicity of wild-type diphtheria toxin is absent (via the G52E mutation in CRM197, or the K51E/E148K mutations of Pecetta et al.

Table 1 also shows the amino acid sequence of protein D (SEQ ID NO:8) from *H. influenzae*. The enhanced carrier protein comprising nnAA residues may have at least 80% sequence identity to SEQ ID NO:8. At least one Lys residue in SEQ ID NO:8 can be replaced by a nnAA. There are 36 Lys residues within SEQ ID NO:8 so several can be replaced by nnAA and then used for conjugation.

Where sequence identity is determined relative to diphtheria or tetanus toxin, it should be determined relative to the processed heavy chain sequence e.g. relative to amino acids 226-567 of P00588-1, or to amino acids 458-1315 of P04958-1 (UniProt sequences).

In some embodiments, the enhanced carrier protein comprising the nnAA residues comprises less than the full native sequence of the carrier protein, and instead comprises at least one or a plurality of T-cell activating epitopes from *Corynebacterium diphtheriae* toxin, *Clostridium tetani* tetanospasmin, *Haemophilus influenzae* protein D (PD, HiD), outer membrane protein complex of serogroup B meningococcus (OMPC), CRMI97, Pfs25, or another suitable native or non-toxic carrier protein. In some embodiments, the toxicity of the enhanced carrier protein is limited by treatment with paraformaldehyde (or by treatment with formaldehyde or glutaraldehyde) followed by a quenching agent. In one embodiment the enhanced carrier protein comprising the nnAA residues is a polypeptide comprising a plurality of T-cell activating epitopes of native CRM197.

TABLE 1

| Native CRM197 and NTHi-D amino acid and nucleic acid sequences | |
|---|---|
| Amino acid | >4AE1_B<br>MGADDVVDSSKSFVMENFSSYHGTKPGYVDSIQKGIQKPKSGTQGNYDDDWKEFYSTDNKYDAAGYS<br>VDNENPLSGKAGGVVKVTYPGLTKVLALKVDNAETIKKELGLSLTEPLMEQVGTEEFIKRFGDGASR<br>VVLSLPFAEGSSSVEYINNWEQAKALSVELEINFETRGKRGQDAMYEYMAQACAGNRVRRSVGSSLS<br>CINLDWDVIRDKTKTKIESLKEHGPIKNKMSESPNKTVSEEKAKQYLEEFHQTALEHPELSELKTVT<br>GTNPVFAGANYAAWAVNVAQVIDSETADNLEKTTAALSILPGIGSVMGIADGAVHHNTEEIVAQSIA<br>LSSLMVAQAIPLVGELVDIGFAAYNFVESIINLFQVVHNSYNRPAYSPGHKTQPFLHDGYAVSWNTV<br>EDSIIRTGFQGESGHDIKITAENTPLPIAGVLLPTIPGKLDVNKSKTHISVNGRKIRMRCRAIDGDV<br>TFCRPKSPVYVGNGVHANLHVAFHRSSSEKIHSNEISSDSIGVLGYQKTVDHTKVNSKLSLFFEIKS<br>(SEQ ID NO: 1) |
| Nucleic acid | >KU521393.1 Synthetic construct clone pUC57-CRM197 toxin CRM197<br>(CRM197) gene, complete cds<br>ATGGGCGCAGACGATGTTGTGGACTCAAGTAAATCATTTGTCATGGAAAACTTCTCCTCATATCACG<br>GCACGAAACCGGGCTACGTTGATAGCATTCAGAAAGGTATCCAAAAACCGAAATCTGGCACGCAGGG<br>TAACTACGATGACGATTGGAAAGAATTCTACAGCACCGACAACAAATATGATGCGGCCGGTTACTCA<br>GTCGACAACGAAAATCCGCTGTCGGGCAAAGCCGGCGGTGTGGTTAAAGTGACGTATCCGGGCCTGA<br>CCAAAGTCCTGGCCCTGAAAGTGGATAATGCAGAAACCATCAAAAAAGAACTGGGTCTGAGCCTGAC<br>GGAACCGCTGATGGAACAGGTTGGCACCGAAGAATTTATCAAACGCTTCGGCGATGGTGCCAGTCGT<br>GTCGTGCTGTCCCTGCCGTTCGCAGAAGGTAGCTCTAGTGTGGAATATATTAACAATTGGGAACAAG<br>CGAAAGCCCTGTCCGTTGAACTGGAAATCAACTTTGAAACCCGCGGCAAACGTGGTCAGGATGCGAT |

TABLE 1-continued

Native CRM197 and NTHi-D amino acid and nucleic acid sequences

```
GTATGAATACATGGCACAAGCTTGCGCGGGTAATCGCGTTCGTCGCAGCGTCGGCTCCTCACTGTCT
TGTATCAACCTGGACTGGGATGTTATCCGTGATAAAACCAAAACGAAAATCGAAAGTCTGAAAGAAC
ATGGCCCGATCAAAAACAAAATGAGCGAATCTCCGAATAAAACGGTGTCCGAAGAAAAAGCTAAACA
GTATCTGGAAGAATTCCACCAAACCGCACTGGAACATCCGGAACTGTCAGAACTGAAAACCGTGACG
GGTACCAACCCGGTTTTTGCCGGCGCAAATTACGCAGCTTGGGCTGTGAACGTTGCGCAAGTGATTG
ACTCGGAAACGGCCGATAATCTGGAAAAAACCACGGCGGCCCTGAGTATTCTGCCGGGCATCGGTTC
CGTTATGGGTATTGCCGACGGCGCAGTCCATCACAACACCGAAGAAATTGTGGCCCAGTCTATCGCA
CTGTCGAGCCTGATGGTTGCTCAAGCGATTCCGCTGGTTGGCGAACTGGTTGATATCGGCTTTGCAG
CTTACAACTTCGTGGAAAGTATTATCAACCTGTTTCAGGTTGTCCACAACTCATATAATCGCCCGGC
CTACTCGCCGGGTCACAAAACCCAACCGTTCCTGCATGACGGCTACGCGGTTAGCTGGAATACGGTC
GAAGATTCTATTATCCGTACCGGCTTTCAGGGTGAATCTGGCCACGACATTAAAATCACGGCTGAAA
ACACCCCGCTGCCGATTGCAGGTGTTCTGCTGCCGACGATCCCGGGTAAACTGGATGTTAACAAATC
AAAAACCCATATCTCGGTCAACGGTCGCAAAATTCGTATGCGCTGCCGTGCGATCGACGGCGATGTG
ACCTTCTGTCGTCCGAAAAGCCCGGTCTATGTGGGCAACGGTGTCCATGCTAATCTGCACGTGGCGT
TTCATCGCTCTAGTTCCGAAAAAATCCATAGTAACGAAATCTCATCGGATTCCATTGGTGTGCTGGG
CTACCAGAAAACCGTGGACCATACCAAAGTGAATAGCAAACTGAGCCTGTTCTTCGAAATCAAATCG
TAA (SEQ ID NO: 2)
```

Amino acid

\>AA24998.1 Haemophilus influenzae protein D
CSSHSSNMANTQMKSDKIIIAHRGASGYLPEHTLESKALAFAQQADYLEQDLAMTKDGRLVVIHDHF
LDGLTDVAKKFPHRHRKDGRYYVIDFTLKEIQSLEMTENFETKDGKQAQVYPNRFPLWKSHFRIHTF
EDEIEFIQGLEKSTGKKVGIYPEIKAPWFHHQNGKDIAAETLKVLKKYGYDKKTDMVYLQTFDFNEL
KRIKTELLPQMGMDLKLVQLIAYTDWKETQEKDPKGYWVNYNYDWMFKPGAMAEVVKYADGVGPGWY
MLVNKEESKPDNIVYTPLVKELAQYNVEVHPYTVRKDALPEFFTDVNQMYDALLNKSGATGVFTDFP
DTGVEFLKGIK (SEQ ID NO: 8)

5a. nnAA-Containing CRM197

As mentioned above, Table 1 shows the amino acid sequence (SEQ ID NO:1) of CRMI97. CRM197 ('cross-reacting material 197'; also known as CRM197) is a non-toxic mutant of diphtheria toxin which is used in many approved glycoconjugate vaccines (e.g. see Broker et al. (2011) *Biologicals* 39:195-204). Preferred carrier proteins for use with the invention comprise an amino acid sequence which has at least 90% sequence identity to SEQ ID NO: 1. For instance, the carrier protein can comprise the amino acid sequence SEQ ID NO:1 except for the presence of one or more nnAA (which may be inserted within SEQ ID NO:1 or may be substituted for one or more amino acid residues within SEQ ID NO:1 e.g. substituted for Lys and/or Phe).

In some embodiments at least one Lys and/or at least one Phe residue in SEQ ID NO:1 is substituted by a nnAA residue. It is preferred to substitute more than one residue in SEQ ID NO:1 with a nnAA and, ideally, only one species of residue in SEQ ID NO:1 is substituted by a nnAA e.g. only Lys residues are substituted. Where more than one residue in SEQ ID NO:1 is substituted for a nnAA it is preferred that the same nnAA is used at each position e.g. pAMF at each substitution position.

Carrier proteins with from 2-9 nnAA residues within SEQ ID NO:1 are preferred, and ideally with from 4-9, 4-8, or 4-6 nnAA residues e.g. 4, 5 or 6 nnAA residues. This permits more extensive attachment of antigens to the carrier than using a single nnAA, thereby increasing the antigen:carrier ratio, while avoiding excessive disruption of the native sequence and structure, which can result in insolubility.

Studies of CRM197 have identified T-cell epitopes within residues P272-D291, V322-G384, and Q412-I458. Thus it is preferred to avoid introducing nnAA within these regions of SEQ ID NO:1. These regions include F274, F356, F361, F369, K420, K441, K446, K448, and K457, so these are the Phe and Lys residues which are less preferred for nnAA substitution in CRM197. The preferred Lys residues for substitution by a nnAA in SEQ ID NO:1 are K25, K34, K38, K40, K213, K215, K228, K245, K265, K386, K523, or K527. Other useful Lys residues for substitution by a nnAA are K1, K38, K83, K104, K105, K126, K158, K173, K222, K237, K243, K475, and K499. The preferred Phe residues for substitution by a nnAA are F13, F54, F124, F128, F141, F168, F251, F390, F531, or F532.

Structural studies of CRM197 reveal two general 3D regions: the first region runs from the N-terminus to Asn-374; and the second region runs from Ser-375 to the C-terminus. Ideally a carrier used with the invention includes at least one nnAA in the first region and at least one nnAA in the second region e.g. at least 2 nnAA in each region, or at least 3 nnAA in each region. This permits conjugated antigens to be spatially separated when attached to the carrier. A carrier with 3 nnAA in the first region and 3 nnAA in the second region is useful.

The first region contains 27 Lys residues, and the second region contains 12 Lys residues. Thus one or more (e.g. 3) Lys residues within the N-terminal 374 amino acids and one or more (e.g. 3) Lys residues within the C-terminal 162 amino acids of SEQ ID NO:1 can be substituted with a nnAA e.g. within pAMF.

Preferred embodiments of nnAA-containing carriers based on CRM197 have the amino acid sequence of SEQ ID NO:1 in which one or more of residues K25, K34, K38, K40, K213, K215, K228, K245, K265, K386, K523, and/or K527 is/are replaced by a nnAA. One such sequence is SEQ ID NO:9, in which each X represents a nnAA (preferably the same nnAA, such as pAMF):

(SEQ ID NO: 9)
MGADDVVDSSKSFVMENFSSYHGTKPGYVDSIQXGIQKPKSGTQGNYDDD

WKEFYSTDNKYDAAGYSVDNENPLSGKAGGVVKVTYPGLTKVLALKVDNA

ETIKKELGLSLTEPLMEQVGTEEFIKRFGDGASRVVLSLPFAEGSSSVEY

INNWEQAKALSVELEINFETRGKRGQDAMYEYMAQACAGNRVRRSVGSSL

SCINLDWDVIRDXTKTKIESLKEHGPIKNKMSESPNKTVSEEKAXQYLEE

FHQTALEHPELSELXTVTGTNPVFAGANYAAWAVNVAQVIDSETADNLEK

TTAALSILPGIGSVMGIADGAVHHNTEEIVAQSIALSSLMVAQAIPLVGE

-continued
LVDIGFAAYNFVESIINLFQVVHNSYNRPAYSPGH<u>X</u>TQPFLHDGYAVSWN

TVEDSIIRTGFQGESGHDIKITAENTPLPIAGVLLPTIPGKLDVNKSKTH

ISVNGRKIRMRCRAIDGDVTFCRPKSPVYVGNGVHANLHVAFHRSSSEKI

HSNEISSDSIGVLGYQKTVDHTKVNS<u>X</u>LSLFFEIKS

This carrier protein has been found to be very well-expressed in a cell-free protein synthesis system, while retaining good solubility and providing good immunogenic responses when conjugated to pneumococcal capsular polysaccharides.

The invention also provides a composition includes multiple different conjugates (e.g. different pneumococcal serotypes) in which each conjugate includes a carrier protein having amino acid sequence SEQ ID NO:9 (ideally in which each X residue is the same nnAA, preferably pAMF).

SEQ ID NO:1 has a N-terminus methionine (which will typically be formylated) that is not present in wild-type CRM197 but is included for initiating translation without requiring the whole native leader sequence. In some embodiments the carrier protein used herein lacks a N-terminus methionine e.g. the N-terminus methionine of SEQ ID NO:1 or SEQ ID NO:9 may be absent. In some embodiments a carrier protein based on CRM197 includes no natural amino acids (and more preferably no amino acids) upstream of the N-terminus of SEQ ID NO: 1 or downstream of the C-terminus of SEQ ID NO: 1.

These nnAA-containing CRM197 carrier proteins are particularly useful for conjugating to pneumococcal capsular polysaccharides. These conjugates can be combined to form multivalent compositions as discussed elsewhere herein.

The invention also provides a protein for preparing an immunogenic polysaccharide-protein conjugate, wherein the protein has an amino acid sequence which has at least 80% sequence identity to SEQ ID NO:1 (e.g. at least 85%, at least 90%, or at least 95%) and includes at least one nnAA, wherein the protein has a N-terminus methionine. The invention also provides an immunogenic polysaccharide-protein conjugate prepared by conjugating a polysaccharide to at least one nnAA in the protein.

The invention also provides a protein for preparing an immunogenic polysaccharide-protein conjugate, wherein the protein comprises the amino acid sequence SEQ ID NO:1 except that at least one (e.g. 2-9) lysine residues is a nnAA. The nnAA is ideally an azido-containing nnAA (such as pAMF, which is preferred), a 1,2,4,5-tetrazinyl-containing nnAA, or an alkenyl-containing nnAA. The invention also provides a conjugate comprising such a protein conjugated to a polysaccharide antigen via at least one of its nnAA.

The invention also provides an immunogenic polysaccharide-protein conjugate, wherein the protein is CRM197 having a N-terminus methionine.

The nnAA-containing CRM197 carriers are typically present in monomeric form when used for preparing conjugates, rather than being associated with other CRM197 subunits to form CRM197 multimers.

6. Carrier Protein Production Methods

General Methods for Polypeptide Production:

The enhanced carrier protein is produced by any method described for production of polypeptides. Methods suitable for production of polypeptides include, but are not limited to, solid phase chemical peptide synthesis, cell-based recombinant protein expression (in *E. coli* or a native host), and cell-free protein expression, and any combination thereof (e.g. expressed protein ligation using a combination of synthetic and recombinant peptide components).

In one embodiment of the enhanced carrier protein production method, the nnAA-bearing enhanced carrier protein is produced by a method that comprises "codon reassignment". In one variation of this embodiment, nnAAs that are close structural analogs of the 20 canonical amino acids (e.g. homoallylglycine, fluorinated leucine, azidohomoalanine) are used. The nnAA is loaded onto its corresponding tRNA using wild-type aminoacyl-tRNA synthetases, and the nnAA completely replaces one of the 20 canonical amino acids specified in a template DNA sequence. To prevent interference from the native amino acid, this generally requires use of a bacterial expression strain that is auxotrophic for the native amino acid being replaced. This strategy is amino acid rather than residue-specific, since all AA residues of a certain type are replaced with the nnAA.

In another embodiment of the enhanced carrier protein production method, the nnAA-bearing enhanced carrier protein is produced by a strategy that comprises "nonsense suppression". In this approach the non-natural amino acid is specified in a template DNA sequence by a rare or "nonsense" codon that does not ordinarily specify an amino acid in nature. One variation of the nonsense suppression approach has been pioneered by Schultz (Noren et al. *Science.* 1989(244): 182-188.) and Chamberlin (Bain et al. *J Am Chem Soc.* 1989(111):8013-8014.), and involves the use of the rare stop codon TAG (the "amber" codon; UAG in the RNA code) along with its tRNA and its corresponding aminoacyl-tRNA synthetase (aaRS) to incorporate nnAAs into a polypeptide in a site-specific manner.

In one embodiment, the "nonsense suppression" approach involves isolating a tRNA/aaRS pair, modifying the tRNA at the anti-codon loop to recognize an orthogonal codon (e.g. the amber codon TAG, the opal codon TGA, or another codon or base sequence not commonly used to specify amino acids in translation), and modifying the aaRS to prefer the nnAA over the aminoacyl-tRNAs native amino acid. In some variations of this embodiment, the tRNA/aminoacyl-tRNA synthetase pair is from the same organism as the translation machinery used for polypeptide synthesis. In other embodiments, the tRNA/aminoacyl-tRNA synthetase pair is from a different species as the translation machinery used for polypeptide synthesis. Methods to modify the tRNA anticodon loop and aaRS active site have been described, as are examples of engineered orthogonal tRNA/aaRS pairs.

In another embodiment of the "nonsense suppression" approach, production of the enhanced carrier protein does not involve the use of an engineered aminoacyl-tRNA synthetase. In this embodiment an orthogonal tRNA alone is isolated and modified at the anti-codon loop to recognize an orthogonal codon (e.g. the amber codon TAG, or another codon or base sequence not commonly used to specify amino acids in translation). The orthogonal engineered tRNA is then acylated in vitro by a suitable chemical method (e.g., the method of Heckler et al. Biochemistry. 1984 Mar. 27; 23(7):1468-73. which involves the use of T4 RNA ligase and mutant tRNAPhe), and supplemented in a cell-free protein synthesis extract. Because this embodiment uses chemically acylated tRNAs, it is only compatible with protein synthesis methods that are cell-free.

Cell-Free Protein Synthesis:

A particularly useful technique for producing nnAA-containing carrier proteins use cell-free protein synthesis. Several cell-free protein expression techniques are known in the art and various nnAA can be incorporated in this way (e.g. see Table 1 of Quast et al. (2015) *FEBS Letters* 589:1703-12) while avoiding potential cytotoxic effects of nnAA. In some embodiments, the enhanced carrier protein is produced by cell-free extract-based protein synthesis. In some embodiments, the cell-free extract comprises an extract of rabbit reticulocytes, wheat germ, or *E. coli*. In further embodiments, the cell-free extract is supplemented with amino acids, energy sources, energy regenerating systems, or cation cofactors, and any combination thereof. In some embodiments, the extract comprises exogenously supplemented mutant tRNA or mutant aaRS (aminoacyl tRNA synthetase), and any combination thereof. In some embodiments the extract comprises lysates from *E. coli* strains genetically encoding mutant tRNA or mutant aaRS, and any combination thereof. In some embodiments the *E. coli* strains used for lysates are RF-1 attenuated strains. Compatible cell-free protein synthesis systems have been described for the insertion of formulas I, II, and III into recombinant polypeptides (e.g., U.S. Pat. No. 8,715,958B2, US20160257946A1, and US 20160257945A1).

In one example U.S. Pat. No. 8,715,958B2 demonstrates a regenerating cell-free *E. coli* based system whereby the tRNA$^{Tyr}$/Tyrosine-synthetase pair from *Methanococcus jannaschii* (Wang et al. (2001) *Science* 292(5516):498-500) is used to introduce the non-natural amino acid p-azido-L-phenylalanine (pAF) into recombinant chloramphenicol acetyltransferase (CAT), GM-CSF, and TetA. Using this system, the tRNA/synthetase pair is either supplemented into the extract, or transformed into bacteria used to make the extract.

In another example, US20160257946A1 demonstrates: (a) how the *Methanococcus jannaschii* Tyrosine-synthetase above is adapted using mutagenesis so that it preferentially loads p-azidomethyl-L-phenylalanine (pAMF) onto an amber-recognizing tRNA, and (b) how a cell-free synthesis system comprising the modified synthetase/tRNA pair is used to selectively incorporate pAMF into antibodies such as trastuzumab.

In a further example, US20160257945A1 demonstrates: (a) how the *Methanococcus jannaschii* Tyrosine-synthetase above is adapted using mutagenesis so that it preferentially loads (S)-2-amino-3-(5-((6-methyl-1,2,4,5-tetrazin-3-ylamino)methyl)pyridin-2-yl)propanoic acid (a pyridyl tetrazine amino acid derivative) onto an amber-recognizing tRNA, and (b) how a cell-free synthesis system comprising the modified synthetase/tRNA pair is used to selectively incorporate (S)-2-amino-3-(5-((6-methyl-1,2,4,5-tetrazin-3-ylamino)methyl)pyridin-2-yl)propanoic acid into recombinant GFP.

In a further embodiment, the disclosure provides for methods of producing polypeptides in a cell-free extract containing 2 or more non-natural amino acids. In this embodiment the polypeptides also have biological activity comparable to the native protein. In other embodiments the polypeptides have improved or enhanced biological activity comparable to the native protein.

One optionally determines the specific activity of a protein in a composition by determining the level of activity in a functional assay, quantitating the amount of protein present in a non-functional assay (e.g. immunostaining, ELISA, quantitation on coomassie or silver stained gel, etc.) and determining the ratio of biologically active protein or non-aggregated protein to total protein. Generally, the specific activity as thus defined will be at least about 5% that of the native protein, usually at least about 10% that of the native protein, and optionally is about 20%, about 40%, about 60% or greater.

In some embodiments, the methods of producing the nnAA-containing polypeptides involve altering the concentrations of nnAA-specific tRNA, nnAA-specific synthetase, nnAA itself, or translation temperature, and any combination thereof. Such conditions optionally allow for fewer translational errors, improved rate of incorporation of the nnAA, improved activity of chaperones necessary for protein folding with incorporation of the nnAA, decreased activity of cellular factors that interfere with nnAA incorporation, or any combination of the aforementioned mechanisms.

In some embodiments of the enhanced polypeptide production methods, nnAA-specific tRNA concentration is increased to a concentration above about 20 µM, leading to an increased fraction of soluble or active polypeptide. In further variations of this embodiment the tRNA concentration is increased while the nnAA concentration is kept below about 2 mM and the nnAA synthetase is maintained below about 5 µM.

In some embodiments of the enhanced polypeptide production methods, the translation mix incubation temperature is between 20 degrees and 30 degrees Celsius, about 20 degrees Celsius, or below 20 degrees Celsius. In some variations, these temperature modifications are independently combined with modifications to the nnAA-specific tRNA concentrations, nnAA concentrations, or nnAA synthetase concentrations described in the preceding paragraph.

7. Sequence Variants

The improved carrier proteins of the present disclosure comprise one or more nnAA substituted at any position within the polypeptide as long as the immunogenic function of one or more T-cell epitopes of the polypeptide is preserved. When basing the improved carrier protein on a known carrier it is usually preferred to substitute some or all of the nnAAs for existing naturally occurring amino acids in the known carrier to minimize the chance of adversely affecting the carrier's properties. It is appreciated, however, that nnAAs may be inserted internally or at a terminus as additions to the starting carrier sequence. In some embodiments the at least one nnAA in the improved carrier protein (e.g., eCRM) is not present within one or more regions of the protein that comprise a T-cell epitope. In another embodiment, no nnAA in the enhanced immunogenic polypeptide is present within one or more regions of the protein that comprise a T-cell epitope.

In some embodiments, the nnAA residue is substituted for one or more of the twenty naturally-encoded amino acids, including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some other embodiments the nnAA residue is substituted for one or more of a specific class of natural amino acid residue, such as aliphatic, aromatic, acidic, basic, hydroxylic, sulfur-containing, or amidic (containing amide group). In some cases, only one specific amino acid (e.g., lysine) is substituted for a nnAA within the polypeptide at one or more positions. In other cases, two or more different amino acids (e.g., lysine, phenylalanine, etc.) are substituted for a nnAA within the polypeptide at two or more positions. Lysine and phenylalanine are preferred for substitution by nnAA because (i) lysine has often been used for conjugation to existing carrier proteins, so the nnAA-containing carrier can maintain the same attachment sites and (ii) many useful nnAA are based on phenylalanine, so the carrier with nnAA can have minimal structural modification compared to a native sequence. Polypeptides in which only a single species of amino acid is substituted for a nnAA are preferred e.g. in which only Lys residues are substituted.

In some embodiments, the nnAA residue is substituted for at least 1, at least 2, at least 3, at least 4, at least 5, at least 6, at least 7, at least 8, at least 9, at least 10, at least 11, at least 12, at least 13, at least 14, or at least 15 natural amino acid residues of a carrier protein. In some embodiments, the nnAA residue is substituted for at least 1, at least 2, at least 3, at least 4, at least 5, at least 6, at least 7, at least 8, at least 9, at least 10, at least 11, at least 12, at least 13, at least 14, or at least 15 natural amino acid residues of a carrier protein. In some embodiments, the nnAA residue is substituted for at least 1, at least 2, at least 3, at least 4, at least 5, at least 6, at least 7, at least 8, at least 9, at least 10, at least 11, at least 12, at least 13, at least 14, or at least 15 natural amino acid residues of SEQ ID NO: 1.

In further aspects the nnAA is substituted for one or more amino acid residues within a carrier protein. The specific amino acid residue that is selected to create single- or multiple-substituted nnAA variants described herein is optionally determined by dividing the protein into subdomains and choosing for substitution a single amino acid or sets of amino acid residues that do not sterically obstruct each other (e.g. such that there is a multi-angstrom distance between the substitution sites). Division of CRM197 into two structural regions is discussed below.

In some embodiments, the nnAA is substituted for a charged amino acid residue. Thus a nnAA can be substituted for an aspartate, glutamate, lysine, arginine or histidine amino acid residue. In some embodiments, the nnAA is substituted for a negatively-charged amino acid residue e.g. for an aspartate or glutamate residue. In some embodiments, the nnAA is substituted for a positively-charged amino acid residue e.g. for a lysine, arginine or histidine residue.

In some embodiments, the nnAA is substituted for one or more lysine residues within an immunogenic polypeptide. For example, an enhanced version of SEQ ID NO: 1 is generated by substituting an nnAA for lysine in the following manner: 1) one residue from the group consisting of K25, K34, K38, and K40; 2) one residue selected from the group consisting of K213 and K215; and 3) 2 to 4 residues selected from the group consisting of K228, K245, K265, K386, K523, and K527. In yet further embodiments the one or more of a specific class of natural amino acid residue substituted is selected from the group consisting of K25, K34, K38, K40, K213, K215, K228, K265, K386, K523 and K527, and any combination thereof of SEQ ID NO: 1. In other embodiments, the nnAA substitution in SEQ ID NO:1 is selected from one or more of K25, K34, K38, K40, K213, K215, K228, K245, K265, K386, K523, and K527. In one embodiment the nnAA substitution comprises six residues consisting of K25, K215, K228, K265, K386, and K523 of SEQ ID NO:1. In some embodiments, the nnAA substitution in SEQ ID NO:1 comprises K265. In other embodiments, the nnAA substitution in SEQ ID NO:1 comprises K386. In another embodiment, the nnAA substitutions in SEQ ID NO:1 comprise K265 and K386. In a further embodiment, the nnAA is substituted for a phenylalanine. Preferred phenylalanines for substitution include F13, F54, F124, F128, F141, F168, F251, F390, F531, or F532 of SEQ ID NO: 1. Because of their proximity, it is generally preferred to not substitute at both F531 and F532.

The binding epitopes for human CD4+ cells on diphtheria toxin that are recognized by most subjects tested encompass residues 271-290, 321-340, 331-350, 351-370, 411-430, or 431-450 (see, Raju et al., *Eur J Immunol.* 1995 Dec.; 25(12):3207-14). Therefore, in some embodiments the one or more nnAA substituted is not within residues 271-290, 321-340, 331-350, 351-370, 411-430, and/or 431-450 of SEQ ID NO: 1. In one embodiment, the one or more nnAA substituted is not within residues 331-350 of SEQ ID NO: 1. In another embodiment, the one or more nnAA substituted is not within residues 321-340 of SEQ ID NO: 1. In yet another embodiment, the one or more nnAA substituted is not within residues 431-450 of SEQ ID NO: 1.

The binding epitopes for human CD4+ cells on tetanus toxin that are recognized by all subjects tested encompass heavy chain residues H176-195, IDKISDVS-TIVPYIGPALNI [SEQ ID NO:3], and H491-510, NNFTVSFWLRVPKVSASHLE [SEQ ID NO:4] (see, Diethelm-Okita et al., *J Infect Dis.* 1997 February; 175(2): 382-91). Thus, in some embodiments the one or more nnAA substituted is not within residues 176-195 and/or 491-510 of the heavy chain peptide component of the tetanus toxin precursor protein. In another embodiment, the one or more nnAA substituted is not within residues 176-195 of the heavy chain peptide component of the tetanus toxin precursor protein. In yet another embodiment, the one or more nnAA substituted is not within residues 491-510 of the heavy chain peptide component of the tetanus toxin precursor protein.

The binding epitopes for human CD4+ cells on *Neisseria meningitidis* outer membrane protein (OMP or PorA) that are recognized by most subjects tested encompass immunodominant T-cell epitopes, which are mostly located outside the variable regions and are conserved among different meningococcal (and gonococcal) strains, e.g., corresponding to conserved putative trans-membrane regions of OMP (Wiertz et al. *J Exp Med* 1992; 176(1): 79-88). Thus, in some embodiments the one or more nnAA substituted is not within a conserved region of OMP.

The binding epitopes for human CD4+ cells on BB, a carrier protein derived from the G protein of *Streptococcus* strain G148, that are recognized by most subjects tested encompass amino acids 25-40 (VSDYYKNLINNAKTVE [SEQ ID NO:5]), 63-78 (DGLSDFLKSQTPAEDT [SEQ ID NO:6]), and 74-89 (AEDTVKSIELAEAKVL [SEQ ID NO:7]) in the BB sequence (Goetsch et al., *Clin Diagn Lab Immunol.* 2003 Jan.; 10(1):125-32). Thus, in some embodiments the one or more nnAA substituted is not within residues 25-40, 63-78, and/or 74-89 of the BB sequence.

In some embodiments the immunogenic polypeptide comprising at least one non-natural amino acid residue further comprises at least one antigen. In some embodiments the immunogenic polypeptide comprising at least one non-natural amino acid is an enhanced carrier protein and further comprises at least one antigen. In some embodiments the immunogenic polypeptide comprising at least one non-natural amino acid is an enhanced carrier protein and further comprises at least one antigen.

8. T-Cell Epitopes

The T-cell epitopes of a carrier protein are optionally determined by any of the known methods. As an aid in designing improved carrier proteins of the present disclosure, T-cell binding epitopes in proteins are predicted using algorithms that take into account various factors, such as amphipathicity profiles of proteins, sequence motifs, quantitative matrices (QM), artificial neural networks (ANN), support vector machines (SVM), quantitative structure activity relationship (QSAR) and molecular docking simulations, etc. (see, Desai et al. *Methods Mol Biol.* 2014; 1184:333-64). For example, the T-cell binding epitopes in diphtheria toxin/CRM have been predicted using the DeLisi & Berzofsky algorithm (see, Bixler et al. WO89/06974 and PNAS 82:7848, 1985). Predicted T-cell epitopes can be experimentally confirmed. For example, the T-cell epitopes of an immunogenic polypeptide of interest can be experimentally determined by synthesizing partially overlapping peptide fragments corresponding to the complete sequence of the immunogenic polypeptide (or predicted regions) and performing proliferation assays of CD4+ cell lines (e.g., peripheral blood mononuclear cells (PBMC)) in the presence of each fragment. This general approach has been employed to map the T-cell epitopes in diphtheria toxin (Raju et al., *Eur J Immunol.* 1995 Dec.; 25(12):3207-14), tetanus toxin (Diethelm-Okita et al., *J Infect Dis.* 1997 February; 175(2):382-91), *Neisseria meningitidis* outer membrane protein (OMP) (J Exp Med. 1992 Jul. 1; 176(1): 79-88), and BB, a carrier protein derived from the G protein of *Streptococcus* strain G148 (Goetsch et al., Clin Diagn Lab Immunol. 2003 Jan.; 10(1):125-32). One can also directly screen the improved carrier proteins of the present disclosure for CD4+ cell proliferation and/or a cytokine response to establish the presence of a T-cell epitope that has not been inactivated by the presence of one or more nnAAs.

9. Methods of Conjugate Production

In one embodiment, the disclosure provides for a method for synthesis of a polypeptide comprising a nnAA in a cell-free expression mixture maintained at a temperature between about 10 degrees Celsius and about 30 degrees Celsius. In another embodiment, the temperature is above about 20 degrees Celsius. In another embodiment, the temperature is below about 20 degrees Celsius. In another embodiment, the temperature is between about 14 degrees Celsius and about 18 degrees Celsius. In another embodiment, the polypeptide is encoded by a nucleic acid comprising a suppression codon. In another embodiment, the cell-free expression mixture comprises an orthogonal tRNA/aminoacyl-tRNA synthetase pair specific for the nnAA. In another embodiment, the tRNA concentration is at least 20 µM. In another embodiment, the nnAA concentration is less than about 2 mM and the concentration of the aminoacyl-tRNA synthetase is less than about 5 µM. In another embodiment, the method comprises conjugating the polypeptide to an active moiety. In another embodiment, the active moiety is selected from the group consisting of a hapten, a bacterial antigen, a viral antigen, a tumor-derived glycan, a peptide toxin, a macrolide, a polyether, and any combination thereof. In another embodiment, the polypeptide is selected from the group consisting of a growth hormone, a clotting factor, a plasma protein, an interleukin, a T-cell receptor extracellular domain, a growth factor extracellular domain, a bacterial antigen, a viral antigen, and any combination thereof. In another embodiment, the expression mixture comprises a cellular extract of *E. coli*, wheat germ, or rabbit reticulocyte. In another embodiment, the expression mixture comprises at least 30% cellular extract. In another embodiment, the polypeptide comprises at least 2, at least 3, at least 4, at least 5, at least 6, at least 7, at least 8, or at least 9 nnAAs. In another embodiment, the nnAA is selected from the group consisting of 2-amino-3-(4-azidophenyl) propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, 2-amino-3-(4-(azidomethyl)phenyl)propanoic acid, and any combination thereof. In another embodiment, the polypeptide produced comprises both a soluble and an insoluble fraction, wherein the ratio of the soluble fraction to the insoluble fraction is at least 40% (w/w). In another embodiment, the polypeptide produced comprises both a soluble and an insoluble fraction, wherein the ratio of the soluble fraction to the insoluble fraction is at least 60% (w/w). In one embodiment, the polypeptide produced by cell-free expression comprises at least 2, at least 3, at least 4, at least 5, at least 6, at least 7, at least 8, or at least 9 nnAAs and the ratio of the soluble fraction to the insoluble fraction is at least at least 20% (w/w), at least 30% (w/w), at least 40% (w/w), at least 50% (w/w), 60% (w/w), at least 70% (w/w), at least 80% (w/w), at least 90% (w/w).

Antigens:

Described herein are immunogenic antigens that are optionally further derivatized with a chemical handle to facilitate attachment to an enhanced carrier protein. In one embodiment, the antigens are any purified natural, synthetic, or recombinantly produced macromolecule or fragment thereof. Examples include, but are not limited to lipids, polysaccharides, nucleic acids, or polypeptides, and any combination thereof (e.g. glycoproteins, glycolipoproteins, glycolipids). For instance, the glycolipid optionally is glycophosphatidylinositol. In another embodiment, the antigen is a T-independent or T-activating antigen (usually a weak T-activating antigen) selected from the group consisting of a bacterial polysaccharide, a bacterial lipopolysaccharide, a tumor-derived glycan, or a hapten.

Bacterially Derived Polysaccharides:

In some embodiments, an antigen comprising a polysaccharide comprises a bacterially-derived polysaccharide, such as a capsular polysaccharide. Such capsular polysaccharides are high molecular mass polymers of gram-positive or gram-negative bacteria that function to protect the microorganisms against immune responses, and as such represent appealing vaccine targets when the goal is production of neutralizing antibodies. Such capsular polysaccharides are generally prepared from whole cell lysates or culture supernatant of the corresponding bacterium via processes that involve diafiltration, protein removal, ethanol precipitation, nucleic acid removal, and freeze drying. Examples include, but are not limited to, the Merieux protocol (Institut Merieux (1980) Brevet Belge 80:26320) and the Yavordios protocol (Yavordios et al. EP0071515A1(1983)).

Capsular Polysaccharides of *S. pneumoniae*:

In some embodiments the capsular polysaccharide comprises a capsular polysaccharide derived from *Streptococcus pneumoniae*. *Streptococcus pneumoniae* is an encapsulated Gram-positive bacterium that can cause pneumonia, bacteremia, and meningitis. There are 90 distinct documented serotypes of *S. pneumoniae* (outlined in e.g. Kalin, M. *Thorax* 1998; 53:159-162) which bear capsular polysaccharides with serotype-specific repeating unit structures. Therefore, in some cases the antigen is a *Streptococcus pneumoniae* capsular polysaccharide selected from 1, 2, 3, 4, 5, 6A, 6B, 7F, 7A, 7B, 7C, 8, 9A, 9L, 9N, 9V, 10F, 10A, 10B, 10C, 11F, 11A, 11B, 11C, 11D, 12F, 12A, 12B, 13, 14, 15F, 15A, 15B, 15C, 16F, 16A, 17F, 17A, 18F, 18A, 18B, 18C, 19F, 19A, 19B, 19C, 20, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48 (Henrichsen *J Clin Microbiol* 1995; 33:2759-2762). However, only a subset of these serotypes are commonly responsible for bacterial infection, which include serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F. Serotypes 6C, 7C, 15A, 15C, 16F, 23A, 23B, 31, 34, 35B, 35F, 37 and 38 have also become of clinical concern, as have serotypes 20A, 20B and 24B. In another embodiment, the antigen is a *Streptococcus pneumoniae* capsular polysaccharide selected from serotypes 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F. In a another embodiment, the antigen is a *Streptococcus pneumoniae* capsular polysaccharide selected from serotypes 6C, 7C, 15A, 15C, 16F, 23A, 23B, 31, 34, 35B, 35F, 37 and 38. The embodiments described herein can also additionally comprise one or more of *Streptococcus pneumoniae* capsular polysaccharide selected from serotypes 20A, 20B and 24B.

As mentioned above, compositions of the invention can include conjugates of capsular polysaccharide from at least 14, 15, 20, 21, 24 or 25, different pneumococcal serotypes. Where a composition includes 14 or more serotypes, these preferably include the 13 serotypes 1, 3, 4, 5, 6A, 6B, 7F, 9V, 14, 18C, 19A, 19F, and 23F. In addition to these 13 serotypes a compositions preferably includes one or more of serotypes 2, 8, 9N, 10A, 11A, 12F, 15B, 17F, 20, 22F, and/or 33F. Alternatively, in addition to the above 13 serotypes, a composition preferably includes one or more serotypes 2, 6C, 8, 9N, 10A, 12F, 15A, 15B, 15C, 16F, 17F, 20, 20A, 20B, 22F, 23A, 23B, 24F, 24B, 31, 33F, 34, 35B, 35F and 38. A useful combination of 15 or more (e.g., 16 or more) serotypes includes each of serotypes 1, 3, 4, 5, 6A, 6B, 7F, 9V, 14, 18C, 19A, 19F, 22F, 23F and 33F, and may also include serotype 8. A useful combination of 20 or more (e.g. 21 or more) serotypes includes each of serotypes 1, 3, 4, 5, 6A, 6B, 7F, 8, 9V, 10A, 11A, 12F, 14, 15B, 18C, 19A, 19F, 22F, 23F and 33F. A useful combination of 24 or more serotypes includes each of serotypes 1, 2, 3, 4, 5, 6A, 6B, 7F, 8, 9V, 9N, 10A, 11A, 12F, 14, 15B, 17F, 18C, 19A, 19F, 20, 22F, 23F and 33F.

The structures of common *S. pneumoniae* serotype capsular polysaccharide repeating units are described in Jones et al. (Jones C et al. *An Acad Bras Ciênc.* 2005 June; 77(2): 293-324):

Type 1
 [→3)-D-AAT-α-Galp-(1→4)-α-D-GalpA(2/3OAc)-(1→3)-α-D-GalpA-(1→]
Type 2
 [→4)-β-D-Glcp-(1→3)-[α-D-GlcpA-(1→6)-α-D-Glcp-(1→2)]-α-L-Rhap-(1→3)-α-L-Rhap-(1→3)β-L-Rhap-(1→]
Type 3
 [→3)-β-D-GlcA-(1→4)-β-D-Glcp-(1→]
Type 4
 [→3)-β-D-ManpNAc-(1→3)-α-L-FucpNAc-(1→3)-α-D-GalpNAc-(1→4)-α-D-Galp2,3(S)Py-(1→]
Type 5
 [→4)-β-D-Glcp-(1→4)-[α-L-PnepNAc-(1→2)-β-D-GlcpA-(1→3)]-α-L-FucpNAc-(1→3)-β-D-Sugp-(1→]
Type 6B
 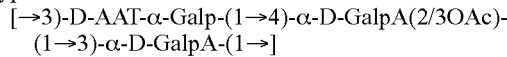
 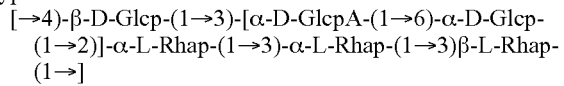

Type 9N
 [→4)-α-D-GlcpA-(1→3)-α-D-Glcp-(1→3)-β-D-ManpNAc-(1→4)-β-D-Glcp-(1→4)-α-D-GlcpNAc-(1→]
Type 9V
 [→4)-α-D-GlcpA(2/3OAc)-(1→3)-α-D-Galp-(1→3)-β-D-ManpNAc(4/6OAc)-(1→4)-β-D-Glcp-(1→4)-α-D-Glcp-(1→]
Type 12F
 [→4)-[α-D-Galp-(1→3)]α-L-FucpNAc-(1→3)-β-D-GlcNAc-(1→4)-[α-D-Glc-(1→2)-α-D-Glc-(1→3)]-3-D-ManNAcA-(→]
Type 14
 [→4)-β-D-Glcp-(1→6)-[β-D-Galp-(1→4)]-β-D-GlcpNAc-(1→3)-β-D-Galp-(→]
Type 18C
 [→4)-β-D-Glcp-(1→4)-[α-D-Glcp(6OAc) (1→2)][Gro-(1→P→3)]-β-D-Galp-(1→4)-α-D-Glcp-(1→3)-β-L-Rhap-(1→]
Type 19F
 [→4)-β-D-ManpNAc-(1→4)-α-D-Glcp-(1→2)-α-L-Rhap-(1→P→]
Type 23F
 [→4)-β-D-Glcp-(1→4)-[α-L-Rhap-(1→2)]-[Gro-(2→P→3)]-β-D-Galp-(1→4)-β-L-Rhap-(1→]

A more extensive discussion of the polysaccharides is found in Geno et al. (2015) *Clin. Microbiol. Rev.* 28:871-99, in which Table 1 shows the structures for 97 known serotypes. This table also discloses the proportion of saccharide residues which are acetylated when acetylation is not complete.

The capsular polysaccharide is optionally O-acetylated. In some embodiments, the capsular polysaccharide from serotype 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F comprises a saccharide which has a degree of O-acetylation of between 10-100%, between 20-100%, between 30-100%, between 40-100%, between 50-100%, between 60-100%, between 70-100%, between 75-100%, 80-100%, 90-100%, 50-90%, 60-90%, 70-90% or 80-90%. In other embodiments, the degree of O-acetylation is greater than 10%, greater than 20%, greater than 30%, greater than 40%, greater than 50%, greater than 60%, greater than 70%, greater than 80%, greater than 90%, or about 100%. The degree of O-acetylation of the polysaccharide is optionally determined, for example, by proton NMR (see for example Lemercinier & Jones (1996) *Carbohydrate Research* 296: 83-96; Jones et al. (2002) *J. Pharmaceutical and Biomedical Analysis* 30:1233-1247). In some embodiments, the presence of O-acetyl groups is determined by ion-HPLC analysis. Normally the polysaccharide in a conjugate will retain O-acetylation levels seen in the starting polysaccharide purified from a bacterium.

In an embodiment, the capsular polysaccharide from serotype 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F has a molecular weight of between 10 kDa and 4,000 kDa. In other such embodiments, the polysaccharide has a molecular weight of between 50 kDa and 4,000 kDa. In other such embodiments, the polysaccharide has a molecular weight of between 50 kDa and 1,400 kDa. In further such embodiments, the polysaccharide has a molecular weight of between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

The capsular polysaccharide is optionally chemically modified relative to the capsular polysaccharide found in nature. For example, the polysaccharide is optionally de-O-acetylated (partially or fully), de-N-acetylated (partially or fully), N-propionated (partially or fully), etc. De-acetylation optionally occurs before, during or after conjugation to a chemical handle or polypeptide, but typically occurs before conjugation.

Polysaccharides of *S. pyogenes*:

In some embodiments, an antigen comprising a polysaccharide comprises a polysaccharide derived from *S. pyogenes*. *S. pyogenes* is a gram-positive bacterium (also known as group A *streptococcus* or 'GAS') responsible for a wide array of infections in humans, including pharyngitis, tonsillitis, scarlet fever, cellulitis, erysipelas, rheumatic fever, post-streptococcal glomerulonephritis, necrotizing fasciitis, myonecrosis and lymphangitis. In an embodiment, the polysaccharide is the capsular polysaccharide of *S. pyogenes*. The capsular polysaccharide of *S. pyogenes* is composed of hyaluronic acid, a high molecular weight polymer where the repeating unit has the structure:

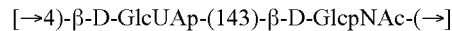

which appears to be invariant between *S. pyogenes* serotypes.

In an embodiment, the capsular polysaccharide from *S. pyogenes* has a molecular weight of between 10 kDa and 4,000 kDa. In other such embodiments, the polysaccharide has a molecular weight of between 50 kDa and 4,000 kDa. In further such embodiments, the polysaccharide has a molecular weight of between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

In another embodiment, the polysaccharide is a non-capsular polysaccharide from *S. pyogenes*. Non-capsular polysaccharides include the group-A-strep cell wall polysaccharide, which comprises a backbone of poly-L-rhamnopyranosyl units connected by alternating α-L-(1→3) and α-L-(1→2) linkages, to which N-acetyl-β-D-glucosamine residues are attached at the 3-position of the rhamnose backbone.

In an embodiment, the group-A-strep cell wall polysaccharide from *S. pyogenes* has a molecular weight of between 10 kDa and 4,000 kDa. In other such embodiments, the polysaccharide has a molecular weight of between 50 kDa and 4,000 kDa. In further such embodiments, the polysaccharide has a molecular weight of between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

Capsular Polysaccharides of *Streptococcus agalactiae*:

In some embodiments, the antigen comprising a polysaccharide comprises a capsular polysaccharide derived from *S. agalactiae*. *S. agalactiae* (also referred to as Group B *Streptococcus* or GBS) is a gram-positive bacterium commonly commensal with mammals that causes septicemia, pneumonia, and meningitis in immunologically vulnerable humans and bovine mastitis in dairy cows. There are at least 10 *S. agalactiae* serotypes with distinct capsular polysaccharide repeating units (Ia, Ib, II-IX); however, only a subset of the serotypes are commonly responsible for disease. These include serotypes Ia, Ib, II, III, and V, and conjugates of capsular polysaccharides from these serotypes can be prepared. The structures for the capsular polysaccharide repeating units of common *S. agalactiae* serotypes have been determined and are:

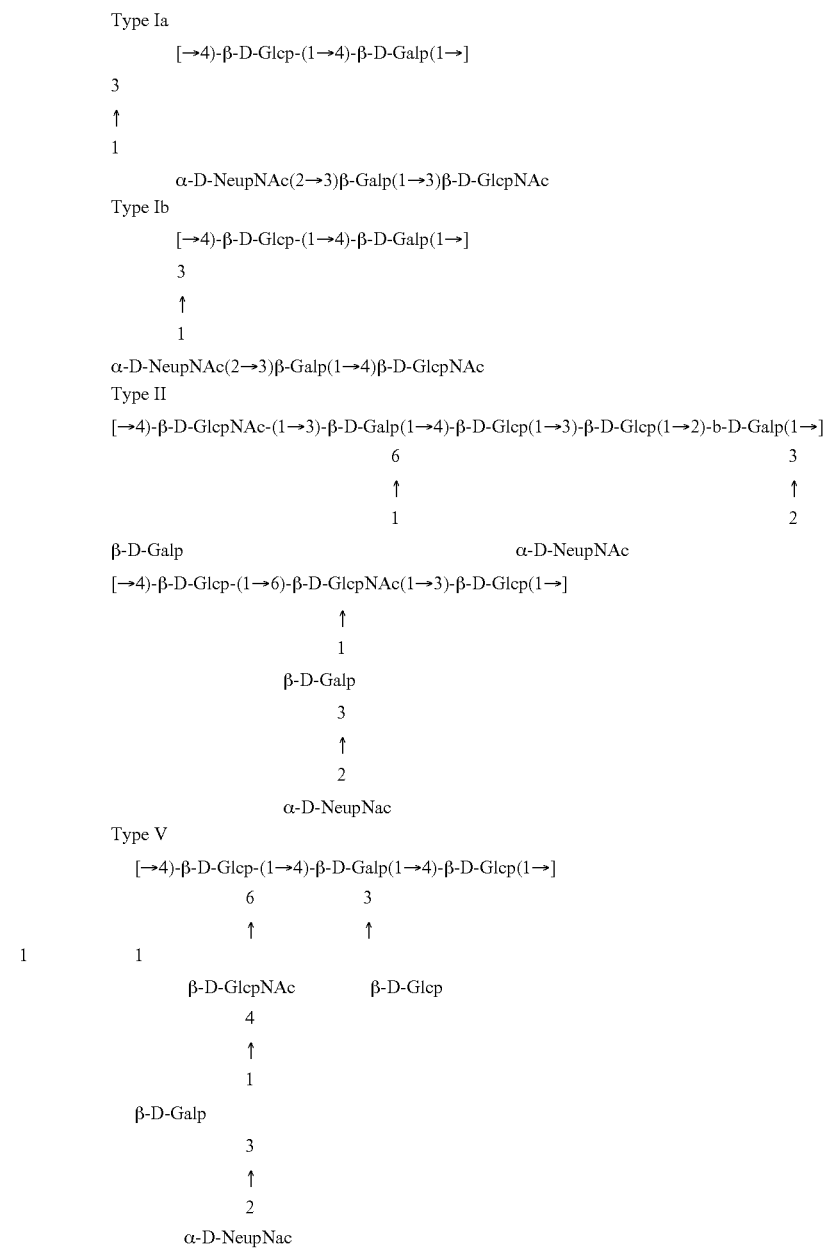

Capsular Polysaccharides of *Haemophilus influenzae*:

In some embodiments, the antigen comprising a polysaccharide comprises a capsular polysaccharide derived from *H. influenzae*. *H. influenzae* is a gram-negative, anaerobic pathogenic bacterium responsible for a wide range of localized and invasive infections including pneumonia, bacteremia, meningitis, epiglottitis, cellulitis and infectious arthritis. There are at least 6 serotypes of *H. influenzae* with distinct capsular polysaccharide chemical structures (types a-f). However, only type a and type b are considered "high-virulence" strains of *H. influenzae*, and the bulk of childhood infections are thought to be caused by type b (Jin et al. Infect. Immun. June 2007 vol. 75 no. 6 2650-2654), which is thus the preferred type of *H. influenzae* polysaccharide for use with the invention. The structure of the repeating unit of the type b capsular polysaccharide has been determined and is:

[→3)-β-D-Ribf-(1→1)-D-Ribitol-(5-OPO$_3^-$→].

Capsular Polysaccharides of *Neisseria meningitidis*:

In some embodiments, the antigen comprising a polysaccharide comprises a capsular polysaccharide derived from *N. meningitidis*. *N. meningitidis* is a gram negative bacterium that is a major causative agent of meningitis and meningococcal septic infection. There are at least 13 serogroups of *N. meningitidis* with distinct capsular polysaccharide chemical structures (serogroups A, B, C, E-29, H, I, K, L, W-135, X, Y, Z, and Z' (29E)). However, only six serogroups (A, B, C, W-135, X, Y) are thought to cause life-threatening disease. The structures of the repeating unit of the capsular polysaccharide for the five main life threat ening serogroups of interest for conjugate preparation have been determined and are:

Type A
[→6)-α-D-ManpNAc(3/4OAc)-(1→OPO3→]

Type C
[→9)-α-D-Neup5Ac(7/8OAc)-(2→]

Type W-135
[→6)-α-D-Galp-(1-4)-α-D-Neup5Ac(9OAc)-α-(2→]

Type X
[→4)-α-D-GlcpNAc-(1-OPO3→]

Type Y
[→6)-α-D-Glcp-(1-4)-α-D-Neup5Ac(9OAc)-α-(2→]

Capsular Polysaccharides of *Porphyromonas gingivalis*:

In another embodiment, the antigen is a capsular polysaccharide derived from one of the six serotypes of *Porphyromonas gingivalis* (e.g., K1, K2, K3, K4, K5 and/or K6). See Van Winkelhoff et al. (1993) *Oral Microbiol. Immunol.* 8:259-265; and Laine et al. (1996) *J. Periodontal Res.* 31: 278-84.

Capsular Polysaccharides of *Salmonella typhi*:

In another embodiment, the antigen is a Vi polysaccharide. Vi is the capsular polysaccharide of *Salmonella typhi* (previously classified as a species itself, but now referred to as the *typhi* serovar of *S. enterica*). Vi may also be found in other serovars of *Salmonella* (such as *S. enterica* serovar paratyphi C or serovar dublin) and in other bacteria, such as *Citrobacter* (e.g. *C. freundii* and *C. youngae*). The Vi polysaccharide is a linear homopolymer of a hexosaminuronic acid, α1,4-N-acetylgalactos-aminouronic acid, which is 60-90% acetylated at the C-3 position. The O-acetyl substitution on Vi is a factor in its ability to elicit a protective immune response. The immunogenicity of Vi is closely related to its degree of O-acetylation. Partial de-O-acetylation can slightly increase immunogenicity; complete de-O-acetylation eliminates the immunogenicity of Vi. The Vi polysaccharide used in the present invention may be chemically modified relative to the capsular polysaccharide as found in nature. For example, the Vi polysaccharide may be partially de-O-acetylated, de-N-acetylated (partially or fully), N-propionated (partially or fully), etc. De-acetylation may occur before, during or after conjugation, but preferably occurs before conjugation. The effect of de-acetylation etc. can be assessed by routine assays.

Saccharides of *Staphylococcus aureus*:

In another embodiment, the antigen is a polysaccharide from *S. aureus*. The polysaccharide can be the exopolysaccharide of *S. aureus*, which is a poly-N-acetylglucosamine (PNAG), or the capsular polysaccharide of *S. aureus*, which can be e.g. type 5, type 8 or type 336.

Surface Polysaccharides of *Clostridium difficile*:

In another embodiment, the antigen is a surface glycan from *C. dificile*, such as PS-I or PS-II.

Glucans:

In another embodiment, the antigen is a glucan containing β-1,3-linkages and/or β-1,6-linkages. These conjugated glucans can be useful for raising an anti-fungal immune response, for example against *Candida albicans*. Glucans are glucose-containing polysaccharides found inter alia in fungal cell walls. β-glucans include one or more β-linkages between glucose subunits. A glucan used in accordance with the invention includes β-linkages, and may contain only β-linkages (i.e. no α linkages). The glucan may comprise one or more β-1,3-linkages and/or one or more β-1,6-linkages. It may also comprise one or more β-1,2-linkages and/or β-1,4-linkages, but normally its only β linkages will be β-1,3-linkages and/or β-1,6-linkages. The glucan may be branched or linear. The glucan may be a fungal glucan. A 'fungal glucan' will generally be obtained from a fungus but, where a particular glucan structure is found in both fungi and non-fungi (e.g. in bacteria, lower plants or algae) then the non-fungal organism may be used as an alternative source. Thus the glucan may be derived from the cell wall of a *Candida*, such as *C. albicans*, or from *Coccidioides immitis*, *Trichophyton verrucosum*, *Blastomyces dermatidis*, *Cryptococcus neoformans*, *Histoplasma capsulatum*, *Saccharomyces cerevisiae*, *Paracoccidioides brasiliensis*, or *Pythiumn insidiosum*. There are various sources of fungal β-glucans. For instance, pure β-glucans are commercially available e.g. pustulan (Calbiochem) is a β-1,6-glucan purified from *Umbilicaria papullosa*. β-glucans can be purified from fungal cell walls in various ways. In some embodiments the glucan is a β-1,3 glucan with some β-1,6 branching, as seen in e.g. laminarins. Laminarins are found in brown algae and seaweeds. The β(1-3):β(1-6) ratios of laminarins vary between different sources e.g. it is as low as 3:2 in *Eisenia bicyclis* laminarin, but as high as 7:1 in *Laminaria digititata* laminarin. Thus the glucan used with the invention may have a β(1-3):β(1-6) ratio of between 1.5:1 and 7.5:1 e.g. about 2:1, 3:1, 4:1, 5:1, 6:1 or 7:1. In other embodiments, the glucan has exclusively or mainly β-1,3 linkages, as seen in curdlan. Thus the glucan may be made solely of β-1,3-linked glucose residues (e.g. linear 13-D-glucopyranoses with exclusively 1,3 linkages). Optionally, though, the glucan may include monosaccharide residues that are not β-1,3-linked glucose residues e.g. it may include β-1,6-linked glucose residues. The ratio of β-1,3-linked glucose residues to these other residues should be at least 8:1 (e.g. ≥9:1, ≥10:1, ≥11:1, ≥12:1, ≥13:1, ≥14:1, ≥15:1, ≥16:1, ≥17:1, ≥18:1, ≥19:1, ≥20:1, ≥25:1, ≥30:1, ≥35:1, ≥40:1, ≥45:1, ≥50:1, ≥75:1, ≥100:1, etc.).

Tumor-Derived Glycans:

In some embodiments, an antigen comprising a polysaccharide comprises a developmentally-inappropriate cell-surface glycan characteristic of tumor cells. Danishefsky (reviewed in Zhu et al. *Expert Rev Vaccines*. 2009(10):1399-1413) among others have discovered that certain oligosaccharide motifs (stage-specific embryonic antigens, SSEAs) are originally expressed on cell surfaces during embryogenesis and "reactivated" in adult tumors. As these are short polysaccharides, they are primarily accessed via chemical synthesis (reviewed in Zhu above). Among these oligosaccharides, the most clearly associated with carcinogenesis (e.g. prostate and breast cancer) are Globo-H, Le$^y$, STn, TF, and Tn.

Haptens:

In some embodiments, an antigen comprises a hapten: a non-polymeric synthetic moiety of molecular weight less than 1,000 Da. The application of haptens in therapeutic protein conjugates is of haptens that mimic drugs of abuse, e.g., nicotine or cocaine (see, e.g., Berkowitz & Spector. *Science*. 1972(178):1290-1292 for morphine; Kosten et al. *Vaccine*. 2002(20): 1196-1204 for cocaine; and Hatsukami et al. *Clin Pharmacol Ther*. 2005(78):456-467). The conjugation of otherwise poorly-immunogenic small molecules to immunogenic polypeptides allows for drug specific antibodies to be raised, which sequester abusive drugs away from the central nervous system.

Methods of Derivatization and Preparation for Antigens and Compositions Resulting Therefrom:

Described herein are antigens containing a chemical handle that is capable of reacting with a corresponding group introduced into a non-natural amino acid of a polypeptide as described earlier herein. In some embodiments, the chemical handle comprises a group suitable for "click"

chemistry reaction with a corresponding group on a polypeptide. Suitable chemical groups for "click" chemistry include, but are not limited to azido (—$N_3$), alkyne (C≡C), a phosphine (e.g. —P(Ph)$_2$), alkene (C=C) and 1,2,4,5-tetrazine

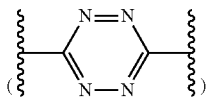

groups.

The chemical handle is introduced via a general process comprising 3 steps: (a) activating the antigen; (b) optionally reacting the antigen with a linker or nucleophilic group to introduce reactivity not normally present in the antigen; and (c) conjugating the antigen to the chemical handle. In some embodiments, two or more of steps (a)-(c) are simultaneous, as in the case where a chemical handle is modified by the addition of a reactive moiety such as N-hydroxysuccinimide. In some embodiments two or more of steps (a)-(c) are discrete, with optional purification of the antigen between steps. In some embodiments step (a) additionally comprises a step to remove a blocking group on the antigen, such that certain functional groups (e.g. hydroxyls, amines, thiols) are more accessible to activation.

The chemical handle is optionally introduced at varying locations with respect to the antigen. In some embodiments, the chemical handle is introduced at a terminus (e.g. reducing and non-reducing ends of a polysaccharide, the N- and C-termini of a polypeptide, or the end of the acyl chain of a glyceride). In some embodiments the chemical handle is introduced at an internal location (e.g. an internal amino acid of a polypeptide, or an internal hydroxyl, amine, or activated hydroxyl of a polysaccharide). In some embodiments the chemical handle is introduced at one or more termini in addition to an internal location. The particular method of activation used for the antigen will affect the locations activated for conjugation, and hence the ultimate location of the conjugated chemical handle on the antigen. It is preferred to introduce multiple chemical handles into an antigen such that it can achieve multiple linkages with carriers.

In a preferred embodiment, a method for conjugating a polypeptide to an antigen via chemical handles is as follows. An antigen is activated to incorporate at least one first chemical handle therein, where the first chemical handle is capable of conjugating to a second chemical handle of an nnAA in the polypeptide. The activated antigen is combined with a polypeptide containing at least one nnAA bearing the second handle under conditions in which the first and second chemical handles react to form an antigen-polypeptide conjugate. The reaction thus enabled is a non-catalytic covalent bioconjugation reaction. The reactive sites on the antigen that serve as the "first chemical handle" are preferably alkynyl groups, where the alkynyl groups may be incorporated in a molecular context that increases reactivity. For instance, the alkynyl groups may be incorporated into a ring, e.g., a cyclooctynyl ring, such as a diaryl-strained cyclooctyne. Preferred reactive sites in the polypeptide, i.e., the "second chemical handle" provided by the nnAA residues, are azido groups. As known in the art, the reaction in this case is a [3+2]cycloaddition referred to in the art as "strain-promoted azide-alkyne cycloaddition" (SPAAC), discussed in further detail infra.

Activation of Antigens:

The antigen is optionally activated using any chemical method described for production of bioconjugates. Such methods include, but are not limited to, periodate oxidation, unmasking of an intrinsic aldehyde (e.g. a reducing terminus of a polysaccharide), 1-cyano-4-dimethylaminopyridinium tetrafluoroborate (CDAP) activation, or hydroxyl activation with 1,1'-carbonyldiimidazole (CDI) followed by nucleophilic addition. Further chemical strategies for saccharide derivatization are described in Hermanson (Hermanson, Greg. *Bioconjugate Techniques* (2008)). Activation can use cyanylating reagents (such as p-nitrophenylcyanate, CDAP, or N-cyanotriethylammonium tetrafluoroborate), active esters, carbodiimides, hydrazides, norborane, p-nitrobenzoic acid, N-hydroxysuccinimide, S-NHS, EDC, TSTU, etc.

The invention provides an antigen (in particular a polysaccharide antigen as disclosed herein, such as a pneumococcal capsular polysaccharide antigen) which is activated according to any of the chemistry discussed below e.g. the product of reacting the antigen with one or more the DBCO and DIFO groups discussed below.

Periodate Activation:

In some embodiments, the antigen is activated by periodate oxidation. In some embodiments, periodate oxidation is used to introduce aldehyde groups into an antigen, and is useful for the addition of aldehydes to: 1) polysaccharides; and 2) N-terminal residues of polypeptides to produce an activated antigen. Periodate cleaves carbon-carbon bonds that possess a primary or secondary hydroxyl or amine on either end, and so activates carbohydrate sugar residues bearing adjacent hydroxyls, or amino acids containing the 2-amino alcohol moiety (N-terminal threonine or serine residues). As the aldehyde moiety has a long half-life, antigens activated by this method are optionally chromatographically purified and/or lyophilized after activation.

For periodate oxidation of antigens: (a) antigens are dissolved in a solution; (b) a source of periodate is added to the antigen from a concentrated stock solution to form an oxidation mixture; (c) the reaction mixture is incubated; and (d) (optional) excess periodate is removed.

Deionized water or a suitable buffered solution is optionally used for the oxidation reaction. In some embodiments, the solution in step (a) is deionized water. In some embodiments, the solution in step (a) comprises an effective amount of a buffer with a pKa around physiological pH. In some embodiments, the solution in step (a) comprises an effective amount of a buffer with a pKa around physiological pH, wherein the buffer does not comprise an amine group. Examples of amine-free buffers include, but are not limited to acetate, formate, and phosphate.

The periodate source in step (b) is optionally selected from any periodate source with appropriate stability in aqueous solution. Examples of periodate sources include, but are not limited to, sodium periodate, potassium periodate, tetrabutylammonium (meta)periodate, barium periodate, sodium hydrogen periodate, sodium (para)periodate, and tetraethylammonium (meta)periodate.

In some embodiments, the level of periodate addition and reaction conditions are adjusted to convert all available diols on a polysaccharide to aldehydes. For example, large excesses of sodium periodate (>1000× excess with respect to the molar concentration of polysaccharide, or a 10 mM solution of sodium periodate) in combination with incubation at room temperature favor total conversion of diols to aldehydes.

In some embodiments, the level of periodate addition and reaction conditions are adjusted to introduce a low amount of oxidation/aldehyde formation into the polysaccharide chain. Less than stoichiometric amounts of sodium periodate (e.g. <1.0 equivalents) in the oxidation reaction favor low amounts of polysaccharide chain oxidation. For example, a bacterial saccharide is activated by 0.001-0.7, 0.005-0.5, 0.01-0.5, 0.1-1.2, 0.1-0.5, 0.1-0.2, 0.5-0.8, 0.1-0.8, 0.3-1.0 or 0.4-0.9 molar equivalents of periodate (see WO2011/110531). In another embodiment, 0.4 molar equivalent of periodate is added to a pH 6.0 solution containing a pneumococcal capsular polysaccharide and incubated for 17 hrs at 25° C. (see WO2011/110531).

In one embodiment, less than 0.001%, 0.01%, 0.1%, 0.5%, 1%, 2%, 5%, 10%, 30% or 50% of the vicinal diols of a bacterial saccharide become oxidized during periodate activation (see WO2011/110531) e.g. between 5-10%. Low reaction temperatures also favor lower amounts of polysaccharide chain oxidation. In some embodiments low periodate concentrations (<0.1 eq) are combined with reactions overnight at 4° C. to minimize polysaccharide chain oxidation of particular capsular polysaccharides, such as S. pneumoniae 19F.

In some embodiments, the level of periodate addition and reaction conditions are adjusted to direct cleavage to selective sugars a polysaccharide chain. For example, 1 mM $NaIO_4$ at 4 degrees Celsius is used in the literature to selectively oxidize sialic acid residues at carbons 7, 8, or 9, while 10 mM $NaIO_4$ at room temperature is used to oxidize a wide variety of sugar residues, including sialic acid, galactose, and mannose residues.

For oxidation of N-terminal serine or methionine residues in protein antigens, milder oxidation conditions (low periodate concentrations and reaction times) are generally used, to avoid oxidative damage to internal side chains of the antigens. In an embodiment, step (b) comprises adding sodium periodate to a final concentration of 2.5 mM and step (c) comprises incubating the reaction mixture at 25 degrees Celsius for 3 minutes.

Because excess unreacted periodate can cause higher than desirable oxidation levels or damage to immunogenic moieties in the antigen, excess periodate is optionally removed in step (d). For large antigens (>10 kDa), excess periodate, in some embodiments, is removed by size exclusion, dialysis, or diafiltration against water or buffer solution using a medium with a suitable molecular weight cutoff or exclusion limit. For small antigens where size-based purification is inconvenient (short peptides or oligosaccharides), and removal of periodate in step (d) comprises adding a quenching agent. Excess periodate is optionally quenched by the addition of glycerol (10% (v/v)), the addition of a molar excess of sodium sulfite, or the addition of a molar excess of N-acetylmethionine.

In some embodiments, a polysaccharide or protein antigen is deprotected to increase accessibility of hydroxyl or amine groups for periodate activation. In one embodiment, O-acetyl or N-acetyl groups on polysaccharides are removed to increase reactivity of adjacent hydroxyls to periodate. For polysaccharide antigens, de-O-acetylation or de-N-acetylation is optionally accomplished by incubation in a mild acid (e.g. low concentration HCl) or alkaline (e.g. sodium bicarbonate) solution, followed by optional heating and adjustment back to physiological pH. In some embodiments, mild acid treatment (<0.1 M HCl or <0.2M AcOH), followed by heating and neutralization is used to partially hydrolyze ("size") polysaccharides of high molecular weight. In some embodiments, mild acid treatment (e.g. <0.1M HCl or <0.2M AcOH), followed by heating (45-95° C.) and neutralization (to pH 5.5-6.0) is used to simultaneously partially hydrolyze ("size") polysaccharides of high molecular weight and deprotect the polysaccharide. In some embodiments, serotypes 3, 4, 18C, and 11A are treated by such an acid/heating/neutralization process to deprotect the polysaccharide, size the polysaccharide, or both. In one embodiment, S. pneumoniae serotype 3 polysaccharide is treated with 0.18M acetic acid, followed by heating at 85° C. for 1 hour. In one embodiment, S. pneumoniae serotype 4 polysaccharide is treated with 0.01M HCl followed by heating at 45° C. for 1 hour. In one embodiment, S. pneumoniae 18C polysaccharide is treated with 0.18M acetic acid, followed by heating at 95° C. for 40 minutes. In one embodiment, S. pneumoniae serotype 11A polysaccharide is treated by 0.18M acetic acid, followed by heating at 80° C. for 1 hour.

In another embodiment, N-formyl groups on purified proteins are removed/amine groups are de-formylated by treatment with a formyl-L-methionyl peptide amidohydrolase in deionized water or a physiological pH buffered solution. In yet another embodiment, N-formyl groups on purified proteins are removed by treatment of lyophilized protein with anhydrous hydrazine vapor at −5° C. (Miyataki et al. Eur. J. Biochem. 212, 785-789 (1993)).

CDAP Activation

In some embodiments, the antigen is activated by forming a transient adduct with cyano-4-dimethylamino pyridinium tetrafluoroborate (CDAP) (see, e.g., WO2011/110531 and US20120321658). In some embodiments, hydroxyl groups on a protein or polysaccharide antigen are activated by reaction with CDAP to form a transient cyanato (—OCN) adduct, which is then be reacted with a suitable nucleophile on a chemical handle or linker to form a carbamimidate linkage. In this embodiment, C—C bonds on the antigen are not cleaved (in contrast with periodate activation). In some embodiments, particular capsular polysaccharides are preferentially activated using CDAP. In particular embodiments, S. pneumoniae serotype 3, 7F, or 10A capsular polysaccharides are activated using CDAP.

For CDAP activation of antigens: (a) the antigen is dissolved in a suitable solvent; (b) CDAP is added to the antigen from a stock solution; (c) a buffering agent is added.

CDAP activation is optionally performed in any suitable solvent. In some embodiments, the solvent in (a) comprises distilled water. In further embodiments, the solvent in (a) additionally comprises an organic solvent such as DMSO or acetonitrile. In particular embodiments, S. pneumoniae serotype 3, 7F, or 10A capsular polysaccharides are activated in water.

In some embodiments, supra- or sub-stoichiometric (with respect to polysaccharide) amounts of CDAP are used for activation. In some embodiments, about 0.1 to about 3 eq of CDAP is used for activation of a polysaccharide. In some embodiments, about 0.2-0.8 eq of CDAP is used for activation of a polysaccharide. In one embodiment, S. pneumoniae serotype 3 capsular polysaccharide is activated using 2.0 eq CDAP. In one embodiment, S. pneumoniae serotype 10A capsular polysaccharide is activated using 0.8 eq CDAP.

In some embodiments, the addition of a buffering agent in (c) is used to dramatically increase the efficiency of CDAP activation (Lees et al. Vaccine. 1996 (14):190-198). In some embodiments, the buffering agent in (c) is triethanolamine (TEA). In some embodiments, about 1 to about 4 eq of TEA (relative to the polysaccharide) is used as a buffering agent. In one embodiment, about 1 to about 4 eq TEA is used as a buffering agent for a CDAP activation reaction involving S. pneumoniae serotype 7F polysaccharide. In some embodiments, 2.5 eq of TEA is used as a buffering agent. In one embodiment, 2.5 eq TEA is used as a buffering agent for a CDAP activation reaction involving *S. pneumoniae* serotype 7F polysaccharide. In some embodiments the buffering agent is sodium borate, sodium carbonate, or sodium hydroxide, and any combination thereof. In some embodiments, the buffering agent has a pKa of between about 8.0 to about 11.0 or the buffering agent is used to adjust the pH of the reaction solution to between about 8.0 to about 11.0. In some embodiments, the buffering agent has a pKa of between about 9.0 to about 9.5 or the buffering agent is used to adjust the pH of the reaction solution to between about 9.0 to about 9.5. In one embodiment, sodium hydroxide adjustment of pH to 9.5 is used for a CDAP activation reaction involving *S. pneumoniae* serotype 3 polysaccharide. In one embodiment, sodium hydroxide adjustment of pH to 9.5 is used for a CDAP activation reaction involving *S. pneumoniae* serotype 10A polysaccharide.

Carbonyldiimidazole (CDI)/Carbonylditriazole (CDT) Activation:

In some embodiments the antigen is activated with carbonyldiimidazole (CDI) or carbonylditriazole (CDT). CDI and CDT, like CDAP, are capable of activating hydroxyl groups on an antigen to form a transient reactive moiety; in this case it is an unstable carbamate

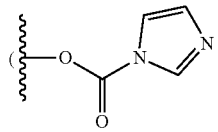 [SMILES: *OC(=O)n1ccnc1]

for CDI and

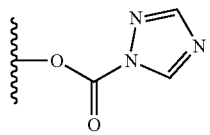

for CDT), which is then optionally reacted with an amine or thiol on a chemical handle or linker to form a carbamate or carbonothioate linkage. The activation should be performed in a dry organic solvent. In some embodiments, CDI/CDT activation is performed in anhydrous dimethylsulfoxide (DMSO). In some embodiments, CDI/CDT activation is performed by adding a molar excess of CDI/CDT with respect to the antigen. In other embodiments, CDI/CDT activation is performed by adding a molar amount of CDI/CDT approximately equal to the molar amount of the antigen.

No Chemical Activation:

In some embodiments, endogenous amines or other nucleophilic moieties (e.g. a primary amine) either naturally present or the result of a deprotection step (e.g. as discussed above) are used to conjugate a given polysaccharide to a chemical handle or carrier protein. Such nucleophilic moieties can be conveniently reacted with a variety of common electrophilic conjugation reagents like succinate derivatives (e.g. N-hydroxysuccinimide (NHS) or sulfo-NHS esters). In such embodiments, it is sometimes advantageous to treat with a periodate protocol as in (i) to promote degradation of antigenic contaminants like *S. pneumoniae* C-polysaccharide. In this embodiment, periodate treatment is followed by a vast excess of sodium borohydride to quench any chemically introduced aldehyde groups. In one embodiment, *S. pneumoniae* serotype 1 polysaccharide is treated with between about 0.05 to about 0.25 eq of sodium periodate at room temperature for between about 12 to about 14 hours, followed by treatment with between about 5 eq to about 15 eq of sodium borohydride. In one embodiment, *S. pneumoniae* serotype 1 polysaccharide is treated with 0.15 eq of sodium periodate at room temperature for 18 hours, followed by treatment with 10 eq of sodium borohydride.

Conjugation to Chemical Handle:

In some embodiments, the antigen is conjugated to the chemical handle using any chemical method compatible with the activation methods described above ("Activation of antigens"). Such methods include, but are not limited to, Schiff-base formation with synthetic antigen aldehydes followed by reductive amination, hydrazone formation, oxime formation, direct nucleophilic addition, and Schiff-base formation with native antigen aldehydes followed by reductive amination. In some embodiments, the absolute polysaccharide concentration in a conjugation reaction with a chemical handle is important to minimize aggregation or cross-reactivity of the polysaccharide. In some embodiments, the absolute polysaccharide/antigen concentration in a conjugation reaction with DBCO (a dibenzocyclo-octyne) or a DBCO derivative is important for polysaccharides activated with periodate or CDAP. In some embodiments, the polysaccharide concentration in a DBCO/DBCO-derivative conjugation reaction is less than 2, less than 5, less than 7, less than 10, less than 15, less than 17.5, or less than 20 μmol/mL. In some embodiments, the polysaccharide concentration in a DBCO/DBCO-derivative conjugation reaction is about 1.5 to about 17.5 μmol/mL.

Reactions with Periodate-Activated Antigens:

In some embodiments the chemical handle is conjugated to an polypeptide or polysaccharide antigen activated as above ("Activation of antigens") with periodate. In these embodiments a chemical handle comprising a functional group that forms a stable or semi-stable adduct with aldehydes is combined with the periodate activated antigen, followed by optional reduction to convert semi-stable adducts to stable adducts (see, e.g., WO2014/111344; Wu et al. *Vaccine* 31(2013): 5623-2626; Hermanson, G. T., *Bioconjugate Techniques*, Second Edition, 2008). In some variations of these embodiments, the chemical handle is added at a large molar excess with respect to the aldehyde groups on the activated antigen, such that all the aldehydes are consumed in the chemical handle/antigen conjugation reaction. In other variations of these embodiments, the chemical handle is added at a lower molar ratio with respect to the aldehydes groups on the activated antigen, and excess unreacted aldehydes on the activated antigen are consumed by further reaction with an excess of an inexpensive aldehyde-reactive nucleophile (e.g. ethanolamine), or by treatment with a reducing agent strong enough to reduce aldehydes to hydroxyl groups (e.g. NaBH$_4$).

In one embodiment, the chemical handle is conjugated to the antigen by Schiff-base formation with synthetic antigen aldehydes followed by reductive amination. This embodiment results in an end-product that has secondary amine linkage between the chemical handle and the antigen: a direct N—C bond between the amine of the chemical handle and a carbon atom on antigen. In this embodiment the chemical handle comprises an amine. In this embodiment the conjugation method comprises: combining the amine-containing handle with periodate-activated antigen in DI water or buffered solution containing DMSO; incubating to form a Schiff base; reducing the Schiff base to a secondary amine using sodium cyanoborohydride (NaBH$_3$CN); and optionally quenching unreacted aldehydes with NaBH$_4$. In some embodiments of this method the chemical handle and antigen are combined at or near 1:1 stoichiometry. In some embodiments of this method the chemical handle and antigen are combined with a molar excess of chemical handle. In some embodiments of this method, the chemical handle and antigen are combined with a molar excess of antigen. In some embodiments sodium cyanoborohydride is substituted for another reducing agent with similar selectivity for reducing C=N bonds such as sodium triacetoxyborohydride.

In one embodiment the chemical handle is conjugated to the antigen via hydrazone formation. In this embodiment the chemical handle comprises a hydrazide (—C(=O)—NH—NH$_2$) group. This embodiment results in an end product that has a hydrazone (—C(=O)—NH—N=C—) or N'-alkyl hydrazide (—C(=O)—NH—NH—C—) linkage between the chemical handle and the antigen carbon. In this embodiment, the conjugation method comprises: combining a molar excess of the hydrazide-containing chemical handle with the antigen in a solution pH 6.0-8.5 and incubating to form a hydrazone (—C(=O)—NH—N=C—). In some further embodiments of this method, sodium cyanoborohydride or sodium triacetoxyborohydride is included in the reaction mixture to reduce the N=C bond, which produces an N'-alkyl hydrazide (—C(=O)—NH—NH—C—).

In one embodiment, the chemical handle is conjugated to the antigen by oxime formation. In this embodiment the chemical handle comprises an aminooxy (—O—NH$_2$) group. This embodiment results in an end product that has an oxime (—O—N=C—) linkage between the chemical handle and an antigen carbon. In this embodiment, the conjugation method comprises: combining a molar excess of the aminooxy-containing chemical handle with the antigen in a solution pH 6.0-8.5 and incubating to form an oxime linkage (—O—N=C—). In some further embodiments of this method, sodium cyanoborohydride or sodium triacetoxyborohydride is included in the reaction mixture to reduce the N=C bond and improve stability; this produces an N'-alkyl hydroxylamine linkage (—O—N=C—).

Reactions with CDAP-Activated Antigens:

In some embodiments the chemical handle is conjugated to a polypeptide or polysaccharide antigen activated as described above ("CDAP activation") with CDAP. In these embodiments, a transient cyanato (—OCN) group produced via CDAP activation is further reacted with an amine-containing chemical handle to produce a carbamimidate linkage (—NH—C(=NH)—O—) between the chemical handle and an antigen carbon.

For CDAP conjugation of chemical handles, hydroxyl groups on the antigen are activated as described above ("CDAP activation"), and a chemical handle comprising an amine is additionally added to the activation mixture. Because the cyanato group is labile, the chemical handle is generally added shortly (within minutes) after activation of the antigen. In some embodiments, the antigen is added 2.5 minutes after CDAP is introduced. In some embodiments, a large molar excess of the amine-containing chemical handle with respect to activated hydroxyl groups on the antigen is added. In other embodiments, the chemical handle is added at a concentration closer to 1:1 molar ratio with respect to the activated hydroxyl groups on the antigen, and excess unreacted cyanato groups are exhausted by addition of an excess of an inexpensive amine (e.g. ethanolamine or hexanediamine).

Reactions with CDI/CDT-Activated Antigens:

In some embodiments the chemical handle is conjugated to a polypeptide or polysaccharide antigen activated as described above ("Carbonyldiimidazole (CDI)/carbonyldiitriazole (CDT) activation") with CDI/CDT. In these embodiments, an unstable carbamate produced by CDI/CDT activation of antigen hydroxyl groups

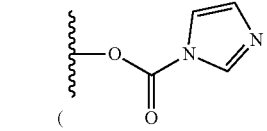 [SMILES: *OC(=O)n1ccnc1]

for CDI and

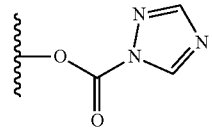 [SMILES: *OC(=O)n1cncn1]

for CDT) is further reacted with a primary amine to produce a stable carbamate (—NH—C(=O)—O—) linkage or primary thiol to produce a stable carbonothioate (—S—C(=O)—O—) linkage between the chemical handle and an antigen carbon. In some embodiments, a large molar excess of the amine/thiol-containing chemical handle with respect to activated hydroxyl groups on the antigen is added. In other embodiments, the chemical handle is added at a concentration closer to 1:1 molar ratio with respect to the activated hydroxyl groups on the antigen. In yet further embodiments, residual CDI/CDT in the reaction is further inactivated by treatment with sodium tetraborate.

Reactions with Non-Activated Antigens:

In some embodiments the chemical handle is conjugated to an endogenous amine or other nucleophilic moiety (e.g. a primary amine) either naturally present or the result of a deprotection step from a polypeptide or polysaccharide antigen as described above. In one embodiment of this, an electrophilic group (e.g. an NHS or sulfo-NHS ester) on a chemical handle is reacted with a primary amine group on the antigen to produce an amide linkage (—C(=O)—NH—) between the chemical handle and the antigen amine. In another embodiment, a carboxylic acid group on a chemical handle is reacted with a primary amine group on the antigen in the presence of standard peptide coupling reagents and conditions to produce an amide linkage between the chemical handle and the antigen amine.

Alkyne-Containing Handles

In some embodiments the chemical handle comprises a moiety that allows for a "click" chemistry reaction with a corresponding group on nnAA residue of a polypeptide. One such moiety is an alkyne group, which is capable of reacting with a nnAA residue comprising an azido group. In the simplest embodiment, this is a propargyl group, such that an alkyne group on an antigen comprises a structure of formula IV:

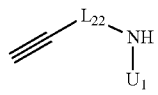

wherein:
  $L_{22}$ is $C_1$-$C_{10}$ alkyl; and
  $U_1$ is at least one moiety of an antigen.
In other embodiments an alkyne group on an antigen comprises a structure of formula IVa:

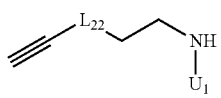

wherein:
  $L_{22}$ is —$(CH_2CH_2O)_{1\text{-}10}$—; and
  $U_1$ is at least one moiety of an antigen.

In some embodiments the alkyne group further comprises additional features that accelerate or facilitate the reaction of the alkyne with an azido group. An example of one such feature is an 8-membered ring structure (e.g., cyclo-octyne), such that an alkyne group on an antigen further comprises a DIFO or DBCO group. In some embodiments, an alkyne group on an antigen comprises a structure of formula V, formula VI, or VIa:

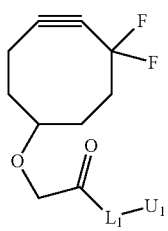
(V)

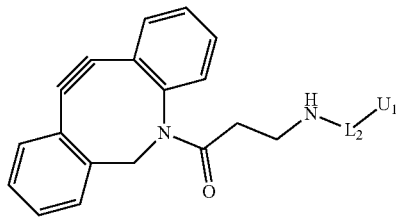
(VI)

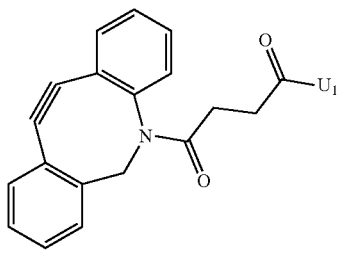
(VIa)

wherein:
  $L_1$ is independently a bond, —NH—, —O—, —S—, —NH($L_{12}$)-, —O($L_{12}$)-, or —S($L_{12}$)-;
  $L_2$ is independently a bond, —C(=O)—, —S(=O)$_2$—, —C(=O)$L_{12}$-, —S(=O)$_2L_{12}$;
  $L_{12}$ is independently $L_{22}$ or $L_{22}$NH—
  $L_{22}$ is independently $C_{1\text{-}10}$ alkyl or —$(CH_2CH_2O)_{1\text{-}10}$—; and
  $U_1$ is independently at least one moiety of an antigen.

In some embodiments, structures of formula V and VIa are conveniently formed from an antigen comprising a nucleophilic group (e.g. a primary amine) and the NHS or sulfo-NHS ester of the corresponding DIFO or DBCO carboxylic acids of structures V and VIa. In some embodiments structures of formula VI are conveniently formed from an activated antigen, and a DBCO derivative such as DBCO-$NH_2$ or DBCO-PEGn-$NH_2$. In some embodiments, DBCO-PEGn-$NH_2$ is DBCO-PEG$_4$-$NH_2$.

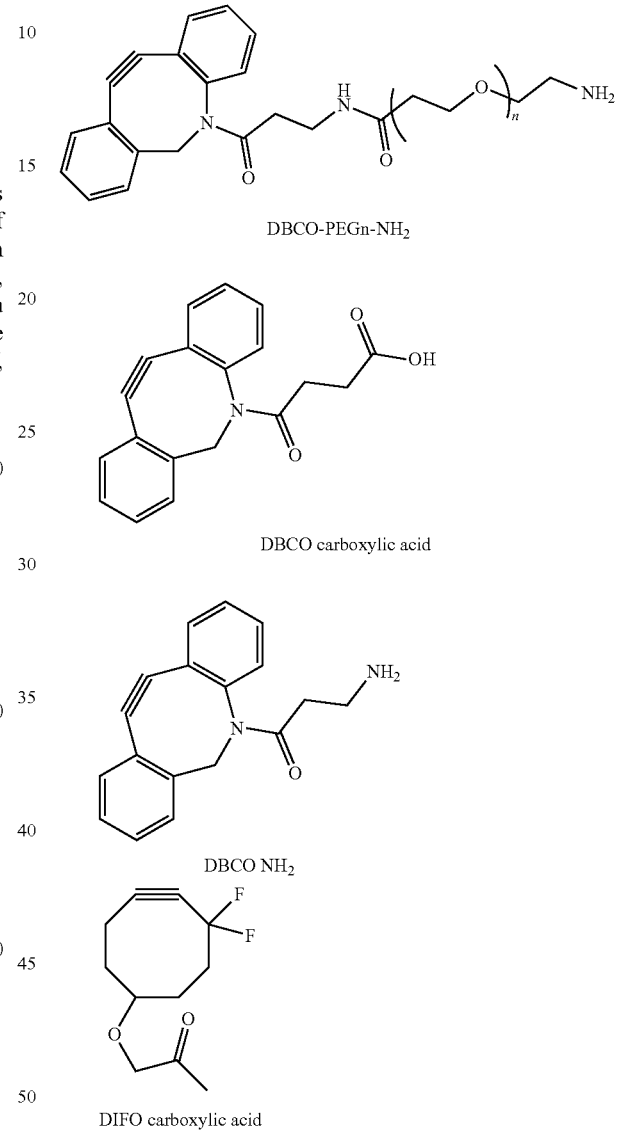

The value of 'n' in 'PEGn' represents the number of oxyethylene repeat units e.g. in the structure shown above, or within formula VII, formula VIIb, formula XI, or moiety 'A', or within the poly(alkyloxy) of $L_{22}$. The value of n is in the range 1-20 e.g. within 2-18, 3-16, or 4-14. Thus n can be, for example, any of 4, 5, 11, 12 or 13.

In some embodiments of formulas IV, V, or VI, the moiety of $U_1$ is at least one polyol of a polysaccharide. In some embodiments the moiety of $U_1$ is at least one polyol of a lipopolysaccharide. In some embodiments the moiety of $U_1$ is at least one amino acid of an antigenic polypeptide.

In further embodiments, an antigen comprising an alkyne comprises a structure of formula VII or VIIa:

(formula VII)

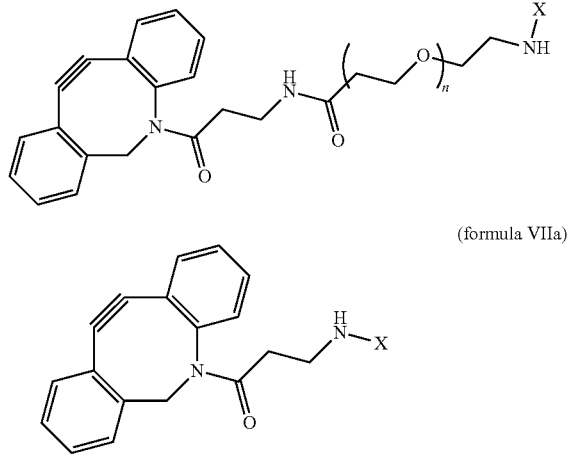

wherein:

X is independently at least one polyol of a polysaccharide; and n is at least 1.

Where a group (e.g. X, Y or $U_1$) is described as being a polyol, this can refer to a chemical attachment to a polyol within the polysaccharide (e.g. to a monosaccharide within the polysaccharide, which monosaccharide is a polyol). The attachment itself can be to any suitable functional group (e.g. to an aldehyde, which may arise from oxidation of a vicinal diol).

In further embodiments, an antigen comprising an alkyne comprises a structure of formula VIIb or VIIc (formula VIIb)

(formula VIIc)

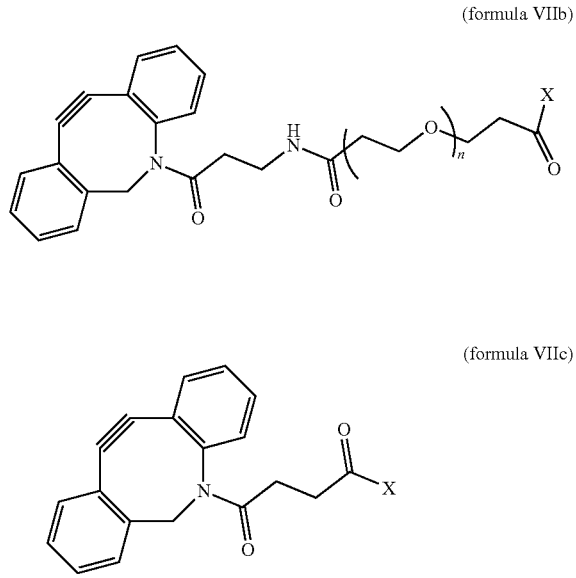

wherein:

X is independently an amine of at least one aminosugar of a polysaccharide; and n is at least 1.

In some embodiments, an antigen comprising an alkyne comprises a polysaccharide according to $(A-X)_z$—Y, wherein:

A is

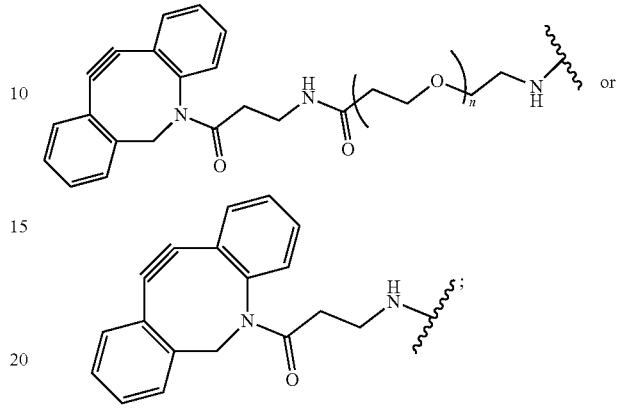

X is independently at least one polyol;

Y is independently at least one polyol of a polysaccharide;

n is at least 1; and z is greater than 1.

In some embodiments, an antigen comprises polysaccharide which further comprises a DBCO group comprises at least 1.5%, at least, 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% (w/w) covalently attached DBCO. In some embodiments, the antigen comprises greater than about 1.5% (w/w) DBCO. In some embodiments, the antigen comprises greater than 3% (w/w) DBCO. In some embodiments the antigen comprises at most 20% at most 19%, at most 18%, at most 17%, at most 16%, at most 15%, at most 14%, at most 13%, at most 12%, at most 11%, at most 10%, at most 9%, at most 8%, at most 7%, at most 6%, at most 5%, at most 4%, at most 3.5%, at most 3.0%, at most 2.5%, at most 2.0%, or at most about 1.7% (w/w) covalently attached DBCO. In some embodiments the antigen comprises less than 20% (w/w) covalently attached DBCO. In other embodiments the antigen comprises less than 10% (w/w) covalently attached DBCO. In some embodiments the antigen comprises between about 1.5 and 20%, 3% and 20%, 3% and 18%, 3% and 16%, 3% and 14%, 3% and 12%, 3% and 10%, 3% and 8%, 3% and 6%, or 3% and 4%, or 1.5 and 9% (w/w) covalently attached DBCO.

In some embodiments, an antigen comprises polysaccharide which further comprises a DBCO group comprises at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% DBCO molecules per 100 polysaccharide repeating units. In some embodiments, the antigen comprises greater than 3% DBCO molecules per polysaccharide 100 repeating units. In some embodiments the antigen comprises at most 20% at most 19%, at most 18%, at most 17%, at most 16%, at most 15%, at most 14%, at most 13%, at most 12%, at most 11%, at most 10%, at most 9%, at most 8%, at most 7%, at most 6%, at most 5%, at most 4%, or at most 3.5% covalently attached DBCO molecules per 100 polysaccharide repeating units. In some embodiments the antigen comprises less than 20% covalently attached DBCO per polysaccharide repeating unit. In other embodiments the antigen comprises less than 10% covalently attached DBCO molecules per 100 polysaccharide repeating units. In some embodiments the antigen comprises between about 3% and 20%, 3% and 18%, 3% and 16%, 3% and 14%, 3% and 12%, 3% and 10%, 3% and 8%, 3% and 6%, or 3% and 4% covalently attached DBCO molecules per 100 polysaccharide repeating units.

In an embodiment, an antigen comprising a polysaccharide is optionally an oligosaccharide. Oligosaccharides have a low number of repeat units (typically 5-15 repeat units) and are typically derived synthetically or by hydrolysis of higher molecular weight polysaccharides.

In an embodiment, an antigen comprising a polysaccharide has a molecular weight of between about 10 kDa and about 10,000 kDa. In other such embodiments, the polysaccharide has a molecular weight of between 50 kDa and 10,000 kDa. In further such embodiments, the polysaccharide has a molecular weight of between 50 kDa and 10,000 kDa; between 50 kDa and 9,500 kDa; between 50 kDa and 9,000 kDa; between 50 kDa and 8,500 kDa; between 50 kDa and 8,000 kDa; between 50 kDa and 7,500 kDa; between 50 kDa and 7,000 kDa; between 50 kDa and 6,500 kDa; between 50 kDa and 6,000 kDa; between 50 kDa and 5,500 kDa; between 50 kDa and 5,000 kDa; between 50 kDa and 4,500 kDa; between 50 kDa and 4,000 kDa; between 50 kDa and 3,500 kDa; between 50 kDa and 3,000 kDa; between 50 kDa and 2,500 kDa; between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; 100 kDa and 10,000 kDa; between 100 kDa and 9,500 kDa; between 100 kDa and 9,000 kDa; between 100 kDa and 8,500 kDa; between 100 kDa and 8,000 kDa; between 100 kDa and 7,500 kDa; between 100 kDa and 7,000 kDa; between 100 kDa and 6,500 kDa; between 100 kDa and 6,000 kDa; between 100 kDa and 5,500 kDa; between 100 kDa and 5,000 kDa; between 100 kDa and 4,500 kDa; between 100 kDa and 4,000 kDa; between 100 kDa and 3,500 kDa; 100 kDa and 3,000 kDa; 100 kDa and 2,500 kDa; 100 kDa and 2,000 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; 200 kDa and 10,000 kDa; between 200 kDa and 9,500 kDa; between 200 kDa and 9,000 kDa; between 200 kDa and 8,500 kDa; between 200 kDa and 8,000 kDa; between 200 kDa and 7,500 kDa; between 200 kDa and 7,000 kDa; between 200 kDa and 6,500 kDa; between 200 kDa and 6,000 kDa; between 200 kDa and 5,500 kDa; between 200 kDa and 5,000 kDa; between 200 kDa and 4,500 kDa; between 200 kDa and 4,000 kDa; between 200 kDa and 3,500 kDa; between 200 kDa and 3,000 kDa; between 200 kDa and 2,500 kDa; between 200 kDa and 2,000 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; or between 200 kDa and 500 kDa. Any whole number integer within any of the above ranges is contemplated as an embodiment of the disclosure.

In an embodiment, an antigen comprising a polysaccharide has a molecular weight of between about 50 kDa and about 1,400 kDa. In an embodiment, an antigen comprising a polysaccharide has a molecular weight of between about 500 kDa and about 3,000 kDa.

Azido-Containing Handles

In some embodiments the chemical handle comprises a moiety that allows for a "click" chemistry reaction with a corresponding group on nnAA residue of a polypeptide. One such moiety is an azido group, which is capable of reacting with a nnAA residue comprising an alkyne group or a phosphine on a polypeptide. In some embodiments, an azido group on an antigen comprises a structure of formula VIII:

(VIII)

$L_{22}$ is a bond, alkyl, or poly(alkyloxy); and
$U_1$ is independently at least one moiety of an antigen.

Alkene-Containing Handles

In some embodiments the chemical handle comprises a moiety that allows for a "click" chemistry reaction with a corresponding group on nnAA residue of a polypeptide. One such moiety is an alkene group, which is capable of reacting with a nnAA residue comprising an 1,2,4,5-tetrazine group. In the simplest embodiments, this is a vinyl group. In one such embodiment, an alkene group on an antigen comprises a structure of formula IX:

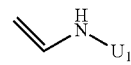

wherein:
$U_1$ is independently at least one moiety of an antigen.

In other embodiments, an alkene group on an antigen comprises a structure of formula IXa:

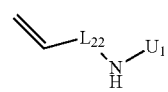

wherein:
$L_{22}$ is $C_{1-10}$ alkyl or $—(CH_2CH_2O)_{1-10}—$; and
$U_1$ is independently at least one moiety of an antigen.

In one embodiment, the disclosure provides for a method for producing a glycoconjugate comprising: (a) providing a nucleic acid encoding a carrier protein, wherein the nucleic acid comprises a suppression codon; (b) creating a reaction mixture by combining the nucleic acid with a cell-free bacterial extract comprising 4-azidomethylphenylalanine (pAMF), a tRNA complementary to the suppression codon, and an aminoacyl-tRNA synthetase; (c) incubating the reaction mixture of (b) under conditions sufficient to selectively incorporate pAMF at a site corresponding to the suppression codon in the carrier protein; and (d) conjugating the pAMF to a polysaccharide by a [2+3] cycloaddition. In another embodiment, the [2+3]cycloaddition comprises the reaction between an azide and an alkyne group. In another embodiment, step (c) comprises incubating the reaction mixture at less than 20 degrees Celsius. In another embodiment, the method additionally comprises purifying the carrier protein immediately after (c). In another embodiment, the suppression codon is selectively substituted at codon 25, 34, 38, 40, 213, 215, 228, 245, 265, 386, 523, or 527 of SEQ ID NO:2. In another embodiment, the reaction mixture in (b) further comprises biological components necessary for protein synthesis. In another embodiment, the tRNA in (b) is capable of being charged with pAMF. In another embodiment, the aminoacyl-tRNA synthetase in (b) preferentially aminoacylates the tRNA with pAMF compared to the 20 natural amino acids. In another embodiment, the alkyne group comprises a DBCO moiety conjugated to the polysaccharide. In another embodiment, the polysaccharide is a capsular polysaccharide of Streptococcus pneumoniae, Neisseria meningitidis, Haemophilus influenzae, Streptococcus pyogenes, or Streptococcus agalactiae. In another embodiment, the polysaccharide is a capsular polysaccharide of a Streptococcus pneumoniae serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, or any combination thereof. In another embodiment, the antigen is a capsular polysaccharide derived from one of the six serotypes of Porphyromonas gingivalis (e.g., K1, K2, K3, K4, K5 and/or K6). In another embodiment, the disclosure provides a glycoconjugate prepared by a process comprising steps (a)-(d). In another embodiment, the pAMF is conjugated to the polysaccharide to generate a conjugate of formula X, Xa, XI, or XIa.

In one embodiment, the disclosure provides for a vaccine comprising the glycoconjugate prepared by steps (a)-(d).

Polypeptide-Antigen Conjugates:

Described herein are polypeptide-antigen conjugates that can be formed between an immunogenic polypeptide as described above and an antigen as described above. In some embodiments the polypeptide-antigen conjugates comprise an enhanced carrier protein and an antigen, wherein the antigen is linked to an nnAA in the enhanced carrier protein. In one embodiment, the antigen is not linked to a natural amino acid of an immunogenic polypeptide. In another embodiment, the antigen is not linked to a lysine within an immunogenic polypeptide. For example, the antigen is not linked to a lysine in SEQ ID NO: 1. In another embodiment, the antigen is only linked to one or more nnAAs of an immunogenic polypeptide. The one or more nnAA is optionally located at the N-terminus, the C-terminus, or anywhere in between the N- and C-terminal ends of an immunogenic polypeptide. In some cases, the antigen is only linked to one or more pAMFs in an immunogenic polypeptide. For example, the antigen is only linked to one or more pAMFs in SEQ ID NO: 1.

In another embodiment, at least one antigen is linked to an amino acid located outside a T-cell epitope of an immunogenic polypeptide. In another embodiment, no antigen is linked to an amino acid located within a T-cell epitope of an immunogenic polypeptide.

The amino acids selected for conjugation within an immunogenic polypeptide optionally comprises one or more surface-accessible residues based on the crystal structure (or other 3D structure, such as a NMR structure) of the polypeptide. Additionally or alternatively, a comprehensive replacement of natural amino acids for nnAAs is performed on an immunogenic polypeptide followed by conjugation, to assess the utility of specific sites on the polypeptide for conjugation.

In one embodiment, the antigen is conjugated to the enhanced carrier protein indirectly (e.g. by first combining the enhanced carrier protein or antigen with a reactive linker, and then combining the enhanced carrier protein-linker or antigen-linker adduct with an antigen or enhanced carrier protein, respectively). In another embodiment, the antigen is conjugated to the enhanced carrier protein directly (e.g. by combining two components comprising the enhanced carrier protein and antigen together in one reaction). Where a conjugate includes a linker, any suitable group can be used. For example, a conjugate can include a linker selected from adipic acid, adipic acid dihydrazide (ADH), β-propionamido, nitrophenyl-ethylamine, haloacyl halides, glycosidic linkages, 6-aminocaproic acid, N-succinimidyl-3-(2-pyridyldithio)-propionate (SPDP), $C_4$ to $C_{12}$ moieties, etc. Linkers resulting from the DBCO and DIFO groups discussed above can also be used e.g. including the residue of a diarylcyclooctyne moiety, such as diarylcyclooctene. The linker will generally be attached to an antigen for conjugation, rather than being attached to a carrier.

Because the antigen-polypeptide conjugates can form large cross-linked complexes, it may not be possible with available analytical methods to directly measure or determine the exact location of some or all conjugations and other physical features. It is understood, however, that such locations or physical features may be reliably inferred from the design of a synthetic scheme, its expected product, and analytical results consistent with that expectation.

Antigen-Polypeptide Conjugation Reaction

In some embodiments, the antigen is conjugated to the enhanced carrier protein using any chemical method suitable for conjugating the non-natural amino acids and chemical handles herein described. Such methods include, but are not limited to, copper(I)-catalyzed alkyne-azide cycloaddition (CuAAC), strain-promoted azide-alkyne cycloaddition (SPAAC), and tetrazine-alkene ligation. As "click" reactions, all of these reactions are able to be performed in aqueous solution. Staudinger ligation between a phosphine and an azide can also be used.

CuAAC: In some embodiments, the antigen is conjugated to the enhanced carrier protein by copper(I)-catalyzed alkyne-azide cycloaddition (CuAAC). In one variation of this embodiment, the enhanced carrier protein comprises a propargyl-containing nnAA and the antigen comprises an azido group. In another variation of this embodiment, the enhanced carrier protein comprises an azido-containing nnAA and the antigen comprises a propargyl group. Suitable conditions for CuAAC conjugation of biomolecules are found, e.g. Presolski et al. Curr Protoc Chem Biol. 2011; 3(4): 153-162, all of which involve the addition of $Cu^{2+}$. In some embodiments, the reaction is accelerated by the addition of a Cu-coordinating ligand, such as THPA. In some embodiments the reaction is accelerated by the addition of a reducing agent to maintain the oxidation state of $Cu^{2+}$. Suitable reducing agents include sodium ascorbate, DTT, or TCEP.

SPAAC: In some embodiments, the antigen is conjugated to the enhanced carrier protein by strain-promoted azide-alkyne cycloaddition (SPAAC). In one variation of these embodiments, the enhanced carrier protein comprises an azido-containing nnAA and the antigen comprises a cyclooctyne group. In another variation of these embodiments, the enhanced carrier protein comprises a cyclooctyne-containing nnAA and the antigen comprises an azido group. As SPAAC requires no additional catalysts or cofactors, this reaction is able to be performed in distilled water, 0.9% saline, PBS, or a physiologically buffered solution. In one embodiment, the enhanced carrier protein and antigen are combined at a mass ratio of 1.20:1 (w/w).

In some embodiments, the antigen is linked to an azido-containing nnAA in the enhanced carrier protein via a structure of formula X or Xa:

(formula X)

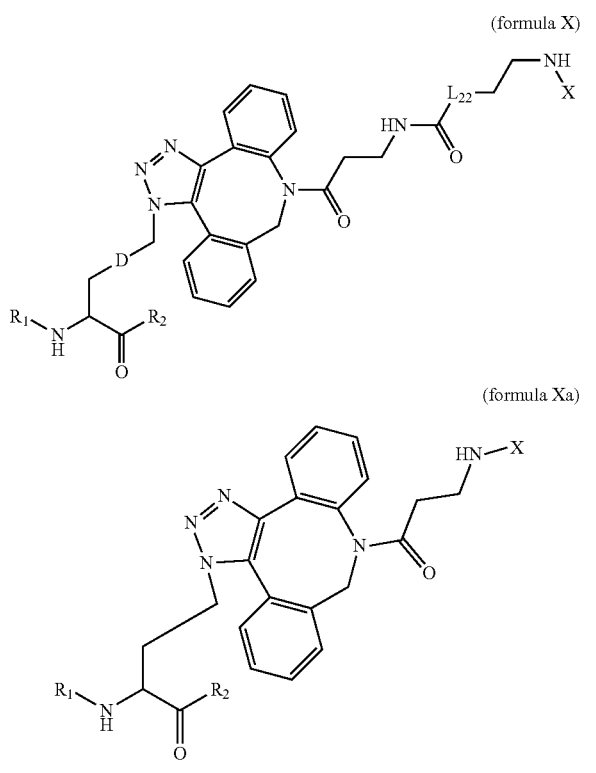

(formula Xa)

wherein:
- R₁ is independently H, formyl, or at least one amino acid of the enhanced carrier protein;
- R₂ is independently OH or at least one amino acid of the enhanced carrier protein;
- D is —Ar—W3- or —W1-Y1-C(O)—Y2-W2-;
- Ar is

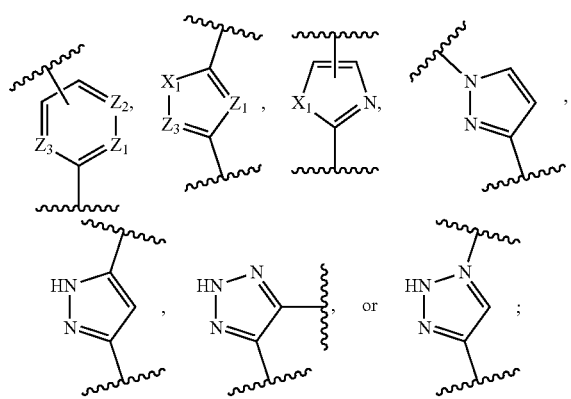

- each of W1, W2, and W3 is independently a single bond or lower alkylene;
- each X1 is independently —NH—, —O—, or —S—;
- each Y1 is independently a single bond, —NH—, or —O—;
- each Y2 is independently a single bond, —NH—, —O—, or an N-linked or C-linked pyrrolidinylene;
- one of Z1, Z2, and Z3 is —N— and the others of Z1, Z2, and Z3 are independently —CH—;
- L22 is independently a bond, alkyl or poly(alkyloxy); and
- X is at least one polyol of a polysaccharide.

In some embodiments, the antigen is linked to an azido-containing nnAA in the enhanced carrier protein via a structure of formula XI or XIa:

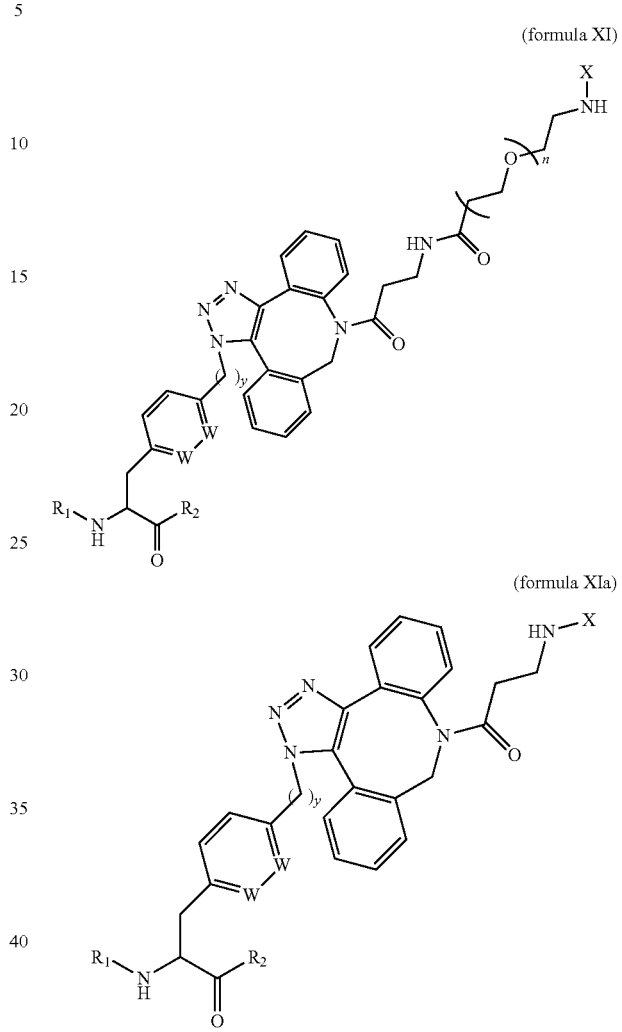

(formula XI)

(formula XIa)

wherein:
- R₁ is independently H, formyl, or at least one amino acid of the enhanced carrier protein;
- R₂ is independently OH or at least one amino acid of the enhanced carrier protein;
- W is C or N;
- y is at least 1;
- n is at least 1; and
- X is independently at least one polyol of a capsular polysaccharide.

The value of 'n' is discussed above in relation to 'PEGn'. The value of 'y' is in the range 1-10, in line with formula XII, and is preferably a lower alkylene e.g. a C1-C4 alkylene.

Tetrazine-Alkyne Ligation:

In some embodiments, the antigen is conjugated to the enhanced carrier protein by tetrazine-alkyne ligation. In one variation of these embodiments, the enhanced carrier protein comprises a 1,2,4,5-tetrazine-containing nnAA and the antigen comprises an alkene group. Similarly to the SPAAC reaction, the tetrazine-alkyne ligation proceeds without the addition of cofactors this and this reaction is able to be performed in distilled water, 0.9% saline, PBS, or a physiologically buffered solution.

Conjugate Characterization

Methods (size exclusion, diafiltration, dialysis): Following the conjugation reaction, the antigen-enhanced carrier protein conjugates of interest are optionally purified according to methods including, but not limited to, chromatography (e.g., ion exchange, affinity, hydrophobic interaction, and size exclusion), molecular size exclusion (dialysis, diafiltration, tangential flow filtration, depth filtration) electrophoretic procedures (e.g., preparative isoelectric focusing), differential solubility (e.g., ammonium sulfate precipitation), or SDS-PAGE (see, e.g., Protein Purification, J. C. Janson & Lars Ryden, editors, VCH Publishers, New York, 1989) to obtain substantially pure conjugates.

The conjugated proteins of interest are optionally quantitated according to methods including, but not limited to, microfluidic electrophoresis, gel electrophoresis, western blotting, immunoassays (e.g., ELISA), and other assays to assess the activity of the conjugated protein.

Exemplary Physical Parameters

One important parameter for antigen-enhanced carrier protein conjugates is the molecular weight of the conjugate. Since conjugates optionally comprise variable numbers of antigen molecules conjugated to each protein molecule as well as variable higher-order crosslinking (protein-antigen-protein linkages, for example) the output molecular weight of a conjugate is not necessarily predictable from the input molecular weights of the enhanced carrier proteins and antigens. A wide body of literature (e.g. Howard et al. *Immunology.* 1971(21): 535-545 and Kabat & Bezer. *Arch Biochem Biophys.* 1958(78) 306-18) suggests that antigenic particle size has an important effect on immunogenicity. Wessels et al. (1998) *Infect Immun* 66:2186-92 report that conjugate size and cross-linking can influence the immunogenicity and protective efficacy of GBS type III conjugates.

In general term, conjugates can be formed by linking a carrier protein to an antigen which has either one or multiple handles per antigen. With multiple handles per antigen a crosslinked conjugate can be formed, involving protein-antigen-protein linkages. With a single handle per antigen (e.g. a terminal group in a polysaccharide) this sort of conjugate lattice does not form because a single antigen cannot bind to multiple carrier protein molecules. Crosslinked conjugates are preferred herein (particularly for pneumococcus) where higher molecular weights are desired, and thus antigens with multiple handles are preferred.

In some embodiments, the antigen-enhanced carrier protein conjugate has a molecular weight of about 750 kDa, about 1,000 kDa, about 1,500 kDa, about 2,000 kDa, about 2,500 kDa, about 3,000 kDa, about 3,500 kDa, about 4,000 kDa, about 4,500 kDa, about 5,000 kDa, about 5,500 kDa, about 6,000 kDa, about 6,500 kDa, about 7,000 kDa, about 7,500 kDa, or about 8,000 kDa. In some embodiments, the antigen-enhanced carrier protein conjugate has a molecular weight of at least about 750 kDa, at least about 1,000 kDa, or at least about 1,500 kDa, In some embodiments, the antigen-enhanced carrier protein conjugate has a molecular weight of between about 750 kDa and about 2,800 kDa. In some embodiments, the antigen-enhanced carrier protein conjugate has a molecular weight of between about 800 kDa and about 2,800 kDa. In some embodiments, the antigen-enhanced carrier protein conjugate has a molecular weight of between about 850 kDa and about 2,800 kDa. In some embodiments, the antigen-enhanced carrier protein conjugate has a molecular weight of between about 900 kDa and about 2,800 kDa. In some embodiments, the antigen-enhanced carrier protein conjugate has a molecular weight of between about 950 kDa and about 2,800 kDa. In some embodiments, the antigen-enhanced carrier protein conjugate has a molecular weight of between about 1,000 kDa and about 2,800 kDa.

Another important parameter for the conjugate vaccines of the present disclosure is the ratio of the antigen (e.g., polysaccharide) to immunogenic polypeptide carrier (e.g., carrier proteins of the present disclosure). Using a polysaccharide-carrier protein conjugate as illustrative of the general principle, the polysaccharide-to-protein (PS:PC) ratio of the purified conjugate is generally expressed in terms of a weight-weight (w/w) ratio. Such ratios conventionally are expressed to include any free polysaccharide that is purified along with individual glycoconjugates. Higher PS:PC ratios of polysaccharide-carrier protein conjugates allow for more polysaccharide antigen to be delivered with a lower amount of enhanced carrier protein. For pneumococcal conjugate vaccines, the ratio is typically in the range 0.3-3.0, but this can vary with the serotype and aspects of the conjugation chemistry (*Annex 2: Recommendations for the production and control of pneumococcal conjugate vaccines*; WHO Technical Report Series, No. 927, 2005). The ratio of the commercial vaccine Prevnar-13 is 0.9 (see, Prevnar 13 Package Insert, M/2016 Revision, pg. 24; www.fda.gov/downloads/biologicsbloodvaccines/vaccines/approvedproducts/ucm201669.pdf), suggesting a preferred range of 1.0-3.0. When formulating a vaccine with more than 13 serotypes, it may be preferred to achieve a ratio of 1.5-3.0, and particularly preferred to employ a ratio of about 1.5 to about 2.0. This can be the average ratio for all conjugates in a composition, which can be achieved by ensuring that all individual conjugates have this ratio, or by ensuring that any conjugates outside this range on one side are balanced by a conjugate outside this range on the other side.

In another embodiment, the ratio (weight by weight) of polysaccharide to enhanced carrier protein in the polysaccharide-enhanced carrier protein conjugate is between 0.5 and 4.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0). In another embodiment, the (w/w) PS:PC ratio in the carrier protein conjugate is between 0.7 and 2.8. In another embodiment, the (w/w) PS:PC ratio in the carrier protein conjugate is between 1.0 and 2.8. In another embodiment, the (w/w) PS:PC ratio in the carrier protein conjugate at least 0.8, at least 0.9, at least 1.0, at least 1.1, at least 1.2, at least 1.3. at least 1.4 or at least 1.5. In another embodiment the ratio of polysaccharide to enhanced carrier protein in the polysaccharide-enhanced carrier protein conjugate is greater than 0.9 (w/w). In another embodiment the ratio of polysaccharide to enhanced carrier protein in the polysaccharide-enhanced carrier protein conjugate is between about 0.9 and about 3.0 (w/w). Mixing of individual conjugates with such PS:PC ratios can yield a combination having a desired overall PS:PC ratio.

Presence of Contaminants (Free Polysaccharide, C-Poly):

An important parameter for polysaccharide-enhanced carrier protein conjugates is the level of free polysaccharide that is not covalently conjugated to the enhanced carrier protein, but is nevertheless present in the conjugate composition. For example, in certain instances, the free polysaccharide is noncovalently associated with (i.e., noncovalently bound to, adsorbed to, or entrapped in or with) the polysaccharide-enhanced carrier protein conjugate. In some embodiments, polysaccharide-enhanced carrier protein conjugates described herein comprise less than about 50%, 45%, 40%, 35%, 30%, 25%, 20%, 15%, or 10% of free polysaccharide compared to the total amount of polysaccharide. In another embodiment the polysaccharide-enhanced carrier proteins described herein comprise less than about 10% of free polysaccharide compared to the total amount of polysaccharide. In another embodiment the polysaccharide-enhanced carrier proteins described herein comprise less than about 25% of free polysaccharide compared to the total amount of polysaccharide. In another embodiment, the polysaccharide-enhanced carrier proteins described herein comprise less than about 30% of free polysaccharide compared to the total amount of polysaccharide. In another embodiment the polysaccharide-enhanced carrier proteins described herein comprise less than about 15% of free polysaccharide compared to the total amount of polysaccharide. Free polysaccharide is optionally measured by any suitable method, including the method of Lei et al. (*Dev Biol* (*Basel*). 2000; 103:259-64), which uses an HCl/deoxycholate-based precipitation method to distinguish the pools of polysaccharide. In preferred compositions the amount of unconjugated bacterial polysaccharide is less than 5%, by weight, of the total amount of bacterial polysaccharide in the composition. In a composition with multiple pneumococcal conjugates it is preferred that the amount of unconjugated bacterial polysaccharide for each serotype is less than 5%, by weight, of the total amount of that serotype's bacterial polysaccharide in the composition.

An important parameter for pneumococcal capsular polysaccharide-enhanced carrier protein conjugates is the level of C-polysaccharide contamination present in preparations of the conjugate. C-polysaccharide is an immunologically unproductive but highly immunogenic cell wall component of *S. pneumoniae* that "rides along" in many pneumococcal capsular polysaccharide preparation methods. As C-polysaccharide immune responses do not generally produce neutralizing antibodies, contamination with C-polysaccharide can interfere with proper assessments of antigen-enhanced carrier protein conjugate effectiveness when administered to animals.

The level of C-polysaccharide is optionally shown by total acid hydrolysis of a polysaccharide conjugate preparation, chromatography of the hydrolysate, and conductometric detection of choline. Alternatively, the non-hydrolyzed polysaccharide is analyzed by NMR for choline. The NMR technique uses the ratio of the choline signal to the rhamnose methyl signal (for capsular polysaccharides containing a rhamnose; a different signal for other capsular polysaccharides) for calculating the C-polysaccharide content. The chromatographic method uses the ratio of the choline signal to either the polysaccharide content determined by conductometric assay or to one of the capsular polysaccharide component peaks to calculate the C-polysaccharide content. In either method, standards of known concentrations of choline allow direct calculation of the level of choline present in a polysaccharide preparation once the choline concentration is known, using the theoretical repeat structure of C-polysaccharide [Hermans, et al., *Recl. Trav. Chim. Pays-Bas,* 107, 600 (1988)], the concentration of C-polysaccharide in a polysaccharide preparation is known.

Polysaccharide concentrations of polysaccharide-enhanced carrier protein conjugate samples are optionally measured by a variety of techniques, for example, total polysaccharide concentration is optionally determined by total hydrolysis of the polysaccharide and measurement of the concentration of a specific monosaccharide. By comparing the C-polysaccharide concentration to total polysaccharide concentration, the degree of C-polysaccharide contamination (w/w) is determined. Levels of C-polysaccharide below 3% (w/w) of total polysaccharide are considered acceptable. In some embodiments, the C-polysaccharide levels are below 1%.

In one embodiment, the disclosure provides for a conjugate comprising a carrier protein and an antigen, wherein the antigen is linked to an nnAA in the carrier protein. In another embodiment, the carrier protein retains a T-cell binding epitope of diphtheria toxoid (DT), tetanus toxoid (T), *Haemophilus influenzae* protein D (PD), outer membrane protein complex of serogroup B meningococcus (OMPC), or CRM197. In another embodiment, the nnAA is 2-amino-3-(4-azidophenyl)propanoic acid (pAF), 2-amino-3-(4-(azidomethyl)phenyl)propanoic acid (pAMF), 2-amino-3-(5-(azidomethyl)pyridin-2-yl)propanoic acid, 2-amino-3-(4-(azidomethyl)pyridin-2-yl)propanoic acid, 2-amino-3-(6-(azidomethyl)pyridin-3-yl)propanoic acid, 2-amino-5-azidopentanoic acid, or 2-amino-3-(4-(azidomethyl)phenyl) propanoic acid, and any combination thereof. In another embodiment, the nnAA is not in a T-cell activating epitope of the carrier protein. In another embodiment, the nnAA is substituted for one or more lysine residues in the carrier protein. In another embodiment, the apparent molecular weight of the conjugate is between about 900 kDa and about 5 MDa. In another embodiment, one or more lysine residues substituted are selected from the group consisting of K25, K34, K38, K40, K213, K215, K228, K265, K386, K523 and K527, and any combination thereof of SEQ ID NO: 1. In another embodiment, the nnAA is not in a T-cell activating epitope of the carrier protein. In another embodiment, the antigen is linked to the carrier protein according to formula XI or XIa:

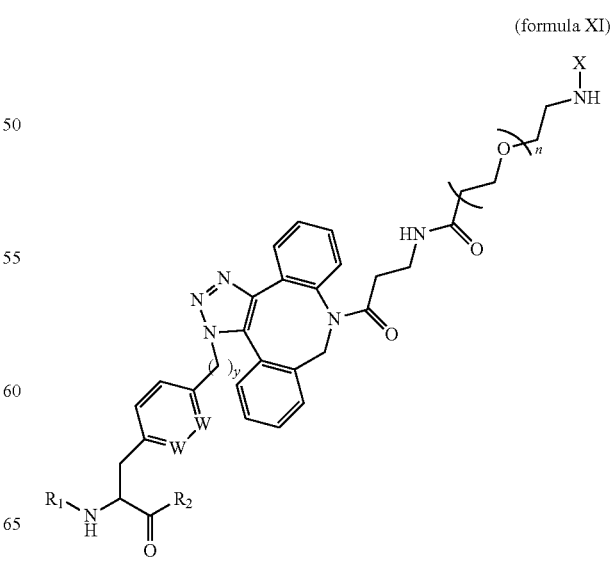

(formula XI)

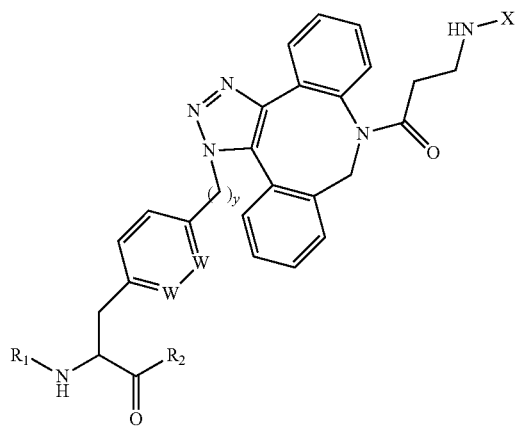

(formula XIa)

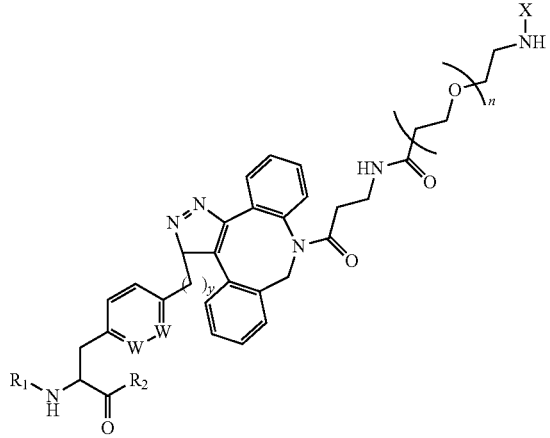

(formula XI)

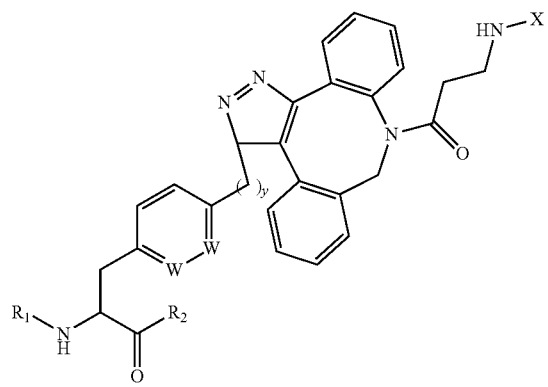

(formula XIa)

wherein
- $R_1$ is independently H, formyl, or at least one amino acid of the carrier protein;
- $R_2$ is independently OH or at least one amino acid of the carrier protein;
- W is C or N;
- y is at least 1;
- n is at least 1; and
- X is independently at least one polyol of a capsular polysaccharide.

In another embodiment, the antigen is a polysaccharide. In another embodiment, the polysaccharide is a capsular polysaccharide of *Streptococcus pneumoniae*, *Neisseria meningitidis*, *Haemophilus influenzae*, *Streptococcus pyogenes*, or *Streptococcus agalactiae*. In another embodiment, the polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the antigen is a capsular polysaccharide derived from one of the six serotypes of *Porphyromonas gingivalis* (e.g., K1, K2, K3, K4, K5 and/or K6).

In one embodiment, the disclosure provides a method for identifying optimal placement of an antigen on a carrier protein to improve a host immune response, comprising: i) introducing into a carrier protein an nnAA substitution; ii) conjugating a polysaccharide to the nnAA to form a glycoconjugate; and iii) measuring the apparent molecular weight of the glycoconjugate. In another embodiment, the nnAA substitution is not in a T-cell activating epitope of the carrier protein. In another embodiment, the carrier protein retains a T-cell binding epitope of diphtheria toxoid (DT), tetanus toxoid (TT), *Haemophilus influenzae* protein D (PD), outer membrane protein complex of serogroup B meningococcus (OMPC), or CRM197. In another embodiment, the antigen is a polysaccharide. In another embodiment, the at least one or more polysaccharides is conjugated to the carrier protein according to formula XI or XIa:

where
- $R_1$ is independently H, formyl, or at least one amino acid of the carrier protein;
- $R_2$ is independently OH or at least one amino acid of the carrier protein; and
- X is independently at least one polyol of a capsular polysaccharide.

In another embodiment, the at least one or more non-natural amino acids substituted for is pAMF. In another embodiment, the disclosure provides for a carrier protein with optimal placement of an antigen identified by the process of i)-iii). In another embodiment, the substitution is introduced at least 2, at least 3, at least 4, at least 5, at least 6, at least 7, at least 8, or at least 9 times. In another embodiment, the polysaccharide is a capsular polysaccharide of a bacterium. In another embodiment, the bacterium is *Streptococcus pneumoniae*, *Neisseria meningitidis*, *Haemophilus influenzae*, *Streptococcus pyogenes*, or *Streptococcus agalactiae*. In another embodiment, the bacterium is *Streptococcus pneumoniae*. In another embodiment, polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the antigen is a capsular polysaccharide derived from one of the six serotypes of *Porphyromonas gingivalis* (e.g., K1, K2, K3, K4, K5 and/or K6).

Modified Polypeptides and Polysaccharides:

In one embodiment, the disclosure provides for a modified polypeptide comprising at least one compound, or salt thereof, comprising Formula XI or XIa:

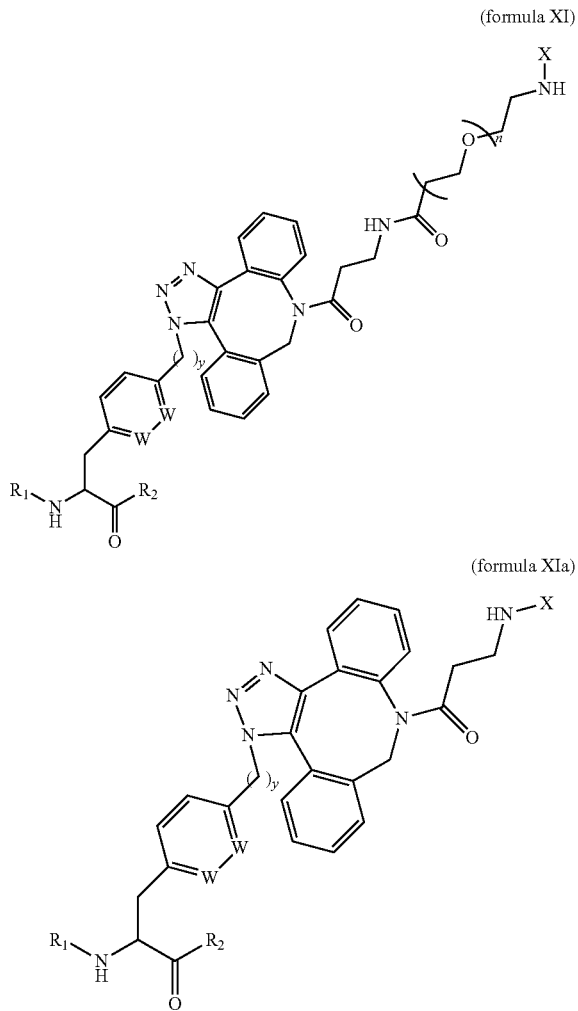

(formula XI)

(formula XIa)

wherein
R₁ is independently H, formyl, or at least one amino acid of a carrier protein;
R₂ is independently OH or at least one amino acid of a carrier protein; and
X is independently at least one polyol of a polysaccharide.

In another embodiment, the carrier protein retains a T-cell binding epitope of diphtheria toxoid (DT), tetanus toxoid (TT), *Haemophilus* protein D (PD), outer membrane protein complex of serogroup B meningococcus (OMPC), or CRM197. In another embodiment, the polysaccharide is a capsular polysaccharide of a bacterial species. In another embodiment, the bacterial species is *Streptococcus pneumoniae*. In another embodiment, the bacterial species is *Streptococcus pneumoniae, Neisseria meningitidis, Haemophilus influenzae, Streptococcus pyogenes*, or *Streptococcus agalactiae*. In another embodiment, the polysaccharide is a capsular polysaccharide of a *Streptococcus pneumoniae* serotype selected from the group selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, R1 and R2 are not amino acids that occur in a T-cell epitope of the carrier protein. In another embodiment, the antigen is a capsular polysaccharide derived from one of the six serotypes of *Porphyromonas gingivalis* (e.g., K1, K2, K3, K4, K5 and/or K6).

In one embodiment, the disclosure provides for a modified polysaccharide, comprising at least one compound, or salt thereof, comprising formula VII or VIIa

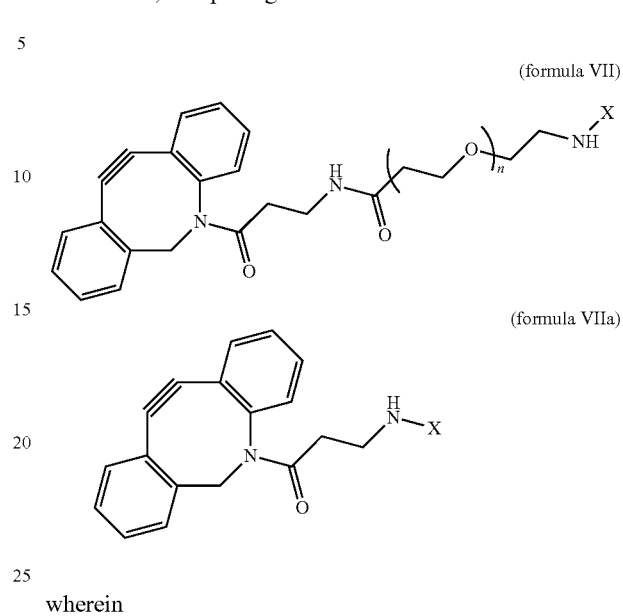

(formula VII)

(formula VIIa)

wherein
X is independently at least one polyol of the capsular polysaccharide; and
n is at least 1.

In another embodiment, the modified polysaccharide of formula VII is further conjugated to a carrier protein comprising at least one nnAA. In another embodiment, the modified polysaccharide is conjugated by a [2+3] cycloaddition. In another embodiment, the polysaccharide is derived from a bacterial species. In another embodiment, bacterial species is *Streptococcus pneumoniae*. In another embodiment, the bacterial species is *Streptococcus pneumoniae, Neisseria meningitidis, Haemophilus influenzae, Streptococcus pyogenes*, or *Streptococcus agalactiae*. In another embodiment, the polysaccharide is a bacterial capsular polysaccharide. In another embodiment, the molar ratio of DBCO to repeating unit of the capsular polysaccharide is greater than 1. In another embodiment, the capsular polysaccharide is of a *Streptococcus pneumoniae* serotype comprising 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the antigen is a capsular polysaccharide derived from one of the six serotypes of *Porphyromonas gingivalis* (e.g., K1, K2, K3, K4, K5 and/or K6).

In one embodiment, the disclosure provides a modified polysaccharide according to $(A-X)_z-Y$
wherein
A is

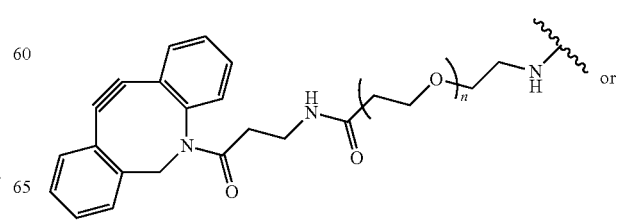

or

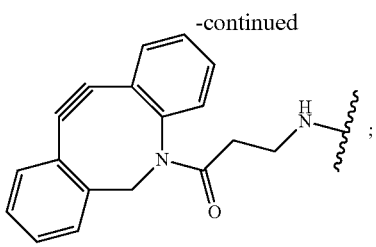

X is independently at least one polyol;
Y is independently at least one polyol of a polysaccharide;
n is at least 1; and
z is greater than 1.

In another embodiment, the polysaccharide is derived from a bacterial species. In another embodiment, the bacterial species is *Streptococcus pneumoniae*. In another embodiment, the bacterial species is *Streptococcus pneumoniae, Neisseria meningitidis, Haemophilus influenzae, Streptococcus pyogenes*, or *Streptococcus agalactiae*. In another embodiment, the polysaccharide is a bacterial capsular polysaccharide. In another embodiment, the capsular polysaccharide is that of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the antigen is a capsular polysaccharide derived from one of the six serotypes of *Porphyromonas gingivalis* (e.g., K1, K2, K3, K4, K5 and/or K6). In another embodiment, the polysaccharide is further conjugated to a carrier protein. In another embodiment, the polysaccharide is conjugated to a carrier protein via a linkage of formula II. In another embodiment, the carrier protein retains a T-cell binding epitope of CRM197. In another embodiment, the polysaccharide is conjugated by a [2+3] cycloaddition. In another embodiment, the carrier protein comprises one or more non-natural amino acids. In another embodiment, the carrier protein retains a T-cell binding epitope of diphtheria toxoid (DT), tetanus toxoid (TT), *Haemophilus influenzae* protein D (PD), outer membrane protein complex of serogroup B meningococcus (OMPC), or CRM197. In another embodiment, the carrier protein is further conjugated to an antigen. In another embodiment, the carrier protein is conjugated to an antigen via a linkage of formula II. In another embodiment, a ratio (w/w) of the polysaccharide to the carrier protein (PS:PC) is between about 1.5 and about 4.

Compositions of Polypeptide-Antigen Conjugates:

Described herein are immunogenic compositions comprising at least one enhanced carrier protein-antigen conjugate together with at least one excipient, wherein the antigen is conjugated to the polypeptide via a nnAA residue in the enhanced carrier protein. In one embodiment, the disclosure provides for a vaccine composition comprising a glycoconjugate described herein. In some embodiments, the conjugate vaccine composition comprising at least one enhanced carrier protein-antigen conjugate as described herein elicits reduced carrier suppression in a subject compared to a conjugate vaccine composition comprising the native carrier protein. In some embodiments, the conjugate vaccine composition comprising at least one enhanced carrier protein-antigen conjugate as described herein improves the overall immune response and/or increases the T-cell dependent response in a subject compared to a conjugate vaccine composition comprising the native carrier protein.

In some embodiments the immunogenic composition comprises a single carrier-protein-antigen conjugate (e.g. a single serotype of pneumococcus). In some embodiments the immunogenic composition comprises multiple carrier-protein antigen conjugates (e.g. multiple serotypes of pneumococcus). In further embodiments, the multiple carrier-protein antigen conjugates optionally comprise: (a) multiple antigens conjugated to a common enhanced carrier protein; or (b) multiple antigens conjugated to different enhanced carrier proteins. In further embodiments, the multiple enhanced carrier protein antigen conjugates comprise antigens derived from different serotypes of the same organism (e.g. *S. pneumoniae*). Where a composition includes multiple different antigens (e.g. capsular polysaccharide from multiple serotypes of pneumococcus, or from multiple serogroups of meningococcus) it is preferred that the same type of carrier protein is used for each antigen e.g. each antigen is individually conjugated to the same nnAA-containing CRM197 variant, and the individual antigen-protein conjugates are then combined to give a multi-antigen composition.

In some embodiments, the overall (weight by weight) ratio of all serotype polysaccharides to carrier protein (PS:PC) in a multivalent serotype polysaccharide conjugate composition is in a certain range. In another embodiment, the ratio (weight by weight) of polysaccharide to enhanced carrier protein in the polysaccharide-enhanced carrier protein conjugate (or in the overall multivalent composition) is between 0.5 and 4.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0). In another embodiment, the (w/w) PS:PC ratio in the carrier protein conjugate (or in the overall multivalent composition) is between 0.7 and 2.8. In another embodiment, the (w/w) PS:PC ratio in the carrier protein conjugate (or in the overall multivalent composition) is between 1.0 and 2.8. In another embodiment, the (w/w) PS:PC ratio in the carrier protein conjugate (or in the overall multivalent composition) is at least 0.8, at least 0.9, at least 1.0, at least 1.1, at least 1.2, at least 1.3. at least 1.4 or at least 1.5 (w/w). In another embodiment the ratio of polysaccharide to enhanced carrier protein in the polysaccharide-enhanced carrier protein conjugate (or in the overall multivalent composition) is greater than 0.9 (w/w). In another embodiment the ratio of polysaccharide to enhanced carrier protein in the polysaccharide-enhanced carrier protein conjugate (or in the overall multivalent composition) is between about 0.9 and about 3.0 (w/w). A preferred composition includes protein-saccharide conjugates of capsular polysaccharides from multiple pneumococcal serotype with an overall mass excess of polysaccharide to protein e.g. a protein:polysaccharide ratio between 1:1.1 and 1:2 (w/w) e.g. between 1:1.5 and 1:1.9.

In some embodiments, the overall molecular weight range of all serotype polysaccharide-carrier protein conjugates in a multivalent serotype polysaccharide-carrier protein conjugate composition is within a particular range. In some embodiments, the antigen-enhanced carrier protein conjugates have a molecular weight of about 750 kDa, about 1,000 kDa, about 1,500 kDa, about 2,000 kDa, about 2,500 kDa, about 3,000 kDa, about 3,500 kDa, about 4,000 kDa, about 4,500 kDa, about 5,000 kDa, about 5,500 kDa, about 6,000 kDa, about 6,500 kDa, about 7,000 kDa, about 7,500 kDa, or about 8,000 kDa. In some embodiments, the antigen-enhanced carrier protein conjugates have a molecular weight of at least about 750 kDa, at least about 1,000 kDa, or at least about 1,500 kDa, In some embodiments, the antigen-enhanced carrier protein conjugates have a molecular weight of between about 750 kDa and about 2,800 kDa. In some embodiments, the antigen-enhanced carrier protein conjugates have a molecular weight of between about 800 kDa and about 2,800 kDa. In some embodiments, the antigen-enhanced carrier protein conjugates have a molecular weight of between about 850 kDa and about 2,800 kDa. In some embodiments, the antigen-enhanced carrier protein conjugates have a molecular weight of between about 900 kDa and about 2,800 kDa. In some embodiments, the antigen-enhanced carrier protein conjugates have a molecular weight of between about 950 kDa and about 2,800 kDa. In some embodiments, the antigen-enhanced carrier protein conjugates have a molecular weight of between about 1,000 kDa and about 2,800 kDa.

In further embodiments, the immunogenic composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 distinct enhanced carrier protein-antigen conjugates.

In any composition which includes multiple conjugates (e.g. a conjugate for each of multiple pneumococcal serotypes) it could be preferred in some instances that the carrier protein in each conjugate is identical. In an alternative embodiment of such compositions with multiple conjugates, it may be preferred to use more than one carrier. While it is possible that each antigen (e.g., capsular polysaccharides from different pneumococcal serotypes) could be conjugated to a different carrier, typically there would be only 2-4 (e.g., 2 or 3) different carriers represented among the individual conjugates in such compositions. By way of illustration and not of limitation, in a composition of 24 different conjugates, each conjugate comprising a capsular polysaccharides from a different pneumococcal serotype, some but not all of the 24 conjugates comprise a first carrier protein (e.g., based on CRM197) and the balance of the 24 conjugates comprise a second protein carrier (e.g., based on HiD). Thus, again by way of example and not of limitation, 12, 13, 15 or 20 of the 24 conjugates could comprise the first carrier protein, and the 12, 11, 9 or 4, respectively, remaining conjugates could comprise the second carrier protein.

In some embodiments, the at least one excipient comprises components suitable for parenteral administration.

In further embodiments, the at least one excipient optionally comprises a buffer or pH adjusting agent. In particular embodiments, the buffer or pH adjusting agent is selected from the group consisting of sodium borate, sodium phosphate, sodium citrate, ammonium sulfate, or succinate, and any combination thereof. Other examples of suitable buffers include acids such as acetic, boric, citric, lactic, phosphoric and hydrochloric acids; bases such as sodium hydroxide, sodium acetate, sodium lactate and tris-hydroxymethylaminomethane; and buffers such as citrate/dextrose, sodium bicarbonate and ammonium chloride. Histidine buffers are also useful in immunogenic compositions.

In further embodiments, the at least one excipient optionally comprises a tonicity agent to bring osmolality of the composition into an acceptable range. In particular embodiments, the tonicity agent is selected from the group consisting of sodium chloride, dextrose, and glycerin, and any combination thereof. Other examples of buffers suitable for parenteral administration include salts having sodium, potassium or ammonium cations and chloride, citrate, ascorbate, borate, phosphate, bicarbonate, sulfate, thiosulfate or bisulfite anions; suitable salts include potassium chloride, sodium thiosulfate, sodium bisulfite and ammonium sulfate.

In further embodiments, the at least one excipient optionally comprises a surface active agent (surfactant). In particular embodiments, the surface active agent is polyoxyethylene sorbitan monolaurate (polysorbate 20 or 'Tween 20'), polyoxyethylene sorbitan monooleate (polysorbate 80 or 'Tween 80'), Brij 35, Triton X-10, Pluronic F127, or sodium dodecyl sulfate (SDS). In some embodiments the surface active agent is present at a concentration between 0.0003% and 0.3% (w/w).

In some embodiments, the at least one excipient optionally comprises an adjuvant, an agent which increases the stimulation of the immune system by enhancing antigen presentation (depot formulation, delivery systems) and/or by providing costimulation signals (immunomodulators). In some variations of this embodiment, the adjuvant is aluminum-salt-based. In particular embodiments, the adjuvant is aluminum potassium phosphate, aluminum hydroxyphosphate sulfate, aluminum hydroxide, or aluminum phosphate, and any combination thereof. In other variations, the adjuvant is an oil-in-water emulsion. In particular embodiments, the adjuvant is AS03, MF59, or AF03, and any combination thereof. In yet other variations the adjuvant is a TLR4-agonist. In a particular embodiment the adjuvant is RC529. Preferred adjuvants for use with the invention are aluminum salts, such as an aluminum phosphate adjuvant (e.g. an aluminum hydroxyphosphate adjuvant). Where a composition includes an aluminum salt adjuvant it is preferred that the concentration of $Al^{3+}$ in the composition is ≤1.25 mg per dose e.g. ≤1.25 mg per 0.5 ml, and ideally ≤0.85 mg per dose. Conjugates within a composition may be adsorbed to the aluminum salt adjuvant. For a mixed composition, conjugates can be adsorbed to an aluminum salt individually and then mixed, or can be added in to an aluminum salt to achieve sequential adsorption, thereby forming the mixed conjugate composition.

A preferred composition comprises (i) one or more conjugates as defined herein e.g. capsular polysaccharide from multiple pneumococcal serotypes conjugated to nnAA-containing carrier proteins and (ii) an aluminum phosphate adjuvant.

In one embodiment, the disclosure provides for a method for increasing the polysaccharide to protein carrier ratio (w/w) (PS:PC) of an immunogenic composition, comprising: (a) introducing into a carrier protein one or more nnAA substitutions; and (b) conjugating a polysaccharide to the carrier protein via the one or more non-natural amino acid substitutions. In another embodiment, the one or more substitutions comprises at least 2, at least 3, at least 4, at least 5, at least 6, at least 7, at least 8, or at least 9 substitutions. In another embodiment, the nnAA substitutions are not in a T-cell activating epitope of the carrier protein. In another embodiment the nnAA is pAMF. In another embodiment, the carrier protein retains a T-cell binding epitope of diphtheria toxoid (DT), tetanus toxoid (TT), *Haemophilus* protein D (PD), outer membrane protein complex of serogroup B meningococcus (OMPC), or CRM197. In another embodiment, the non-natural amino acid substitutions occur at lysine residues. In another embodiment, the lysine residues are selected from the group consisting of K25, K34, K38, K40, K213, K215, K228, K265, K386, K523 and K527, and any combination thereof of SEQ ID NO: 1. In another embodiment, the polysaccharide is conjugated to the carrier protein via a linkage of formula XI or XIa:

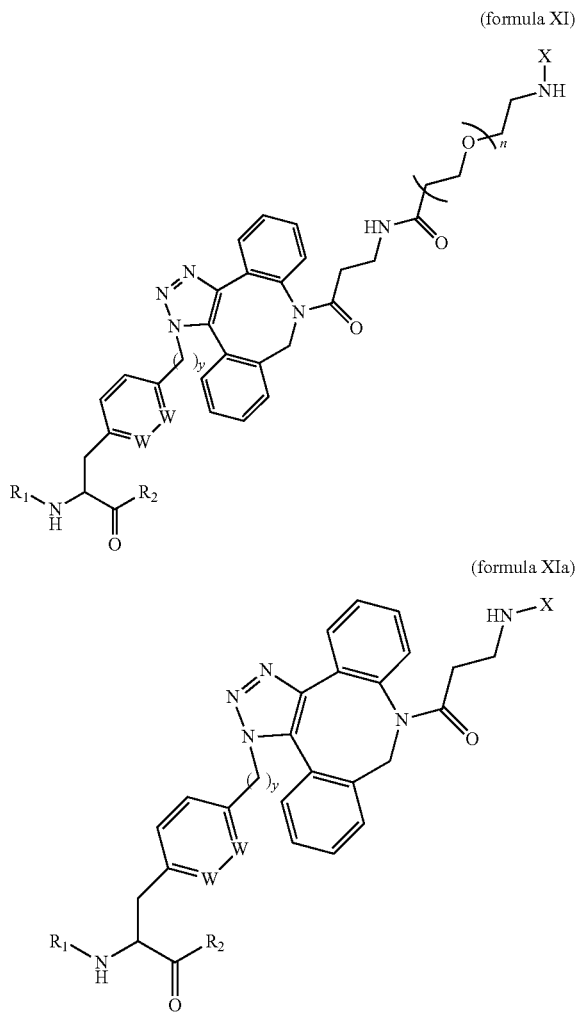

wherein

R₁ is independently H, formyl, or at least one amino acid of the carrier protein;

R₂ is independently OH or at least one amino acid of the carrier protein; and

X is independently at least one polyol of a capsular polysaccharide.

In another embodiment, the PS:PC ratio is between about 1.5 and about 4. In another embodiment, the polysaccharide is a capsular polysaccharide of a *Streptococcus pneumoniae* serotype selected from the group consisting of 1, 2, 3, 4, 5, 6A, 6B, 7F, 8, 9V, 9N, 10A, 11A, 12F, 13, 14, 15B, 16, 17F, 18C, 19A, 19F, 20, 22F, 23F, 24F, 31, and 33F, and any combination thereof. In another embodiment, the antigen is a capsular polysaccharide derived from one of the six serotypes of *Porphyromonas gingivalis* (e.g., K1, K2, K3, K4, K5 and/or K6). In another embodiment, the polysaccharide is a capsular polysaccharide of *Streptococcus pneumoniae, Neisseria meningitidis, Haemophilus influenzae, Streptococcus pyogenes,* or *Streptococcus agalactiae.* In another embodiment, the disclosure provides a glycoprotein prepared by a process comprising steps (a)-(b).

10. Raising Immune Responses

Provided herein are a method of eliciting an immunoprotective antibody response to an antigen in a subject by administering to the subject a conjugate or composition as described herein. The conjugate or composition will typically be combined with an excipient suitable for parenteral administration.

Also provided are the conjugates and compositions for use in eliciting an immunoprotective antibody response to an antigen. Also provided are the use of conjugates and compositions for the manufacture of a medicament for eliciting an immunoprotective antibody response to an antigen.

The immunoprotective antibody response means that the conjugate and compositions can be used, for example, to provide active immunization for the prevention of invasive disease caused by *S. pneumoniae*, for the prevention of otitis media caused by *S. pneumoniae*, for the prevention of pneumonia caused by *S. pneumoniae*, for active immunization of subjects at risk of exposure to *N. meningitidis* to prevent invasive disease, etc.

The invention is illustrated in the following examples. The materials, methods, and examples are illustrative only and not intended to be limiting. Numerous variations, changes, and substitutions will occur to those skilled in the art without departing from the invention. The examples are carried out using well known and routine techniques to those of skill in the art, except where otherwise described in detail.

EXAMPLES

Example 1: Synthesis of Single-Site eCRM Moieties K11TAG, K25TAG, K34TAG, K38TAG, K40TAG, K52TAG, K60TAG, K77TAG, K83TAG, K91TAG, K96TAG, and K103TAG eCRM was expressed in a cell-free protein synthesis (CFPS) extract provided by Sutro Biopharma, Inc. (South San Francisco, Calif.). Features and preparation of such an extract are described in other publications; in this case the extract was generally prepared as described in Zawada et al., 2011, *Biotechnol. Bioeng.,* 108(7), 1570-1578 with the following modifications from US2016/0257946: (1) cell-free extract was prepared from an OmpT sensitive RF-1 attenuated strain engineered to overexpress *E. coli* DsbC; (2) cell-free extract was prepared from a similar RF-1 attenuated *E. coli* strain engineered to produce an orthogonal CUA-encoding tRNA for insertion of a non-natural amino acid at an amber stop codon; (3) the cell-free extracts from (1) and (2) were blended (at a ratio of 85:15) and treated with 50 µM iodoacetamide for 30 min at RT (20° C.); and (4) the blended extracts were added to a premix containing all other components of a cell-free protein synthesis system except for DNA encoding eCRM. The final concentration in the cell-free protein synthesis reaction was 30% (by volume) cell extract, 2 mM para-methylazido-L-phenylalanine (pAMF) (RSP Amino Acids, Shirley, Mass.), 5 µM pAMF-specific tRNA synthetase ('RS'), 2 mM GSSG (oxidized glutathione), 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for tyrosine and phenylalanine), 4 mM sodium oxalate, 1 mM putrescine, 1.5 mM spermidine, 15 mM potassium phosphate, 100 nM T7 RNAP, and 2.5 µM eCRM plasmid encoding the nnAA variants. The cell-free synthesis reactions were initiated by the addition of the plasmid DNA encoding eCRM.

The reactions were incubated 14 h on a shaker at 650 rpm in 48-well Flower plates (m2p-labs # MTP-48-B). After the incubation period, the reaction was held at 4° C. until it was processed for purification or analysis. Following the cell-free protein synthesis reaction, the mixture containing pAMF-eCRM was transferred to a 96-well plate (DyNa Block™, 2 mL; Labnet, Edison, N.J.) and centrifuged at 5000×g for 15 minutes at 40° C.

First, an optimization experiment was performed to assess the best temperature and additives for the CFPS production of eCRM. CFPS reactions were performed at 30, 25, and 20, degrees Celsius, with additional supplementation of CUA-encoding tRNA (0, 1, 2, 4, 8, 12% v/v) and nnAA/synthetase mix (50, 100, 150, 200 µg/ml) at each of the three temperatures. Samples of CFPS mixture pre- and post-centrifugation were collected and analyzed by SDS-PAGE electrophoresis, and bands were quantitated by densitometry to assess the amount of soluble protein (post-centrifugation sample) of total protein (pre-centrifugation sample) produced in each condition.

FIG. 1 shows yield of nnAA-eCRM produced in each condition as assessed by quantitative densitometry. While CFPS reactions at 30 degrees produced a relatively small fraction of soluble protein (max ~0.33 of total among all conditions), the yield of soluble protein was enhanced (>~0.40 soluble/total among all conditions) at 25 degrees and further enhanced (>~0.60 soluble/total among all conditions) at 20 degrees. At both of the "low" temperature conditions, soluble protein yield is further enhanced by increasing the tRNA concentration (1-12× show increasing yield), whereas increasing the nnAA/synthetase concentration had a detrimental to no effect on soluble yield.

Based on the experiment of FIG. 1, temperatures less than 20 degrees and tRNA concentration of at least 20 µM were chosen for the synthesis of K11TAG, K25TAG, K34TAG, K38TAG, K40TAG, K52TAG, K60TAG, K77TAG, K83TAG, K91TAG, K96TAG, and K103TAG variants.

Figure 2A:
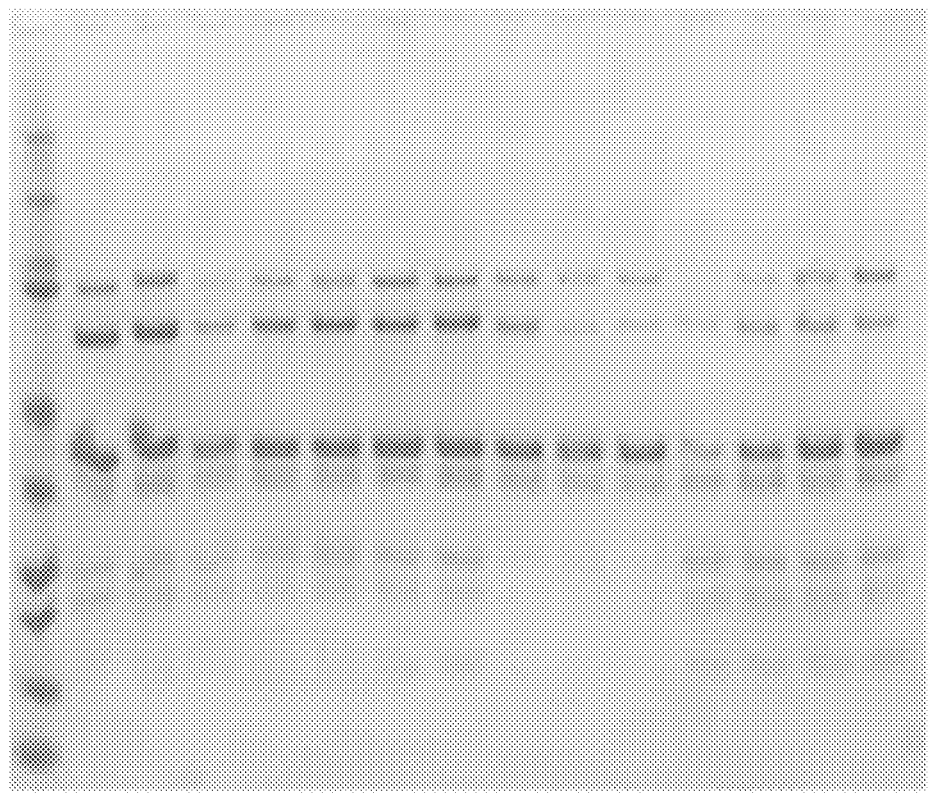
FIG. 2A shows a coumassie gel image and FIG. 2B shows a fluorescent gel image demonstrating the relative yield of synthesized protein (FIG. 2A) and the ability of pAMF incorporated into eCRM to react with DBCO-fluorescein (FIG. 2B) for single-site eCRM produced in cell-free protein synthesis (CFPS) reactions.
Figure 2B:
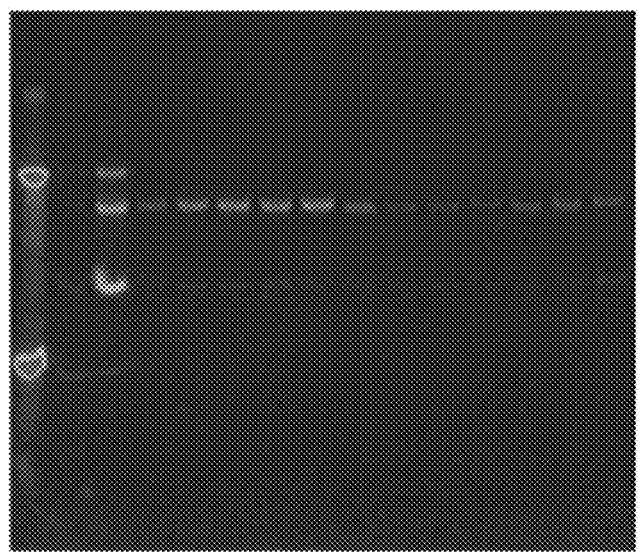

CFPS reactions were performed as above. For convenience of purification in these preliminary experiments a histidine tag (GSGHHHHHH; SEQ ID NO:10) was fused to the C-terminus of the carrier protein sequence via the expression vector, and purification of eCRM variants from the post-centrifugation supernatant was carried out by using IMAC Phytips (Phynexus, San Jose, Calif.) containing 40 µL resin. The resin bed was pre-equilibrated in IMAC equilibration buffer (1×PBS and 10 mM imidazole) and the clarified supernatant was pipetted up and down 10 times through equilibrated IMAC Phytips at a flow rate of 4.2 µL/min. The bound protein was washed with IMAC equilibration buffer, and then eluted with 125 µL IMAC elution buffer (1×PBS and 0.5M imidazole). The histidine tag is not essential and is omitted for larger-scale purification.

nnAA incorporation and reactivity was assessed by SDS-PAGE and fluorescent analysis after reaction with DBCO-fluorescein (FIG. 2). 2-12 µM eCRM was incubated with 50 µM DBCO-fluorescein for 16 hours, subjected to nonreducing SDS-PAGE, and visualized with coomassie blue (visible light) and a Sypro-ruby filter set (fluorescent, fluorescein). FIG. 2 shows the corresponding coomassie (left) and fluorescent (right) gel images showing the ability of pAMF incorporated into eCRM to react with DBCO. K25, K34, K38, and K40 amber substitutions show high expression and conjugation efficiency, while others do not.

Example 2: Design of Multiple nnAA eCRM

Multiple nnAA eCRM variants were selected as described in the detailed description above. Variants were synthesized via CFPS and tested along the lines of Example 1.

TABLE 2

Multiple nnAA eCRM variants

| Variant # | K25 | K34 | K38 | K40 | K213 | K215 | K228 | K245 | K265 | K386 | K523 | K527 |
|---|---|---|---|---|---|---|---|---|---|---|---|---|
| 1 | ✓ | | | | ✓ | | ✓ | | ✓ | ✓ | ✓ | |
| 2 | ✓ | | | | ✓ | | ✓ | | ✓ | ✓ | | ✓ |
| 3 | ✓ | | | | ✓ | | | ✓ | ✓ | ✓ | ✓ | |
| 4 | ✓ | | | | ✓ | | | ✓ | ✓ | ✓ | | ✓ |
| 5 | ✓ | | | | | ✓ | ✓ | | ✓ | ✓ | ✓ | |
| 6 | ✓ | | | | | ✓ | ✓ | | ✓ | ✓ | | ✓ |
| 7 | ✓ | | | | | ✓ | | ✓ | ✓ | ✓ | ✓ | |
| 8 | ✓ | | | | | ✓ | | ✓ | ✓ | ✓ | | ✓ |
| 9 | | ✓ | | | ✓ | | ✓ | | ✓ | ✓ | ✓ | |
| 10 | | ✓ | | | ✓ | | ✓ | | ✓ | ✓ | | ✓ |
| 11 | | ✓ | | | ✓ | | | ✓ | ✓ | ✓ | ✓ | |
| 12 | | ✓ | | | ✓ | | | ✓ | ✓ | ✓ | | ✓ |
| 13 | | ✓ | | | | ✓ | ✓ | | ✓ | ✓ | ✓ | |
| 14 | | ✓ | | | | ✓ | ✓ | | ✓ | ✓ | | ✓ |
| 15 | | ✓ | | | | ✓ | | ✓ | ✓ | ✓ | ✓ | |
| 16 | | ✓ | | | | ✓ | | ✓ | ✓ | ✓ | | ✓ |
| 17 | | | ✓ | | ✓ | | ✓ | | ✓ | ✓ | ✓ | |
| 18 | | | ✓ | | ✓ | | ✓ | | ✓ | ✓ | | ✓ |
| 19 | | | ✓ | | ✓ | | | ✓ | ✓ | ✓ | ✓ | |
| 20 | | | ✓ | | ✓ | | | ✓ | ✓ | ✓ | | ✓ |
| 21 | | | ✓ | | | ✓ | ✓ | | ✓ | ✓ | ✓ | |
| 22 | | | ✓ | | | ✓ | ✓ | | ✓ | ✓ | | ✓ |
| 23 | | | ✓ | | | ✓ | | ✓ | ✓ | ✓ | ✓ | |
| 24 | | | ✓ | | | ✓ | | ✓ | ✓ | ✓ | | ✓ |
| 25 | | | | ✓ | ✓ | | ✓ | | ✓ | ✓ | ✓ | |
| 26 | | | | ✓ | ✓ | | ✓ | | ✓ | ✓ | | ✓ |
| 27 | | | | ✓ | ✓ | | | ✓ | ✓ | ✓ | ✓ | |
| 28 | | | | ✓ | ✓ | | | ✓ | ✓ | ✓ | | ✓ |
| 29 | | | | ✓ | | ✓ | ✓ | | ✓ | ✓ | ✓ | |
| 30 | | | | ✓ | | ✓ | ✓ | | ✓ | ✓ | | ✓ |

TABLE 2-continued

Multiple nnAA eCRM variants

| Variant # | K25 | K34 | K38 | K40 | K213 | K215 | K228 | K245 | K265 | K386 | K523 | K527 |
|---|---|---|---|---|---|---|---|---|---|---|---|---|
| 31 | | ✓ | | | ✓ | | | ✓ | ✓ | ✓ | ✓ | |
| 32 | | ✓ | | | ✓ | | | ✓ | ✓ | ✓ | | ✓ |

Further variants including different numbers of Lys→pAMF substitutions were prepared. In general it was found that higher numbers of substitutions gave carriers which led to higher MW conjugates (e.g. for serotype 14, rising from 998 kDa with 2 substitutions to 1238 kDa with 3 substitutions, to 1789 kDa with 4 substitutions, and to 2547 kDa with 5 substitutions) but the carriers had lower solubility. Carriers with six pAMF residues generally provided both good solubility (>>50 mg/mL) and immunogenicity. The high solubility was surprising because replacement of charged Lys residues in the native sequence with hydrophobic pAMF residues increased the hydrophobicity of CRM197, which is a protein whose hydrophobicity has already been reported to affect its solubility (Orr et al. 1999 *Infect Immun* 67:4290-4). Thus these results show that it is possible to maintain the same attachment sites which have been used in known CRM197 conjugates (namely Lys residues) without causing insolubility when the charged residues are lost.

Studies of CRM197 have identified T-cell epitopes within residues P272-D291, V322-G384, and Q412-I458 of SEQ ID NO:1. These epitope regions include Lys residues K420, K441, K446, K448, and K457, so substitution of these lysine residues might disrupt T-cell epitopes which underpin CRM197's activity. Preferred Lys residues for substitution by a nnAA in SEQ ID NO:1 are thus K25, K34, K38, K40, K213, K215, K228, K245, K265, K386, K523, and K527, as shown in Table 2 above.

It is desirable that conjugated polysaccharides are not localized too tightly in one area of the CRM197 surface. Thus, within closely-spaced residues, it is preferred to pick (i) only one of K25, K34, K38, and K40 and (ii) either K213 or K215. Moreover, going beyond its primary structure, studies of CRM197's 3D structure identify two general regions (the first running to Asn-374 and the second running from Ser-375), so it is also preferred to pick residues in both of these regions e.g. for 6 substitutions, to pick 3 in each region. This general guidance permits polysaccharides to be spatially separated when attached to the CRM197 carrier.

One sequence which has been particularly useful in creating pneumococcal conjugates is variant 12 in Table 2, in which K34, K213, K245, K265, K386 and K527 are replaced by a nnAA. This protein has amino acid sequence SEQ ID NO:9 where each X is pAMF (a preferred nnAA). This protein is used for preparing the conjugates described below.

Lysine residues are useful because they are the amino acids which have been used in known CRM197 conjugates, so nnAAs at these positions permit conjugation to occur at the same sites as are already known to be compatible with CRM197. As mentioned above, however, loss of charged lysine can lead to structural changes, increased hydrophobicity, and lower solubility. Modification of phenylalanine residues to phenylalanine-based nnAAs (such as para-azido-Phe, para-azido-methyl-Phe, para-fluoro-Phe, para-acetyl-Phe, or para-benzoyl-Phe) would reduce the risk of these changes. Thus residues F13, F54, F124, F128, F141, F168, F251, F390, F531, or F532 are also selected for substitution, singly and in combination. Substitution of up to five Phe residues by pAMF was tested and provided soluble conjugates, but with a tendency for lower MW conjugates than achieved with the same number of multiple Lys substitutions.

Rather than substituting amino acids within CRM197 it is also possible to insert nnAA within the CRM197 sequence. For example, a TAG codon encoding pAMF is inserted directly downstream of lysine residues K34, K213, K245, K265, K386 and K527, either individually (to create six point insertions) or in combination (inserting 2, 3, 4, 5 or 6 nnAA). Carriers with inserted nnAA, such as these, are useful for making the conjugates and multivalent compositions as described above.

Example 3: Identification of T-Cell Epitopes in Pfs25

The T-cell activating epitopes of malaria ookinete specific surface protein Pfs25 are determined experimentally along the lines of the methods described in, e.g., Diethelm-Okita et al., *J Infect Dis.* 1997 February; 175(2):382-91. Briefly, peptide fragments of 20 amino acids and overlapping by 5 amino acids are synthesized corresponding to the complete expressed sequence of Pfs25. CD8+-depleted and CD4+-enriched human peripheral blood lymphocytes (PBL) are obtained from multiple subjects. The PBLs are plated in triplicate and cultured with the individual synthetic peptides spanning the Pfs25 sequence serving as experimental stimuli. The proliferation of PBLs in response to each peptide fragment is measured by pulsing the cultures with [$^3$H]-thymidine and compared across cultures originating from different individuals. Pfs25 fragments that stimulate proliferation are identified to comprise a T-cell epitope. Fragments that stimulate proliferation of PBLs from a plurality or all subjects are classified as comprising a universal or immunodominant T-cell epitope in Pfs25.

Example 4: General Protocol for Polysaccharide Activation with Sodium Meta-Periodate Serotype polysaccharides (~30 μmol) were dissolved in aqueous solution (10 mM HCl). The solution was then heated at 45° C. for 30 min and then cooled, at which time NaOH solution was added to adjust pH to 6.70. The reaction mixture was dialyzed using AMICON ultra centrifuge (30 kDa MWCO) against HPLC grade water. The supernatant was transferred to a 50 mL of falcon tube, acetate buffer (pH 5.35) was added to 25 mM, and 0.5 eq $NaIO_4$ was added. The mixture was stirred at 25° C. for 17 hours, after which the time, the oxidized sample was optionally treated with an excess of sodium borohydride (10 eq) and purified using AMICON ultra centrifuge (30 kDa MWCO) against several changes of HPLC grade water to give oxidized polysaccharide solution.

Example 5: General Procedure for Periodate-Oxidized Polysaccharide Derivatization with DBCO Oxidized polysaccharide (~30 μmol) was combined with DBCO-$PEG_4$-$NH_2$ (~30 μmol) or DBCO-$NH_2$ (~30 μmol) in 72 mM sodium phosphate pH 6.79 containing 16% DMSO at 25° C. The reaction mixture was then stirred at 25° C. for 30 min, after which time sodium cyanoborohydride solution (16 mg/ml solution in water, 59.54 µmol, 20 equivalents) was added and kept stirring for overnight-2 days at 25° C. The reaction mixture was then washed 3× with ethyl acetate, transferred to an AMICON ultra centrifuge (30 kDa MWCO), and then dialyzed using 6 exchanges of 20% ethanol in water followed by 3 exchanges with water to give a solution of type the polysaccharide-DBCO derivative. The polysaccharide-DBCO derivative was then compounded with 10:1 (w/w) sucrose and lyophilized to give a white powder for use in the next conjugation reaction.

Example 6: General Protocol for Polysaccharide Activation with CDAP

Capsular polysaccharide (30 mg) (PS 3) was dissolved in aqueous solution (13.5 mL $H_2O$ with 1.5 mL 2M acetic acid). The mixture was heated at 85° C. for 1 hour and an excess of magnesium chloride was added from a 1M solution after cooling to ambient temperature. The resultant polysaccharide was purified using Amicon centrifugal 30 kDa MWCO dialysis using 6 exchanges of water.

Prepared polysaccharide was then dissolved in pH 7.0 water and cyanylation reagent CDAP (1-Cyano-4-dimethylaminopyridinium tetrafluoroborate, in acetonitrile) was added. The solution was then adjusted to pH 9.5 or trimethylamine (2.5 eq) was added. DBCO-$PEG_4$-$NH_2$ or DBCO-$NH_2$ was then added to the solution. Solution was adjusted to 5% DMSO and stirred overnight at 25° C. The solution was washed 3× with 20 mL ethyl acetate, and purified using Amicon 30 kDa MWCO dialysis units using 7 exchanges with 3% DMSO, 20% ethanol, 0.9% sodium chloride and 3 exchanges with water. The polysaccharide-DBCO derivative was then compounded 10:1 (w/w) with sucrose and lyophilized.

Example 7: General Procedure for Conjugation of Polysaccharide-DBCO with eCRM Polysaccharide—DBCO sample lyophilized and compounded with 10:1 w/w sucrose (prepared by the procedure of examples 4 or 5) was dissolved in 0.9% NaCl and mixed with eCRM in solution to provide a PS:eCRM input mass ratio of 1:1 (w/w). The reaction mixture was gently mixed by hand before gently mixing on an orbital shaker at room temperature (20° C.) for 18 hours. The click reaction was quenched by the addition of an excess of sodium azide solution. The conjugated PS-eCRM mixture was transferred to a prewashed dialysis tube (SpectrumLab Float-A-Lyzer G2, Cat. No. G235060, 300K MWCO) and then dialyzed against 5 exchanges of 0.9% sodium chloride solution over 24 hours. The dialyzed solution was filtered through a Millex-GP (0.22 µm, 33 mm polyethersulfone) to give a PS-eCRM conjugate solution.

Example 8: Preparation of Pneumococcal PS Serotype 1 Conjugates to an eCRM from Table 2

1. Oxidation
   Purity of type 1 PS: 80% (uronic)
   Mol. wt: 625 g $mol^{-1}$ (per repeating unit)
Reaction Procedure:
   The native polysaccharide (19.7 mg, corrected to 80%, 15.8 mg, 25.2 µmol) was dissolved in 9.85 mL of aqueous solution (7.0 mL water and 2.85 mL acetate buffer, 200 mM, pH 5.5). To this solution was added 300 µL of sodium periodate solution (104 µg, 3.78 µmol, 0.15 eq). The mixture was stirred at 25° C. for 18 hours after which time a large molar excess of sodium borohydride (10 mol. eq) was added. The oxidized PS was purified using Amicon centrifugal 30 k Da MWCO dialysis using at least 6 exchanges with water to give purified PS-1 solution.

| Mol eq of $NaIO_4$ | PS 1 (mg) | Vol. after purification (mL) | Uronic assay (µM) | % Oxidation (BCA) | % Oxidation (aldehyde assay) | PS yield (%) | Note |
|---|---|---|---|---|---|---|---|
| 0.15 | 19.7 | 2.86 | 11040 | 1.4 | n/d | 100 | N/A |

2. DBCO Derivatization
Reaction Procedure:
   PS1-OX (15.8 mg, 25.2 µmol) was dissolved in phosphate buffer (3.6 mL, 50 mM pH 7.0) to which was added DBCO-$PEG_4$-NHS ester (1.0 eq., 649.1 g $mol^{-1}$ in DMSO, 0.35 mL). The reaction mixture was stirred at 37° C. for two days in a thermostatted water bath followed by extraction with ethyl acetate (3×20 mL). The DBCO derivative was purified by centrifugal dialysis units (Amicon 30 kDa MWCO) using 6 exchanges with 20% ethanol in water followed by 3 exchanges with water (12 mL each) to give type the 1-DBCO derivative. To this solution (2.20 mL, 9.59 mg) was added a solution of sucrose (96 mg in 1 mL water). The combined solution were divided into three equal portions and each lyophilized to give three samples of white powder. Each sample contained 3.18 mg of 1 DBCO and 32 mg of sucrose for use in the next conjugation reaction.

| oxidized PS 1 (mg) | Vol. after purification (mL) | Uronic assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 15.8 | 2.20 | 6976 | 0.280 × 4 | 116.16 | 1.67 | 65 | 602 |

3. Conjugation of PS 1-DBCO Derivative with eCRM
   PS 1-DBCO: 3.18 mg (with 32 mg sucrose) lyophilized powder
   % DBCO: 1.67%
   CRM concentration: 6.5 mg/mL solution
   PS:CRM (input ratio): 1:1
Reaction Procedure:
   1-DBCO was dissolved in azido-functionalized eCRM solution (0.51 mL) to provide a PS1:CRM input mass ratio of 1:1 (w/w). Further dilution with 0.9% sodium chloride solution (0.22 µm filtered) was necessary to 1.0 mg $mL^{-1}$ to mitigate gel formation. The solution was very gently mixed by hand before gently mixing on an orbital shaker at room temperature (20° C.) for 18 hours. The click reaction was quenched by the addition of sodium azide solution (10 mg/mL, 50 µL). The CRM conjugate was transferred to two pre-washed dialysis tubes (SpectrumLab Float-A-Lyzer G2, 300K MWCO) and then dialyzed with 0.9% sodium chloride solution for 24 hours (3 exchanges, 800 ml each). The dialyzed solution was filtered through a Millex-GP syringe filter (0.22 μm, 33 mm polyethersulfone) to give a 1-CRM conjugate solution.

| PS 1-DBCO (mg) | CRM (mg) | Vol. after purification (mL) | Anthrone (mg/mL) | PS recovery (%) | BCA (CRM) (mg/mL) | CRM recovery (%) | PS:CRM CJD* Ratio | Free PS (%) | SEC-MALS MDa |
|---|---|---|---|---|---|---|---|---|---|
| 3.18 | 3.315 | 7.17 | 0.177 | 40 | 0.099 | 21 | 1.79:1 | 9.39 | 2.13 |

*CJD = dialysed conjugate

Example 9: Preparation of Pneumococcal PS Serotype 2 Conjugates to an eCRM from Table 2

1. Oxidation
   Purity of type 2 PS: 80%
   Mol. wt: 960.84 g mol$^{-1}$
   Reaction Procedure:
   The native polysaccharide (25.5 mg, 26.5 μmol) was dissolved in 12.75 mL of aqueous solution (9.24 mL water and 3.51 mL acetate buffer, 200 mM, pH 5.5). To this solution was added 216 μL of sodium periodate solution (5.26 mg/ml, 0.20 eq). The mixture was stirred at 25° C. for 18 hours with monitoring by UV absorption at 222 nm for NaIO$_4$. The oxidized PS was purified using Amicon centrifugal 100 kDa MWCO dialysis using at least 6 exchanges with water to give purified PS-2 solution.

| Mol eq of NaIO$_4$ | PS 2 (mg) | Vol. after purification (mL) | Anthrone assay (μM) | % Oxidation (BCA) | % Oxidation (aldehyde assay) | PS yield (%) | Note |
|---|---|---|---|---|---|---|---|
| 0.20 | 25.5 | 2.28 | 9041 | 22.8 | 5.4 | 78 | N/A |

2. DBCO Derivatization
Reaction Procedure:
   PS2-OX (18.1 mg, 18.8 μmol) in 2.14 mL water was diluted with phosphate buffer (1.95 mL, 200 mM pH 6.0) to which was added DBCO-PEG$_4$-NH$_2$ (9.85 mg, 1 eq., in DMSO, 0.197 mL). After 25 minutes NaCNBH$_3$ (2.36 mg, 2 eq. 59 μL from a solution in H$_2$O) was added. The reaction mixture was stirred at 25° C. for two days in a thermostatted water bath followed by addition of phosphate buffer (0.5 mL of 200 mM pH=6). To this was added NaBH$_4$ (60 μL of a 10 mg/mL aqueous solution, 1 eq.) After stirring for 30 min the mixture was extraction with ethyl acetate (4×5 mL). The residual ethyl acetate was removed by bubbling with nitrogen gas and the mixture transferred to 100 kDa MWCO Amicon centrifuge filters. The DBCO derivative was purified by centrifugal dialysis using 1 exchange of water followed by 6 exchanges with 20% ethanol in water followed by 3 exchanges with water (12 mL each) to give type the 2-DBCO derivative. To this solution (2.14 mL, 14.3 mg) was added a solution of sucrose (100 mg in 1 mL water). The combined solution were divided into three almost equal portions and each lyophilized to give three samples of white powder (4.96 mg, 4.96 mg and 4.4 mg).

| oxidized PS 2 (mg) | Vol. after purification (mL) | Anthrone assay (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 18.1 | 2.14 | 1956 | 0.848 × 4 | 315.5 | 4.03 | 89 | 375 |

3. Conjugation of PS 2-DBCO Derivative with eCRM
   PS 2-DBCO: 4.4 mg (with 32 mg sucrose) lyophilized powder
   % DBCO: 4.03%
   CRM concentration: 3.18 mg/mL solution
   PS:CRM (input ratio): 1.5:1
   Reaction Procedure:
   PS2-DBCO was dissolved in 0.9% NaCl (3.01 mL) and DMSO (0.44 mL) was added. Then azido-functionalized eCRM solution (0.95 mL) was added to provide a PS2:CRM input mass ratio of 1.5:1 (w/w). The solution was very gently mixed by hand before gently mixing on an orbital shaker at room temperature (20° C.) for 18 hours. The click reaction was quenched by the addition of sodium azide solution (10 mg/mL, 100 μL). The CRM conjugate was transferred to two pre-washed dialysis tubes (SpectrumLab Float-A-Lyzer G2, 300K MWCO) and then dialyzed with 0.9% sodium chloride solution for 24 hours (5 exchanges, 1000 ml each). The dialyzed solution was filtered through a Millex-GP syringe filter (0.22 μm, 33 mm polyethersulfone) to give a 2-CRM conjugate solution.

| PS 2-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 4.4 | 2.93 | 4.77 | 0.683 | 91 | 0.387 | 75 | 1.76:1 | LLOQ | 1.37 |

Example 10: Preparation of Pneumococcal PS Serotype 3 Conjugates to an eCRM from Table 2

1. Hydrolysis

Purity of type 3 PS: 86% (anthrone)

Mol. wt: 360.3 g mol$^{-1}$

Reaction Procedure:

The native polysaccharide 3 (30.0 mg) was dissolved in 15.0 mL of aqueous solution (13.5 mL water and 1.5 mL acetic acid, 2M). The mixture was heated at 85° C. for 1 hour after which time magnesium chloride solution was added (1.5 mL, 1 M) after cooling for ambient temperature. The hydrolyzed PS was purified using Amicon centrifugal 30 k Da MWCO dialysis using at least 6 exchanges with water to give purified PS-3 solution which was then lyophilized in two equal aliquots.

| PS 3 (mg) | Water (mL) | AcOH, 2 M (mL) | Anthrone assay (µM) | PS yield (%) | MALS (kDa) |
|---|---|---|---|---|---|
| 30.0 | 13.5 | 1.50 | 10477.22 | 85 | 294 |

2. DBCO Derivatization

Reaction Procedure:

Hydrolyzed PS3 (12.75 mg, 35.4 µmol) was dissolved in water (6.4 mL) adjusted to pH 7.0 with sodium hydroxide solution (0.2M, 100 µL). The cyanylation reagent, CDAP, was then added dropwise (0.426M in acetonitrile, 0.2 eq., 16.7 µL). After 90 s, the solution was quickly adjusted to pH 9.5 with sodium hydroxide solution (0.2M, 300 µL). DBCO-PEG$_4$-NH$_2$ (0.032M in DMSO, 0.1 eq., 523 g mol$^{-1}$, 0.110 mL) was added immediately, dropwise. Additional DMSO was added to give 5% (v/v) DMSO (0.320 mL). The reaction mixture was stirred at 25° C. overnight in a thermostatted water bath followed by filtration through a 0.22 µm PES syringe filter. The filtrate was extracted with ethyl acetate (3×20 mL). The DBCO derivative was purified by centrifugal dialysis units (Amicon 30 kDa MWCO) using a total of 7 exchanges with 3% DMSO, 20% ethanol in water, 0.9% sodium chloride followed by 3 exchanges with water (12 mL each) to give type the 3-DBCO derivative. The aqueous solution was then filtered through a 0.45 µm PVDF syringe filter. To this solution (3.84 mL, 8.52 mg) was added a 10-fold mass excess of sucrose (85 mg in 0.85 mL water). The combined solution was divided into three portions which were lyophilized to give three samples of white powder. Two samples contained 5.0 mg of 3-DBCO and 50 mg of sucrose for use in the next conjugation reaction, with 8.5 mg in the remaining sample, for a total of three.

| hydrolyzed PS 3 (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 12.8 | 4.04 | 2063.47 | 1.095 × 3 | 102.64 | 5.0 | 70 | 409 |

3. Conjugation of PS 3-DBCO Derivative with eCRM

PS 3-DBCO: 5.0 mg (with 50 mg sucrose) lyophilized powder

% DBCO: 5.0%

CRM concentration: 4.0 mg/mL solution

PS:CRM (input ratio): 1:1

Reaction Procedure:

3-DBCO was dissolved in 0.9% sodium chloride solution (6.39 mL, 0.22 µm filtered), phosphate buffer (pH 7.0, 0.5M, 0.333 mL) and DMSO (0.833 mL). Azido-functionalized eCRM solution (0.770 mL) was added dropwise to provide a PS3:CRM input mass ratio of 1:1 (w/w). The solution was very gently mixed by hand before gently mixing on an orbital shaker at room temperature (20° C.) for 18 hours. The click reaction was quenched by the addition of sodium azide solution (10 mg/mL, 50 µL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give a 3-CRM conjugate solution.

| PS 3-DBCO (mg) | CRM (mg) | Vol. after purification (mL) | Anthrone (mg/mL) | PS recovery (%) | BCA (CRM) (mg/mL) | CRM recovery (%) | PS:CRM CJF* Ratio | Free PS (%) | SEC-MALS MDa |
|---|---|---|---|---|---|---|---|---|---|
| 5.0 | 5.0 | 3.63 | 0.402 | 70 | 0.423 | 74 | 0.95:1 | 2.55 | 3.2 |

*CJF = dialysed and filtered conjugate

Example 11: Preparation of Pneumococcal PS Serotype 3 Conjugates to an eCRM from Table 2

1. Oxidation
Purity of type 3 PS: 86% (anthrone)
Mol. wt: 360.3 g mol$^{-1}$
Reaction Procedure:

The native polysaccharide 3 (14.4 mg, corrected to 86%, 12.4 mg, 34.4 µmoles) was dissolved in 7.2 mL of aqueous solution (5.9 mL water and 1.3 mL acetate buffer, 200 mM, pH 5.5). To this solution was added 300 µL of sodium periodate solution (1.10 mg, 5.16 µmol, 0.15 eq.). The mixture was stirred at 25° C. for 18 hours. The oxidized PS was purified using Amicon centrifugal 30 k Da MWCO dialysis using at least 6 exchanges with water to give purified PS3-OX solution.

| Mol eq of NaIO$_4$ | PS 3 (mg) | Vol. after purification (mL) | Anthrone assay (µM) | % Oxidation (BCA) | % Oxidation (aldehyde assay) | PS yield (%) |
|---|---|---|---|---|---|---|
| 0.15 | 14.4 | 1.84 | 15940.33 | 3.9 | 0.8 | 73 |

2. DBCO Derivatization
Reaction Procedure:

PS3-OX (9.05 mg, 25.1 µmol) was dissolved in phosphate buffer (2.11 mL, 50 mM, pH 6.7) to which was added DBCO-PEG$_4$-NH$_2$ (1.0 eq., 523 g mol$^{-1}$ in DMSO, 0.40 mL). The reaction mixture was stirred at 25° C. for 25 mins. prior to the addition of a solution of sodium cyanoborohydride (2 eq., 44.5 mg/mL, 35 µL) and stirred for two days. At this time the reaction mixture was extracted with ethyl acetate (3×20 mL). The DBCO derivative was purified by centrifugal dialysis units (Amicon 30 kDa MWCO) using 6 exchanges with 20% ethanol in water followed by 3 exchanges with water (12 mL each) to give type the 3-DBCO derivative. To this solution (3.20 mL, 8.60 mg) was added a 10-fold mass excess of sucrose (86 mg in 0.86 mL water). The combined solution was divided into four portions and each lyophilized to give three samples of white powder. Three samples contained 2.0 mg of 3-DBCO and 20 mg of sucrose for use in the next conjugation reaction, with 2.6 mg in the remaining sample, for a total of four.

| oxidized PS 3 (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 15.8 | 2.76 | 2681.28 | 0.683 × 3 | 64.47 | 2.3 | 95 | 304 |

3. Conjugation of PS 3-DBCO Derivative with eCRM
PS 3-DBCO: 2.0 mg (with 20 mg sucrose) lyophilized powder
% DBCO: 2.3%
CRM concentration: 4.0 mg/mL solution
PS:CRM (input ratio): 1:1
Reaction Procedure:

3-DBCO was dissolved in 0.9% sodium chloride solution (0.400 mL, 0.22 µm filtered) and DMSO (0.100 mL). Azido-functionalized eCRM solution (0.330 mL) was added dropwise to provide a PS3:CRM input mass ratio of 1:1 (w/w). The solution was very gently mixed by hand before gently mixing on an orbital shaker at room temperature (20° C.) for 48 hours. The click reaction was quenched by the addition of sodium azide solution (10 mg/mL, 50 µL). The CRM conjugate was transferred to two pre-washed dialysis tubes (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give a 3-CRM conjugate solution.

| PS 3-DBCO (mg) | CRM (mg) | Vol. after purification (mL) | Anthrone (mg/mL) | PS recovery (%) | BCA (CRM) (mg/mL) | CRM recovery (%) | PS:CRM CJF ratio | Free PS (%) | SEC-MALS MDa |
|---|---|---|---|---|---|---|---|---|---|
| 2.0 | 2.0 | 3.63 | 0.226 | 41 | 0.307 | 59 | 0.74:1 | 21.0 | 3.42 |

Example 12: Preparation of Pneumococcal PS Serotype 4 Conjugates to an eCRM from Table 2

1. Oxidation

Purity of type 4 PS: 80% (Anthrone)
Mol. wt: 825.78
Reaction Procedure:

Type 4 PS (27.5 mg, 33.30 µmol) powder was dissolved in 13.75 mL of aqueous solution (12.38 mL of water and 1.37 mL of 0.1 M HCl). The solution was then heated at 45° C. for 30 min and then cooled, at which time, NaOH solution (0.1 M, 1.37 mL) was added to adjust pH to 6.70. The reaction mixture was dialyzed using AMICON ultra centrifuge (30 kDa MWCO 6-12 mL) by 3 exchanges with HPLC grade water (12 mL each). The supernatant was transferred to a 50 mL of falcon tube with 9.84 mL of water. To this solution was added 3.43 mL of 200 mM acetate buffer (pH 5.35) and 632 µL of NaIO$_4$ solution (3.56 mg, 16.65 µmol, 0.5 eq). The mixture was stirred at 25° C. for 17 hours, after which the time, the oxidized sample was purified using AMICON ultra centrifuge (30 kDa MWCO 6-12 mL) 6 exchanges (12 mL) of HPLC grade water to give oxidized PS-4 solution.

| Mol eq of NaIO$_4$ | mg of PS 4 | Vol. after purification ml | Anthrone uM | % oxidation (BCA) | % oxidation (aldehyde assay) | PS yield (%) |
|---|---|---|---|---|---|---|
| 0.5 | 27.5 | 2.71 | 12078 | 10.8 | 2.58 | 101 |

2. DBCO Derivatization

Reaction Procedure:

To a solution of oxidized (assume 10% oxidation level) Type 4 PS (24.58 mg, 29.77 µmol, 2.4 mL water) was added buffer solution (1.8 mL of 200 mM phosphate buffer, pH=6.79), DMSO (0.6 mL) and a solution of DBCO-PEG-4-NH$_2$ (15 mg in 200 µL of DMSO; 28.65 µmol, 9.6 equivalent) all at 25° C. The reaction mixture was then stirred at 25° C. for 30 min, after which time 224 µL of a sodium cyanoborohydride solution (5.0 mg in 300 µL of water; 59.54 µmol, 20 equivalent) was added and kept stirring for 2 days at 25° C. The reaction mixture was diluted with phosphate buffer (500 µL of 200 mM solution, pH=6) before adding 225 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water followed by 3 exchanges with water (12 mL each) to give a solution of type the 4 DBCO derivative. To this solution (4.75 mL, 15.25 mg) was added a solution of sucrose (153 mg in 1 mL water). The combined solution were divided into three portions and each lyophilized to give three samples of white powder. Two samples contained 5.35 mg of 4 DBCO and 54 mg of sucrose and one sample contained 4.55 mg of 4 DBCO and 45 mg of sucrose for use in the next conjugation reaction.

| mg of oxidized PS 4 | Vol. after purification ml | Anthrone uM | DBCO derivatization 309 nm Abs | DBCO derivatization uM | % DBCO (%) | PS-DBCO yield (%) | SEC-MALS kDa |
|---|---|---|---|---|---|---|---|
| 24.58 | 5.25 | 3897 | 0.472 × 3 | 137.16 | 3.52 | 69 | 343 |

3. Conjugation of PS 4-DBCO Derivative with eCRM

PS 4-DBCO: 5.35 mg (with 54 mg of sucrose) white powder
% DBCO: 3.52%
CRM concentration: 4 mg/mL solution
PS:CRM (input ratio): 1.20:1
Reaction Procedure:

Type 4-DBCO sample (5.35 mg white powder with 54 mg of sucrose) was dissolved in 0.67 mL of 0.9% of NaCl solution and then azido-functionalized eCRM solution (0.74 mL) was added. After 10 min, another portion of azido-functionalized eCRM (0.37 mL) was added providing a PS4:CRM mass ratio of 1.20:1 (w/w). The reaction mixture was gently mixed by hand before gently mixing on an orbital shaker at room temperature (20° C.) for 2 days. The conjugated PS-CRM mixture was transferred to a prewashed dialysis tube (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 µm, 33 mm polyethersulfone) to give a Type 4 PS-CRM conjugate solution.

| PS 4-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.35 | 4.46 | 5.31 | 0.595 | 65 | 0.360 | 45 | 1.65:1 | 23.63 | 4.55 |

Example 13: Preparation of Pneumococcal PS Serotype 5 Conjugates to an eCRM from Table 2

1. Oxidation

Purity of type 5 PS: 89% (Uronic Acid)
Mol. wt: 919.32
Reaction Procedure:

Type 5 PS (22.8 mg, 24.36 µmol) powder was dissolved in 8.26 mL of water and 3.14 mL of 200 mM acetate buffer (pH 5.26) and 163 µL of NaIO$_4$ solution (1.3 mg, 6.1 µmol, 0.25 eq). The mixture was stirred at 25° C. for 18 hours, after which the time, the oxidized sample was purified using AMICON ultra centrifuge (100 kDa MWCO 6-12 mL) 6 exchanges (12 mL) of HPLC grade water to give oxidized PS-5 solution.

| Mol eq of NaIO$_4$ | PS 5 (mg) | Vol. after purification (mL) | Uronic Acid (µM) | % Oxidation (BCA) | % Oxidation (aldehyde assay) | PS yield (%) |
|---|---|---|---|---|---|---|
| 0.25 | 22.8 | 2.44 | 6735.97 | 84.87 | 5.71 | 68 |

2. DBCO Derivatization

Reaction Procedure:

To a solution of oxidized (assume 10% oxidation level) Type 5 PS (6.25 mg, 6.68 µmol, 0.992 mL water) was added buffer solution (0.063 mL of 200 mM phosphate buffer, pH=6.74), DMSO (25 µL) and a solution of DBCO-PEG-4-NH$_2$ (3.5 mg in 100 µL of DMSO; 6.68 µmol, 10 equivalent) all at 25° C. The reaction mixture was then stirred at 37° C. for 30 min, after which time 84 µL of a sodium cyanoborohydride solution (0.84 mg in 84 µL of water; 13.36 µmol, 20 equivalents) was added and kept stirring for 24 hr at 37° C. The reaction mixture was extracted with ethyl acetate (6×10 mL). The extract was transferred to an AMICON ultra centrifuge filter (30 kDa MWCO 6-12 mL) and then dialyzed using 8 exchanges with 20% ethanol in water (12 mL each) followed by 3 exchanges with water (12 mL each) to give type the 5 DBCO derivative. To this solution (5.35 mL, 6.0 mg) was added a solution of sucrose (60 mg in 0.6 mL water). The combined solution was divided into two equal portions and each lyophilized to give two samples of white powder. Each sample contained 3.0 mg of 5 DBCO and 30 mg of sucrose for use in the next conjugation reaction.

| oxidized PS 5 (mg) | Vol. after purification (mL) | Uronic Acid (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 6.25 | 5.38 | 1219.4 | 0.688 × 3 | 63.044 | 5.17 | 98 | 300 |

3. Conjugation of PS 5-DBCO Derivative with eCRM

PS 5-DBCO: 3.0 mg (with 30 mg of sucrose) white powder
% DBCO: 5.17%
CRM concentration: 3.25 mg/mL solution
PS:CRM (input ratio): 1:1
Reaction Procedure:

5-DBCO derivative (3.0 mg white powder with 30 mg of sucrose) was dissolved in 0.9% sodium chloride solution (4.48 mL) and DMSO (0.6 mL). Azido-functionalized eCRM solution (0.92 mL) was added providing a PS5:CRM mass ratio of 1:1 (w/w). The reaction mixture was gently mixed before gently mixing on an orbital shaker at room temperature (20° C.) for 5 hours. Sodium azide solution (20 µL, 10 mg/mL in water) was added. After 30 min the conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 µm, 33 mm polyethersulfone) to give 5 PS-CRM conjugate solution.

| PS 5-DBCO (mg) | CRM (mg) | Vol. after purification (mL) | Uronic Acid (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 3.0 | 3.0 | 5.466 | 0.231 | 46 | 0.239 | 48 | 0.97 | LLOQ | 2.74 |

Example 14: Preparation of Pneumococcal PS Serotype 6A Conjugates to an eCRM from Table 2

1. Oxidation

Type 6A PS Mol. wt: 706
NaIO$_4$ solution in water (10 mg/mL)
Reaction Procedure:

PS-6A (15 mg, 21.2 μmol) powder was dissolved in 7.5 mL of aqueous solution (10 mM sodium acetate solution, PH 4.5). To this solution was added 36.3 μL of NaIO$_4$ solution (0.363 mg, 1.69 μmol, 0.08 eq). The mixture was stirred at 4° C. for 18 hours, after which the time, the oxidized sample was transferred to a prewashed dialysis tube (SpectrumLab Float-A-Lyzer G2, Cat. No. G235057, 20K MWCO) and then dialyzed with 50 mm PB buffer, PH 6.8 for 24 hours (4 exchanges, 600 ml each) to give oxidized PS-6A solution. After dialysis, add DMSO to make PS-6A in 10% DMSO with 50 mm PB buffer, PH 6.8.

| Mol eq of NaIO$_4$ | PS 6 A (mg) | Vol. after purification (mL) | Anthrone (μM) | % Oxidation (BCA) | PS yield (%) |
|---|---|---|---|---|---|
| 0.08 | 15 | 4 | 4780 | 9.0 | 90 |

2. DBCO Derivatization

Final concentration of PS: 3.37 mg/ml,
Final concentration of buffer: 10% DMSO in 50 mM PB (pH 6.8)
Reaction Procedure:

To a solution of oxidized Type 6A PS (13.5 mg, 19.1 μmol, 4 mL in 10% DMSO, 50 Mm PB, PH 6.8), a solution of DBCO-PEG$_4$-NH$_2$ (10.01 mg in 100.1 μL of DMSO; 19.1 μmol, 10 equivalent) was added at 25° C. The reaction mixture was then stirred at 25° C. for 60 min, after which time sodium cyanoborohydride solution (1.2 mg in 120 μL of water; 19.1 μmol, 10 equivalent) was added and kept stirring for 24 hours at 25° C. The reaction mixture was then transferred to a prewashed dialysis tube (SpectrumLab Float-A-Lyzer G2, Cat. No. G235057, 20K MWCO) and then dialyzed using 4 exchanges with 20% ethanol in 50 mM PB buffer followed by 3 exchanges with 50 mM PB buffer to give type the 6A DBCO derivative.

| oxidized PS 6A (mg) | Vol. after purification (mL) | Anthrone (μM) | DBCO derivatization (μM) | DBCO incorporation (%) | PS-DBCO yield (%) | SEC-MALS kDa |
|---|---|---|---|---|---|---|
| 13.5 | 8 | 1685 | 148 | 8.78 | 70 | 193 |

3. Conjugation of PS 6A-DBCO Derivative with eCRM

PS 6A-DBCO: 7.1 mg (with 71 mg of sucrose) white powder
DBCO: 9%
CRM concentration: 2.617 mg/mL solution
PS:CRM (input ratio): 2:1
Final concentration of PS: 5.2 mg/ml
Reaction Procedure:

Azido-functionalized eCRM solution (1.4 mL) was added to 6A DBCO derivative (7.1 mg white powder with 71 mg of sucrose) providing a PS 6A:CRM mass ratio of 2:1 (w/w). The reaction mixture was gently mixed by hand before gently mixing on an orbital shaker at room temperature (23° C.) for 17 hours. The mixture was then put into an incubator (37° C.) for 3 hours. After reaction, the mix was diluted 2 fold by 0.9% sodium chloride solution and reduced by sodium borohydride (1.9 mg in 191 μL of water; 50.2 μmol, 50 equivalent) for 3 hours. The conjugated PS-CRM mixture was transferred to a prewashed dialysis tube (SpectrumLab Float-A-Lyzer G2, Cat. No. G235072, 300K MWCO) and then dialyzed with PBS, PH 7 for 24 hours (3 exchanges, 1000 ml each). The dialyzed solution was filtered through a Millex-GP (0.22 μm, 33 mm polyethersulfone) to give a 6A PS-CRM conjugate solution.

| PS 6A-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 7.1 | 3.6 | 10 | 0.424 | 60 | 0.170 | 47 | 2.5:1 | 16.1 | 1.15 |

Example 15: Preparation of Pneumococcal PS Serotype 6B Conjugates to an eCRM from Table 2

1. Oxidation

Purity of type 6B PS: 80% (Anthrone)
Mol. wt: 706.18
NaIO4 solution in water (5.45 mg/mL)
Reaction Procedure:

PS-6B (27.28 mg corrected to 80%, 21.82 mg, 30.9 µmol) powder was dissolved in 14 mL of aqueous solution (9.5 mL of water and 4.5 mL of 0.2 M acetate buffer; pH=5.5). To this solution was added 145 µL of NaIO$_4$ solution (0.79 mg, 3.71 µmol, 0.12 eq). The mixture was stirred at 25° C. for 18 hours, after which the time, the oxidized sample was purified using AMICON ultra centrifugal device (30 kDa MWCO 6-12 mL) 6 exchanges (12 mL) of HPLC grade water to give oxidized PS-6B solution.

| Mol eq of NaIO$_4$ | PS 6B (mg) | Vol. after purification (mL) | Anthrone (µM) | % Oxidation (BCA) | % Oxidation (aldehyde assay) | PS yield (%) |
|---|---|---|---|---|---|---|
| 0.12 | 27.28 | 3.54 | 7783 | 8.1 | 7.33 | 89 |

2. DBCO Derivatization

Final concentration of PS: 3.5 mg/ml
Final concentration of buffer: 53 µM (pH 6.0)
Reaction Procedure:

To a solution of oxidized (assume 10% oxidation level) Type 6B PS (18.4 mg, 27.6 µmol, 3.35 mL water) was added buffer solution (1.4 mL of 200 mM phosphate buffer, pH=6.01), DMSO (700 µL) and a solution of DBCO-PEG-4-NH$_2$ (14.43 mg in 295 µL of DMSO; 27.6 µmol, 10 equivalent) all at 25° C. The reaction mixture was then stirred at 25° C. for 30 min, after which time 75 µL of a sodium cyanoborohydride solution (9.39 mg in 200 µL of water, 55.6 µmol, 20 equivalent) was added and kept stirring for 2 days at 25° C. The reaction mixture was diluted with phosphate buffer (500 µL of 200 mM solution, pH=6) before adding 104 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water followed by 3 exchanges with water (12 mL each) to give a solution of type the 6B DBCO derivative. To this solution (2.96 mL, 20.1 mg) was added a solution of sucrose (200 mg in 1 mL water). The combined solution were divided into three equal portions and each lyophilized to give three samples of white powder. Each sample contained 6.7 mg of 6B DBCO and 67 mg of sucrose for use in the next conjugation reaction.

| oxidized PS 6B (mg) | Vol. after purification (mL) | Anthrone (µM) | DBCO derivatization 309 nm Abs | DBCO derivatization (µM) | DBCO incorporation (%) | PS-DBCO yield (%) | SEC-MALS KDa |
|---|---|---|---|---|---|---|---|
| 18.4 | 3.11 | 9620 | 0.796 × 4 | 311.17 | 3.2 | 115 | 403 |

3. Conjugation of PS 6B-DBCO Derivative with eCRM

PS 6B-DBCO: 6.7 mg (with 67 mg of sucrose) white powder
% DBCO: 3.2%
CRM concentration: 2.617 mg/mL solution
PS:CRM (input ratio): 2:1
Final concentration of PS: 5.23 mg/ml
Reaction Procedure:

Azido-functionalized eCRM solution (1.28 mL) was added to 6B-DBCO derivative (6.70 mg white powder with 67 mg of sucrose) providing a PS6B:CRM mass ratio of 2:1 (w/w). The reaction mixture was gently mixed by hand before gently mixing on an orbital shaker at room temperature (20° C.) for 17 hours. The mixture was then put into an oven (37° C.) for 2 hours. The conjugated PS-CRM mixture was transferred to a prewashed dialysis tube (SpectrumLab Float-A-Lyzer G2, Cat. No. G235071, 100K MWCO) and then dialyzed with 0.9% sodium chloride solution for 24 hours (3 exchanges, 800 ml each). The dialyzed solution was filtered through a Millex-GP (0.22 µm, 33 mm polyethersulfone) to give a 6B PS-CRM conjugate solution.

| PS 6B-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 6.70 | 3.35 | 6.18 | 0.68 | 67 | 0.347 | 67 | 1.96:1 | 8.72 | 1.30 |

Example 16: Preparation of Pneumococcal PS Serotype 7F Conjugates to an eCRM from Table 2

1. CDAP Activation and DBCO Crosslink

Purity PS 7F: n.d. % (Anthrone)—assumed 100%
Mol. wt: 1227 g mol$^{-1}$ (repeat unit)

Reaction Procedure:

PS7F (6.2 mg, 5.1 μmol) was dissolved in water (3.1 mL) to which was added CDAP (2.0 eq., 100 mg/mL in acetonitrile, 24 μL). The reaction mixture was stirred at room temperature (RT) for 30 s. At this time, triethylamine (TEA, 2.5 eq., 0.2M, 63 μL) was added and the reaction mixture was stirred for 120 s. DBCO-PEG$_4$-NH$_2$ (1.0 eq., 28.7 μmol/mL in DMSO, 180 μL) was added along with borate buffer (0.1M, pH8.5, 1.0 mL) and stirred at RT overnight. The DBCO-derivatized PS7F was purified by ethanol precipitation and by centrifugal dialysis (Amicon 100 kDa MWCO) using 3 exchanges with water. After analysis by UV absorbance spectroscopy, anthrone assay and SEC, this solution (3.61 mL, 3.05 mg) was diluted with a sucrose solution (10-fold mass content, 100 mg/mL) and lyophilized to a white powder.

| PS 7F (mg) | Vol. after purification (mL) | Anthrone assay (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 6.2 | 3.61 | 686.3 | 0.619 | 55.52 | 8.1 | 49 | n.d. |

2. Conjugation of PS 7F-DBCO Derivative with eCRM
 PS 7F-DBCO: 2.62 mg (with 26.2 mg sucrose) lyophilized powder
 % DBCO: 8.1%
 CRM: 5.0 mg/mL in PBS buffer
 PS:CRM (input mass ratio): 1.73:1

Reaction Procedure:

Lyophilized 7F-DBCO was dissolved in brine (0.9% (w/v), 0.938 mL), phosphate buffer (0.5 M, pH 7.0, 58 μL) and DMSO (144 μL) to which was added eCRM solution (0.300 mL) to provide a PS7F:CRM input mass ratio of 1.73:1.00 (w/w). The solution was very gently mixed by hand before gently mixing on an orbital shaker at room temperature (20° C.) for 17 hours. The CRM conjugate was transferred to two pre-washed dialysis tubes (SpectrumLab Float-A-Lyzer G2, 300K MWCO) and then dialyzed with 0.9% sodium chloride solution for 24 hours (3 exchanges, 800 ml each). The dialyzed solution was sterile-filtered through a Millex-GP syringe filter (0.22 μm, 33 mm polyethersulfone) to give a 7F-CRM conjugate solution.

| PS 7F-DBCO (mg) | CRM (mg) | Vol. after purification (mL) | Anthrone (mg/mL) | PS recovery (%) | BCA (CRM) (mg/mL) | PS:CRM CJF ratio | Free PS (%) | SEC-MALS MDa |
|---|---|---|---|---|---|---|---|---|
| 2.62 | 1.5 | 7.17 | 0.450 | 65 | 0.224 | 2.0:1.0 | LLOQ (<21.4 ug/mL) | 1.95 |

Example 17: Preparation of Pneumococcal PS Serotype 8 Conjugates to an eCRM from Table 2

1. Oxidation
 Purity of type 8 PS 84%
 Mol. Wt: 684.54 g mol$^{-1}$

Reaction Procedure:

The native polysaccharide (42 mg, 61.3 μmol) was dissolved in 21 mL of aqueous solution (14.7 mL water and 6.3 mL acetate buffer, 200 mM, pH 5.5). To this solution was added a sodium periodate solution (calculated for 2.63 mg, 0.20 eq.). The mixture was stirred at 25° C. for 18 hours with monitoring by UV absorption at 222 nm for NaIO$_4$. The oxidized PS was purified using Amicon centrifugal 30 kDa MWCO dialysis using at least 6 exchanges with water to give purified PS-8 solution.

| Mol eq of NaIO$_4$ | PS 8 (mg) | Vol. after purification (mL) | Anthrone assay (μM) | % Oxidation (BCA) | % Oxidation (aldehyde assay) | PS yield (%) |
|---|---|---|---|---|---|---|
| 0.20 | 42 | 3.26 | 15724 | 8.96 | 2.28 | 84 |

2. DBCO Derivatization
Reaction Procedure:

PS8-OX (33.8 mg, 49.4 μmol) in 3.14 mL water was diluted with phosphate buffer (789 μL, 0.5 M pH 6.0), 1 mL of H$_2$O and DMSO (313 μL) to which was added DBCO-PEG$_4$-NH$_2$ (25 mg, 1 eq., in DMSO, 250 μL). After 10 minutes NaCNBH$_3$ (6.2 mg, 2 eq. by adding 132 μL from 9.43 mg in 200 μL H$_2$O) was added. The reaction mixture was stirred at 25° C. for two days in a thermostatted water bath followed by addition of phosphate buffer (0.5 mL of 200 mM pH=6). To this was added NaBH$_4$ (1 eq.). After stirring for 30 min the mixture was extraction with ethyl acetate (3×5 mL). The residual ethyl acetate was removed by bubbling with nitrogen gas and the mixture transferred to 100 kDa MWCO Amicon centrifuge filters. The DBCO derivative was purified by centrifugal dialysis using 6 exchanges with 20% EtOH and 3 exchanges with water (12 mL each) to give type the 8-DBCO derivative. To this solution (5.63 mL, 25 mg) was added a solution of sucrose and lyophilized.

| oxidized PS 8 (mg) | Vol. after purification (mL) | Anthrone assay (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 33.8 | 5.63 | 6492 | 0.813 × 3 | 232 | 3.57 | 74 | 392 |

3. Conjugation of PS 8-DBCO Derivative with eCRM

PS 8-DBCO: 3.77 mg (with 38 mg sucrose) lyophilized powder
% DBCO: 3.57%
CRM concentration: 5.966 mg/mL solution
PS:CRM (input ratio): 1.5:1

Reaction Procedure:

PS8—DBCO was dissolved in 0.9% NaCl (2.28 mL), phosphate buffer (0.126 mL, 0.5 M pH 7.0) and DMSO (0.314 mL) was added. Then azido-functionalized eCRM solution (0.42 mL) was added to provide a PS8:CRM input mass ratio of 1.5:1 (w/w). The solution was very gently mixed by hand before gently mixing on an orbital shaker at room temperature (20° C.) for 1 hour and then put in oven at 37° C. overnight. The click reaction was quenched by the addition of sodium azide solution (10 mg/mL, 100 μL). The CRM conjugate was transferred to pre-washed dialysis tube (SpectrumLab Float-A-Lyzer G2, 300K MWCO) and then dialyzed with 0.9% sodium chloride solution for 48 hours (8 exchanges, 1000 ml each). The dialyzed solution was filtered through a Millex-GP syringe filter (0.22 μm, 33 mm polyethersulfone) to give a 8-CRM conjugate solution.

| PS 8-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 3.77 | 2.51 | 7.13 | 0.372 | 70 | 0.237 | 67 | 1.57:1 | 11.53 | 1.2 |

Example 18: Preparation of Pneumococcal PS Serotype 9N Conjugates to an eCRM from Table 2

1. Oxidation

Purity of type 9N PS: 75%
Mol. Wt: 928.29 g mol$^{-1}$

Reaction Procedure:

The native polysaccharide (19.0 mg, 20.4 μmol) was dissolved in 9.49 mL of aqueous solution (7.12 mL water and 2.37 mL acetate buffer, 200 mM, pH 5.5). To this solution was added a sodium periodate solution (1.31 mg, 0.30 eq., 56 μL from a 23.65 mg in 1.0 mL aqueous solution). The mixture was stirred at 25° C. for 18 hours with monitoring by UV absorption at 222 nm for NaIO$_4$. The oxidized PS was purified using Amicon centrifugal 30 kDa MWCO dialysis using 4 exchanges with water to give purified PS-9 solution.

| Mol eq of NaIO$_4$ | PS 9N (mg) | Vol. after purification (mL) | Anthrone assay (μM) | % Oxidation (BCA) | % Oxidation (aldehyde assay) | PS yield (%) |
|---|---|---|---|---|---|---|
| 0.30 | 19.0 | 1.643 | 9229 | 7.0 | N.D. | 71 |

2. DBCO Derivatization

Reaction Procedure:

PS9N-OX (12.6 mg, 13.6 μmol) in 1.643 mL water was diluted with phosphate buffer (0.945 mL, 200 mM pH 6.0 containing 94.5 mg sucrose) and DMSO (0.33 mL) to which was added DBCO-PEG$_4$-NH$_2$ (7.2 mg, 1 eq., in DMSO, 0.142 mL). After 10 minutes NaCNBH$_3$ (1.71 mg, 2 eq. by adding 47 μL from 7.36 mg in 200 μL H$_2$O) was added. The reaction mixture was stirred at 25° C. for two days in a thermostatted water bath followed by addition of phosphate buffer (0.4 mL of 200 mM pH=6). To this was added NaBH$_4$ (0.51 mg, 1 eq.) After stirring for 30 min the mixture was extraction with ethyl acetate (5×5 mL). The residual ethyl acetate was removed by bubbling with nitrogen gas and the mixture transferred to 30 kDa MWCO Amicon centrifuge filters. The DBCO derivative was purified by centrifugal dialysis using 3 exchanges with water (12 mL each) followed by 6 exchanges with 20% aqueous ethanol (12 mL each) and finally 3 exchanges with water (12 mL each) to give type the 9N-DBCO derivative. To this solution (2.388 mL, 9.05 mg) was added a solution of sucrose and lyophilized.

| oxidized PS 9N (mg) | Vol. after purification (mL) | Anthrone assay (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 12.6 | 2.388 | 1485 | 0.782 | 72.8 | 4.9 | 78 | 474 |

3. Conjugation of PS 9N-DBCO Derivative with eCRM
  PS 9N-DBCO: 4.5 mg (with 45 mg sucrose) lyophilized powder
  % DBCO: 4.9%
  CRM concentration: 3.0 mg/mL solution
  PS:CRM (input ratio): 1.5:1
Reaction Procedure:

PS9N-DBCO was dissolved in 0.9% NaCl (1.30 mL) along with pH=7 phosphate buffer (96 µL of 0.5 M) and DMSO (0.24 mL) was added. Then azido-functionalized eCRM solution (0.60 mL) was added to provide a PS:CRM input mass ratio of 1.5:1 (w/w). The solution was very gently mixed by hand before gently mixing on an orbital shaker at room temperature (20° C.) for 18 hours. The click reaction was quenched by the addition of sodium azide solution (10 mg/mL, 100 µL). The CRM conjugate was transferred to two pre-washed dialysis tubes (SpectrumLab Float-A-Lyzer G2, 300K MWCO) and then dialyzed with 0.9% sodium chloride solution with 3 mL of pH=7 buffer added to it, for 24 hours (7 exchanges, 1000 ml each). The dialyzed solution was filtered through a Millex-GP syringe filter (0.22 µm, 33 mm polyethersulfone) to give a 9N-CRM conjugate solution.

2. DBCO Derivatization
Reaction Procedure:

To a solution of oxidized type 9V PS (21.64 mg, 22.78 µmol, 4.27 mL), buffer solution (0.541 mL of 0.5 M phosphate buffer pH 6.0), DMSO (66 µL) and a solution of DBCO-PEG$_4$-NH$_2$ (11.9 mg in 475 µL DMSO; 22.78 µmol, 1 mol eq.) were added. The reaction mixture was stirred at 25° C. for 30 min, after which time 140 µL of a sodium cyanoborohydride solution (2.86 mg in 140 µL of water; 45.56 µmol, 2 mol eq.) was added. The reaction mixture was wrapped in aluminum foil and kept stirring in a water bath set to 25° C. for 2 days. The reaction was halted on the second day by the addition of 163 µL of a sodium borohydride solution (1.72 mg in 163 µL of water; 45.56 µmol, 2 mol eq.). After stirring for 30 minutes (when observable bubbling had ceased), the reaction mixture was extracted with ethyl acetate (2×10 mL) followed by dichloromethane (2×10 mL). The extract was bubbled with N$_2$ for 20 minutes to remove residual dichloromethane and was then trans-

| PS 9N-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 4.5 | 3.0 | 5.28 | 0.77 | 90 | 0.407 | 72 | 1.89:1 | 10.9 | 1.17 |

Example 19: Preparation of Pneumococcal PS Serotype 9V Conjugates to an eCRM from Table 2

1. Oxidation
  Purity of type 9V PS: 85% (Anthrone)
  Mol. wt: 704 kDa (Repeat Unit=971.8 g/mol)
Reaction Procedure:

Type 9V PS (35.90 mg, 37.80 µmol) powder was dissolved in 17.95 mL of aqueous solution (12.565 mL of water and 5.385 mL of 0.2 M Acetate buffer, pH 5.5) in a 50-mL polystyrene sample tube with stirring bar. Once the PS was solubilized, 852 µL of NaIO$_4$ solution (2.83 mg, 13.23 µmol, 0.35 mol eq.) was added. The reaction tube was wrapped in foil and placed in a water bath at 24° C. The mixture was stirred at 24° C. After 18 hrs, the reaction mixture was dialyzed using three AMICON® Ultra-15 centrifugal filter devices (30 kDa MWCO; 15 mL) by 4 exchanges with HPLC-grade water (15 mL each) to render oxidized PS-9V solution.

ferred to 2 AMICON® Ultra-15 centrifugal filter devices (50 kDa MWCO; 15 mL). Dialysis was performed by conducting three exchanges with a 3% DMSO solution (15 mL each), three exchanges with a 20% ethanol solution (15 mL each), and two exchanges with HPLC-grade water (15 mL each) to give the 9V DBCO derivative. To this solution (4.40 mL, 12.144 mg) was added a solution of sucrose (121.44 mg 1.214 mL water). This combined solution was divided into three fractions (2×5 mg and 1×2.14 mg) and each lyophilized to give a fine, white powder. All fractions were stored at 4° C. until needed for the conjugation reaction.

| Oxidized PS 9V (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 21.6 | 4.40 | 949.00 | 0.341 | 28.00 | 3.0 | 56 | 267 |

3. Conjugation of PS 9V-DBCO Derivative with eCRM
  PS 9V-DBCO: 5 mg (with 50 mg of sucrose) white powder
  % DBCO: 3.0%
  CRM concentration: 6.009 mg/mL solution
  PS:CRM (input ratio): 1.5:1
Reaction Procedure:

9V DBCO derivative (5.0 mg white powder with 50 mg of sucrose) was dissolved in 0.9% sodium chloride solution (0.881 mL), phosphate buffer pH 7 (0.067 mL, 0.5 M) and DMSO (0.167 mL). Azido-functionalized eCRM solution (0.555 mL solution) was added providing a PS9V:CRM mass ratio of 1.5:1 (w/w). The reaction mixture was gently mixed on an orbital shaker at room temperature (20° C.) for

| Mol eq of NaIO$_4$ | PS 9V (mg) | Vol. after purification (mL) | Anthrone (µM) | % Oxidation (BCA) | % Oxidation (aldehyde assay) | PS yield (%) |
|---|---|---|---|---|---|---|
| 0.35 | 35.90 | 4.55 | 5213.14 | 9.06 | 7.30 | 64 |

18 hours then for a further 2 hours at 37° C. After the total reaction time, a volume of sodium azide was added to the conjugation mixture (0.33 mg; 5.15 µmol). The reaction mixture was then diluted with 0.9% sodium chloride solution (2.83 mL) and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 µm, 33 mm polyethersulfone) to give 9V PS-CRM conjugate solution.

| PS 9V-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.0 | 3.33 | 1.67 | 0.86 | 87 | 0.450 | 68 | 1.9 | 14.2 | 0.94 |

Example 20: Preparation of Pneumococcal PS Serotype 9V Conjugates to an eCRM from Table 2

1. Oxidation

Purity of type 9V PS: 81% (Anthrone)
Mol. wt: 949.83
NaIO$_4$ solution in water (5.41 mg/mL)
Reaction Procedure:

PS-9V (21.15 mg corrected to 81%, 17.13 mg, 18.04 µmol) powder was dissolved in 10.57 mL of aqueous solution (7.4 mL of water and 3.17 mL of 0.2 M acetate buffer; pH=5.5). To this solution was added 214 µL of NaIO$_4$ solution (1.16 mg, 5.41 µmol, 0.3 eq). The mixture was stirred at 25° C. for 20 hours. The oxidized sample was purified via an AMICON ultra centrifuge filter (30 kDa MWCO 6-12 mL) using 6 exchanges (12 mL) of HPLC grade water to give oxidized PS-9V solution.

| Mol eq of NaIO$_4$ | PS 9V (mg) | Vol. after purification (mL) | Anthrone (µM) | % Oxidation (BCA) | % Oxidation (aldehyde assay) | PS yield (%) |
|---|---|---|---|---|---|---|
| 0.30 | 21.15 | 2.49 | 7352 | 7.4 | 9.6 | 82 |

2. DBCO Derivatization

Reaction Procedure:

To a solution of oxidized (assume 10% oxidation level) Type 9V PS (15.36 mg, 16.17 µmol, 2.20 mL water) was added buffer solution (1.4 mL of 200 mM phosphate buffer, pH=6.01), DMSO (500 µL) and a solution of DBCO-PEG-4-NH$_2$ (8.46 mg in 131 µL of DMSO; 16.17 µmol, 10 equivalent) all at 25° C. The reaction mixture was then stirred at 25° C. for 30 min, after which time 41 µL of a sodium cyanoborohydride solution (15.5 mg in 200 µL of water, 32.34 µmol, 20 equivalent) was added and kept stirring for 2 days at 25° C. The reaction mixture was diluted with phosphate buffer (500 µL of 200 mM solution, pH=6) before adding 62 µL solution of sodium borohydride (0.01 mg/µL, 10 equiv) in water. After stirring for 30 min, the reaction mixture was extracted with ethyl acetate (3×20 mL). The extract was transferred to an AMICON ultra centrifuge filter (30 kDa MWCO 6-12 mL) and then dialyzed using 6 exchanges with 20% ethanol in water (12 mL each) followed by 3 exchanges with water (12 mL each) to give type the 9V DBCO derivative. To this solution (4.0 mL, 10.08 mg) was added a solution of sucrose (100 mg in 1 mL water). The combined solution were divided into two equal portions and each lyophilized to give three samples of white powder. Each sample contained 5.04 mg of 9V DBCO and 50 mg of sucrose for use in the next conjugation reaction.

| oxidized PS 9V (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 15.36 | 5.42 | 2642 | 0.216 × 4 | 90.32 | 3.42 | 89 | 324 |

3. Conjugation of PS 9V-DBCO Derivative with eCRM

PS 9V-DBCO: 5.04 mg (with 50 mg of sucrose) white powder
% DBCO: 3.42%
CRM concentration: 3.923 mg/mL solution
PS:CRM (input ratio): 1.11:1
Reaction Procedure:

Azido-functionalized eCRM solution (CRM in 0.1.156 mL solution) was added to the 9V DBCO derivative (5.04 mg white powder with 50 mg of sucrose) providing a PS9V:CRM mass ratio of 1.11:1 (w/w). The reaction mixture was gently mixed by hand before gently mixing on an orbital shaker at room temperature (20° C.) for 18 hours. The conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 µm, 33 mm polyethersulfone) to give a 9V PS-CRM conjugate solution.

| PS 9V-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.04 | 4.53 | 5.73 | 0.61 | 69 | 0.298 | 39 | 2.05:1 | 14.64 | 1.26 |

Example 21: Preparation of Pneumococcal PS Serotype 10A Conjugates to an eCRM from Table 2

1. CDAP Activation and DBCO Crosslink
   Purity PS 10A: 77% (Anthrone)
   Mol. wt: 1227 g mol-1 (repeat unit)
Reaction Procedure:

PS10A (18.7 mg, 15.2 µmol) was dissolved in water (7.9 mL) to which was added CDAP (0.8 eq., 100 mg/mL in acetonitrile, 30 µL). The reaction mixture was stirred at room temperature (RT) for 30 s. At this time, sodium hydroxide solution (0.2 M, 200 µL) was added to achieve pH 9.5 and the reaction mixture was stirred for 150 s. DMSO (1.2 mL) was then added, followed by DBCO-PEG$_4$-NH$_2$ (0.5 eq., 32.0 µmol/mL in DMSO, 238 µL) and stirred at RT overnight. The DBCO-derivatized PS10A was purified by solvent extraction and by centrifugal dialysis (Amicon 30 kDa MWCO) using 3 exchanges of 3% (v/v) DMSO, 2 exchanges with 0.9% (v/v) brine and 3 exchanges with water. After analysis by UV absorbance spectroscopy, anthrone assay and SEC, this solution (3.18 mL, 13.5 mg) was diluted with a sucrose solution (10-fold mass content, 100 mg/mL) and lyophilized to a white powder.

| PS 10A (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 18.7 | 3.18 | 1150.41 | 1.081 | 101.26 | 8.8 | 72 | 579 |

2. Conjugation of PS 10A-DBCO Derivative with eCRM
   PS 10A-DBCO: 5.00 mg (with 50.0 mg sucrose) lyophilized powder
   % DBCO: 8.8%
   CRM: 5.0 mg/mL in PBS buffer
   PS:CRM (input mass ratio): 1.75:1
Reaction Procedure:

Lyophilized 10A-DBCO was dissolved brine (0.9% (w/v), 3.759 ml), phosphate buffer (0.5 M, pH 7.0, 200 µL) and DMSO (500 µL) to which was added eCRM solution (0.541 mL) to provide a PS10A:CRM input mass ratio of 1.75:1.00 (w/v). The solution was very gently mixed by hand before gently mixing on an orbital shaker at room temperature (20° C.) for 17 hours. The CRM conjugate was transferred to two pre-washed dialysis tubes (SpectrumLab Float-A-Lyzer G2, 300K MWCO) and then dialyzed with 0.9% sodium chloride solution for 24 hours (3 exchanges, 800 ml each). The dialyzed solution was sterile-filtered through a Millex-GP syringe filter (0.22 µm, 33 mm polyethersulfone) to give a 10A-CRM conjugate solution.

| PS 10A-DBCO (mg) | CRM (mg) | Vol. after purification (mL) | Anthrone (mg/mL) | PS recovery (%) | BCA (CRM) (mg/mL) | PS:CRM CJF ratio | Free PS (%) | SEC-MALS MDa |
|---|---|---|---|---|---|---|---|---|
| 5.00 | 2.86 | 6.86 | 0.678 | 93 | 0.311 | 2.18:1.0 | 5.64 | 1.048 |

Example 22: Preparation of Pneumococcal PS Serotype 11A Conjugates to an eCRM from Table 2

1. Hydrolysis
   Purity of type 11A PS: 69% (anthrone)
   Mol. wt: 908.7 g mol$^{-1}$ Reaction Procedure:

The native polysaccharide 11A (35.0 mg) was dissolved in 17.5 mL of aqueous solution (15.75 mL water and 1.75 mL acetic acid, 2M). The mixture was heated at 80° C. for 1 hour after which time sodium hydroxide solution was added to pH 5.5 (3.2 mL, 1M) after cooling to ambient temperature. The hydrolyzed PS was purified using Amicon centrifugal 30 k Da MWCO dialysis using at least 6 exchanges with water to give purified PS-3 solution which was then lyophilized as one aliquot.

| PS 11A (mg) | Water (mL) | AcOH, 2 M (mL) | Anthrone assay (µM) | PS yield (%) | MALS (kDa) |
|---|---|---|---|---|---|
| 35.0 | 15.75 | 1.75 | 6294.58 | 85 | 461 |

2. Oxidation
Reaction Procedure:

To the hydrolyzed polysaccharide solution (5.027 mL, 28.75 mg, 31.6 µmoles) was further added water (5.75 mL) and acetate buffer (0.2M, pH 5.5, 3.6 mL). To this solution was added 135 µL of sodium periodate solution dropwise (1.35 mg, 6.32 µmol, 0.20 eq.). The mixture was stirred at 25° C. for 18 hours. The oxidized PS was purified using Amicon centrifugal 100 k Da MWCO dialysis using at least 6 exchanges with water to give purified PS-11A-OX solution.

| Mol eq of NaIO$_4$ | PS 11A (mg) | Vol. after purification (mL) | Anthrone assay (µM) | % Oxidation (BCA) | % Oxidation (aldehyde assay) | PS yield (%) |
|---|---|---|---|---|---|---|
| 0.20 | 28.75 | 2.42 | 9525.39 | 10.2 | 4.82 | 73 |

3. DBCO Derivatization
Reaction Procedure:

PS11A-OX (22.0 mg, 24.2 µmol, 2.235 mL) was added to phosphate buffer (1.37 mL, 200 mM, pH 6.0) to which was added DBCO-PEG$_4$-NH$_2$ (1.0 eq., 523 g mol$^{-1}$ in DMSO, 100 mg/mL, 127 µL) and an additional quantity of DMSO (560 µL). The reaction mixture was stirred at 25° C. for 25 mins. prior to the addition of a solution of sodium cyanoborohydride (2 eq., 44.5 mg/mL, 68 µL) and stirred for two days. The reaction mixture was extracted with ethyl acetate (3×20 mL) and filtered through a 0.45 µm syringe filter. The DBCO derivative was purified by centrifugal dialysis units (Amicon 100 kDa MWCO) using 7 exchanges with 20% ethanol in water followed by 3 exchanges with water (12 mL each) to give type the 11A-DBCO derivative. To this solution (2.535 mL, 15.00 mg) was added a solution of sucrose (150 mg in 1.5 mL water). The combined solution was divided into three equal portions and each lyophilized to give three samples of white powder. Each sample contained 5.00 mg of 11A-DBCO and 50 mg of sucrose for use in the next conjugation reaction.

| hydrolyzed PS 11A (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 22.0 | 3.44 | 1628.30 | 1.000 × 4 | 93.93 | 5.77 | 93 | 543 |

4. Conjugation of PS 11A-DBCO Derivative with eCRM
PS 11A-DBCO: 5.0 mg (with 50 mg sucrose) lyophilized powder
% DBCO: 5.77%
CRM concentration: 5.42 mg/mL solution
PS:CRM (input ratio): 1.5:1
Reaction Procedure:
11A-DBCO was dissolved in 0.9% sodium chloride solution (7.656 mL, 0.22 µm filtered), phosphate buffer (pH 7.0, 0.5M, 0.385 mL) and DMSO (0.962 mL). Azido-functionalized eCRM solution (5.42 mg/mL, 0.617 mL) was added dropwise to provide a PS 1A:CRM input mass ratio of 1.5:1 (w/w). The solution was very gently mixed by hand before gently mixing on an orbital shaker at room temperature (20° C.) for 17 hours. The click reaction was quenched by the addition of sodium azide solution (10 mg/mL, 50 µL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give an 11A-CRM conjugate solution.

| PS 11A-DBCO (mg) | CRM (mg) | Vol. after purification (mL) | Anthrone (mg/mL) | PS recovery (%) | BCA (CRM) (mg/mL) | CRM recovery (%) | PS:CRM CJF ratio | Free PS (%) | SEC-MALS MDa |
|---|---|---|---|---|---|---|---|---|---|
| 5.0 | 3.33 | 9.14 | 0.454 | 83 | 0.271 | 74 | 1.68:1 | 0.92 | 0.987 |

Example 23: Preparation of Pneumococcal PS Serotype 12F Conjugates to an eCRM from Table 2

1. Oxidation
Purity of type 12F PS: 82% (anthrone)
Mol. wt: 1094 g mol-1
Reaction Procedure:
Type 12F PS (21.8 mg, 20 µmol) powder was dissolved in 10.9 mL of aqueous solution (8.175 mL of water and 2.725 mL of 0.2 M acetate buffer, pH 5.5) in a 50-mL polystyrene sample tube with stirring bar. Once the PS was solubilized, 160 µL of NaIO$_4$ solution (0.64 mg, 3 µmol, 0.15 mol. eq.) was added. The reaction tube was wrapped in foil and placed in a water bath at 25° C. The mixture was stirred at 25° C. After 18 hrs, the reaction mixture was dialyzed using two AMICON® Ultra-15 centrifugal filter devices (30 kDa MWCO; 15 mL) by 6 exchanges with HPLC-grade water (15 mL each) to render oxidized PS-12F solution.

| Mol eq of NaIO$_4$ | PS 12F (mg) | Vol. after purification (mL) | Anthrone assay (µM) | % Oxidation (BCA) | % Oxidation (aldehyde assay) | PS yield (%) |
|---|---|---|---|---|---|---|
| 0.15 | 21.8 | 3.06 | 4462.11 | 37 | 5.62 | 69 |

2. DBCO Derivatization
Reaction Procedure:
PS12F—OX (13.1 mg, 12 µmol, 2.68 mL) was added to phosphate buffer (1.00 mL, 200 mM, pH 6.0) to which was added DBCO-PEG$_4$-NH$_2$ (1.0 eq., 523 g mol$^{-1}$ in DMSO, 33 mg/mL, 199 µL) and an additional quantity of DMSO (500 µL). The reaction mixture was stirred at 25° C. for 25 mins. prior to the addition of a solution of sodium cyanoborohydride (2 eq., 52.5 mg/mL, 29 µL) and stirred for two days. The reaction mixture was extracted with ethyl acetate (3×20 mL) and bubbled free of solvent. The DBCO derivative was purified by centrifugal dialysis units twice (Amicon 30 kDa MWCO) using 6 exchanges with 20% ethanol in water followed by 3 exchanges with water each time (12 mL each) to give the 12F-DBCO derivative. To this solution (2.2 mL, 10.45 mg) was added a solution of sucrose (104.5 mg in 1.05 mL water). The combined solution was divided into two equal portions and each lyophilized to give three samples of white powder. Each sample contained 5.0 mg of 12F-DBCO and 50 mg of sucrose for use in the conjugation reaction.

| PS 12F-OX (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 13.1 | 2.20 | 1447.92 | 0.302 × 3 | 28.2 | 2.0 | 80 | 544 |

3. Conjugation of PS 12F-DBCO Derivative with eCRM
 PS 12F-DBCO: 5.0 mg (with 50 mg sucrose) lyophilized powder
 % DBCO: 2.0%
 CRM concentration: 5.29 mg/mL solution
 PS:CRM (input ratio): 1.5:1

Reaction Procedure:

12F-DBCO was dissolved in 0.9% sodium chloride solution (6.542 mL, 0.22 µm filtered), phosphate buffer (pH 7.0, 0.5M, 0.334 mL) and DMSO (0.834 mL). Azido-functionalized eCRM solution (5.29 mg/mL, 0.630 mL) was added dropwise to provide a PS 12F:CRM input ratio of 1.5:1 (w/w). The solution was very gently mixed by hand before gently mixing on an orbital shaker at room temperature (20° C.) for 17 hours. The click reaction was quenched by the addition of sodium azide solution (10 mg/mL, 50 µL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give a sterile 12F-CRM conjugate solution.

| PS 12F-DBCO (mg) | CRM (mg) | Vol. after purification (mL) | Anthrone (mg/mL) | PS recovery (%) | BCA (CRM) (mg/mL) | CRM recovery (%) | PS:CRM CJF ratio | Free PS (%) | SEC-MALS MDa |
|---|---|---|---|---|---|---|---|---|---|
| 5.0 | 3.33 | 8.06 | 0.547 | 88 | 0.200 | 48 | 2.73:1 | 13.3 | 0.931 |

Example 24: Preparation of Pneumococcal PS Serotype 14 Conjugates to an eCRM from Table 2

1. Oxidation

Purity of type 14 PS: 91% (Anthrone)
Mol. wt: 689.25
NaIO$_4$ solution in water (7.8 mg/mL)

Reaction Procedure:

PS-14 (28.3 mg corrected to 80%, 25.75 mg, 37.36 µmol) powder was dissolved in 14 mL of aqueous solution (10 mL of water and 4 mL of 0.2 M acetate buffer, pH=5.5). To this solution was added 110 µL of NaIO$_4$ solution (0.86 mg, 4.05 µmol, 0.13 eq). The mixture was stirred at 25° C. for 3 hours, after which the time, the oxidized sample was purified using AMICON ultra centrifuge (30 kDa MWCO 6-12 mL) 6 exchanges (12 mL) of HPLC grade water to give oxidized PS-14 solution.

| Mol eq of NaIO$_4$ | PS 14 (mg) | Vol. after purification (mL) | Anthrone (µM) | % Oxidation (BCA) | % Oxidation (aldehyde assay) | PS yield (%) |
|---|---|---|---|---|---|---|
| 0.13 | 28.3 | 3.042 | 10189 | 6.59 | 3.67 | 83 |

2. DBCO Derivatization

Reaction Procedure:

To a solution of oxidized (assume 10% oxidation level) Type 14 PS (20.5 mg, 29.74 µmol, 2.92 mL water) was added buffer solution (1.3 mL of 200 mM phosphate buffer, pH=6.8), DMSO (550 µL) and a solution of DBCO-PEG-4-NH$_2$ (11.68 mg in 150 µL of DMSO; 22.3 µmol, 0.75 equivalent) all at 25° C. The reaction mixture was then stirred at 25° C. for 30 min, after which time 70 µL of a sodium cyanoborohydride solution (6.39 mg in 120 µL of water, 59.48 µmol, 20 equivalents) was added and kept stirring for 2 days at 25° C. The reaction mixture was diluted with phosphate buffer (500 µL of 200 mM solution, pH=6) before adding 100 µL solution of sodium borohydride (1.13 mg 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 7 exchanges with 20% ethanol in water (12 mL each) followed by 3 exchanges with water (12 mL each) to give type the 14 DBCO derivative. To this solution (3.78 mL, 17.7 mg) was added a solution of sucrose (177 mg in 1.17 mL water). The combined solution were divided into three equal portions and each lyophilized to give three samples of white powder. Each sample contained 5.9 mg of 14 DBCO and 59 mg of sucrose for use in the next conjugation reaction.

| oxidized PS 14 (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 20.5 | 3.91 | 1694.06 | 0.622 × 4 | 238 | 3.51 | 91 | 463 |

3. Conjugation of PS 14-DBCO Derivative with eCRM

PS 6B-DBCO: 5.9 mg (with 59 mg of sucrose) white powder
 % DBCO: 3.5%
 CRM concentration: 5.06 mg/mL solution
 PS:CRM (input ratio): 1.5:1

Reaction Procedure:

Azido-functionalized eCRM solution (0.779 mL) was added to 14 DBCO derivative (5.9 mg white powder with 59 mg of sucrose) providing a PS14:CRM mass ratio of 1.5:1 (w/w). The reaction mixture was gently mixed by hand before gently mixing on an orbital shaker at room temperature (20° C.) for 18 hours. The conjugated PS-CRM mixture was transferred to a prewashed dialysis tube (SpectrumLab Float-A-Lyzer G2, Cat. No. G235071, 100K MWCO) and then dialyzed with 0.9% sodium chloride solution for 48 hours (8 exchanges, 800 ml each). The dialyzed solution was filtered through a Millex-GP (0.22 µm, 33 mm polyethersulfone) to give a 14 PS-CRM conjugate solution.

| PS 14-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.9 | 3.94 | 4.27 | 0.648 | 93 | 0.283 | 61 | 2.29:1 | 5.29 | 0.925 |

Example 25: Preparation of Pneumococcal PS Serotype 14 Conjugates to an eCRM from Table 2

1. Oxidation

Purity of type 14 PS: 91% (Anthrone)
Mol. wt: 689.25
NaIO4 solution in water (10.19 mg/mL)
Reaction Procedure:
PS-14 (23.5 mg corrected to 80%, 21.38 mg, 31.02 µmol) powder was dissolved in 11.75 mL of aqueous solution (8.2 mL of water and 3.55 mL of 0.2 M acetate buffer; pH=5.5). To this solution was added 97 µL of NaIO$_4$ solution (0.95 mg, 4.03 µmol, 0.13 eq). The mixture was stirred at 25° C. for 18 hours, after which the time, the oxidized sample was purified using AMICON ultra centrifuge (30 kDa MWCO 6-12 mL) 6 exchanges (12 mL) of HPLC grade water to give oxidized PS-14 solution.

| Mol eq of NaIO$_4$ | PS 14 (mg) | Vol. after purification (mL) | Anthrone (µM) | % Oxidation (BCA) | % Oxidation (aldehyde assay) | PS yield (%) | Note |
|---|---|---|---|---|---|---|---|
| 0.13 | 23.5 | 3.76 | 5994 | 6.60 | 2.28 | 73 | N/A |

2. DBCO Derivatization
Reaction Procedure:
To a solution of oxidized (assume 10% oxidation level) Type 14 PS (14.3 mg, 20.75 µmol, 3.46 mL water) was added buffer solution (1.3 mL of 200 mM phosphate buffer, pH=6.8), DMSO (637 µL) and a solution of DBCO-PEG-4-NH$_2$ (10.86 mg in 263 µL of DMSO; 20.75 µmol, 10 equivalent) all at 25° C. The reaction mixture was then stirred at 25° C. for 30 min, after which time 51 µL of a sodium cyanoborohydride solution (10.2 mg in 200 µL of water, 41.50 µmol, 20 equivalent) was added and kept stirring for 2 days at 25° C. The reaction mixture was diluted with phosphate buffer (500 µL of 200 mM solution, pH=6) before adding 78 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water (12 mL each) followed by 3 exchanges with water (12 mL each) to give type the 14 DBCO derivative. To this solution (4.12 mL, 12.24 mg) was added a solution of sucrose (12 mg in 1 mL water). The combined solution were divided into three equal portions and each lyophilized to give three samples of white powder. Each sample contained 6.12 mg of 14 DBCO and 6 mg of sucrose for use in the next conjugation reaction.

| oxidized PS 14 (mg) | Vol. after purification (mL) | Anthrone (µM) | DBCO derivatization 309 nm Abs | DBCO derivatization (µM) | DBCO incorporation (%) | PS-DBCO yield (%) |
|---|---|---|---|---|---|---|
| 14.3 | 4.43 | 4307 | 0.621 × 3 | 190.14 | 4.42 | 92 |

3. Conjugation of PS 14-DBCO Derivative with eCRM

PS 6B-DBCO: 6.12 mg (with 62 mg of sucrose) white powder
% DBCO: 4.42%
CRM concentration: 2.617 mg/mL solution
PS:CRM (input ratio): 1.8:1
Reaction Procedure:

Azido-functionalized eCRM solution (1.3 mL) was added to 14 DBCO derivative (6.12 mg white powder with 62 mg of sucrose) providing a PS14:CRM mass ratio of 1.8:1 (w/w). The reaction mixture was gently mixed by hand before gently mixing on an orbital shaker at room temperature (20C) for 17 hours. The conjugated PS-CRM mixture was transferred to a prewashed dialysis tube (SpectrumLab Float-A-Lyzer G2, Cat. No. G235071, 100K MWCO) and then dialyzed with 0.9% sodium chloride solution for 24 hours (3 exchanges, 800 ml each). The dialyzed solution (1.5 mL) was filtered through a Millex-GP (0.22 µm, 33 mm polyethersulfone) to give a 14 PS-CRM conjugate solution.

| PS 14-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa | Lot# |
|---|---|---|---|---|---|---|---|---|---|---|
| 6.12 | 3.4 | 4.85 | 1.24 | 98 | 0.472 | 67 | 2.63:1 | 3.48 | 2.5 | CJD |
| 6.12 | 3.4 | 2.31 | 0.24 |  | 0.094 |  | 2.55:1 | N/A | 1.56 | CJF |

Example 26: Preparation of Pneumococcal PS Serotype 15B Conjugates to an eCRM from Table 2

1. Oxidation
Purity of type 15B PS: 71% (Anthrone)
Mol. wt: 1185 kDa (Repeat Unit=1069.80 g/mol)
Reaction Procedure:
Type 15B PS (14.6 mg, 13.65 μmol) powder was dissolved in 7.30 mL of aqueous solution (5.1 mL of water and 2.2 mL of 0.2 M Acetate buffer, pH 5.5) in a 50-mL polystyrene sample tube with stirring bar. Once the PS was solubilized, 160 μL of NaIO₄ solution (0.59 mg, 2.75 μmol, 0.20 mol eq.) was added. The reaction tube was wrapped in foil and placed in a water bath to stir at 24° C. After 3.5 hours, the reaction mixture was dialyzed using one AMICON® Ultra-15 centrifugal filter device (30 kDa MWCO; 15 mL) by 6 exchanges with HPLC-grade water (15 mL each) to render oxidized PS-15B solution.

| Mol eq of NaIO₄ | PS 15B (mg) | Vol. after purification (mL) | Anthrone (μM) | % Oxidation (BCA) | % Oxidation (Aldehyde assay) | PS yield (%) |
|---|---|---|---|---|---|---|
| 0.20 | 14.6 | 1.521 | 5560.34 | 27.01 | 9.52 | 62 |

2. DBCO Derivatization
Reaction Procedure:
To a solution of oxidized type 15B PS (7.56 mg, 7.07 μmol, 1.271 mL), buffer solution (0.640 mL of 0.5 M phosphate buffer pH 6.0), DMSO (0.063 mL), and a solution of DBCO-PEG₄-NH₂ (17 mg in 221 μL DMSO; 7.07 μmol, 1 mol eq.) were added. The reaction mixture was stirred at 25° C. for 30 min, after which time 350 μL of a sodium cyanoborohydride solution (0.90 mg in 350 μL of water, 2 mol eq.) was added. The reaction mixture was wrapped in aluminum foil and kept stirring in a water bath set to 25° C. for 2 days. The reaction was halted on the second day by the addition of 163 μL of a sodium borohydride solution (0.27 mg; 7.07 μmol, 2 mol eq.). After stirring for 30 minutes, the reaction mixture was extracted with dichloromethane (3×15 mL). The extract was bubbled with N₂ for 20 minutes to remove residual dichloromethane and was then transferred to one AMICON® Ultra-15 centrifugal filter device (30 kDa MWCO; 15 mL). Dialysis was performed by conducting three exchanges with a 3% DMSO solution (15 mL each), three exchanges with a 20% ethanol solution (15 mL), and three exchanges with HPLC-grade water (15 mL each) to give the 15B DBCO derivative. To this solution (1.982 mL, 6.86 mg) was added a solution of sucrose (68.6 mg in 0.686 mL water). This combined solution was divided into two fractions and each lyophilized to give a fine, white powder. All fractions were stored at 4° C. after lyophilized to dryness until needed for the conjugation reaction.

| Oxidized PS 15B (mg) | Vol. after purification (mL) | Anthrone (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 7.56 | 1.982 | 1122.13 | 0.732 | 66.71 | 5.9 | 91 | n/a |

3. Conjugation of PS 15B-DBCO Derivative with eCRM
PS 15B-DBCO: 3.85 mg (with 38.5 mg of sucrose) white powder
% DBCO: 5.9%
CRM concentration: 6.009 mg/mL solution
PS:CRM (input ratio): 1.5:1
Reaction Procedure:
15B DBCO derivative (3.85 mg white powder with 38.5 mg of sucrose) was dissolved in 0.9% sodium chloride solution (4.302 mL), phosphate buffer pH 7 (0.220 mL, 0.5 M) and DMSO (0.550 mL). Azido-functionalized eCRM solution (0.467 mL solution) was added providing a PS15B:CRM mass ratio of 1.5:1 (w/w). The reaction mixture was gently mixed on an orbital shaker at room temperature (20° C.) for 18 hours then for a further 2 hours at 37° C. The conjugation reaction was terminated with the addition of sodium azide (0.23 mg; 3.60 μmol). The reaction mixture was then diluted with 0.9% sodium chloride solution to a final volume of 7 mL and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 μm, 33 mm polyethersulfone) to give the 15B PS-CRM conjugate solution.

| PS 15B-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 3.85 | 2.57 | 7.52 | 0.515 | 100 | 0.289 | 85 | 1.8:1 | 7.68 | 2.40 |

Example 27: Preparation of Pneumococcal PS Serotype 17F Conjugates to an eCRM from Table 2

1. Oxidation

Purity of type 17F PS: 84% (Anthrone)
Mol. wt: 1274 kDa (Repeat Unit=1203.00 g/mol)
Reaction Procedure:

Type 17F PS (28.50 mg, 23.69 µmol) powder was dissolved in 14.25 mL of aqueous solution (9.925 mL of water and 4.275 mL of 0.2 M Acetate buffer, pH 5.5) in a 50-mL polystyrene sample tube with stirring bar. Once the PS was solubilized, 53.8 µL of $NaIO_4$ solution (0.65 mg, 3.03 µmol, 0.128 mol eq.) was added. The reaction tube was wrapped in foil and placed in a water bath to stir at 24° C. After 1 hour, the reaction mixture was dialyzed using two AMICON® Ultra-15 centrifugal filter device (30 kDa MWCO; 15 mL) by 5 exchanges with HPLC-grade water (15 mL each) to render oxidized PS-17F solution.

| Mol eq of $NaIO_4$ | PS 17F (mg) | Vol. after purification (mL) | Anthrone (µM) | % Oxidation (BCA) | Oxidation (Aldehyde assay) | PS yield (%) |
|---|---|---|---|---|---|---|
| 0.128 | 28.50 | 2.63 | 7378.81 | 12.60 | 6.81 | 82 |

2. DBCO Derivatization

Reaction Procedure:

To a solution of oxidized type 17F PS (22.0 mg, 18.29 µmol, 2.48 mL), buffer solution (1.31 mL of 0.5 M phosphate buffer pH 6.0), and a solution of $DBCO-PEG_4-NH_2$ (9.58 mg in 95.8 µL DMSO; 18.29 µmol, 1 mol eq.) were added. The reaction mixture was stirred at 25° C. for 30 min, after which time sodium cyanoborohydride solution (2.30 mg in 200 µL of water, 36.60 µmol; 2 mol eq.) was added. The reaction mixture was wrapped in aluminum foil and kept stirring in a water bath set to 25° C. for 2 days. The reaction was halted on the second day by the addition of sodium borohydride solution (0.48 mg; 18.29 µmol, 1 mol eq.). After stirring for 30 minutes, the reaction mixture was extracted with dichloromethane (3×15 mL). The extract was bubbled with $N_2$ for 20 minutes to remove residual dichloromethane and was then transferred to one AMICON® Ultra-15 centrifugal filter device (30 kDa MWCO; 15 mL). Dialysis was performed by conducting five exchanges with a 20% ethanol solution (15 mL) and three exchanges with HPLC-grade water (15 mL each) to give the 17F DBCO derivative. To this solution (3.27 mL, 11.58 mg) was added a solution of sucrose (115.8 mg in 1.158 mL water). This combined solution was divided into three fractions (2×5 mg; 1×1.58 mg) and each lyophilized to give a fine, white powder. All fractions were stored at 4° C. after lyophilized to dryness until needed for the conjugation reaction.

| Oxidized PS 17F (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 22 | 4.40 | 978.16 | 0.350 | 30.45 | 3.1 | 53 | 209 |

3. Conjugation of PS 17F-DBCO Derivative with eCRM

PS 17F-DBCO: 5 mg (with 50 mg of sucrose) white powder
% DBCO: 3.1%
CRM concentration: 5.996 mg/mL solution
PS:CRM (input ratio): 1.5:1
Reaction Procedure:

17F DBCO derivative (5 mg white powder with 50 mg of sucrose) was dissolved in 0.9% sodium chloride solution (3.742 mL), phosphate buffer pH 7 (0.200 mL, 0.5 M) and DMSO (0.500 mL). Azido-functionalized eCRM solution (0.558 mL solution) was added providing a PS17F:CRM mass ratio of 1.5:1 (w/w). The reaction mixture was gently mixed on an orbital shaker at room temperature (20° C.) for 19 hours. The conjugation reaction was terminated with the addition of sodium azide (0.27 mg; 4.16 µmol; 1 mol eq.). The reaction mixture was then diluted with 0.9% sodium chloride solution to a final volume of 8 mL and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 µm, 33 mm polyethersulfone) to give the 17F PS-CRM conjugate solution.

| PS 17F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5 | 3.33 | 6.71 | 461.30 | 99 | 0.349 | 70 | 1.59:1 | 9.41 | 1.072 |

Example 28: Preparation of Pneumococcal PS Serotype 18C Conjugates to an eCRM from Table 2

1. Oxidation

Purity of type 18C PS: 72% (Anthrone)
Mol. wt: 970.76
$NaIO_4$ solution in water (5.41 mg/mL)
Reaction Procedure:

Type 18C PS (61 mg, 62.84 µmol) powder was dissolved in 30.5 mL of aqueous solution (27.45 mL of water and 3.05 mL of 2 M Acetic acid). The solution was then heated at 95° C. for 40 min and then cooled, at which time; NaOH solution (1 N, 5.2 mL) was added to adjust pH to 6.0. The reaction mixture was dialyzed using AMICON ultra centrifuge (100 kDa MWCO 6-12 mL) by 3 exchanges with HPLC grade water (12 mL each). The supernatant was transferred to a 50 mL of falcon tube with 12.4 mL of water. To this solution was added 5.15 mL water and 5.8 mL of 200 mM acetate buffer (pH 5.35) and 153 µL of NaIO$_4$ solution (1.53 mg, 7.175 µmol, 0.15 eq). The mixture was stirred at 25° C. for 3 hours, after which the time, the oxidized sample was purified using AMICON ultra centrifuge (100 kDa MWCO 6-12 mL) 6 exchanges (12 mL) of HPLC grade water to give oxidized PS-18C solution.

| Mol eq of NaIO$_4$ | PS 18C (mg) | Vol. after purification (mL) | Anthrone (µM) | % Oxidation (BCA) | % Oxidation (aldehyde assay) | PS yield (%) |
|---|---|---|---|---|---|---|
| 0.15 | 61 | 5.29 | 6480.2 | 4.84 | | 7.1 | 55 |

2. DBCO Derivatization
Reaction Procedure:
To a solution of oxidized (assume 10% oxidation level) Type 18C PS (10.0 mg, 10.3 µmol, 1.55 mL water) was added buffer solution (0.211 mL of 200 mM phosphate buffer, pH=6.74), DMSO (141 µL) and a solution of DBCO-PEG-4-NH$_2$ (5.4 mg in 54 µL of DMSO; 16.17 µmol, 10 equivalent) all at 25° C. The reaction mixture was then stirred at 25° C. for 30 min, after which time 130 µL of a sodium cyanoborohydride solution (1.3 mg in 130 L of water, 20.6 µmol, 20 equivalents) was added and kept stirring for 2 days at 370C. The reaction mixture was diluted with phosphate buffer (500 µL of 200 mM solution, pH=6) before adding 80 µL solution of sodium borohydride (0.01 mg/µL, 10 equiv) in water. After stirring for 30 min, the reaction mixture was extracted with dichloromethane (2×10 mL) followed by ethyl acetate (10 mL). The extract was transferred to an AMICON ultra centrifuge filter (100 kDa MWCO 6-12 mL) and then dialyzed using 4 exchanges with 20% ethanol in water (12 mL each) followed by 3 exchanges with water (12 mL each) to give type the 18C DBCO derivative. To this solution (1.31 mL, 7.0 mg) was added a solution of sucrose (70 mg in 0.7 mL water). The combined solution was divided into two equal portions and each lyophilized to give two samples of white powder. Each sample contained 3.5 mg of 18C DBCO and 35 mg of sucrose for use in the next conjugation reaction.

3. Conjugation of PS 18C-DBCO Derivative with eCRM
PS 18C-DBCO: 3.5 mg (with 35 mg of sucrose) white powder
% DBCO: 5.32%
CRM concentration: 2.76 mg/mL solution
PS:CRM (input ratio): 1.5:1
Reaction Procedure:
18C DBCO derivative (3.5 mg white powder with 35 mg of sucrose) was dissolved in 0.9% sodium chloride solution (0.661 mL), phosphate buffer pH 7 (0.07 mL, 0.5 M) and DMSO (0.175 mL). Azido-functionalized eCRM solution (0.844 mL solution) was added providing a PS18C:CRM mass ratio of 1.5:1 (w/w). The reaction mixture was gently mixed before gently mixing on an orbital shaker at room temperature (20° C.) for 2 hours. Then the reaction mixture was diluted with 0.9% sodium chloride solution (0.661 mL), phosphate buffer pH 7 (0.07 mL, 0.5 M) and DMSO (0.175 mL) to make the PS-18 final concentration to 1 mg/mL and allowed to react for 18 hours. Sodium azide solution (23 µL, 10 mg/mL in water) was added. After 30 min the conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 48 hours (8 exchanges, 800 ml each). The dialyzed solution was filtered through a Millex-GP (0.22 µm, 33 mm polyethersulfone) to give 18C PS-CRM conjugate solution.

| PS 18C-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 3.5 | 2.33 | 4.11 | 0.287 | 34 | 0.168 | 29.6 | 1.7 | 13.7 | 1.97 |

Example 29: Preparation of Pneumococcal PS Serotype 18C Conjugates to an eCRM from Table 2

1. Oxidation
Type 18C PS Repeating unit Mol. wt: 1012
NaIO$_4$ solution in water (10 mg/mL)
Reaction Procedure:
PS-18C (20 mg, 19.76 µmol) powder was dissolved in 3 mL of aqueous solution (10 mM sodium acetate solution, PH 4.5). To this solution was added 63.4 µL of NaIO$_4$ solution (0.634 mg, 2.96 µmol, 0.15 eq). The mixture was stirred at 23° C. for 18 hours, after which the time, the oxidized sample was transferred to a prewashed dialysis tube (SpectrumLab Float-A-Lyzer G2, Cat. No. G235057, 20K MWCO) and then dialyzed with 50 mm PB buffer, PH 6.8 for 24 hours (4 exchanges, 600 ml each) to give oxidized PS-18C solution. After dialysis, add DMSO to make PS-18C in 10% DMSO with 50 mm PB buffer, PH 6.8.

| oxidized PS 18C (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 10.0 | 1.52 | 5469.4 | 1.031 × 3 | 291 | 5.32 | 81 | 203 |

| Mol eq of NaIO$_4$ | PS 18C (mg) | Vol. after purification (mL) | Anthrone (μM) | % Oxidation (BCA) | PS yield (%) |
|---|---|---|---|---|---|
| 0.15 | 20 | 4 | 3705 | 7.05 | 75 |

2. DBCO Derivatization
  Final concentration of PS: 3.75 mg/ml,
  Final concentration of buffer: 10% DMSO in 50 mM PB (pH 6.8)
Reaction Procedure:
  To a solution of oxidized Type 18C PS (15 mg, 14.8 μmol, 4.4 mL in 10% DMSO 50 mM PB, PH 6.8), a solution of DBCO-PEG$_4$-NH$_2$ (7.76 mg in 77.6 μL of DMSO; 14.8 μmol, 10 equivalent) was added at 25° C. The reaction mixture was then stirred at 25° C. for 60 min, after which time sodium cyanoborohydride solution (0.93 mg in 93 μL of water; 14.8 μmol, 10 equivalent) was added and kept stirring for 24 hours at 25° C. The reaction mixture was then transferred to a prewashed dialysis tube (SpectrumLab Float-A-Lyzer G2, Cat. No. G235057, 20K MWCO) and then dialyzed using 4 exchanges with 20% ethanol in 50 mM PB buffer followed by 3 exchanges with 50 mM PB buffer to give type the 18C DBCO derivative.

| Oxidized PS 18C (mg) | Vol. after purification (mL) | Anthrone (μM) | DBCO derivatization (μM) | DBCO incorporation (%) | PS-DBCO yield (%) | SEC-MALS kDa |
|---|---|---|---|---|---|---|
| 15 | 5 | 2460.4 | 75.12 | 3.05 | 83 | 350 |

3. Conjugation of PS 18C-DBCO derivative with eCRM
  PS 18C-DBCO: 6 mg (with 60 mg of sucrose) white powder
  DBCO: 3%
  eCRM concentration: 6.5 mg/mL
  PS:CRM (input ratio): 1.5:1
  Final concentration of PS: 2 mg/ml
Reaction Procedure:
  Azido-functionalized eCRM solution (0.615 mL) was added to 18C DBCO derivative (6 mg white powder pre-dissolve in 3 mL Water, 5.9 μmol) providing a PS 18C:CRM mass ratio of 1.5:1 (w/w). The reaction mixture was gently mixed by hand before gently mixing on an orbital shaker at room temperature (23° C.) for 17 hours. The mixture was then put into an incubator (37° C.) for 3 hours. After reaction, the mix was dilute 2 fold by 0.9% sodium chloride solution and reduced by sodium borohydride (1.12 mg in 112 μL of water; 29.64 μmol, 50 equivalent) for 3 hours. The conjugated PS-CRM mixture was transferred to a prewashed dialysis tube (Spectrum Lab Float-A-Lyzer G2, Cat. No. G235072, 300K MWCO) and then dialyzed with PBS, PH 7 for 24 hours (3 exchanges, 1000 ml each). The dialyzed solution was filtered through a Millex-GP (0.45 μm and 0.22 μm, 33 mm polyethersulfone) to give a 18C PS-CRM conjugate solution.

Example 30: Preparation of Pneumococcal PS Serotype 19A Conjugates to an eCRM from Table 2

1. Oxidation
  Purity of type 19A PS: 90% (Anthrone)
  Mol. wt: 614.44
  NaIO$_4$ solution in water (5.69 mg/mL)
Reaction Procedure:
  PS-19A (22.10 mg corrected to 90%, 19.89 mg, 32.37 μmol) powder was dissolved in 11.05 mL of aqueous solution (7.73 mL of water and 3.32 mL of 0.2 M acetate buffer; pH=5.5). To this solution was added 304 μL of NaIO$_4$ solution (1.73 mg, 8.09 μmol, 0.25 eq). The mixture was stirred at 25° C. for 18 hours, after which the time, the oxidized sample was purified using AMICON ultra centrifuge (30 kDa MWCO 6-12 mL) 6 exchanges (10 mL) of HPLC grade water to give oxidized PS-19A solution.

| Mol eq of NaIO$_4$ | PS 19A (mg) | Vol. after purification (mL) | Anthrone (μM) | % Oxidation (BCA) | % Oxidation (aldehyde assay) | PS yield (%) |
|---|---|---|---|---|---|---|
| 0.25 | 22.10 | 2.72 | 11148 | 11.5 | 6.1 | 99.39 |

2. DBCO Derivatization
Reaction Procedure:
  To a solution of oxidized (assume 10% oxidation level) Type 19A PS (17.14 mg, 27.9 μmol, 2.50 mL water) was added buffer solution (1.0 mL of 200 mM phosphate buffer, pH=6.01), DMSO (0.4 mL) and a solution of DBCO-PEG-4-NH$_2$ (14.61 mg in 190 μL of DMSO; 27.9 μmol, 10 equivalent) all at 25° C. The reaction mixture was then stirred at 25° C. for 30 min, after which time 70.2 μL of a sodium cyanoborohydride solution (15.6 mg in 313 μL of water; 55.8 μmol, 20 equivalent) was added and kept stirring for 2 days at 25° C. The reaction mixture was diluted with phosphate buffer (500 μL of 200 mM solution, pH=6) before adding 105 μL solution of sodium borohydride (0.01 mg/μL, 10 equiv) in water. After stirring for 30 min, the reaction mixture was extracted with ethyl acetate (3×20 mL ethyl acetate) and then transferred to an AMICON ultra centrifuge

| PS 18C-DBCO (mg) | CRM (mg) | Vol. after purification (mL) | Anthrone (mg/mL) | PS recovery (%) | BCA (CRM) (mg/mL) | PS:CRM CJD ratio | Free PS (%) | SEC-MALS MDa (0.22 μm filtered) |
|---|---|---|---|---|---|---|---|---|
| 6 | 4 | 10 | 0.42 | 70 | 0.15 | 2.65:1 | 14.80 | 8.25 |

(30 kDa MWCO 6-12 mL) and then dialyzed using 6 exchanges with 20% ethanol in water followed by 3 exchanges with water (12 mL each) to give type the 19A DBCO derivative. To this solution (3.12 mL, 11.4 mg) was added a solution of sucrose (114 mg in 1 mL water). The combined solution were divided into two equal portions and each lyophilized to give two samples of white powder. Each sample contained 5.70 mg of 19A DBCO and 57 mg of sucrose for use in the next conjugation reaction.

| oxidized PS 19A (mg) | Vol. after purification (mL) | Anthrone (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 17.14 | 4.87 | 5976 | 0.482 × 4 | 197.76 | 3.31 | 105 | 139 |

3. Conjugation of PS 19A-DBCO Derivative with eCRM
   PS 19A-DBCO: 5.7 mg (with 57 mg of sucrose) white powder
   % DBCO: 3.31%
   CRM concentration: 6.5 mg/mL solution
   PS:CRM (input ratio): 1.8:1

Reaction Procedure:
Azido-functionalized eCRM solution (0.49 mL) was added to 19A DBCO derivative (5.7 mg white powder with 57 mg of sucrose) providing a PS19A:CRM mass ratio of 1.8:1 (w/w). The reaction mixture was gently mixed by hand before gently mixing on an orbital shaker at room temperature (20° C.) for 18 hours. The conjugated PS-CRM mixture was transferred to a prewashed dialysis tube (SpectrumLab Float-A-Lyzer G2, Cat. No. G235060, 300K MWCO) and then dialyzed with 0.9% sodium chloride solution for 24 hours (3 exchanges, 800 ml each). The dialyzed solution was filtered through a Millex-GP (0.22 μm, 33 mm polyethersulfone) to give a 19A PS-CRM conjugate solution.

| PS 19A-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.7 | 3.185 | 5.42 | 0.62 | 70 | 0.40 | 61 | 1.55:1 | 25.23 | 1 |

Example 31: Preparation of Pneumococcal PS Serotype 19A Conjugates to an eCRM from Table 2

1. Oxidation
   Purity of type 19A PS: 90% (Anthrone)
   Mol. wt: 614.44
   $NaIO_4$ solution in water (5.45 mg/mL)

Reaction Procedure:
PS-19A (20.83 mg corrected to 90%, 18.75 mg, 30.5 μmol) powder was dissolved in 9.5 mL of aqueous solution (6.5 mL of water and 3 mL of 0.2 M acetate buffer, pH=5.5). To this solution was added 305 μL of $NaIO_4$ solution (1.63 mg, 7.62 μmol, 0.25 eq). The mixture was stirred at 25° C. for 18 hours, after which the time, the oxidized sample was purified using AMICON ultra centrifuge (30 kDa MWCO 6-12 mL) 6 exchanges (10 mL) of HPLC grade water to give oxidized PS-19A solution.

| Mol eq of $NaIO_4$ | PS 19A (mg) | Vol. after purification (mL) | Anthrone (μM) | % Oxidation (BCA) | % Oxidation (aldehyde assay) | PS yield (%) | Note |
|---|---|---|---|---|---|---|---|
| 0.25 | 20.83 | 2.95 | 9858 | 7.2 | 4.2 | 95.32 | N/A |

2. DBCO Derivatization

Reaction Procedure:

To a solution of oxidized (assume 10% oxidation level) Type 19A PS (17.57 mg, 28.59 µmol, 2.90 mL water) was added buffer solution (0.87 mL of 200 mM phosphate buffer, pH=6.01), DMSO (0.7 mL) and a solution of DBCO-PEG-4-NH$_2$ (14.97 mg in 306 µL of DMSO; 28.59 µmol, 10 equivalent) all at 25° C. The reaction mixture was then stirred at 25° C. for 30 min, after which time 79 µL of a sodium cyanoborohydride solution (9.39 mg in 200 µL of water, 57.2 µmol, 20 equivalent) was added and kept stirring for 2 days at 25° C. The reaction mixture was diluted with phosphate buffer (500 µL of 200 mM solution, pH=6) before adding 110 µL solution of sodium borohydride (0.01 mg/µL, 10 equiv) in water. After stirring for 30 min, the reaction mixture was extracted with ethyl acetate (3×20 mL ethyl acetate) and then transferred to an AMICON ultra centrifuge (30 kDa MWCO 6-12 mL) and then dialyzed using 6 exchanges with 20% ethanol in water followed by 3 exchanges with water (12 mL each) to give type the 19A DBCO derivative. To this solution (3.56 mL, 11.9 mg) was added a solution of sucrose (120 mg in 1 mL water). The combined solution were divided into two equal portions and each lyophilized to give two samples of white powder. Each sample contained 5.95 mg of 19A DBCO and 60 mg of sucrose for use in the next conjugation reaction.

| oxidized PS 19A (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 17.57 | 3.76 | 5424 | 0.831 × 3 | 254.1 | 4.68 | 71 | 111 |

3. Conjugation of PS 19A-DBCO Derivative with eCRM

PS 19A-DBCO: 5.95 mg (with 60 mg of sucrose) white powder

% DBCO: 4.68%

CRM concentration: 6.5 mg/mL solution

PS:CRM (input ratio): 1.8:1

Reaction Procedure:

Azido-functionalized eCRM solution (0.51 mL) was added to 19A DBCO derivative (5.95 mg white powder with 60 mg of sucrose) providing a PS19A:CRM mass ratio of 1.8:1 (w/w). The reaction mixture was gently mixed by hand before gently mixing on an orbital shaker at room temperature (20° C.) for 18 hours. The mixture was then put into an oven (37° C.) for 2 hours. The conjugated PS-CRM mixture was transferred to a prewashed dialysis tube (SpectrumLab Float-A-Lyzer G2, Cat. No. G235071, 100K MWCO) and then dialyzed with 0.9% sodium chloride solution for 24 hours (3 exchanges, 800 ml each). The dialyzed solution was filtered through a Millex-GP (0.22 µm, 33 mm polyethersulfone) to give a 19A PS-CRM conjugate solution.

Example 32: Preparation of Pneumococcal PS Serotype 19F Conjugates to an eCRM from Table 2

1. Oxidation

Purity of type 19F PS: 90.7% (Anthrone)

Mol. wt: 614.44

NaIO$_4$ solution in water (5.21 mg/mL)

Reaction Procedure:

PS-19F (22.0 mg, 35.8 µmol) powder was dissolved in 13.75 mL of aqueous solution (11 mL of water and 2.75 mL of 0.2 M acetate buffer; pH=5.5). To this solution was added 117 µL of NaIO$_4$ solution (0.61 mg, 2.86 µmol, 0.08 eq). The mixture was stirred at 4° C. in a fridge for 17 hours, after which the time, the oxidized sample was purified using AMICON ultra centrifuge (30 kDa MWCO 6-12 mL) 6 exchanges (12 mL) of 10 mM phosphate buffer pH 6.7 to give oxidized PS-19F solution.

| Mol eq of NaIO$_4$ | PS 19F (mg) | Vol. after purification (mL) | Anthrone (µM) | % Oxidation (BCA) | % Oxidation (aldehyde assay) | PS yield (%) |
|---|---|---|---|---|---|---|
| 0.08 | 22.0 | 2.89 | 8786.24 | 5.56 | N/A | 99.39 |

2. DBCO Derivatization

Reaction Procedure:

To a solution of oxidized (assume 10% oxidation level) Type 19F PS (13.7 mg, 22.3 µmol, 2.50 mL water) was added buffer solution (1.0 mL of 200 mM phosphate buffer, pH=6.0), DMSO (0.483 mL) and a solution of DBCO-PEG-4-NH$_2$ (11.68 mg in 117 µL of DMSO; 22.3 µmol, 10 equivalent) all at 25° C. The reaction mixture was then stirred at 25° C. for 30 min, after which time 70.2 µL of a sodium cyanoborohydride solution (2.8 mg in 280 µL of water, 44.6 µmol, 20 equivalents) was added and kept stirring overnight at 25° C. The reaction mixture was diluted with phosphate buffer (500 µL of 200 mM solution, pH=6) before adding 84 µL solution of sodium borohydride (0.01 mg/µL, 10 equiv) in water. After stirring for 30 min, the reaction mixture was extracted with ethyl acetate (5×12 mL ethyl acetate) and then transferred to an AMICON ultra centrifuge (30 kDa MWCO 6-12 mL) and then dialyzed using 5 exchanges with 20% ethanol in water followed by 3 exchanges with 5 mM phosphate buffer pH 7.0 (12 mL each) to give type the 19F DBCO derivative. To this solution (1.11 mL, 7.0 mg) was added a solution of sucrose (70 mg in 1 mL water). The combined solution was divided into two portions of 4 mg and 3 mg each and lyophilized to give two samples of white powder. These lyophilized sample of 19F DBCO were used in the next conjugation reaction.

| PS 19A-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.95 | 3.305 | 6.821 | 0.53 | 61 | 0.314 | 65 | 1.68:1 | 9.48 | 0.752 |

| oxidized PS 19F (mg) | Vol. after purification (mL) | Anthrone (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 13.7 | 1.92 | 1714 | 0.920 × 4 | 1714 | 5.14 | 88 | 93 |

3. Conjugation of PS 19F-DBCO Derivative with eCRM

PS 19F-DBCO: 4.0 mg (with 40 mg of sucrose) white powder
% DBCO: 5.14%
CRM concentration: 5.0 mg/mL solution
PS:CRM (input ratio): 1.6:1

Reaction Procedure:

Azido-functionalized eCRM solution (0.5 mL) was added to 19F DBCO derivative (4.0 mg white powder with 40 mg of sucrose) providing a PS19F:CRM mass ratio of 1.6:1 (w/w). The reaction mixture was gently mixed by hand before gently mixing on an orbital shaker at room temperature (20° C.) for 18 hours followed by 37° C. for 1 hour. 42 μL of sodium azide (0.42 mg, 1 equivalent) was added. After 30 min the conjugated PS-CRM mixture was transferred to a prewashed dialysis tube (SpectrumLab Float-A-Lyzer G2, Cat. No. G235060, 300K MWCO) and then dialyzed with 0.9% sodium chloride solution for 2 days (8 exchanges, 800 ml each). The dialyzed solution was filtered through a Millex-GP (0.22 μm, 33 mm polyethersulfone) to give a 19F PS-CRM conjugate solution.

| Mol eq of NaIO$_4$ | PS 19F (mg) | Vol. after purification (mL) | Anthrone (M) | % Oxidation (BCA) | PS yield (%) | Note |
|---|---|---|---|---|---|---|
| 0.1 | 10 | 2 | 6769 | 9.0 | 83 | N/A |

2. DBCO Derivatization

Final concentration of PS: 3.32 mg/ml,
Final concentration of buffer: 10% DMSO in 50 mM PB (pH 6.8)

Reaction Procedure:

To a solution of oxidized Type 19F PS (8.3 mg, 13.53 μmol, 2.5 mL in 10% DMSO 50 Mm PB, PH 6.8), a solution of DBCO-PEG$_4$-NH$_2$ (7.08 mg in 70.84 μL of DMSO; 13.53 μmol, 10 equivalent) was added at 25° C. The reaction

| PS 19F-DBCO (mg) | CRM (mg) | Vol. after purification (mL) | Anthrone (mg/mL) | PS recovery (%) | BCA (CRM) (mg/mL) | CRM recovery (%) | PS:CRM ratio | Free PS (%) | SEC-MALS MDa |
|---|---|---|---|---|---|---|---|---|---|
| 4.0 | 2.5 | 3.75 | 0.84 | 79 | 0.52 | 77 | 1.63:1 | 16.55 | 1.89 |

Example 33: Preparation of Pneumococcal PS Serotype 19F Conjugates to an eCRM from Table 2

1. Oxidation

Type 19F PS Mol. wt: 613
NaIO$_4$ solution in water (10 mg/mL)

Reaction Procedure:

PS-19F (10 mg, 16.31 μmol) powder was dissolved in 2 mL of aqueous solution (10 mM sodium acetate solution, PH 4.5). To this solution was added 34.9 μL of NaIO$_4$ solution (0.349 mg, 1.63 μmol, 0.1 eq). The mixture was stirred at 4° C. for 18 hours, after which the time, the oxidized sample was transferred to a prewashed dialysis tube (SpectrumLab Float-A-Lyzer G2, Cat. No. G235057, 20K MWCO) and then dialyzed with 50 mm PB buffer, PH 6.8 for 24 hours (4 exchanges, 600 ml each) to give oxidized PS-19F solution. After dialysis, add DMSO to make PS-19F in 10% DMSO with 50 mm PB buffer, PH 6.8.

mixture was then stirred at 25° C. for 60 min, after which time sodium cyanoborohydride solution (0.85 mg in 85 μL of water; 13.53 μmol, 10 equivalent) was added and kept stirring for 24 hours at 25° C. The reaction mixture was then transferred to a prewashed dialysis tube (SpectrumLab Float-A-Lyzer G2, Cat. No. G235057, 20K MWCO) and then dialyzed using 4 exchanges with 20% ethanol in 50 mM PB buffer followed by 3 exchanges with 50 mM PB buffer to give type the 19F DBCO derivative.

| oxidized PS 19F (mg) | Vol. after purification (mL) | Anthrone (μM) | DBCO derivatization (μM) | DBCO incorporation (%) | PS-DBCO yield (%) | SEC-MALS KDa |
|---|---|---|---|---|---|---|
| 8.3 | 4 | 3385 | 235.4 | 7.15 | 78 | 186 |

3. Conjugation of PS 19F-DBCO Derivative with eCRM

PS 19F-DBCO: 6 mg (with 60 mg of sucrose) white powder
DBCO: 7%
CRM concentration: 2.617 mg/mL solution
PS:CRM (input ratio): 2:1
Final concentration of PS: 5.2 mg/ml Reaction Procedure:

Azido-functionalized eCRM solution (1.15 mL) was added to 19F DBCO derivative (6 mg white powder with 60 mg of sucrose, 9.7 μmol) providing a PS 19F:CRM mass ratio of 2:1 (w/w). The reaction mixture was gently mixed by hand before gently mixing on an orbital shaker at room temperature (23° C.) for 17 hours. The mixture was then put into an incubator (37° C.) for 3 hours. After reaction, the mix was dilute 2 fold by 0.9% sodium chloride solution and reduced by sodium borohydride (1.849 mg in 184.9 µL of water, 48.9 µmol, 50 equivalent) for 3 hours. The conjugated PS-CRM mixture was transferred to a prewashed dialysis tube (SpectrumLab Float-A-Lyzer G2, Cat. No. G235071, 100K MWCO) and then dialyzed with PBS, PH 7 for 24 hours (3 exchanges, 1000 ml each). The dialyzed solution was filtered through a Millex-GP (0.22 µm, 33 mm polyethersulfone) to give a 19F PS-CRM conjugate solution.

| PS 19F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS KDa |
|---|---|---|---|---|---|---|---|---|---|
| 6 | 3 | 12 | 0.241 | 48 | 0.166 | 66 | 1.5:1 | 15.12 | 736 (1.05 mDa-414 KDa) |

Example 34: Preparation of Pneumococcal PS Serotype 20 Conjugates to an eCRM from Table 2

1. Oxidation
Purity of type 20 PS: 68% (anthrone)
Mol. wt: 1157.9 g mol$^{-1}$
Reaction Procedure:
Type 20 PS (30.1 mg, 26 µmol) powder was dissolved in 15.00 mL of aqueous solution (11.25 mL of water and 3.75 mL of 0.2 M acetate buffer, pH 5.5) in a 50-mL polystyrene sample tube with stirring bar. Once the PS was solubilized, 160 µL of NaIO$_4$ solution (1.11 mg, 5.2 µmol, 0.20 mol. eq.) was added. The reaction tube was wrapped in foil and placed in a water bath at 25° C. The mixture was stirred at 25° C. After 18 hrs, the reaction mixture was dialyzed using three AMICON® Ultra-15 centrifugal filter devices (30 kDa MWCO; 15 mL) by 5 exchanges with HPLC-grade water (15 mL each) to render oxidized PS-20 solution.

| Mol eq of NaIO$_4$ | PS 20 (mg) | Vol. after purification (mL) | Anthrone assay (µM) | % Oxidation (BCA) | % Oxidation (aldehyde assay) | PS yield (%) | Note |
|---|---|---|---|---|---|---|---|
| 0.20 | 30.1 | 2.6 | 6254.57 | 59.06 | 10.34 | 63 | — |

2. DBCO Derivatization
Reaction Procedure:
PS20-OX (11.7 mg, 10.1 µmol, 1.61 mL) was added to phosphate buffer (0.600 mL, 200 mM, pH 6.0) to which was added DBCO-PEG$_4$-NH$_2$ (1.0 eq., 523 g mol$^{-1}$ in DMSO, 33 mg/mL, 160 µL) and an additional quantity of DMSO (207 µL). The reaction mixture was stirred at 25° C. for 25 mins. prior to the addition of a solution of sodium cyanoborohydride (2 eq., 52.5 mg/mL, 24 µL) and stirred for one day. After capping with 1 eq. of sodium borohydride solution, the reaction mixture was extracted with ethyl acetate (3×20 mL) and bubbled free of solvent. The DBCO derivative was purified by centrifugal dialysis units twice (Amicon 30 kDa MWCO) using 5 exchanges with 20% ethanol in water followed by 3 exchanges with water each time (12 mL each) to give the 20-DBCO derivative. To this solution (2.09 mL, 13.65 mg) was added a solution of sucrose (136.5 mg in 1.37 mL water). The combined solution was divided into two equal portions and each lyophilized to give three samples of white powder. Each sample contained 6.0 mg of 20-DBCO and 60 mg of sucrose for use in the conjugation reaction.

| PS 20-OX (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS KDa |
|---|---|---|---|---|---|---|---|
| 11.7 | 2.09 | 1112.43 | 0.336 × 4 | 29.04 | 2.6 | 123 | 610 |

3. Conjugation of PS 20-DBCO Derivative with eCRM
   PS 20-DBCO: 5.0 mg (with 50 mg sucrose) lyophilized powder
   % DBCO: 2.0%
   CRM concentration: 5.29 mg/mL solution
   PS:CRM (input ratio): 1.5:1

Reaction Procedure:

20-DBCO was dissolved in 0.9% sodium chloride solution (2.684 mL, 0.22 µm filtered), phosphate buffer (pH 7.0, 0.5M, 0.160 mL) and DMSO (0.400 mL). Azido-CRM solution (5.29 mg/mL, 0.756 mL) was added dropwise to provide a PS20:CRM input ratio of 1.5:1 (w/w). The solution was very gently mixed by hand before gently mixing on an orbital shaker at room temperature (20° C.) for 36 hours. The click reaction was quenched by the addition of sodium azide solution (10 mg/mL, 50 µL). The CRM conjugate was transferred to a pre-washed dialysis tube (SpectrumLab Float-A-Lyzer G2, 300K MWCO) and then dialyzed with 0.9% sodium chloride solution for 48 hours (4 exchanges, 1 L each). The dialyzed solution was filtered through a Millex-GP syringe filter (0.22 µm, 33 mm polyethersulfone) to give a sterile 20-CRM conjugate solution.

| PS 20-DBCO (mg) | CRM (mg) | Vol. after purification (mL) | Anthrone (mg/mL) | PS recovery (%) | BCA (CRM) (mg/mL) | CRM recovery (%) | PS:CRM CJF ratio | Free PS (%) | SEC-MALS MDa |
|---|---|---|---|---|---|---|---|---|---|
| 6.0 | 4.0 | 7.00 | 0.640 | 75 | 0.366 | 64 | 1.75:1 | LLOQ | 1.224 |

Example 35: Preparation of Pneumococcal PS Serotype 22F Conjugates to an eCRM from Table 2

1. Oxidation
   Purity of type 22F PS: 89% (Anthrone)
   Mol. wt: 996.88
   $NaIO_4$ solution in water (5 mg/mL)

Reaction Procedure:

Type 22F PS (30.2 mg, 30.3 µmol) powder was dissolved in 10.5 mL of water and 4.5 mL of 200 mM acetate buffer (pH 5.26) and 132 µL of $NaIO_4$ solution (0.65 mg, 3.03 µmol, 0.1 eq). The mixture was stirred at 25° C. for 18 hours, after which the time, the oxidized sample was purified using AMICON ultra centrifuge (100 kDa MWCO 6-12 mL) 6 exchanges (12 mL) of HPLC grade water to give oxidized PS-22F solution.

2. DBCO Derivatization
Reaction Procedure:

| Mol eq of $NaIO_4$ | PS 22F (mg) | Vol. after purification (mL) | Anthrone (µM) | % Oxidation (BCA) | % Oxidation (aldehyde assay) | PS yield (%) |
|---|---|---|---|---|---|---|
| 0.10 | 30.2 | 3.351 | 7389.41 | 20.02 | 3.3 | 81.73 |

To a solution of oxidized (assume 10% oxidation level) Type 22F PS (7.0 mg, 7.02 µmol, 0.956 mL water) was added buffer solution (0.525 mL of 200 mM phosphate buffer, pH=6.0), DMSO (151 µL) and a solution of DBCO-PEG-4-$NH_2$ (3.67 mg in 112 µL of DMSO; 7.02 µmol, 10 equivalent) all at 25° C. The reaction mixture was then stirred at 25° C. for 30 min, after which time 17 µL of a sodium cyanoborohydride solution (0.88 mg in 17 µL of water; 14.06 µmol, 20 equivalents) was added and kept stirring for 2 days at 25° C. The reaction mixture was diluted with phosphate buffer (250 µL of 200 mM solution, pH=6) before adding 9 µL solution of sodium borohydride (31 mg/mL, 10 equiv) in water. After 30 min the reaction mixture was extracted with ethyl acetate (4×5 mL). The extract was transferred to an AMICON ultra centrifuge filter (100 kDa MWCO 6-12 mL) and then dialyzed using 6 exchanges with 20% ethanol in water (12 mL each) followed by 3 exchanges with water (12 mL each). SEC-HPLC shows free DBCO therefore the sample was redialyzed using 3 exchanges with 20% ethanol in water (12 mL each) followed by 3 exchanges with water (12 mL each) to give type the 22F DBCO derivative. To this solution (2.35 mL, 5.2 mg) was added a solution of sucrose (52 mg in 0.520 mL water). The combined solution was divided into two portions and each lyophilized to give two samples of white powder. The sample contained 2.4 mg and 2.8 mg of 22F DBCO and 24 mg and 28 mg of sucrose respectively for use in the next conjugation reaction.

| oxidized PS 22F (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 7.0 | 2.53 | 739.74 | 0.144 × 3 | 27.57 | 1.24 | 80 | 844 |

3. Conjugation of PS 22F-DBCO derivative with eCRM
   PS 22F-DBCO: 2.4 mg (with 24 mg of sucrose) white powder
   % DBCO: 1.24%
   CRM concentration: 4 mg/mL solution
   PS:CRM (input ratio): 1.4:1

Reaction Procedure:

22F DBCO derivative (2.4 mg white powder with 24 mg of sucrose) was dissolved in 0.9% sodium chloride solution (0.075 mL). Azido-functionalized eCRM solution (0.142 mL solution) was added providing a PS22F:CRM mass ratio of 1.4:1 (w/w). The reaction mixture was gently mixed before gently mixing on an orbital shaker at room temperature (20° C.) for 48 hours. Sodium azide solution (16 µL, 10 mg/mL in water) was added. After 30 min the conjugated PS-CRM mixture was transferred to a prewashed dialysis device (SpectrumLab Float-A-Lyzer G2, Cat. No. G235060, 300K MWCO) and then dialyzed with 0.9% sodium chloride solution for 24 hours (5 exchanges, 800 ml each). The dialyzed solution was filtered through a Millex-GP (0.22 µm, 33 mm polyethersulfone) to give 22F PS-CRM conjugate solution.

| PS 22F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 2.4 | 1.71 | 3.834 | 0.29 | 55 | 0.37 | 49 | 1.53 | 20.6 | 2.42 |

Example 36: Preparation of Pneumococcal PS Serotype 23F Conjugates to an eCRM from Table 2

1. Oxidation

Purity of type 23F PS: 85% (Anthrone)
Mol. wt: 792.62
$NaIO_4$ solution in water (5.86 mg/mL)
Reaction Procedure:

PS-23F (20.21 mg corrected to 85%, 17.18 mg, 26.7 µmol) powder was dissolved in 10 mL of aqueous solution (7.5 mL of water and 2.5 mL of 0.2 M acetate buffer; pH=5.5). To this solution was added 119 µL of $NaIO_4$ solution (0.695 mg, 4.0 µmol, 0.15 eq). The mixture was stirred at 25° C. for 4 hours. The oxidized sample was then purified using an AMICON ultra centrifuge filter (30 kDa MWCO 6-12 mL) 6 exchanges (12 mL) of HPLC grade water to give oxidized PS-23F solution.

| Mol eq of $NaIO_4$ | PS 23F (mg) | Vol. after purification (mL) | Anthrone (µM) | % Oxidation (BCA) | % Oxidation (aldehyde assay) | PS yield (%) | Note |
|---|---|---|---|---|---|---|---|
| 0.15 | 20.21 | 2.41 | 7967 | 4.11 | 3.51 | 88 | N/A |

2. DBCO Derivatization

Reaction Procedure:

To a solution of oxidized (assume 10% oxidation level) Type 23F PS (13.51 mg, 17.0 µmol, 2.14 mL water) was added buffer solution (0.85 mL of 200 mM phosphate buffer, pH=6.01), DMSO (310 µL) and a solution of DBCO-PEG-4-$NH_2$ (8.93 mg in 170 µL of DMSO; 17.0 µmol, 10 equivalent) all at 25° C. The reaction mixture was then stirred at 25° C. for 30 min, after which time 42 µL of a sodium cyanoborohydride solution (6.1 mg in 120 µL of water; 34.0 µmol, 20 equivalent) was added and kept stirring for 2 days at 25° C. The reaction mixture was extracted with ethyl acetate (3×20 mL ethyl acetate) and then transferred to an AMICON ultra centrifuge filter (30 kDa MWCO 6-12 mL) and then dialyzed using 6 exchanges with 20% ethanol (12 ml each) in water followed by 3 exchanges with water (12 mL each) to give type 23F DBCO derivative. To this solution (7.58 mL, 13.8 mg) was added a solution of sucrose (138 mg in 1 mL water). The combined solution were divided into two equal portions and each lyophilized to give three samples of white powder. Each sample contained 6.9 mg of 23F DBCO and 69 mg of sucrose for use in the next conjugation reaction.

| oxidized PS 23F (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 13.51 | 7.61 | 2292 | 0.601 × 2 | 116.98 | 5.1 | 102 | 361 |

3. Conjugation of PS 23F-DBCO Derivative with eCRM
  PS 23F-DBCO: 6.90 mg white powder with 69 mg of sucrose
  % DBCO: 5.1%
  CRM concentration: 2.617 mg/mL solution
  PS:CRM (input ratio): 2:1

Reaction Procedure:

Azido-functionalized eCRM solution (1.32 mL solution) was added to 23F DBCO derivative (6.90 mg white powder with 69 mg of sucrose) providing a PS23F:CRM mass ratio of 2:1 (w/w). The reaction mixture was gently mixed by hand before gently mixing on an orbital shaker at room temperature (20° C.) for 17 hours. The mixture was then put into an oven (37° C.) for 3 hours. The conjugated PS-CRM mixture was transferred to a prewashed dialysis filter (SpectrumLab Float-A-Lyzer G2, Cat. No. G235071, 100K MWCO) and then dialyzed with 0.9% sodium chloride solution for 24 hours (3 exchanges, 800 ml each). The dialyzed solution was filtered through a Millex-HV filter (0.45 µm, 33 mm polyethersulfone) to give 23F PS-CRM conjugate solution.

| PS 23F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 6.90 | 3.45 | 5.65 | 0.87 | 71 | 0.422 | 69 | 2.06:1 | 23.62 | 1.4 |

Example 37: Preparation of Pneumococcal PS Serotype 33F Conjugates to an eCRM from Table 2

1. Oxidation
  Purity of type 33F PS: 75% (Anthrone)
  Mol. wt: 973

Reaction Procedure:

Type 33F PS (34.0 mg, 35.0 µmol) powder was dissolved in 17.0 mL of aqueous solution (12.0 mL of water and 5.0 mL of 0.2 M acetate buffer, pH 5.5) in a 50-mL polystyrene sample tube with stirring bar. Once the PS was solubilized, 59 µL of NaIO$_4$ solution (1.49 mg, 7.0 µmol, 0.20 mol eq.) was added. The reaction tube was wrapped in foil and placed in a water bath at 4° C. The mixture was stirred at 4° C. After 18 hrs, the reaction mixture was dialyzed using three AMICON® Ultra-15 centrifugal filter devices (100 kDa MWCO; 15 mL) by 4 exchanges with HPLC-grade water (15 mL each) to render oxidized PS-33F solution.

| Mol eq of NaIO$_4$ | PS 33F (mg) | Vol. after purification (mL) | Anthrone (µM) | % Oxidation (BCA) | % Oxidation (aldehyde assay) | PS yield (%) |
|---|---|---|---|---|---|---|
| 0.20 | 34.0 | 2.74 | 4637.58 | 47.90 | 7.62 | 36 |

2. DBCO Derivatization

Reaction Procedure:

To a solution of oxidized type 33F PS (11.2 mg, 11.51 µmol, 2.49 mL), buffer solution (0.114 mL of 0.5 M phosphate buffer pH 6.0), A solution of DBCO-PEG$_4$-NH$_2$ (6.039 mg in 200 µL DMSO; 6.33 µmol, 0.55 eq.) were added. The reaction mixture was stirred at 25° C. for 30 min, after which time 63 µL of a sodium cyanoborohydride solution (4.5 mg in 100 µL of water; 34.54 µmol, 2.0 eq.) was added. The reaction mixture was wrapped in aluminum foil and kept stirring in a water bath set to 25° C. for 2 days. The reaction was halted on the second day by the addition of 44 µL of a sodium borohydride solution (3.12 mg in 312 µL of water, 11.51 µmol, 1.0 eq.). After stirring for 30 minutes, the reaction mixture was extracted with dichloromethane (3×10 mL) followed by ethyl acetate (3×10 mL). The extract was bubbled with N$_2$ for 20 minutes to remove residual ethyl acetate and was then transferred to 2 AMICON® Ultra-15 centrifugal filter devices (100 kDa MWCO; 15 mL). Dialysis was performed by conducting three exchanges with a 3% DMSO solution (15 mL each), six exchanges with a 20% ethanol solution (15 mL each), and three exchanges with HPLC-grade water (15 mL each) to give the 33F DBCO derivative. To this solution (1.23 mL, 4.0 mg) was added a solution of sucrose (40 mg 0.4 mL water). This combined solution was lyophilized to give a fine, white powder. PS33F DB sample was stored at 4° C. until needed for the conjugation reaction.

| Oxidized PS 33F (mg) | Vol. after purification (mL) | Anthrone (μM) | DBCO derivatization 309 nm Abs | DBCO derivatization (μM) | DBCO incorporation (%) | PS-DBCO yield (%) | SEC-MALS kDa |
|---|---|---|---|---|---|---|---|
| 11.2 | 2.44 | 1112.4 | 0.390 | 32.85 | 3.0 | 71 | 1290 |

3. Conjugation of PS 33F-DBCO Derivative with eCRM

PS 33F-DBCO: 4 mg (with 40 mg of sucrose) white powder
% DBCO: 3.0%
CRM concentration: 6.009 mg/mL solution
PS:CRM (input ratio): 1.5:1

Reaction Procedure:

33F DBCO derivative (4.0 mg white powder with 40 mg of sucrose) was dissolved in 0.9% sodium chloride solution (5.32 mL), phosphate buffer pH 7 (0.267 mL, 0.5 M) and DMSO (0.667 mL). Azido-functionalized eCRM solution (0.445 mL solution) was added providing a PS33F:CRM mass ratio of 1.5:1 (w/w). The reaction mixture was gently mixed on an orbital shaker at room temperature (20° C.) for 19 hours. The click reaction was quenched by the addition of sodium azide solution (10 mg/mL, 50 μL). The reaction mixture was then diluted with 0.9% sodium chloride solution (7.0 mL) and transferred to a prewashed dialysis device (SpectrumLab Float-A-Lyzer G2, Cat. No. G235060, 300K MWCO). The sample underwent dialysis in 0.9% sodium chloride solution for 48 hours (8 exchanges, 800 ml each). The dialyzed solution was filtered through a Millex-GP (0.22 μm, 33 mm polyethersulfone) to give 33F PS-CRM conjugate solution.

| PS 33F-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 4.0 | 2.67 | 7.82 | 0.545 | 106 | 0.212 | 62 | 2.57 | LLOQ | 1.87 |

Example 38: Preparation of Pneumococcal PS Serotype 7F Conjugates to an eCRM from Table 2

1. Oxidation

Purity of type 7F PS: 86% (anthrone, CRB-21-20)
Mol. wt: 1227 g mol$^{-1}$

Reaction Procedure:

The native polysaccharide (19.5 mg, corrected to 86%, 16.8 mg, 13.7 μmol) was dissolved in 3.9 mL water. To this solution was added 4.58 mL water and 0.293 mL sodium acetate buffer (1.5 M, pH 5.4). Then 30 μL of sodium periodate solution (300 μg, 1.4 μmol, 0.1 eq) was added to the stirring solution. The reaction was stirred at 22° C. for 3 hours. The oxidized PS was then concentrated two-fold using a spin concentrator (Amicon 30 k Da MWCO). The concentrated PS was then buffer exchanged into water using gel filtration columns (GE Healthcare PD-10, spin method).

| Mol eq of NaIO$_4$ | PS 7F (mg) | Vol. after purification (mL) | Anthrone assay (μM) | % Oxidation (BCA) | % Oxidation (aldehyde assay) | PS yield (%) | Note |
|---|---|---|---|---|---|---|---|
| 0.1 | 16.8 | 4.0 | 3260 | 6.2 | n/d | 95 | N/A |

2. DBCO Derivatization

Reaction Procedure:

To 7F-OX (1.9 mL of 4.0 mg/mL; 7.6 mg, 6.2 µmol) was added 0.15 mL sodium phosphate (1 M, pH 6.3). Then 0.23 mL DBCO-PEG$_4$-NH$_2$ (27.1 mM in DMSO, lot 1730; 6.2 µmol, 1.0 eq) was added to the stirring solution. After 5 min stirring, 0.039 mL of NaCNBH$_3$ (20 mg/mL in water; 12.4 µmol, 2.0 eq) was added to the stirring solution. The reaction was stirred at 22° C. for 40 hours. To the solution was then added 0.024 mL sodium borohydride (10 mg/mL in water; 6.3 µmol, 1.0 eq). After 15 min of stirring, the PS was purified by buffer exchange into water via gel filtration columns (Thermo Zeba Columns, 40 kDa MWCO).

| Mol eq of NaIO$_4$ | PS 1 (mg) | Vol. after purification (mL) | Uronic assay (µM) | % Oxidation (BCA) | % Oxidation (aldehyde assay) | PS yield (%) |
|---|---|---|---|---|---|---|
| 0.50 | 20.2 | 2.61 | 10777.6 | 2.3 | 2.16 | 87 |

2. DBCO Derivatization

Reaction Procedure:

To a solution of oxidized (assume 10% oxidation level) type-1 PS (16 mg, 25.6 µmol, 2.4 mL water) was added buffer solution (0.424 mL of 500 mM phosphate buffer, pH=6.74), DMSO (572 µL) and a solution of DBCO-PEG$_4$-

| Oxidized PS 7F (mg) | Vol. after purification (mL) | Anthrone assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 7.6 | 2.3 | 2282 | 0.14 × 2 | 111 | 4.8 | 85 | 175 |

3. Conjugation of PS 7F-DBCO Derivative with eCRM

PS 7F-DBCO: 2.8 mg (2.8 mg/mL in water)
% DBCO: 4.8%
CRM concentration: 4.7 mg/mL solution
PS:CRM (input ratio): 1.6:1

Reaction Procedure:

To 7F-DBCO (1 mL of 2.8 mg/mL in water) in a 5 mL centrifuge tube was added 0.128 mL potassium phosphate (0.5 M, pH 7.5). To this solution was then added 0.372 mL azide-functionalized eCRM (4.7 mg/mL in 20 mM potassium phosphate, pH 7.1, 7.5% sucrose), thus giving an input mass ratio of 1.6:1 (w/w). The solution was placed on an orbital rocker and rocked (such that solution moved from end to end of tube) for 16 hours at 22° C. The conjugate was then dialyzed into 0.9% sodium chloride using a 300 kDa dialysis membrane (SpectrumLab Float-A-Lyzer G2, 1 mL) for 48 hours with dialysate changes (500 mL) after 1 hour and 4 hours. The dialyzed solution was filtered through a syringe filter (Pall Acrodisc Supor, 0.22 µm, 13 mm diameter) to give 7F-CRM conjugate solution.

NH$_2$ (13.4 mg in 134 µL of DMSO; 25.6 µmol, 10 eq). The reaction mixture was then stirred at 25° C. for 30 min, after which time 32 µL of a sodium cyanoborohydride solution (3.2 mg in 32 µL of water; 51.2 µmol, 20 eq) was added and kept stirring for 3 days at 25° C. Buffer solution (0.300 mL of 200 mM phosphate buffer, pH=6.0) was added followed by sodium borohydride (0.97 mg in 100 µL, 25.6 µmol, 10 eq) and stirred for 30 min at 25° C. The reaction mixture was extracted with dichloromethane (4×5 mL). The aqueous extract was transferred to two AMICON ultra centrifuge filters (30 kDa MWCO 6-12 mL) and then dialyzed using 5 exchanges with 20% ethanol in water (12 mL each) followed by 3 exchanges with 3% DMSO in water (12 mL each), 3 exchanges with 0.9% sodium chloride and 3 exchanges with water to give type 1 DBCO derivative. To this solution (1.37 mL, 10.0 mg) was added a solution of sucrose (100 mg in 1 mL water). The combined solution was divided into two equal portions and each lyophilized to give two samples of white powder. Each sample contained 5.0 mg of 1-DBCO and 50 mg of sucrose for use in the next conjugation reaction.

| Oxidized PS 1 (mg) | Vol. after purification (mL) | Uronic Acid assay (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 16 | 2.0 | 2909.0 | 0.784 × 4 | 290.19 | 2.5 | 91 | 315 |

Example 39: Preparation of Pneumococcal PS Serotype 1 Conjugates to an eCRM from Table 2

1. Oxidation

Purity of type 1 PS: 80% (Uronic acid assay)
Mol. wt: 625 g mol$^{-1}$

Reaction Procedure:

The native polysaccharide (20.2 mg, 32.32 µmol) was dissolved in 9.5 mL of aqueous solution (7.0 mL water and 2.5 mL acetate buffer, 200 mM, pH 5.24). To this solution was added 492 µL of sodium periodate solution (3.45 mg, 16.16 µmol, 0.5 eq). The mixture was stirred at 25° C. for 18 hours. The oxidized PS was purified using Amicon centrifugal 30 kDa MWCO dialysis using 6 exchanges with water to give purified PS-1 solution.

3. Conjugation of PS 1-DBCO Derivative with eCRM

PS 1-DBCO: 5.0 mg (with 50 mg sucrose) lyophilized powder
% DBCO: 2.5%
CRM concentration: 4.86 mg/mL solution
PS:CRM (input ratio): 1.7:1

Reaction Procedure:

The lyophilized type 1-DBCO powder (5 mg) was dissolved in a solution of filtered 0.9% sodium chloride (5.39 mL) and phosphate buffer (250 µL, 0.5 M, pH 7.0). Azido-functionalized eCRM solution (0.47 mL) was added to provide a PS-1:CRM input mass ratio of 1.7:1 (w/w). The solution was very gently mixed by hand before gently mixing on an orbital shaker at room temperature (20° C.) for 18 hours. The click reaction was quenched by the addition of sodium azide solution (10 mg/mL, 52 µL). The CRM conjugate was transferred to pre-washed dialysis tubes (SpectrumLab Float-A-Lyzer G2, 300K MWCO, 10 mL) and then dialyzed with 0.9% sodium chloride solution for 48 hours (8 exchanges, 800 ml each). The dialyzed solution was filtered through a Millex-GP syringe filter (0.22 µm, 33 mm polyethersulfone) to give a 1-CRM conjugate solution.

then transferred to one AMICON® Ultra-15 centrifugal filter device (30 kDa MWCO; 15 mL). Dialysis was performed by conducting three exchanges with a 3% DMSO solution (15 mL each), three exchanges with a 20% ethanol solution (15 mL), two exchanges with 0.9% sodium chloride solution, and two exchanges with HPLC-grade water (15

| PS 1-DBCO (mg) | CRM (mg) | Vol. after purification (mL) | Uronic Acid (mg/mL) | PS recovery (%) | BCA (CRM) (mg/mL) | CRM recovery (%) | PS:CRM CJD ratio | Free PS (%) | SEC-MALS MDa |
|---|---|---|---|---|---|---|---|---|---|
| 5.0 | 2.94 | 6.47 | 0.56 | 72 | 0.283 | 62 | 1.98:1 | 8.25 | 1.02 |

Example 40: Preparation of Pneumococcal PS Serotype 10A Conjugates to an eCRM from Table 2

1. Oxidation

PS Serotype 10A lot #: 63662302 (ATCC)
Purity PS 10A: 77% (Anthrone)
Mol. wt: 1013 kDa (Repeat Unit=1227 g/mol)

Reaction Procedure:

Type 10A PS (25.99 mg, 21.18 µmol) powder was dissolved in 12.995 mL of aqueous solution (9.746 mL of water and 3.249 mL of 0.2 M Acetate buffer, pH 5.5) in a 50-mL polystyrene sample tube with stirring bar. Once the PS was solubilized, 135 µL of NaIO$_4$ solution (0.27 mg, 1.26 µmol, 0.06 mol eq.) was added. The reaction tube was wrapped in foil and placed in a refrigerator to stir at 4° C. After 45 minutes, the reaction mixture was dialyzed using three AMICON® Ultra-15 centrifugal filter devices (30 kDa MWCO; 15 mL) by 6 exchanges with HPLC-grade water (15 mL each) to render oxidized PS-10A solution.

| Mol eq of NaIO$_4$ | PS 10A (mg) | Vol. after purification (mL) | Anthrone (µM) | % Oxidation (BCA) | % Oxidation (Aldehyde assay) | PS yield (%) |
|---|---|---|---|---|---|---|
| 0.06 | 25.99 | 2.381 | 6757.20 | 16.58 | 3.13 | 76 |

2. DBCO Derivatization

Reaction Procedure:

To a solution of oxidized type 10A PS (18.15 mg, 14.79 µmol, 3.371 mL), buffer solution (0.259 mL of 0.5 M phosphate buffer pH 6.0), DMSO (0.145 mL) and a solution of DBCO-PEG$_4$-NH$_2$ (7.7 mg in 154 µL DMSO; 14.79 µmol, 1 mol eq.) were added. The reaction mixture was stirred at 4° C. for 30 min, after which time 101 µL of a sodium cyanoborohydride solution (1.9 mg in 101 µL of water, 2 mol eq.) was added. The reaction mixture was wrapped in aluminum foil and kept stirring in a refrigerator at 4° C. for 2 days. The reaction was halted on the second day by the addition of 85 µL of a sodium borohydride solution (0.56 mg; 14.79 µmol, 1 mol eq.). After stirring for 30 minutes, the reaction mixture was extracted with dichloromethane (3×15 mL). The extract was bubbled with N$_2$ for 15 minutes to remove residual dichloromethane and was mL each) to give the 10A DBCO derivative. To this solution (3.371 mL, 15.06 mg) was added a solution of sucrose (150.6 mg in 1.506 mL water). This combined solution was divided into three equal fractions, and each lyophilized to give a fine, white powder. After lyophilization, all fractions were stored at 4° C. until needed for the conjugation reaction.

| Oxidized PS 10A (mg) | Vol. after purification (mL) | Anthrone (µM) | DBCO derivatization 309 nm Abs | DBCO derivatization (µM) | DBCO incorporation (%) | PS-DBCO yield (%) | SEC-MALS kDa |
|---|---|---|---|---|---|---|---|
| 18.15 | 3.371 | 1290.30 | 0.333 | 27.21 | 2.1 | 88 | 540 |

3. Conjugation of PS 10A-DBCO Derivative with eCRM

PS 10A-DBCO: 5.20 mg (with 52.0 mg sucrose) lyophilized powder
% DBCO: 2.1%
CRM: 4.962 mg/mL in 20 mM Histidine pH 7.1 (7.5% Sucrose)
PS:CRM (input mass ratio): 1.25:1

Reaction Procedure:

The 10A DBCO derivative (5.2 mg white powder with 52.0 mg of sucrose) was dissolved in 0.9% sodium chloride solution (1.502 mL), phosphate buffer pH 7 (0.104 mL, 0.5 M), and DMSO (0.156 mL). Azido-functionalized eCRM solution (0.838 mL solution) was added providing a PS10A:CRM mass ratio of 1.25:1 (w/w). The reaction mixture, at a concentration of 2.0 mg/mL PS, was gently mixed on an orbital shaker at room temperature (22° C.) for 2 hours. The reaction mixture was then diluted to 1.0 mg/mL and left stirring at 22° C. for a further 20 hrs. The conjugation reaction was terminated with the addition of sodium azide (7.5 mg, 115 µmol). The reaction mixture was then diluted with 0.9% sodium chloride solution to a final volume of 7 mL and transferred to a prewashed dialysis device (SpectrumLab Float-A-Lyzer G2, Cat. No. G235060, 300K MWCO). The sample underwent dialysis in 0.9% sodium chloride solution for 48 hours (2 exchanges, 1 L each; 1 exchange, 4 L). The dialyzed solution was filtered through a Millex-GP (0.22 µm, 33 mm polyethersulfone) to give the 10A PS-CRM conjugate solution.

| PS 10A-DBCO (mg) | CRM (mg) | Vol. after purification (mL) | Anthrone (mg/mL) | PS recovery (%) | BCA (CRM) (mg/mL) | CRM recovery (%) | PS:CRM CJD ratio | Free PS (%) | SEC-MALS (MDa) |
|---|---|---|---|---|---|---|---|---|---|
| 5.20 | 4.16 | 8.21 | 0.553 | 87 | 0.229 | 45 | 2.4:1 | 17.71 | 1.047 |

Example 41: Evaluation of DBCO-PEG$_4$-Amine and DBCO-Amine Incorporation into Pneumococcal Polysaccharides A variety of pneumococcal polysaccharides were oxidized as described above and reacted with DBCO-PEG$_4$-amine (DBCO or DB) or DBCO-amine (DBCA or DA) under the same conditions to determine the effect of the linker on incorporation efficiency. The below table shows that in all but one of the serotypes tested, DBCO-amine incorporates at a higher efficiency as compared to DBCO-PEG$_4$-amine per 100 polysaccharide repeating units.

| Oxidized PS Sample | PS DB/DA Sample | DB/DA Reaction Conditions | DBCO/DBCA % incorporation | DB/DA-PS Yield % | DB/DA-PS Size, kDa |
|---|---|---|---|---|---|
| 5-OX | 5-DB (15.5 mg) | 5 mg/mL, 1 eq of DBCO, 10% DMSO, Phos. Buffer 50 mM, pH 6.7, 25 C, 3 d | 4.9 | 89 | |
| | 5-DA (15.5 mg) | 5 mg/mL, 1 eq of DBCA, 10% DMSO, Phos. Buffer 50 mM, pH 6.7, 25 C, 3 d | 8.3 | 83 | |
| 9V-OX | 9V-DB (17.1 mg) | 5.0 mg/mL, 2 d, 50 mM phos buff, pH 6.0, 1 mol eq. DBCO, 15% DMSO, 25° C. | 3.9 | 56 | |
| | 9V-DA (17.1 mg) | 5.0 mg/mL, 2 d, 50 mM phos buff, pH 6.0, 1 mol eq. DBCA, 15% DMSO, 25° C. | 6 | 80 | |
| 14-OX | 14-DB (15.65 mg) | 5.0 mg/mL, 50 mM phos buffer pH 6.7, 1.0 mol. eq. DBCO, 15% DMSO, 25° C. 48 h | 8 | 80 | |
| | 14-DA (15.65 mg) | 5.0 mg/mL, 50 mM phos buffer pH 6.7, 1.0 mol. eq. DBCA, 15% DMSO, 25° C. 48 h | 4.6 | 67 | |
| 23F-OX | 23F-DB (22.3 mg) | 4 mg/ml, 48 h, 100 mM pH 6.0, 0.8 eq DBCO, 15% DMSO, 25° C. | 5.5 | 68 | |
| | 23F-DA (22.3 mg) | 4 mg/ml, 48 h, 100 mM pH 6.0, 0.8 eq DBCA, 15% DMSO, 25° C. | 7.5 | 63 | |
| 22F-OX | 22F-DB (7.0 mg) | 2 mg/mL, 1 eq of DBCO, 15% DMSO, pH 6, 25° C. 48 h. | 0.8 | 101 | |
| | 22F-DA (7.0 mg) | 2 mg/mL, 1 eq of DBCA, 15% DMSO, pH 6, 25° C. 48 h. Ppt purification. | 4.3 | 104 | |
| 22F-OX | 22F-DB (7.0 mg) | 4 mg/mL, 1 eq of DBCO, 15% DMSO, pH 6, 25° C. 48 h. | 1.2 | 80 | 838 |
| | 22F-DA (14.0 mg) | 4 mg/mL, 1 eq of DBCA, 15% DMSO, pH 6, 25° C. 48 h. Ppt purification. | 4.3 | 73 | 790 |
| 10A-OX | 10A-DB (14.60 mg) | 7 mg/mL, 10% DMSO, 50 mM phos buff, pH 6.0, 1 mol eq. DBCO, 4° C., 2 d | 1.5 | 88 | |
| | 10A-DA (14.60 mg) | 7 mg/mL, 10% DMSO, 50 mM phos buff, pH 6.0, 1 mol eq. DBCA, 4° C., 2 d | 3.8 | 82 | |
| 7F-OX | 7F-DB (12 mg) | 2.9 mg/mL 1 eq DBCO (lot#1730), 99 mM phosphate pH 6.3, 21 h @ RT, 10% DMSO | 1.9 | 78 | 160 |
| | 7F-DA (12 mg) | 2.9 mg/mL 1 eq DBCA (lot#1818), 99 mM phosphate pH 6.3, 21 h @ RT, 10% DMSO | 4.5 | 76 | 177 |

Example 42: Comparison of DBCO-PEG$_4$-Amine and DBCO-Amine Conjugation to eCRM Pneumococcal polysaccharides linked to DBCO-PEG$_4$-amine (DB) or DBCO-amine (DA) were conjugated to the same eCRM from Table 2 under identical reaction conditions along the lines of the above examples to assess the effect of the linker on conjugation efficiency. The below table shows that conjugates formed with polysaccharide linked to DBCO-amine generally result in less free polysaccharide and larger conjugate size.

| DBCO PS | PS Scale (mg) | PS conc. mg/mL | Prot. Conc., mg/mL | Input Ratio | Conjugation Reaction Conditions | Yield % (PS) | PS:Prot Ratio | Free PS % | Conjugate Size MDa |
|---|---|---|---|---|---|---|---|---|---|
| 22F-DB | 2.4 | 3.2 | 2.3 | 1.4 | 3.2 mg/mL, 10% DMSO, 48 h, rt, 300 KDa dialysis, filter Millex-GP | 53 | 1.5 | 20.5 | 3.6 |
| 22F-DA | 2 | 3.2 | 2.3 | 1.4 | 3.2 mg/mL, 10% DMSO, 48 h, rt, 300 KDa dialysis, filter Millex-GP | 37 | 1.7 | LLOQ <9.2% | 6.2 |
| 7F-DB | 4 | 2.6 | 1.6 | 1.6 | 2.6 mg/mL, 18 h, RT, 300 kDa dialysis, filter Millex-MP | 94 | 2 | 31 | 1.3 |
| 7F-DA | 4 | 2.6 | 1.6 | 1.6 | 2.6 mg/mL, 18 h, RT, 300 kDa dialysis, filter Millex-MP | 84 | 2 | 14 | 1.8 |

Example 43: Immunogenicity of Pneumococcal PS Serotype-eCRM Conjugates

Experiments were conducted to determine the total IgG and functional OPA antibody responses in mice or rabbits following administration of a variety of monovalent pneumococcal polysaccharide-eCRM conjugates produced according to the present disclosure. Opsonophagocytic activity (OPA) assays were used to measure functional antibodies in murine sera specific for various *S. pneumonia* serotypes. OPA measurements were based on Moon H. Nahm & Robert L. Burton, "Protocol for opsonophagocytic killing assay for antibodies against Group B *Streptococcus* (UAB GBS OPA)," Version B.04, March 2016 (Original Version A.01 posted September 2011) (www.vaccine.uab.edu/uploads/mdocs/UAB-GBS-OPA.pdf) and "Protocol for multiplexed opsonophagocytic killing assay (UAB-MOPA) for antibodies against *Streptococcus pneumoniae*" Version E.02, December 2014 (www.vaccine.uab.edu/uploads/mdocs/UAB-MOPA.pdf). FIG. 3 shows opsonophagocytic (OPA) activity following administration of monovalent pneumococcal polysaccharide-eCRM conjugates in mice. The total polysaccharide binding antibody (IgG) specific to each pneumococcal polysaccharide was also measured according to the methods described in Yu et al., "Development of an Automated and Multiplexed Serotyping Assay for *Streptococcus pneumoniae*," *Clin Vaccine Immunol.* 2011,18(11): 1900-7. FIG. 4 shows IgG responses following administration of monovalent pneumococcal polysaccharide-eCRM conjugates in mice.

As summarized in the below tables, every conjugate tested elicited IgG and functional antibody responses in mice or rabbits that were comparable or superior to the OPA and IgG results shown in FIG. 3 and FIG. 4.

| PS Types | Immunogenicity in Mice | | PS Types | Immunogenicity in Mice or Rabbits | |
|---|---|---|---|---|---|
| | IgG | OPA | | IgG | OPA |
| 1 | ✔ | ✔ | 22F | ✔ | ✔ |
| 3 | ✔ | ✔ | 33F | ✔ | ✔ |
| 4 | ✔ | ✔ | 15B | ✔ | ✔ |
| 5 | ✔ | ✔ | 2 | ✔ | ✔ |
| 6A | ✔ | ✔ | 9N | ✔ | ✔ |
| 6B | ✔ | ✔ | 11A | ✔ | ✔ |
| 7F | ✔ | ✔ | 12F | ✔ | ✔ |
| 9V | ✔ | ✔ | 20 | ✔ | ✔ |
| 14 | ✔ | ✔ | 10A | ✔ | ✔ |
| 18C | ✔ | ✔ | 8 | ✔ | ✔ |
| 19A | ✔ | ✔ | 17F | ✔ | ✔ |
| 19F | ✔ | ✔ | | | |
| 23F | ✔ | ✔ | | | |

A combination of conjugates for each of 24 pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F was prepared using CRM197 derivative SEQ ID NO:9 as the carrier in each conjugate. The immunogenicity of this composition was tested using a 3-dose schedule in groups of 7 rabbits. It was also compared to the conjugated 13-valent Prevnar™ vaccine and to the unconjugated 23-valent Pneumovax™ vaccine, to which unconjugated serotype 6A polysaccharide had been added to assist the comparison. The three compositions had equivalent polysaccharide doses per serotype (except for 6B, where Prevnar™ includes a double dosage), which involved diluting the Prevnar™ and Pneumovax™. All three compositions included 60 μg aluminum phosphate adjuvant per dose, which involved adding the adjuvant to Pneumovax™.

The conjugation techniques disclosed herein led to a composition with a lower amount of CRM197 carrier than in the approved Prevnar-13™ vaccine, while also including capsular polysaccharides from 11 additional serotypes. The overall weight ratio of capsular polysaccharide to CRM197 in the conjugated 24-valent composition was about double that seen in 13-valent Prevnar™.

Figure 5:
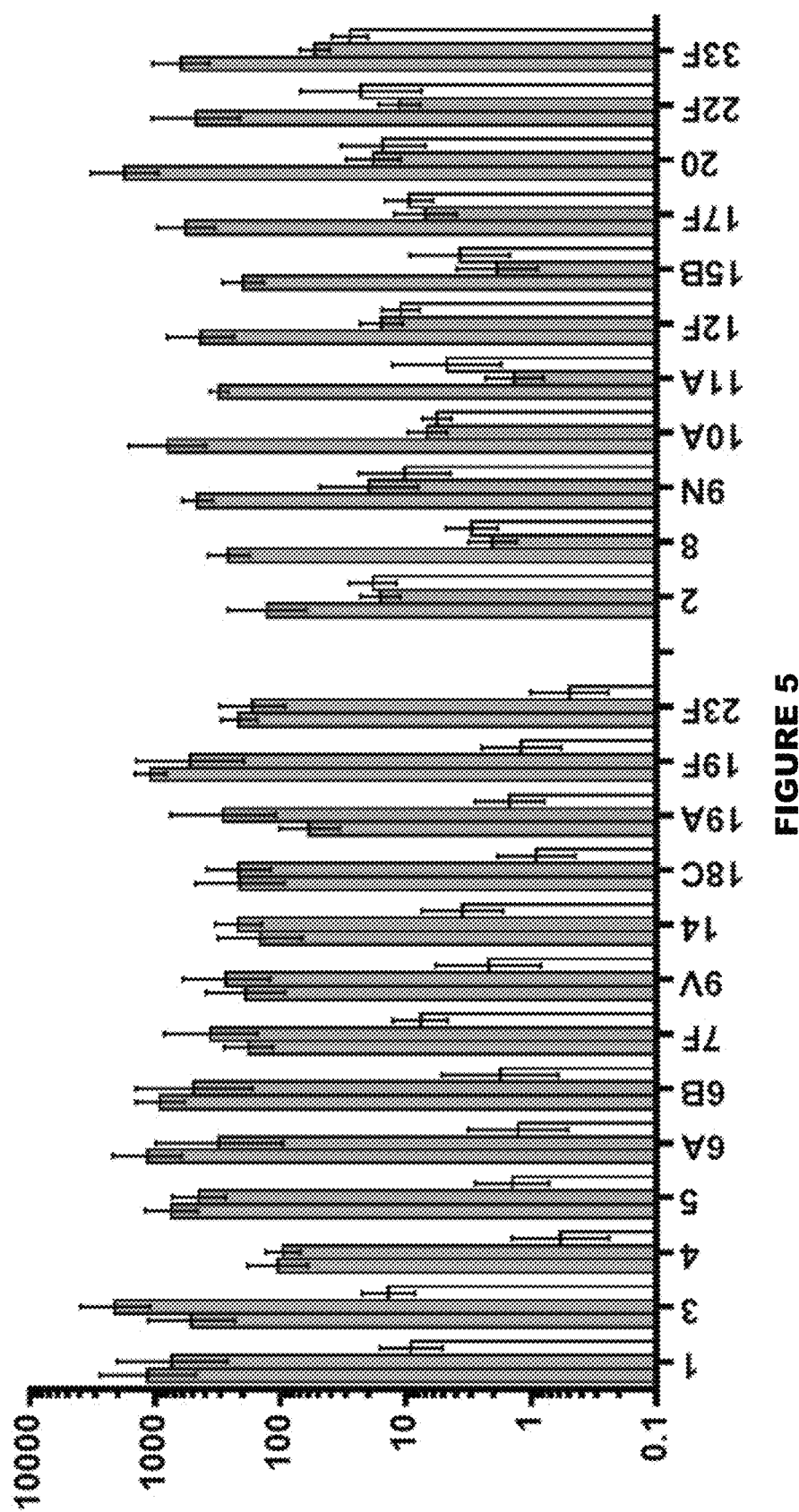
FIG. 5 shows IgG responses (GMT) following administration of multivalent pneumococcal vaccines in rabbits. Each serotype (X-axis) has data for a 24-valent conjugate vaccine of the invention (left), Prevnar-13™ (middle), and a 24-valent unconjugated vaccine (right). The data are means +/−95% confidence interval.
Figure 6:
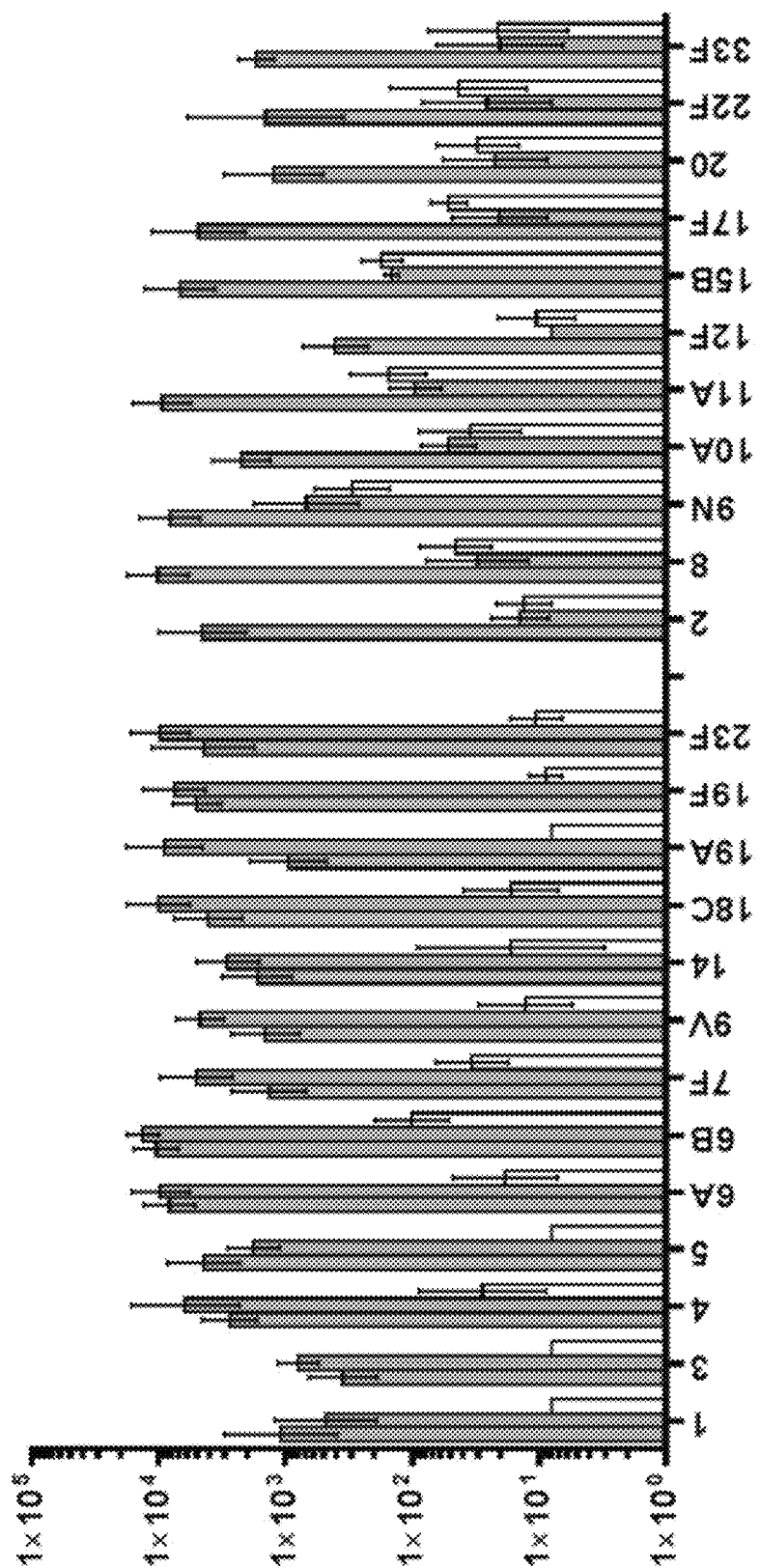
FIG. 6 is similar to FIG. 5 but shows OPA responses (GMT).

Responses after the third dose are shown in FIG. 5 (IgG responses) and FIG. 6 (OPA responses). As expected, responses using the two conjugated vaccines were much greater than with the unconjugated vaccine. Moreover, IgG and OPA responses using the 24-valent vaccine were comparable to those achieved using Prevnar-13™ in the serotypes covered by the approved vaccine, but in addition were superior against the 11 serotypes which are not included in Prevnar-13. Surprisingly, there was no evidence of carrier induced epitopic suppression.

Example 44: Preparation of a Conjugate Vaccine for Periodontitis

A vaccine against *Porphyromonas gingivalis* is prepared by conjugating capsular polysaccharides (CPS) from *P. gingivalis* serotypes K1, K2, K3, K4, K5 and/or K6 to an eCRM carrier protein as follows.

*P. gingivalis* is grown and handled by any suitable method. See, e.g., Huang et al., *Mol Oral Microbiol.* 30:438-50 (2015). CPS are purified by any method of choice. See, e.g., Gonzalez et al., *Infect. Immun.* 71:2283-2287 (2003); Schifferle et al., *J. Immunol.* 143:3035-3042 (1989); Pantosti et al., *Infect. Immun.* 59:2075-2082 (1991). Briefly, *P. gingivalis* is collected by centrifugation, rinsed with saline, suspended in water, and subjected to hot phenol-water extraction. The aqueous phase is collected, extracted with ether, and dialyzed against sterile filtered water. The aqueous material is adjusted to pH 5.5 and digested overnight with a nuclease cocktail consisting of DNase I and RNase A (Sigma). The pH is adjusted to neutrality and proteinase K (1 mg/ml; Sigma) is added to the sample and incubated overnight at 37° C. with gentle shaking. Then a second proteinase K digestion is performed and the resulting carbohydrate concentrated using a 10,000-molecular-weight cutoff membrane. CPS is precipitated with cold ethanol, suspended in deoxycholate buffer, and isolated using an S-400 gel filtration column (Pharmacia, Uppsala, Sweden). Fractions containing high-molecular-mass CPS (via SEC-MALS) are pooled, and fractions that contain LPS are discarded. The pooled fractions are concentrated, precipitated, dialyzed, and lyophilized.

To a buffered polysaccharide solution is added X molar equivalents (to polysaccharide repeating unit; X determined by screening) of 1-cyano-4-dimethylaminopyridinium tetrafluoroborate (CDAP; from 100 mg/mL solution in acetonitrile) with vigorous stirring. Five minutes after addition of CDAP, 0.5 molar equivalents of the dibenzocyclooctyne-amine linker (from DMSO stock solution) is added. After an additional, hour glycine is added to quench any unreacted cyanate esters. Alternatively, CPS may be modified using periodate or TEMPO/NCS chemistry. The derivatized polysaccharide is then purified via dialysis or UF/DF. The polysaccharide concentration is measured using an anthrone colorimetric assay, and dibenzocyclooctyne concentration is measured using absorbance at 309 nm. These two values can be combined to give an estimate of the percentage of polysaccharide derivatized with a dibenzycyclooctyne functional group.

The conjugate is prepared by mixing the derivatized polysaccharide with an eCRM protein of choice, such as those in Table 2. After 18 h incubation, one molar equivalent of sodium azide is added to quench any unreacted dibenzocyclooctyne functional groups. The conjugate is then purified via dialysis or UF/DF to remove unreacted eCRM protein. The conjugate is then analyzed to determine polysaccharide concentration (colorimetric), protein concentration (colorimetric) and the free/unconjugated saccharide percentage calculated. The molecular weight is measured using SEC-MALS.

Polysaccharide:protein conjugates are precipitated by the addition of 1% deoxycholate solution (pH 6.8) and incubation on ice for 30 minutes. Following incubation, 1M HCl is added and the mixture is centrifuged for 20 minutes at 10,000 rpm. The remaining supernatant contains unconjugated polysaccharide. To determine the polysaccharide concentration, anthrone dissolved in sulfuric acid is added to the samples and heated to 95° C. for 10 minutes. The mixture is cooled and the absorbance at 620 nm is measured. The concentration is calculated using a standard curve of the monosaccharide components of the polysaccharide.

The embodiments described herein are provided by way of example only, and various alternatives to the embodiments are not excluded in practicing the embodiments described herein.

The invention claimed is:

1. A composition comprising at least 21 distinct crosslinked carrier protein-antigen conjugates, wherein each of the distinct crosslinked carrier protein-antigen conjugates comprises:
   (i) an antigen, wherein the antigen is a distinct serotype of a capsular polysaccharide antigen from *Streptococcus pneumoniae*,
      wherein there is a distinct crosslinked carrier protein-antigen conjugate for each of the capsular polysaccharide antigens of serotypes 1, 3, 4, 5, 6A, 6B, 7F, 9V, 14, 18C, 19A, 19F and 23F and a distinct crosslinked carrier protein-antigen conjugate for each of at least eight additional capsular polysaccharide antigens of serotypes selected from the group consisting of 2, 6C, 8, 9N, 10A, 11A, 12F, 15A, 15B, 15C, 16F, 17F, 20, 20A, 20B, 22F, 23A, 23B, 24F, 24B, 31, 33F, 34, 35B, 35F and 38; and
   (ii) a carrier protein, wherein the carrier protein comprises a polypeptide comprising at least one T-cell activating epitope and at least 95% sequence identity to SEQ ID NO: 1, wherein a 2-amino-3-(4-(azidomethyl)phenyl) propanoic acid (pAMF) non-natural amino acid (nnAA) is substituted for a naturally occurring amino acid at residues 34, 213, 245, 265, 386, and 527 numbered according to SEQ ID NO:1,
   wherein the capsular polysaccharide antigen is conjugated to the nnAAs in the carrier protein.

2. The composition of claim 1, wherein the at least 21 distinct crosslinked carder protein-antigen conjugates comprise
   (i) at least 21 distinct crosslinked carrier protein-antigen conjugates wherein there is a distinct crosslinked carrier protein-antigen conjugate comprising a capsular polysaccharide for each of *Streptococcus pneumoniae* serotypes 1, 3, 4, 5, 6A, 6B, 7F, 8, 9V, 10A, 11A, 12F, 14, 15B, 18C, 19A, 19F, 22F, 23F, and 33F; or
   (ii) at least 24 distinct crosslinked carrier protein-antigen conjugates wherein there is a distinct crosslinked carrier protein-antigen conjugate comprising a capsular polysaccharide for each of *Streptococcus pneumonia* serotypes 1, 2, 3, 4, 5, 6A, 6B, 7F, 8, 9V, 9N, 10A, 11A, 12F, 14, 15B, 17F, 18C, 19A, 19F, 20, 22F, 23F, and 33F.

3. The composition of claim 2, wherein the antigen is linked to the carrier protein according to formula XI or XIa:

7. The composition according to claim 2, wherein the composition additionally comprises a distinct crosslinked carrier protein-antigen conjugate wherein the antigen is a capsular polysaccharide of *Streptococcus pneumoniae* serotype 6C or 7C.

8. The composition of claim 1, wherein the overall (weight by weight) ratio of all serotype polysaccharides to carrier protein in the composition is at least 1.1.

9. The composition of claim 1, wherein the overall (weight by weight) ratio of all serotype polysaccharides to carrier protein in the composition is at least 1.2.

10. The composition of claim 1, wherein the antigen is linked to the carrier protein according to formula XI or XIa:

(formula XI)

(formula XIa)

wherein
- $R_1$ is H, formyl, or at least one amino acid of the carrier protein;
- $R_2$ is OH or at least one amino acid of the carrier protein;
- W is C;
- y is 1;
- n is at least 1; and
- X is one monosaccharide within the capsular polysaccharide.

4. The composition of claim 3, wherein n is 3-16.

5. The composition according to claim 2, wherein the *Streptococcus pneumoniae* serotype 20 is serotype 20B.

6. The composition according to claim 5, wherein the composition additionally comprises a distinct crosslinked carrier protein-antigen conjugate wherein the antigen is a capsular polysaccharide of *Streptococcus pneumoniae* serotype 6C or 7C.

wherein
R$_1$ is H, formyl, or at least one amino acid of the carrier protein;
R$_2$ is OH or at least one amino acid of the carrier protein;
W is C;
y is 1;
n is at least 1; and
X is one monosaccharide within the capsular polysaccharide.

11. The composition of claim 10, wherein n is 3-16.

12. The composition of claim 1, wherein the *Streptococcus pneumoniae* capsular polysaccharides are conjugated to the nnAAs via a linking moiety, wherein the *Streptococcus pneumoniae* capsular polysaccharides comprise a cyclooctyne group and are conjugated to the pAMF nnAAs.

13. The composition of claim 12, wherein the antigen is linked to the carrier protein according to formula XI or XIa:

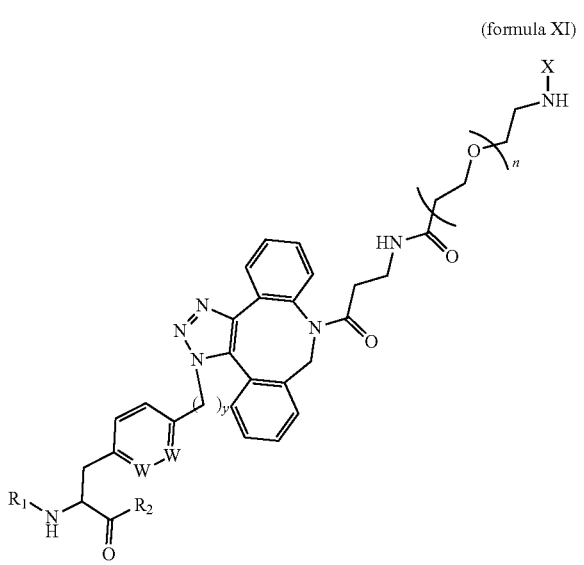

(formula XI)

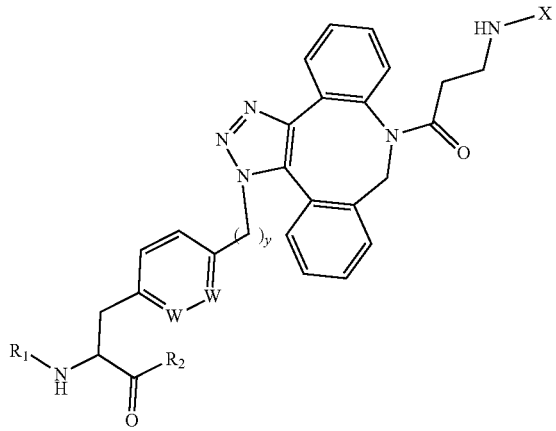

(formula XIa)

wherein
R$_1$ is H, formyl, or at least one amino acid of the carrier protein;
R$_2$ is OH or at least one amino acid of the carrier protein;
W is C;
y is 1;
n is at least 1; and
X is one monosaccharide within the capsular polysaccharide.

14. The composition of claim 13, wherein n is 3-16.

15. The composition of claim 1, wherein the overall (weight by weight) ratio of all serotype polysaccharides to carrier protein in the composition is at least 1.0.

16. The composition of claim 1, wherein there is less than about 25% (by weight) total free capsular polysaccharide present in the composition.

17. The composition according to claim 1, wherein the composition additionally comprises a distinct crosslinked carrier protein-antigen conjugate wherein the antigen is a capsular polysaccharide of *Streptococcus pneumoniae* serotype 6C or 7C.

* * * * *

SEQUENCE LISTING

```
<160> NUMBER OF SEQ ID NOS: 10

<210> SEQ ID NO 1
<211> LENGTH: 536
<212> TYPE: PRT
<213> ORGANISM: Corynebacterium diphtheriae

<400> SEQUENCE: 1

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45
```

-continued

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
    450                 455                 460

-continued

```
Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
        515                 520                 525

Ser Leu Phe Phe Glu Ile Lys Ser
    530                 535

<210> SEQ ID NO 2
<211> LENGTH: 1611
<212> TYPE: DNA
<213> ORGANISM: Corynebacterium diphtheriae

<400> SEQUENCE: 2
atgggcgcag acgatgttgt ggactcaagt aaatcatttg tcatggaaaa cttctcctca     60
tatcacggca cgaaaccggg ctacgttgat agcattcaga aaggtatcca aaaaccgaaa    120
tctggcacgc agggtaacta cgatgacgat tggaaagaat tctacagcac cgacaacaaa    180
tatgatgcgg ccggttactc agtcgacaac gaaaatccgc tgtcgggcaa agccggcggt    240
gtggttaaag tgacgtatcc gggcctgacc aaagtcctgg ccctgaaagt ggataatgca    300
gaaaccatca aaaaagaact gggtctgagc ctgacggaac cgctgatgga acaggttggc    360
accgaagaat ttatcaaacg cttcggcgat ggtgccagtc gtgtcgtgct gtccctgccg    420
ttcgcagaag gtagctctag tgtggaatat attaacaatt gggaacaagc gaaagccctg    480
tccgttgaac tggaaatcaa ctttgaaacc cgcggcaaac gtggtcagga tgcgatgtat    540
gaatacatgg cacaagcttg cgcgggtaat cgcgttcgtc gcagcgtcgg ctcctcactg    600
tcttgtatca acctggactg ggatgttatc cgtgataaaa ccaaaacgaa aatcgaaagt    660
ctgaaagaac atggcccgat caaaaacaaa atgagcgaat ctccgaataa aacggtgtcc    720
gaagaaaaag ctaaacagta tctggaagaa ttccaccaaa ccgcactgga acatccggaa    780
ctgtcagaac tgaaaaccgt gacgggtacc aacccggttt ttgccggcgc aaattacgca    840
gcttgggctg tgaacgttgc gcaagtgatt gactcggaaa cggccgataa tctggaaaaa    900
accacggcgg ccctgagtat tctgccgggc atcggttccg ttatgggtat tgccgacggc    960
gcagtccatc acaacaccga agaaattgtg gcccagtcta tcgcactgtc gagcctgatg   1020
gttgctcaag cgattccgct ggttggcgaa ctggttgata tcggctttgc agcttacaac   1080
ttcgtggaaa gtattatcaa cctgtttcag gttgtccaca actcatataa tcgcccggcc   1140
tactcgccgg gtcacaaaac ccaaccgttc ctgcatgacg gctacgcggt tagctggaat   1200
acggtcgaag attctattat ccgtaccggc tttcagggtg aatctggcca cgacattaaa   1260
atcacggctg aaaacacccc gctgccgatt gcaggtgttc tgctgccgac gatcccgggt   1320
aaactggatg ttaacaaatc aaaaaaccat atctcggtca acggtcgcaa aattcgtatg   1380
cgctgccgtg cgatcgacgg cgatgtgacc ttctgtcgtc cgaaaagccc ggtctatgtg   1440
ggcaacggtg tccatgctaa tctgcacgtg gcgtttcatc gctctagttc cgaaaaaatc   1500
catagtaacg aaatctcatc ggattccatt ggtgtgctgg gctaccagaa aaccgtggac   1560
cataccaaag tgaatagcaa actgagcctg ttcttcgaaa tcaaatcgta a            1611

<210> SEQ ID NO 3
```
<211> LENGTH: 19
<212> TYPE: PRT
<213> ORGANISM: Clostridium tetani

<400> SEQUENCE: 3

Asp Lys Ile Ser Asp Val Ser Thr Ile Val Pro Tyr Ile Gly Pro Ala
1 5 10 15

Leu Asn Ile

<210> SEQ ID NO 4
<211> LENGTH: 20
<212> TYPE: PRT
<213> ORGANISM: Clostridium tetani

<400> SEQUENCE: 4

Asn Asn Phe Thr Val Ser Phe Trp Leu Arg Val Pro Lys Val Ser Ala
1 5 10 15

Ser His Leu Glu
20

<210> SEQ ID NO 5
<211> LENGTH: 16
<212> TYPE: PRT
<213> ORGANISM: Streptococcus G148

<400> SEQUENCE: 5

Val Ser Asp Tyr Tyr Lys Asn Leu Ile Asn Asn Ala Lys Thr Val Glu
1 5 10 15

<210> SEQ ID NO 6
<211> LENGTH: 16
<212> TYPE: PRT
<213> ORGANISM: Streptococcus G148

<400> SEQUENCE: 6

Asp Gly Leu Ser Asp Phe Leu Lys Ser Gln Thr Pro Ala Glu Asp Thr
1 5 10 15

<210> SEQ ID NO 7
<211> LENGTH: 16
<212> TYPE: PRT
<213> ORGANISM: Streptococcus G148

<400> SEQUENCE: 7

Ala Glu Asp Thr Val Lys Ser Ile Glu Leu Ala Glu Ala Lys Val Leu
1 5 10 15

<210> SEQ ID NO 8
<211> LENGTH: 346
<212> TYPE: PRT
<213> ORGANISM: Haemophilus influenzae

<400> SEQUENCE: 8

Cys Ser Ser His Ser Ser Asn Met Ala Asn Thr Gln Met Lys Ser Asp
1 5 10 15

Lys Ile Ile Ile Ala His Arg Gly Ala Ser Gly Tyr Leu Pro Glu His
20 25 30

Thr Leu Glu Ser Lys Ala Leu Ala Phe Ala Gln Gln Ala Asp Tyr Leu
35 40 45

Glu Gln Asp Leu Ala Met Thr Lys Asp Gly Arg Leu Val Val Ile His
50 55 60

Asp His Phe Leu Asp Gly Leu Thr Asp Val Ala Lys Lys Phe Pro His

```
                65                  70                  75                  80
Arg His Arg Lys Asp Gly Arg Tyr Tyr Val Ile Asp Phe Thr Leu Lys
                    85                  90                  95
Glu Ile Gln Ser Leu Glu Met Thr Glu Asn Phe Glu Thr Lys Asp Gly
                    100                 105                 110
Lys Gln Ala Gln Val Tyr Pro Asn Arg Phe Pro Leu Trp Lys Ser His
                    115                 120                 125
Phe Arg Ile His Thr Phe Glu Asp Glu Ile Glu Phe Ile Gln Gly Leu
                    130                 135                 140
Glu Lys Ser Thr Gly Lys Lys Val Gly Ile Tyr Pro Glu Ile Lys Ala
145                 150                 155                 160
Pro Trp Phe His His Gln Asn Gly Lys Asp Ile Ala Ala Glu Thr Leu
                    165                 170                 175
Lys Val Leu Lys Lys Tyr Gly Tyr Asp Lys Lys Thr Asp Met Val Tyr
                    180                 185                 190
Leu Gln Thr Phe Asp Phe Asn Glu Leu Lys Arg Ile Lys Thr Glu Leu
                    195                 200                 205
Leu Pro Gln Met Gly Met Asp Leu Lys Leu Val Gln Leu Ile Ala Tyr
        210                 215                 220
Thr Asp Trp Lys Glu Thr Gln Glu Lys Asp Pro Lys Gly Tyr Trp Val
225                 230                 235                 240
Asn Tyr Asn Tyr Asp Trp Met Phe Lys Pro Gly Ala Met Ala Glu Val
                    245                 250                 255
Val Lys Tyr Ala Asp Gly Val Gly Pro Gly Trp Tyr Met Leu Val Asn
                    260                 265                 270
Lys Glu Glu Ser Lys Pro Asp Asn Ile Val Tyr Thr Pro Leu Val Lys
                    275                 280                 285
Glu Leu Ala Gln Tyr Asn Val Glu Val His Pro Tyr Thr Val Arg Lys
                    290                 295                 300
Asp Ala Leu Pro Glu Phe Phe Thr Asp Val Asn Gln Met Tyr Asp Ala
305                 310                 315                 320
Leu Leu Asn Lys Ser Gly Ala Thr Gly Val Phe Thr Asp Phe Pro Asp
                    325                 330                 335
Thr Gly Val Glu Phe Leu Lys Gly Ile Lys
                    340                 345

<210> SEQ ID NO 9
<211> LENGTH: 536
<212> TYPE: PRT
<213> ORGANISM: Artificial Sequence
<220> FEATURE:
<223> OTHER INFORMATION: Modified carrier protein
<220> FEATURE:
<221> NAME/KEY: MOD_RES
<222> LOCATION: (34)..(34)
<223> OTHER INFORMATION: Xaa is a non-natural amino acid
<220> FEATURE:
<221> NAME/KEY: MOD_RES
<222> LOCATION: (213)..(213)
<223> OTHER INFORMATION: Xaa is a non-natural amino acid
<220> FEATURE:
<221> NAME/KEY: MOD_RES
<222> LOCATION: (245)..(245)
<223> OTHER INFORMATION: Xaa is a non-natural amino acid
<220> FEATURE:
<221> NAME/KEY: MOD_RES
<222> LOCATION: (265)..(265)
<223> OTHER INFORMATION: Xaa is a non-natural amino acid
<220> FEATURE:
<221> NAME/KEY: MOD_RES
<222> LOCATION: (386)..(386)
```

<223> OTHER INFORMATION: Xaa is a non-natural amino acid
<220> FEATURE:
<221> NAME/KEY: MOD_RES
<222> LOCATION: (527)..(527)
<223> OTHER INFORMATION: Xaa is a non-natural amino acid

<400> SEQUENCE: 9

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Xaa Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Xaa Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Xaa Gln Tyr Leu Glu Glu Phe His Gln Thr Ala Leu
                245                 250                 255

Glu His Pro Glu Leu Ser Glu Leu Xaa Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380
```

```
His Xaa Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
                420                 425                 430

Val Leu Leu Pro Thr Ile Pro Gly Lys Leu Asp Val Asn Lys Ser Lys
                435                 440                 445

Thr His Ile Ser Val Asn Gly Arg Lys Ile Arg Met Arg Cys Arg Ala
                450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
                500                 505                 510

Leu Gly Tyr Gln Lys Thr Val Asp His Thr Lys Val Asn Ser Xaa Leu
                515                 520                 525

Ser Leu Phe Phe Glu Ile Lys Ser
    530                 535

<210> SEQ ID NO 10
<211> LENGTH: 9
<212> TYPE: PRT
<213> ORGANISM: Artificial Sequence
<220> FEATURE:
<223> OTHER INFORMATION: Histidine tag

<400> SEQUENCE: 10

Gly Ser Gly His His His His His His
1               5
```